United States Patent
Hofstadler et al.

(10) Patent No.: US 9,194,877 B2
(45) Date of Patent: Nov. 24, 2015

(54) SYSTEMS FOR BIOAGENT INDENTIFICATION

(75) Inventors: Steven A. Hofstadler, Vista, CA (US); Jose R. Gutierrez, San Marcos, CA (US); James C. Hannis, Vista, CA (US); Jared J. Drader, Carlsbad, CA (US); Rex O. Bare, Lake Forest, CA (US); Jeffrey C. Smith, Irvine, CA (US); Paul J. Gleason, Laguna Niguel, CA (US); Jared Nathanson, Misson Viejo, CA (US); Ronald K. Bergold, Misson Viejo, CA (US); Robert D. Miller, Costa Mesa, CA (US); Kevin S. Oberkramer, Placentia, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 923 days.

(21) Appl. No.: 12/837,191

(22) Filed: Jul. 15, 2010

(65) Prior Publication Data
US 2012/0115213 A1    May 10, 2012

Related U.S. Application Data

(63) Continuation of application No. PCT/US2010/042159, filed on Jul. 15, 2010.

(60) Provisional application No. 61/226,537, filed on Jul. 17, 2009.

(51) Int. Cl.
*C12M 1/34* (2006.01)
*C12M 3/00* (2006.01)
(Continued)

(52) U.S. Cl.
CPC ............. *G01N 35/0092* (2013.01); *B01L 7/52* (2013.01); *G01N 35/0095* (2013.01); *G01N 2035/00534* (2013.01)

(58) Field of Classification Search
CPC ............ B01J 2219/00722; B01J 2219/00659; B01L 2300/0636; B01L 7/52; C40B 40/06
USPC ....................... 435/287.2; 422/68.1
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |

(Continued)

FOREIGN PATENT DOCUMENTS

| | | |
|---|---|---|
| DE | 19732086 A1 | 1/1999 |
| DE | 19802905 A1 | 7/1999 |

(Continued)

OTHER PUBLICATIONS

Aaserud D.J., et al., "Accurate Base Composition of Double-Strand DNA by Mass Spectrometry," American Society for Mass Spectrometry, 1996, vol. 7 (12), pp. 1266-1269.
(Continued)

*Primary Examiner* — Michael Hobbs
(74) *Attorney, Agent, or Firm* — David A. Casimir; Casimir Jones, S.C.

(57) ABSTRACT

The present invention provides systems and methods for analysis of samples, particularly biological and environmental sample to detect biomolecules of interest contained therein. A variety of system components are described herein, including, but not limited to, components for sample handling, mixing of materials, sample processing, transfer of materials, and analysis of materials. The invention further provides mechanisms for combining and integrating the different components and for housing, moving, and storing system components or the system as a whole. The systems may include any one or more or all of these components. The system finds particular use when employed for analysis of nucleic acid molecule using mass spectrometry, however, the invention is not limited such specific uses.

29 Claims, 128 Drawing Sheets

(51) Int. Cl.
   *G01N 35/00*   (2006.01)
   *B01L 7/00*   (2006.01)

(56) References Cited

U.S. PATENT DOCUMENTS

| | | |
|---|---|---|
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,366,896 A | 11/1994 | Margrey et al. |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |

(56) References Cited

U.S. PATENT DOCUMENTS

| | | |
|---|---|---|
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,485,913 B1 | 11/2002 | Becker et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,476,313 B2 | 1/2009 | Siddiqi |
| 7,501,251 B2 | 3/2009 | Köster et al. |
| 7,502,665 B2 | 3/2009 | Giles et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0127727 A1* | 9/2002 | Bach et al. .................. 436/48 |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |

(56) References Cited

U.S. PATENT DOCUMENTS

| | | |
|---|---|---|
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0068360 A1 | 3/2006 | Boulais |
| 2006/0121520 A1 | 6/2006 | Ecker et al. |
| 2006/0171853 A1 | 8/2006 | Moore et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2007/0087336 A1* | 4/2007 | Sampath et al. ............. 435/5 |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0117620 A1 | 5/2009 | Fritchie et al. |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0171590 A1 | 7/2009 | Puskas et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |
| 2010/0128558 A1* | 5/2010 | Hofstadler et al. ........ 366/142 |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| WO | WO8803957 A1 | 6/1988 |
| WO | WO9015157 A1 | 12/1990 |
| WO | WO9205182 A1 | 4/1992 |
| WO | WO9208117 A1 | 5/1992 |
| WO | WO9209703 A1 | 6/1992 |
| WO | WO9219774 A1 | 11/1992 |
| WO | WO9303186 A1 | 2/1993 |
| WO | WO9305182 A1 | 3/1993 |
| WO | WO9308297 A1 | 4/1993 |
| WO | WO9416101 A2 | 7/1994 |
| WO | WO9419490 A1 | 9/1994 |
| WO | WO9421822 A1 | 9/1994 |
| WO | WO9504161 A1 | 2/1995 |
| WO | WO9511996 A1 | 5/1995 |
| WO | WO9513395 A1 | 5/1995 |
| WO | WO9513396 A2 | 5/1995 |
| WO | WO9531997 A1 | 11/1995 |
| WO | WO9606187 A1 | 2/1996 |
| WO | WO9616186 A1 | 5/1996 |
| WO | WO9629431 A2 | 9/1996 |
| WO | WO9632504 A2 | 10/1996 |
| WO | WO9635450 A1 | 11/1996 |
| WO | WO9637630 A1 | 11/1996 |
| WO | WO9733000 A1 | 9/1997 |
| WO | WO9734909 A1 | 9/1997 |
| WO | WO9737041 A2 | 10/1997 |
| WO | WO9747766 A1 | 12/1997 |
| WO | WO9803684 A1 | 1/1998 |
| WO | WO9812355 A1 | 3/1998 |
| WO | WO9814616 A1 | 4/1998 |
| WO | WO9815652 A1 | 4/1998 |
| WO | WO9820020 A2 | 5/1998 |
| WO | WO9820157 A2 | 5/1998 |
| WO | WO9820166 A2 | 5/1998 |
| WO | WO9826095 A1 | 6/1998 |
| WO | WO9831830 A1 | 7/1998 |
| WO | WO9835057 A1 | 8/1998 |
| WO | WO9840520 A1 | 9/1998 |
| WO | WO9854571 A1 | 12/1998 |
| WO | WO9854751 A1 | 12/1998 |
| WO | WO9905319 A2 | 2/1999 |
| WO | WO9912040 A2 | 3/1999 |
| WO | WO9913104 A1 | 3/1999 |
| WO | WO9914375 A2 | 3/1999 |
| WO | WO9929898 A2 | 6/1999 |
| WO | WO9931278 A1 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A2 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0112853 A1 | 2/2001 |
| WO | WO0120018 A2 | 3/2001 |
| WO | WO0123604 A2 | 4/2001 |
| WO | WO0123608 A2 | 4/2001 |
| WO | WO0132930 A1 | 5/2001 |
| WO | WO0140497 A2 | 6/2001 |
| WO | WO0146404 A2 | 6/2001 |
| WO | WO0151661 A2 | 7/2001 |
| WO | WO0151662 A1 | 7/2001 |
| WO | WO0157263 A1 | 8/2001 |
| WO | WO0157518 A2 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |

(56) References Cited

FOREIGN PATENT DOCUMENTS

| | | |
|---|---|---|
| WO | WO02070664 A2 | 9/2002 |
| WO | WO02070728 A2 | 9/2002 |
| WO | WO02070737 A2 | 9/2002 |
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03018636 A2 | 3/2003 |
| WO | WO03020890 A2 | 3/2003 |
| WO | WO03033732 A2 | 4/2003 |
| WO | WO03054162 A2 | 7/2003 |
| WO | WO03054755 A2 | 7/2003 |
| WO | WO03060163 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | WO2004003511 A2 | 1/2004 |
| WO | WO2004009849 A1 | 1/2004 |
| WO | WO2004011651 A1 | 2/2004 |
| WO | WO2004013357 A2 | 2/2004 |
| WO | WO2004040013 A1 | 5/2004 |
| WO | WO2004044123 A2 | 5/2004 |
| WO | WO2004044247 A2 | 5/2004 |
| WO | WO2004052175 A2 | 6/2004 |
| WO | WO2004053076 A2 | 6/2004 |
| WO | WO2004053141 A2 | 6/2004 |
| WO | WO2004053164 A1 | 6/2004 |
| WO | WO2004060278 A2 | 7/2004 |
| WO | WO2004070001 A2 | 8/2004 |
| WO | WO2004072230 A2 | 8/2004 |
| WO | WO2004072231 A2 | 8/2004 |
| WO | WO2004101809 A2 | 11/2004 |
| WO | WO2005003384 A1 | 1/2005 |
| WO | WO2005009202 A2 | 2/2005 |
| WO | WO2005012572 A1 | 2/2005 |
| WO | WO2005024046 A2 | 3/2005 |
| WO | WO2005036369 A2 | 4/2005 |
| WO | WO2005054454 A1 | 6/2005 |
| WO | WO2005075686 A1 | 8/2005 |
| WO | WO2005086634 A2 | 9/2005 |
| WO | WO2005091971 A2 | 10/2005 |
| WO | WO2005098047 A2 | 10/2005 |
| WO | WO2005116263 A2 | 12/2005 |
| WO | WO2006089762 A1 | 8/2006 |
| WO | WO2006094238 A2 | 9/2006 |
| WO | WO2006135400 A2 | 12/2006 |
| WO | WO2007014045 A2 | 2/2007 |
| WO | WO2007086904 A2 | 8/2007 |
| WO | WO2008104002 A2 | 8/2008 |
| WO | WO2008118809 A1 | 10/2008 |

OTHER PUBLICATIONS

Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.

Adam E., et al., "Characterization of Intertype Specific Epitopes on Adenovirus Hexons," Archives of Virology, 1998, vol. 143 (9), pp. 1669-1682.

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucleotides for the Detection of Infectious Bronchitis Virus by Thepolymerase Chain Reaction," Avian Pathology, 1996, vol. 25 (4), pp. 817-836.

Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.

Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "VIDA: A Virus Database System for the Organization of Animal Virus Genome Open Reading Frames," Nucleic Acids Research, 2001, vol. 29 (1), pp. 133-136.

Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.

Allawi H.T., et al., "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Hames B.D., ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in *Staphylococci*," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnositic Microbiology and Infectious Diseases, 2001, vol. 40 (1-2), pp. 5-10.

Archer G.L., et al., "Detection of Methicillin Resistance in *Staphylococci* by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

(56) References Cited

OTHER PUBLICATIONS

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.
Aronsson F., et al., "Persistence of the Influenza A/WSN/33 Virus RNA at Midbrain Levels of Immunodefective Mice," Journal of Neurovirology, 2001, vol. 7 (2), pp. 117-124.
Ausubel F.M., et al., Eds., Current Protocols in Molecular Biology, vol. 1, John Wiley & Sons Inc., 2004, Table of Contents.
Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.
Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.
Avellon A., et al., "Rapid and Sensitive Diagnosis of Human Adenovirus Infections by a Generic Polymerase Chain Reaction," Journal of Virological Methods, 2001, vol. 92 (2), pp. 113-120.
Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.
Baba T., et al., "Genome and Virulence Determinants of High Virulence Community-Acquired MRSA," Lancet, 2002, vol. 359 (9320), pp. 1819-1827.
Bahrmahd A.R., et al., "Polymerise Chain Reaction of Bacterial Genomes with Single Universal Primer: Application to Distinguishing *Mycobacteria* Species," Molecular and Cellular Probes, 1996, vol. 10 (2), pp. 117-122.
Bahrmahd A.R., et al., "Use of Restriction Enzyme Analysis of Amplified DNA Coding for the hsp65 Gene and Polymerase Chain Reaction with Universal Primer for Rapid Differtiation of *Mycobacterium* Species in the Clinical Laboratory," Scandinavian Journal of Infectious Diseases, 1998, vol. 30 (5), pp. 477-480.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Baker G.C., et al., "Review and Re-Analysis of Domain-Specific 16S Primers," Journal of Microbiological Methods, 2003, vol. 55 (3), pp. 541-555.
Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.
Barbour A.G., et al., "Identification of an Uncultivatable Borrelia Species in the Hard Tick Amblyomma Americanum: Possible Agent of a Lyme Disease-Like Illness," The Journal of Infectious Diseases, 1996, vol. 173 (2), pp. 403-409.
Barns S.M., et al., "Detection of Diverse New Francisella-like Bacteria in Environmental Samples," Applied and Environmental Microbiology, 2005, vol. 71 (9), pp. 5494-5500.
Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.
Barr I.G., et al., "An Influenza A(H3) Reassortant was Epidemic in Australia and New Zealand in 2003," Journal of Medical Virology, 2005, vol. 76 (3), pp. 391-397.
Barski P., et al., "Rapid Assay for Detection of Methicillin-Resistant *Staphylococcus aureus* Using Multiplex PCR," Molecular and Cellular Probes, 1996, vol. 10 (6), pp. 471-475.
Bastia T., et al., "Organelle DNA Analysis of Solanum and Brassica Somatic Hybrids by PCR with Universal Primers," Theoretical and Applied Genetics, 2001, vol. 102 (8), pp. 1265-1272.
Batey R.T., et al., "Preparation of Isotopically Labeled Ribonucleotides for Multidimensional NMR Spectroscopy of RNA," Nucleic Acids Research, 1992, vol. 20 (17), pp. 4515-4523.
Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.
Beall B., et al., "Sequencing emm-Specific PCR Products for Routine andAccurate Typing of Group A *Streptococci*," Journal of Clincal Microbiology, 1996, vol. 34 (4), pp. 953-958.
Beall B., et al., "Survey of emm Gene Sequences and T-Antigen Types from Systemic *Streptococcus pyogenes* Infection Isolates Collected in San Francisco, California; Atlanta, Georgia; and Connecticut in 1994 and 1995," Journal of Clincal Microbiology, 1997, vol. 35 (5), pp. 1231-1235.
Benko, M. et al., "Family Adenoviridae," Virus taxonomy. VIIIth report of the International Committee on Taxonomy of Viruses, 2004, Academic Press, New York, pp. 213-228.
Benson D.A., et al., "GenBank," Nucleic Acids Research, 1999, vol. 27 (1), pp. 12-17.
Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.
Berencsi G., et al., "Molecular Biological Characterization of Adenovirus DNA," Acta Microbiologica et Immunologica Hungarica, 1998, vol. 45 (3-4), pp. 297-304.
Bishop M.J., et al., "Molecular Sequence Databases" in: Nucleic Acid and Protein Sequence Analysis, 4th Chapter, Bishop M.J., et al., Eds, IRL Press, 1987, pp. 83-113.
Bisno A.L., "*Streptococcus pyogenes*" in: Infectious Diseases and Their Etiologic Agents, vol. 2, Mandell, Eds., Churchill Livingston, New York, pp. 1786-1799.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Blaiotta G., et al., "PCR Detection of *Staphylococcal enterotoxin* Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.
BLAST Search results, Mar. 7, 2006.
Boivin-Jahns V., et al., "Bacterial Diversity in a Deep-Subsurface Clay Environment," Applied and Environmental Microbiology, 1996, vol. 62 (9), pp. 3405-3412.
Bolton E.T., et al., "A General Method for the Isolation of RNA Complementary to DNA," Proceedings of the National Academy of Sciences, 1962, vol. 48, pp. 1390-1397.
Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Boubaker K., et al., "Panton-Valentine Leukocidin and *Staphyloccoccal* Skin Infections in Schoolchildren," Emerging Infectious Diseases, 2004, vol. 10 (1), pp. 121-124.
Bowen J.E., et al., "The Native Virulence Plasmid Combination Affects the Segregational Stability of a Thetareplicating Shuttle Vector in Bacillus Anthracis Var," Journal of Applied Microbiology, 1999, vol. 87 (2), pp. 270-278.
Bowers K.M., et al., "Screening for Methicillin Resistance in *Staphylococars aureus* and Coagulasenegative *Staphylococci*: Evaluation of Three Selective and Mastalex-MRSA latex Agglutination," British Journal of Biomedical Science, 2003, vol. 60 (2), pp. 71-74.
Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and

(56) References Cited

OTHER PUBLICATIONS

Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the *Staphylococcal* mecA Gene from BACTEC BloodCulture Bottles by the Polymerase Chain Reaction," American Journal of Clincal Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escerichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of *Staphylococcus aureus* from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.
Chen C.H., et al., Laser Desorption Mass Spectrometry for FastDNA Sequencing [online], Nov. 1994, Retrieved from the Internet:<URL:http://www.ornl.gove/sci/techresources/Human_Genome/publicat/94SANTA/sequencing/seqtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N.H., et al., "Mass Spectrometry of Single-Stranded Restriction Fragments Captured by an Undigested Complementary Sequence," Nucleic Acids Research, 2000, vol. 28 (8), p. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus Saccharomonospora," International Journal of Systematic Bacteriology, 1998, vol. 48 (4), pp. 1223-1230.

(56) References Cited

OTHER PUBLICATIONS

Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.
Cornel A.J., et al., "Polymerase Chain Reaction Species Diagnostic Assay for Anopheles Quadrimaculatus Cryptic Species (Diptera:Culicidae) Based on Ribosomal DNA ITS2 Sequences," Journal of Medical Entomology, 1996, vol. 33 (1), pp. 109-116.
Couto I., et al., "Development of Methicillin Resistance in Clinical Isolates of *Staphylococcus Sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Deforce D.L., et al., "Analysis of Oligonucleotides by ESI-MS," Advances in Chromatography, 2000, vol. 40, pp. 539-566.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.
Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.

(56) References Cited

OTHER PUBLICATIONS

Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71- 81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.
Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Severe Acute Respiratory Syndrome," New England Journal of Medicine, 2003, vol. 348 (20), pp. 1967-1976.
Dubernet S., et al., "A PCR-Based Method for Identification of Lactobacilli at to Genus Level," FEMS Microbiology Letters, 2002, vol. 214 (2), pp. 271-275.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Edwards K.M., et al., "Adenovirus Infections in Young Children," Pediatrics, 1985, vol. 76 (3), pp. 420-424.
Ellis J.S., et al., "Molecular Diagnosis of Influenza," Reviews in Medical Virology, 2002, vol. 12 (6), pp. 375-389.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.
Elsayed S., et al., "Development and Validation of a Molecular Beacon Probe-Based Real-Time Polymerase Chain Reaction Assay for Rapid Detection of Methicillin Resistance in *Staphylococcus aureus*," Archives of Pathology and Laboratory Medicine, 2003, vol. 127 (7), pp. 845-849.
EMBL "Arabidopsis Thaliana T-DNA Flanking Sequence, Left Border, Clone 346C06," Accession No. AJ552897, Mar. 29, 2003.
EMBL "Dog (Clone: CXX.147) Primer for STS 147, 3" End, Sequence Tagged Site," Accession No. L15697, Mar. 4, 2000.
EMBL "Human, muscle, Mitochondrial Mutant, 22 nt, segment 2 of 2," Accession No. S90302, Sep. 1, 2004.
EMBL "Sequence 10 from U.S. Pat. No. 6,563,025," Accession No. AR321656, Aug. 18, 2003.
EMBL "Synthetic Construct DNA, Reverse Primer for Human STS sts-AA031654 at 1p36" Accession No. AB068711, May 21, 2003.
Enright M.C., et al., "A Multilocus Sequence Typing Scheme for *Streptococcus pneumoniae*: Identification of Clones Associated with Serious Invasive Disease," Microbiology, 1998, vol. 144 (Pt 11), pp. 3049-3060.
Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.
Enright M.C., et al., "Multilocus Sequence Typing of *Streptococcus pyogenes* and theRelationships between Emm Type and Clone," Infection and Immunity, 2001, vol. 69 (4), pp. 2416-2427.
Enright M.C., et al., "The Evolutionary History of Methicillin-Resistant *Staphylococcus aureus* (MRSA)," Proceedings of the National Academy of Sciences, 2002, vol. 99 (11), pp. 7687-7692.
Enright M.C., "The Evolution of a Resistant Pathogen—the Case of MRSA," Current Opinion in Pharmacology, 2003, vol. 3 (5), pp. 474-479.
Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.
Erlich H.A., Ed., PCR Technology: Principles and Applications for DNA Amplification, W.H. Freeman and Company, 1989.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
European Search Report for Application No. EP10175659.1, mailed on Feb. 9, 2011, 4 pages.
Evans P., et al., "Practical Algorithms for Universal DNA Primer Design: An Exercise in Algorithm Engineering," Currents in Computational Molecular Biology, 2001, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.

(56) References Cited

OTHER PUBLICATIONS

Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Jun. 7, 2011 for U.S. Appl. No. 11/930,108 filed Oct. 31, 2007.
Examiner Interview Summary mailed Aug. 10, 2004 for U.S. Appl. No. 09/798,007, filed Mar. 2, 2001.
Examiner Interview Summary mailed Aug. 10, 2004 for U.S. Appl. No. 09/891,793, filed Jun. 26, 2001.
Examiner Interview Summary mailed Aug. 10, 2004 for U.S. Appl. No. 10/156,608, filed May 24, 2002.
Examiner Interview Summary mailed Aug. 10, 2004 for U.S. Appl. No. 10/326,642, filed Dec. 18, 2002.
Examiner Interview Summary mailed May 19, 2003 for U.S. Appl. No. 09/891,793, filed Jun. 26, 2001.
Examiner Interview Summary mailed Oct. 24, 2008 for U.S. Appl. No. 11/582,859, filed Oct. 17, 2006.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011, 5 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Facklam R., et al., "Emm Typing and Validation of Provisional M Types for Group A *Streptococci*," Emerging Infectious Diseases, 1999, vol. 5 (2), pp. 247-253.
Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.
Farlow J., et al., "Francisella tularensis Strain Typing Using Multiple-Locus, Variable-Number Tandem Repeat Analysis," Journal of Critical Microbiology, 2001, vol. 39 (9), pp. 3186-3192.
Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.
Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.
Fedele C.G., et al., "Quantitation of Polyomavirus DNA by a Competitive Nested Polymerase Chain Reaction," Journal of Virological Methods, 2000, vol. 88 (1), pp. 51-61.
Feng P., "Impact of Molecular Biology on the Detection of Food Pathogens," Molecular Biotechnology, 1997, vol. 7 (3), pp. 267-278.
Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Oct. 14, 2009 for U.S. Appl. No. 10/943,344, filed Sep. 17, 2004.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20, 2009 for U.S. Appl. No. 11/331,987, filed Jan. 13, 2006.
Final Office Action mailed Jun. 23, 2010 for U.S. Appl. No. 11/930,017, filed Oct. 30, 2007.
Final Office Action mailed Feb. 26, 2009 for U.S. Appl. No. 11/582,863, filed Oct. 17, 2006.
Final Office Action mailed Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin-Resistant *Staphylococcus aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of *Brucell canis* from Other *Brucella* Spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of Mycoplasma genitalium," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.

(56) References Cited

OTHER PUBLICATIONS

Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in *Staphylococcus aureus* Clinicallsolates and In Vitro Selection of Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gall J.G., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp. 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.
GenBank, "{Deletion 6} [Human, Muscle, Mitochondrial Mutant, 22 nt, Segment 2 of 2]," Accession No. S90302.1, Jun. 10, 1992.
GenBank, "Acinetobacter Genomosp. 10 Strain CIP 70.12 RNA Polymerase Subunit B (rpoB) Gene, Complete Cds," Accession No. 78099429, Mar. 11, 2006.
GenBank, "Bovine Parainfluenza Virus 3 Strain Shipping Fever, Complete Genome," Accesion No. AF178655, Sep. 19, 2000.
GenBank, "Clostridium Tetani E88, Complete Genome," Accession No. AE015927.1, Feb. 4, 2003.
GenBank, "*E. coli* Operon rpoBC Coding for the Beta- and Beta"-Subunits of RNA Polymerase (Genes rpoC and rpoB), and Genes rpIL, rIpJ, rpIA, and rpIK Coding for 50S Ribosomal Subunit Proteins L7/L12, L10, L1, and L11, Respectively. (Map position 89-90 min.)," Accession No. 42813, Feb. 28, 1992.
GenBank, "*E.coli* 16S Ribosomal RNA," Accession No. 174375, Aug. 11, 1995.
GenBank, "*E.coli* Open Reading Frame Upstream of Leu Operon," Accession No. M21150, Sep. 15, 1990.
GenBank, "*E.coli* rRNA Operon (rrnB) Coding for Glu-tRNA-2, 5S, 16S and 23S rRNA," Accession No. 147581, Sep. 14, 1992.
GenBank, "Enterococcus malodoratus Strain ATCC43197 Elongation Factor Tu (tufA) Gene, Partial Cds," Accession No. AF274728, Dec. 11, 2000.
GenBank "*Escherichia coli* str. K-12 substr. MG1655, Complete Genome," Accession No. NC000913, Oct. 15, 2001.
GenBank, "*Homo sapiens* Haplotype V Mitochondrion, Complete Genome", Accession No. AF381990.1, Dec. 28, 2001.
GenBank, "Human Adenovirus Type 4 Hexon Gene," for Accession No. X84646, Jun. 30, 1995.
GenBank, "Human Coronavirus 229E, Complete Genome," Accession No. AF304460, Jul. 11, 2001.
GenBank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5—similar to SW:COX3_Human P00414 Cytochrome C Oxidase Polypeptide III ;, mRNA sequence", Accession No. BQ581956.1, Jun. 20, 2002.
GenBank, "Influenza B Virus B/Panama/45/90 Polymerase (PB2) mRNA, Complete Cds", Accession No. AF005737, Oct. 4, 1997, pp. 1-3.
GenBank, "Mastadenovirus h7 Hexon Gene," Accession No. Z48571, Apr. 18, 2005.
GenBank, "or72a01.s1 NCI_CGAP_Lu5 *Homo sapiens* cDNA Clone Image:1601352 3-similar to SW:COX1_Human P00395 Cytochrome C Oxidase Polypeptide I ;, mRNA sequence", Accession No. A1002209.1, Jun. 10, 1998.
GenBank "*Staphylococcus aureus* RN4220 ErmC Gene, Partial Cds," Accession No. 18542231, Sep. 16, 2003.
GenBank "*Staphylococcus aureus* Strain MSSA476, Complete Genome," Accession No. BX571857.1, Jun. 24, 2004.
GenBank, "*Staphylococcus aureus* Subsp. *aureus* Mu50, Complete Genome," Accession No. 15922990, Oct. 4, 2001.
GenBank "*Staphylococcus aureus* Subsp. *aureus* MW2, Complete Genome," Accession No. G121281729, May 31, 2002.
GenBank, "*Staphylococcus epidermidis* ATCC 12228, Complete Genome," Accession No. AE015929.1, Jan. 2, 2003.
GenBank "*Streptococcus agalactiae* 2603V/R, Complete Genome," Accession No. AE009948.1, Aug. 28, 2002.
GenBank, "*Streptococcus anginosus* Elongation Factor Tu (tuf) Gene, Partial cds," Accession No. AF276257.1, Jul. 1, 2001.
GenBank, "*Streptococcus pneumoniae* Isolate 95.1In00S DNA Gyrase Subunit B (gyrB) Gene, Complete Cds," Accession No. 73916349, Sep. 30, 2005.
GenBank, "*Streptococcus pyogenes* Strain MGAS8232, Complete Genome," Accession No. AE009949.1, Apr. 3, 2002.
GenBank, "Venezuelan Equine Encephalitis Virus Nonstructural Polyprotein and Structural Polyprotein Genes, Complete Cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.
Giles R.E., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain," Journal of Bacteriology, 2005, vol. 187 (7), pp. 2426-2438.
Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.
Ginther C., et al., "Identifying Individuals by Sequencing Mitochondrial DNA from Teeth," Nature Genetics, 1992, vol. 2 (2), pp. 135-138.
Gjoen K.V., et al., "Specific Detection of Coxsackie Viruses A by the Polymerase Chain Reaction," Clinical and Diagnostic Virology, 1997, vol. 8 (3), pp. 183-188.
Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.

(56) References Cited

OTHER PUBLICATIONS

Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.

Gravet A., et al., "Characterization of a Novel Structural Member, LukE-LukD, of the Bi-Component *Staphylococcal leucotoxins* Family," FEBS Letters, 1998, vol. 436 (2), pp. 202-208.

Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.

Greenberg B.D., et al., "Intraspecific Nucleotide Sequence Variability Surrounding the Origin of Replicationin Human Mitochondrial DNA," Gene, 1983, vol. 21, pp. 33-49.

Griffey, et al., "Detection of Base Pair Mismatches in Duplex DNA and RNA Oligonucleotides Using Electrospray Mass Spectrometry," SPIE, 1997, vol. 2985, pp. 82-86.

Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.

Grundmann H., et al., "Emergence and Resurgence of Meticillin-Resistant *Staphylococcus aureus* as a Public-Health Threat," Lancet, 2006, vol. 368 (9538), pp. 874- 885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCR for Quantitative Detection of Human Adenovirus," Journal of Clinical Microbiology, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are We Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.

Hamel S., et al., "Consensus PCR and Microarray for Diagnosis of the Genus *Staphylococcus*, Species, and Methicillin Resistance," Biotechniques, 2001, vol. 31 (6), pp. 1364-1372.

Hammerle T., et al., "A Sensitive PCR Assay System for the Quantitation of Viral Genome Equivalents:Hepatitis C Virus (HCV)," Archives of Virology, 1996, vol. 141 (11), pp. 2103- 2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Hanssen A.M., et al., "Sccmecin *Staphylococci*: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.

Hassan A.A., et al., "Inter- and Intraspecies Variations of the 16S-23S rDNA Intergenic Spacer Region of Various *Streptococcal* Species," Systematic and Applied Microbiology, 2003, vol. 26 (1), pp. 97-103.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Virology, 2003, vol. 70, pp. 228-239.

Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.

Herrmann B., et al., "Differentiation of *Chiamydia* spp. by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant *Staphylococcusaureus*," Trends Microbiology, 2001, vol. 9 (10), pp. 486-493.

Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses," Archives of Virology, 2001, vol. 146 (12), pp. 2275-2289.

(56) References Cited

OTHER PUBLICATIONS

Hofstadler S.A., et al., "TIGER: The Universal Biosensor," International Journal of Mass Spectrometry, 2005, vol. 242, pp. 23-41.
Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis—Validation and Use for Forensic Casework," Forensic Science Review, 1999, vol. 11 (1), pp. 22-50.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Honda K., et al., "Universal Method of Hypersensitive Nested PCR Toward Forensic DNA typing," International Congress Series, 1998, vol. 7, pp. 28-30.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.
Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time Pcr Assay for Rapid Detection of Methicillin-Resistant*staphylococcus aureus* Directly from Specimens Containing a Mixture of *Staphylococci*," Journal of Clinical Microbiology, 2004, vol. 42 (5), pp. 1875-1884.
Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.
Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, mailed on Jun. 11, 2003, 6 pages.
International Preliminary Examination Report for Application No. PCT/US2002/20336, mailed on Apr. 26, 2004, 8 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Aug. 20, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US2006/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/020045 mailed on Jan. 8, 2009, 18 pages.
International Search Report and Written Opinion for Application No. PCT/US2008/054926, mailed on Jan. 26, 2009, 15 pages.
International Search Report and Written Opinion for Application No. PCT/US2008/057901, mailed on Aug. 28, 2008, 14 pages.
International Search Report and Written Opinion for Application No. PCT/US2008/064891, mailed on Jun. 29, 2009, 15 pages.
International Search Report and Written Opinion for Application No. PCT/US2010/042159, mailed on Sep. 14, 2010, 14 pages.
International Search Report for Application No. PCT/US04/007236, mailed on Feb. 24, 2006, 2 pages.
International Search Report for Application No. PCT/US2002/06763, mailed on Oct. 23, 2002, 2 pages.
International Search Report for Application No. PCT/US2002/20336, mailed on Feb. 3, 2003, 4 pages.
International Search Report for Application No. PCT/US2003/009802, mailed on Aug. 3, 2004, 2 pages.
International Search Report for Application No. PCT/US2003/038505, mailed on Apr. 12, 2005, 2 pages.

(56) References Cited

OTHER PUBLICATIONS

International Search Report for Application No. PCT/US2003/038830, mailed on Aug. 25, 2004, 4 pages.
International Search Report for Application No. PCT/US2003/22835, mailed on Dec. 12, 2003, 1 page.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/065332, mailed on Nov. 28, 2008, 4 pages.
International Search Report for Application No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of *Staphylococcal* Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.

James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for Tsst-1 in *Staphylococcal* Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of *Francisella* species and Subspecies and Development of a Specific PCR that Distinguishes the Two Major Subspecies of *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of B. Subtilis and B. Atrophaeus, Closely Related Species of *bacilli*," Journal of Microbiological Methods, 2000, vol. 40 (3), pp. 241-254.
Jonas D., et al., "Rapid PCR-Based Identification of Methicillin-Resistant *Staphylococcus aureus*from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal *eubacterium* Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.

(56) References Cited

OTHER PUBLICATIONS

Katayama Y., et al., "Genetic Organization of the Chromosome Region Surrounding mecA inClinical *Staphylococcal* Strains: Role of IS431-Mediated mecI Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant *Staphylococci* by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. by Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.

Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of *Mycobacterial* Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.

Kitagawa Y., et al., "Rapid Diagnosis of Methicillin-Resistant *Staphylococcus aureus* bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive *Staphylococci*," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as an Augmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus* isolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin Causes Necrotizing Pneumonia," ScienceExpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine Encephalitis Viruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Ampli-

(56) References Cited

OTHER PUBLICATIONS fication than their Nonmodified Counterparts," Genetic Analysis: Biomolecular Engineering, 1996, vol. 13 (1), pp. 15-21.
Lednicky J.A., et al., "Polyomaviruses and Human Tumors: A Brief Review of Current Concenpts and Interpretations," Frontiers Bioscience, 1999, vol. 4, pp. D153-164.
Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.
Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.
Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.
Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.
Leroy E.M., et al., "Diagnosis of Ebola Haemorrhagic Fever by RT-PCR in an Epidemic Setting," Journal of Medicinal Virology, 2000, vol. 60 (4), pp. 463-467.
Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.
Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.
Levison P.R., et al., "Recent Developments of Magnetic Beads for Use in Nucleic Acid Purification," Journal of Chromatography, 1998, vol. A816, pp. 107-111.
Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.
Li C., et al., "Evolution of H9N2 Influenza Viruses from Domestic Poultry in Mainland China," Virology, 2005, vol. 340 (1), pp. 70-83.
Li J., et al., "Single Nucleotide Polymorphism Determination Using Primer Extension and Time-of-Flight Mass Spectrometry," Electrophoresis, 1999, vol. 20 (6), pp. 1258-1265.
Li Q., et al., "Genetic Variability of Hexon Loops 1 and 2 between Seven Genome Types of Adenovirus Serotype 7," Archives of Virology, 1999, vol. 144 (9), pp. 1739-1749.
Li Q., et al., "Screening of the High Yield Influenza B Virus on MDCK c14d Cloning of its Whole Genome," International Congress Series, 2004, vol. 1263, pp. 610-614.
Li Q.G., et al., "Analysis of 15 Different Genome Types of Adenovirus Type 7 Isolated on FiveContinents," Journal of Virology, 1986, vol. 60 (1), pp. 331-335.
Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.
Liebermann H., et al., "Mapping of Epitopes on the Fiber Knobs of Human Adenovirus Serotypes 8 and 15," Intervirology, 2002, vol. 45 (1), pp. 59-66.
Liebermann H., et al., "Mapping of Linear Epitopes on Fibre Knob of Human Adenovirus Serotype 5," Virus Research, 2001, vol. 73 (2), pp. 145-151.
Lim L.P., et al., "The MicroRNAs of Caenorhabditis Elegans," Genes and Development, 2003, vol. 17 (8), pp. 991-1008.
Limbach P.A., et al., "Enzymatic Sequencing of Oligonucleotides with Electrospray Mass Spectrometry," 42nd ASMS Conference on Mass Spectrometry, 1994.
Limoncu M.N., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.
Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.
Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.
Lina G., et al., "Bacterial Competition for Human Nasal Cavity Colonization: Role of *Staphylococcalagr* alleles," Applied and Environmental Microbiology, 2003, vol. 69 (1), pp. 18-23.
Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.
Linssen B., et al., "Development of Reverse Transcription-PCR Assays Specific for Detection of Equine Encephalitis Viruses," Journal of Clinical Microbiology, 2000, vol. 38 (4), pp. 1527-1535.
Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.
Little D.P., et al, "Rapid Sequencing of Oligonucleotides by High-Resolution Mass Spectrometry," Journal of the American Chemical Society, 1994, vol. 116 (11), pp. 4893-4897.
Liu C., et al., "Improving the Microdialysis Procedure for Electrospray Ionization Mass Spectrometry of Biological Samples," Journal of Mass Spectrometry, 1997, vol. 32 (4), pp. 425-431.
Liu J.H., et al., "Interregional Transmission of the Internal Protein Genes of H2 Influenza Virus in Migratory Ducks from North America to Eurasia," Virus Genes, 2004, vol. 29 (1), pp. 81-86.
Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.
Livermore D.M., "The Threat from the Pink Corner," Annals of Medicine, 2003, vol. 35 (4), pp. 226-234.
Loakes D., et al., "Nitroindoles as Universal Bases," Nucleosides and Nucleotides, 1995, vol. 14 (3-5), pp. 1001-1003.
Loo J.A., et al., "Applying Charge Discrimination with Electrospray Ionization-Mass Spectrometry to Protein Analysis," Journal of American Society for Mass Spectrometry, 1995, vol. 6, pp. 1098-1104.
Lott T.J., et al., "Nucleotide Sequence Analysis of the 5-8s rDNA and Adjacent ITS2 Region of Candidaalbicans and Related Species," Yeast, 1993, vol. 9, pp. 1199-1206.
Louie L., et al., "Evaluation of Three Rapid Methods for Detection of Methicillin Resistance in *Staphylococcus aureus*," Journal of Clinical Microbiology, 2000, vol. 38 (6), pp. 2170-2173.
Love B.C., et al., "Cloning and Sequence of the GroESL Heat-Shock Operon of Pasteurella Multocida," Gene, 1995, vol. 166 (1), pp. 179-180.
Lovseth A., et al., "Modified Multiplex PCR Method for Detection of Pyrogenic Exotoxin Genes in *Staphylococcal* Isolates," Journal of Clinical Microbiology, 2004, vol. 42 (8), pp. 3869-3872.
Lowe T., et al., "A Computer Program for Selection of Oligonucleotide Primers for Polymerase Chain Reactions," Nucleic Acids Research, 1990, vol. 18 (7), pp. 1757-1761.
Lu X., et al., "Molecular Typing of Human Adenoviruses by PCR and Sequencing of a Partial Region of the Hexon Gene," Archives of Virology, 2006, vol. 151 (8), pp. 1587-1602.
Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Ludwig S.L., et al., "Prevalence of Antibodies to Adenovirus Serotypes 4 and 7 among Unimmunized US Army Trainees: Results

(56) References Cited

OTHER PUBLICATIONS of a Retrospective Nationwide Seroprevalence Survey," The Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiolofy Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.
Ma X.X., et al., "Novel Type of *Staphylococcal* Cassette Chromosome Mec Identified in Community-Acquired Methicillin-Resistant *Staphylococcus aureus* Strains," Antimicrobial Agents and Chemotherapy, 2002, vol. 46 (4), pp. 1147-1152.
Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by Tag DNA Polymerase: Implications for PCR-Based Genotyping and Cloning," BioTechniques, 1996, vol. 21 (4), pp. 700-709.
Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.
Malasig M.D., et al., "Simplified Microneutralization Test for Serotyping Adenovirus Isolates," Journal of Clinical Microbiology, 2001, vol. 39 (8), pp. 2984-2986.
Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.
Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.
Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Marmur J., et al., "Strand Separation and Specific Recombination in Deoxyribonucleic Acids: Biological Studies," Proceedings of the National Academy of Sciences, 1960, vol. 46 (4), pp. 453-461.
Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.
Martineau F., et al., "Development of a PCR Assay for Identification of *Staphylococci* at Genus and Species Levels," Journal of Clinical Microbiology, 2001, vol. 39 (7), pp. 2541-2547.
Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.
Martin-Lopez J.V., et al., "Simultaneous PCR Detection of Ica Cluster and Methicillin and Mupirocinresistance Genes in Catheter-Isolated *Staphylococcus*," International Microbiology, 2004, vol. 7 (1), pp. 63-66.
Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.
Matray T.J., et al., "Synthesis and Properties of RNA Analogs-Oligoribonucleotide N3—>p5 Phosphoramidates," Nucleic Acids Research, 1999, vol. 27 (20), pp. 3976-3985.
Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.C., "Percent Sequence Identity: The Need to be Explicit," Structure, 2004, vol. 12 (5), pp. 737-738.
McCabe K.M., et al., "Bacterial Species Identification After DNA Amplification with a Universal Primer Pair," Molecular Genetics and Metabolism, 1999, vol. 66 (3), pp. 205-211.
McLafferty F.W., et al., "Comparison of Algorithms and Databases for Matching Unknown Mass Spectra," Journal of the American Society for Mass Spectrometry, 1998, vol. 9 (1), pp. 92-95.
McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Mehrotra M., et al., "Multiplex PCR for Detection of Genes for *Staphylococcus aureus* enterotoxins, Exfoliative Toxins, Toxic Shock Syndrome Toxin 1, and Methicillin Resistance," Journal of Clinical Microbiology, 2000, vol. 38 (3), pp. 1032-1035.
Meiyu F., et al., "Detection of Flaviviruses by Reverse Transcriptase-Polymerase Chain Reaction with the Universal Primer Set," Microbiology and Immunology, 1997, vol. 41 (3), pp. 209-213.
Mellor J., et al., "Genotype Dependence of Hepatitis C Virus Load Measurement in Commercially Available Quantitative Assays," Journal of Clinical Microbiology, 1999, vol. 37 (8), pp. 2525-2532.
Merlino J., et al., "New Chromogenic Identification and Detection of *Staphylococcus aureus* and Methicillin-Resistant *S. aureus*," Journal of Clinical Microbiology, 2000, vol. 38 (6), pp. 2378-2380.
Merlino J., et al., "Rapid Detection of Non-Multidrug-Resistant and Multidrug-Resistant Methicillin-Resistant *Staphylococcus aureus* Using Cycling Probe Technology for the mecA Gene," European Journal of Clinical Microbiology and Infectious Diseases, 2003, vol. 22 (5), pp. 322-323.
Messmer T.O., et al., "Discrimination of *Streptococcus pneumoniae* from Other Upper respiratory tract *Streptococci* by Arbitrary Primed PCR," Clinical Biochemistry, 1995, vol. 28 (6), pp. 567-572.
Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.
Miller K.W., et al., "A Compendium of Human Mitochondria! DNA Control Region: Development of an International Standard Forensic Database," Croatian Medical Journal, 2001, vol. 42 (3), pp. 315-327.
Miragaia M., et al., "Genetic Diversity among Methicillin-Resistant *Staphylococcus epidermidis*(MRSE)," Microbial Drug Resistance, 2005, vol. 11 (2), pp. 83-93.
Miura-Ochiai R., et al., "Quantitative Detection and Rapid Identification of Human Adenoviruses," Journal of Clinical Microbiology, 2007, vol. 45 (3), pp. 958-967.
Mollet C., et al., "RpoB Sequence Analysis as a Novel Basis for Bacterial Identification," Molecular Microbiology, 1997, vol. 26 (5), pp. 1005-1011.
Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.
Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.
Moricca S., et al., "Detection of *Fusarium oxysporum* f.sp. *vasinfectum* in Cotton Tissue by Polymerase Chain Reaction," Plant Pathology, 1998, vol. 47 (4), pp. 486-494.
Morinaga N., et al., "Purification, Cloning and Charactarizarion of Variant LukE-LukD with Strong Leukocidal Activity of *Staphylococcal* Bi-Component *Leukotoxin* Family," Microbiology and Immunology, 2003, vol. 47 (1), pp. 81-90.
Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.
Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

(56) References Cited

OTHER PUBLICATIONS

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole Time-of-Flight Mass Spectrometry and Quadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of *Staphylococci* by Polymerase Chain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.

Nagy M., et al., "Sequence Analysis of Porcine Adenovirus Serotype 5 Fibre Gene: Evidence for Recombination," Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene Sequences and Specific Detection for Panton-Valentine Leukocidin," Biochemical and Biophysical Research Communications, 2005, vol. 328 (4), pp. 995-1002.

Nakao H., et al., "Development of a Direct PCR Assay for Detection of the Diphtheria Toxin Gene," Journal of Clinical Microbiology, 1997, vol. 35 (7), pp. 1651-1655.

Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.

Naumov G.I., et al., "Discrimination Between the Soil Yeast Species *Williopsis saturnus* and *Williopsis suaveolens* by the Polymerase Chain Reaction with the Universal Primer N21," Microbiology, 2000, vol. 69 (2), pp. 229-233.

NEB Catalog, 1998/1999, pp. 1, 79, 121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.

Non-Final Office Action mailed Feb. 2, 2007 for U.S. Appl. No. 10/844,938, filed May 12, 2004.

Non-Final Office Action mailed Oct. 2, 2009 for U.S. Appl. No. 11/929,707, filed Oct. 30, 2007.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Aug. 7, 2007 for U.S. Appl. No. 10/844,938, filed May 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Oct. 13, 2010 for U.S. Appl. No. 10/754,415, filed Jan. 9, 2004.

Non-Final Office Action mailed Sep. 16, 2009 for U.S. Appl. No. 11/233,630, filed Sep. 21, 2005.

Non-Final Office Action mailed Apr. 17, 2009 for U.S. Appl. No. 12/211,641, filed Sep. 16, 2008.

Non-Final Office Action mailed Nov. 19, 2003 for U.S. Appl. No. 09/798,007, filed Mar. 2, 2001.

Non-Final Office Action mailed Aug. 20, 2007 for U.S. Appl. No. 11/582,863, filed Oct. 17, 2006.

Non-Final Office Action mailed May 20, 2008 for U.S. Appl. No. 10/844,938, filed May 12, 2004.

Non-Final Office Action mailed Oct. 20, 2004 for U.S. Appl. No. 09/891,793, filed Jun. 26, 2001.

Non-Final Office Action mailed Feb. 23, 2009 for U.S. Appl. No. 10/660,122, filed Sep. 11, 2003.

Non-Final Office Action mailed May 26, 2010 for U.S. Appl. No. 11/869,449, filed Oct. 9, 2007.

Non-Final Office Action mailed Jul. 27, 2006 for U.S. Appl. No. 11/209,439, filed Aug. 8, 2005.

Non-Final Office Action mailed Jun. 28, 2010 for U.S. Appl. No. 11/930,002, filed Oct. 30, 2007.

Non-Final Office Action mailed Sep. 28, 2009 for U.S. Appl. No. 11/930,017, filed Oct. 30, 2007.

Non-Final Office Action mailed Dec. 29, 2010 for U.S. Appl. No. 12/616,422, filed Nov. 11, 2009.

Non-Final Office Action mailed Apr. 30, 2010 for U.S. Appl. No. 11/930,108, filed Oct. 31, 2007.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Notice of Allowance mailed Apr. 1, 2011 for U.S. Appl. No. 11/233,630, filed Sep. 21, 2005.

Notice of Allowance mailed Jun. 3, 2009 for U.S. Appl. No. 11/331,978, filed Jan. 13, 2006.

Notice of Allowance mailed Aug. 5, 2010 for U.S. Appl. No. 11/233,630, filed Sep. 21, 2005.

(56) References Cited

OTHER PUBLICATIONS

Notice of Allowance mailed Aug. 6, 2009 for U.S. Appl. No. 10/728,486, filed Dec. 5, 2003.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed May 25, 2011 for U.S. Appl. No. 11/929,707, filed Oct. 30, 2007.
Notice of Allowance mailed Oct. 29, 2009 for U.S. Appl. No. 10/660,122, filed Sep. 11, 2003.
Nubel U.,et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415, filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996, filed Sep. 12, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.

(56) References Cited

OTHER PUBLICATIONS

Office Action mailed Jun. 7, 2010 for European Application No. 06800205.4 filed Jul. 27, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Jun. 12, 2009 for Chinese Application No. 200480016187.9 filed May 13, 2004.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.

(56) References Cited

OTHER PUBLICATIONS

Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.

(56) References Cited

OTHER PUBLICATIONS

Office Action mailed Feb. 27, 2003 for U.S. Appl. No. 09/798,007, filed Mar. 2, 2001.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Aug. 30, 2007 for U.S. App. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
O''Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element in Methicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run to Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.
Peng X., et al., "Rapid Detection of Shigella Species in Environmental Sewage by an Immunocapture PCR with Universal Primers," Applied and Environmental Microbiology, 2002, vol. 68 (5), pp. 2580-2583.
Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.
Peters S.E., et al., "Quantification of the Detection of Pneumocystis Carinii by DNA Amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: A Powerful Tool for the Mass and Sequence

(56) References Cited

OTHER PUBLICATIONS

Analysis of Natural and Modified Oligonucleotides, 787 reexamination," Nucleic Acids Research, 1993, vol. 21 (14), pp. 3191-3196.
Pillai S.D., et al., "Rapid Molecular Detection of Microbial Pathogens: Breakthroughs and Challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of Adenovirus using PCR and Molecular Beacon," Journal of Virological Methods, 1999, vol. 82 (1), pp. 19-26.
Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-Based Detection and Typing of Human Adenoviruses in Clinical Samples," Research in Virology, 1997, vol. 148 (3), pp. 225-231.
Promega. T4 Polynucleotide Kinase, Technical Bulletin No. 519, 2002.
Puthavathana P., et al., "Molecular Characterization of the Complete Genome of Human Influenza H5N1 Virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Ramisse V., et al., "Identification and Characterization of Bacillus Anthracis by Multiplex PCR Analysis of Sequences on Plasmids pX01 and pX02 and Chromosomal DNA," FEMS Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of Bacillus Subtilis and Bacillus Mojavensis," Evolution, 1995, vol. 49 (6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleoprotein Gene of Influenza B/Ann Arbor/1/86," Nucleic Acids Research, 1989, vol. 17 (9), pp. 3595.
Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus mutans* by using Competitive Polymerasechain Reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates," Journal of Clinical Microbiology, 2006, vol. 44 (10), pp. 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative *Staphylococci* in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and Molecular Characterization of Ebola Viruses Causing Disease in Human and Nonhuman Primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the *Alphavirus* Genus," Journal of Virological Methods, 2001, vol. 95 (1-2), pp. 153-161.
Santos S.R., et al., "Identification and Phylogenetic Sorting of Bacterial Lineages with Universally Conserved Genes and Proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.

(56) References Cited

OTHER PUBLICATIONS

Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.N., et al., "Polymerase Chain-Reaction-Based mRNA Quantification Using an Internal Standard: Analysis of Oncogene Expression," Methods in Enzymology, 1993, vol. 218, pp. 446-473.
Schlecht N.F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a Marine Pikoplankton Community by 16s rRNA Gene Cloning and Sequencing," Journal of Bacteriology, 1991, vol. 173 (14), pp. 4371-4378.
Schmitz F.J., et al., "Development of a Multiplex-PCR for Direct Detection of the Genes for Enterotoxin B and C, and Toxic Shock Syndrome Toxin-1 in Staphylococcus aureus Isolates," Journal of Medical Microbiology, 1998, vol. 47 (4), pp. 335-340.
Schmitz F.J., et al., "Development of Resistance to Ciprofloxacin, Rifampin, and Mupirocin in Methicillin-Susceptible and -Resistant Staphylococcus aureus Isolates," Antimicrobial Agents and Chemotherapy, 2000, vol. 44 (11), pp. 3229-3231.
Schmitz F.J., et al., "Specific Information Concerning Taxonomy, Pathogenicity and Methicillin Esistance of Staphylococci Obtained by a Multiplex PCR," Journal of Medical Microbiology, 1997, vol. 46 (9), pp. 773-778.
Schram K.H., et al., "Mass Spectrometry of Nucleic Acid Components," Methods of Biochemical Analysis, 1990, vol. 34, pp. 203-280.
Schultz J.C., et al., "Polymerise Chain Reaction Products Analyzed by Charge Detection Mass Spectrometry," Rapid Communications in Mass Spectrometry, 1999, vol. 13 (1), pp. 15-20.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.
Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of Bacilus Subtilis Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the Gene for Toxic Shock Syndrome Toxin 1 in *Siaphylococcusaureus* by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus*," Journal of Clinical Microbiology, 1994, vol. 32 (8), pp. 1866-1869.
Shrestha N.K., et al., "Rapid Identification of *Staphylococcus aureus* and the MecA Gene from BacT/Alert Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and the Avian H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and

(56) References Cited

OTHER PUBLICATIONS

Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of *Staphylococci*," Journal of Clinical Pathology, 2003, vol. 56 (10), pp. 782-785.
Sumner J.W., et al., "PCR Amplification and Comparison of Nucleotide Sequences from the groESL Heat Shock Operon of *ehrlichia* Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, mailed on Jul. 7, 2008, 8 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary Partial European Search Report for Application No. EP02709785.6, mailed Sep. 1, 2005, 5 pages.
Supplementary Partial European Search Report for Application No. EP05751872.2, mailed on Jan. 28, 2008, 8 pages.
Supplementary Partial European Search Report for Application No. EP05856582.1, mailed on Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.
Takagaki Y., et al., "Four Factors are Required for 3"—End Cleavage of Pre-mRNAs," Genes and Development, 1989, vol. 3 (11), pp. 1711-1724.
Takahashi H., et al., "Characterization of gryA, gryB, grlA and grlB Mutations in Fluoroquinolone-Resistant Clinical Isolates of *Staphylococcus aureus*," The Journal of Antimicrobial Chemotherapy, 1998, vol. 41 (1), pp. 49-57.
Takahata M., et al., "Mutations in the GyrA and Gr1A Genes of Quinolone-Resistant Clinical Isolates of Methicillin-Resistant *Staphylococcus aureus*," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.

Talaat A.M., et al., "Genome-Directed Primers for Selective Labeling of Bacterial Transcripts for DNA Microarray Analysis," Nature Biotechnology, 2000, vol. 17, pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al, Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.
Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.
Top F.H Jr., "Control of Adenovirus Acute Respiratory Disease in U.S. Army Trainees," The Yale Journal of Biology and Medicine, 1975, vol. 48 (3), pp. 185-195.
Torroni A., et al., "Classification of European mtDNAs from an Analysis of Three European Populations," Genetics, 1996, vol. 144 (4), pp. 1835-1850.
Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.

(56) References Cited

OTHER PUBLICATIONS

Tsuneyoshi T., et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.
Udo E.E., et al., "Rapid Detection of Methicillin Resistance in *Staphylococci* Using a Slide Latex Agglutination Kit," International Journal of Antimicrobial Agents, 2000, vol. 15 (1), pp. 19-24.
Unal S., et al., "Detection of Methicillin-Resistant *Staphylococci* by Using the Polymerase Chain Reaction," Journal of Clinical Microbiology, 1992, vol. 30 (7), pp. 1685-1691.
Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.
Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.
Van Aerschot A., et al., "In Search of Acyclic Analogues as Universal Nucleosides in Degenerate Probes," Nucleosides and Nucleotides, 1995, vol. 14 (3-5), pp. 1053-1056.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Der Zee H., et al., "Rapid and Alternative Screening Methods for Microbiological Analysis," Journal of AOAC International, 1997, vol. 80 (4), pp. 934-940.
Van Dinten L.C., et al., "Proteolytic Processing of the Open Reading Frame Ib-EncodedPart of Arterivirus Replicase is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," The British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Ert M.N., et al., "Mass Spectrometry Provides Accurate Characterization of Two Genetic Marker Types in Bacillus Anthracis," Bio Techniques, 2004, vol. 37 (4), pp. 642-651.
Van Leeuwen W.B., et al., "Multilocus Sequence Typing of *Staphylococcus aureus* with DNA Array Technology," Journal of Clinical Microbiology, 2003, vol. 41 (7), pp. 3323-3326.
Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Vannuffel P., et al., "Specific Detection of Methicillin-Resistant *Staphylococcus* Species by Multiplex PCR," Journal of Clinical Microbiology, 1995, vol. 33 (11), pp. 2864-2867.
Verma S., et al., "Modified Oligonucleotides: Synthesis and Strategy for Users," Annual Review of Biochemistry, 1998, vol. 67, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.
Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative *Staphylococci*," The Lancet Infectious Diseases, 2002, vol. 2 (11), pp. 677-685.
Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.
Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease VIII," DNA Repair, 2003, vol. 2 (5), pp. 441-453.
Wallet F., et al., "Choice of a Routine Method for Detecting Methicillin-Resistance in *Staphylococci*," The Journal of Antimicrobial Chemotherapy, 1996, vol. 37 (5), pp. 901-909.
Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.
Wang G., et al., "Targeted Mutagenesis in Mammalian Cells Mediated by Intracellular Triple Helix Formation," Molecular and Cellular Biology, 1995, vol. 15 (3), pp. 1759-1768.
Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: The gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-

(56) References Cited

OTHER PUBLICATIONS

ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant *Staphylococcus aureus*," Journal of Clinical Microbiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of *Salmonellae* in Fecal Samples," Journal of Clinical Microbiology, 1992, vol. 30 (12), pp. 3195-3199.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.
Woo T.H., et al., "Identification of Leptospira Inadai by Continuous Monitoring of Fluorescence during Rapid Cycle PCR," Systematic and Applied Microbiology, 1998, vol. 21 (1), pp. 89-96.
Wood S.R., et al., "Rapid Detection and Serotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.
Written Opinion for Application No. PCT/US2004/33742, mailed on May 15, 2006, 5 pages.
Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Wunschel D., et al., "Discrimination Among the B. Cereus Group, in Comparison to B. Subtilis, by Structural Carbohydrate Profiles and Ribosomal RNA Spacer Region PCR," Systematic and Applied Microbiology, 1994, vol. 17, pp. 625-635.
Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.
Wunschel D.S., et al., "Heterogeneity in Bacillus Cereus PCR Products Detected by ESI-FTICR Mass Spectrometry," Analytical Chemistry, 1998, vol. 70 (6), pp. 1203-1207.
Wunschel D.S., et al., "Mass spectrometric characterization of DNA for molecular biological applications: advances using MALDI and ESI," Advances in Mass Spectrometry, 1998, vol. 14, Elsevier, pp. 377-406.
Xu L., et al., "Electrophore Mass Tag Dideoxy DNA Sequencing," Analytical Chemistry, 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1 N2) Reassortant Viruses During the 2001-2002 Influenza Season," The Journal of Infectious Diseases, 2002, vol. 186 (10), pp. 1490-1493.
Yao Z.P., et al., "Mass Spectrometry Based Proteolytic Mapping for Rapid Virus Identification," Analytical Chemistry, 2002, vol. 74 (11), pp. 2529-2534.
Yasui T., et al., "A Specific Oligonucleotide Primer for the Rapid Detection of Lactobacillus Lindneri by Polymerase Chain Reaction," Canadian Journal of Microbiology, 1997, vol. 43 (2), pp. 157-163.
Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.
Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.
Zeng Z.B., "Precision Mapping of Quantitative Trait Loci," Genetics, 1994, vol. 136 (4), pp. 1457-1468.
Zhang J., et al., "PowerBLAST: A New Network Blast Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of *Staphylococcus aureus* from Coagulase-Negative *Staphylococci*," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.
Final Office Action mailed Jun. 14, 2011 for U.S. Appl. No. 12/616,422, filed Nov. 11, 2009.
International Preliminary Report on Patentability and Written Opinion for Application No. PCT/US04/007236, mailed on Mar. 16, 2006, 7 pages.
International Preliminary Report on Patentability for Application No. PCT/US2005/018031, mailed on Nov. 29, 2006, 1 page.
Notice of Allowance mailed Jun. 9, 2011 for U.S. Appl. No. 11/331,987, filed Jan. 13, 2006.
Notice of Allowance mailed Jun. 9, 2011 for U.S. Appl. No. 11/491,376, filed Jul. 21, 2006.
Ecker Supporting Information [online], May 23, 2005 [retrieved on Jul. 31, 2011]. Retrieved from the Internet< URL: http://www.pnas.org/content/102/22/8012/suppl/DC1>.

* cited by examiner

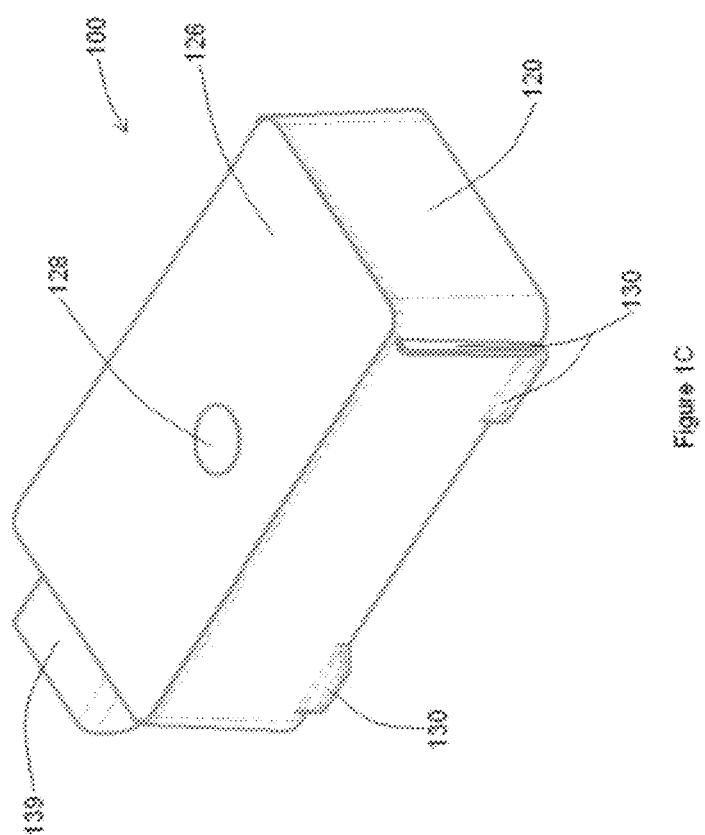

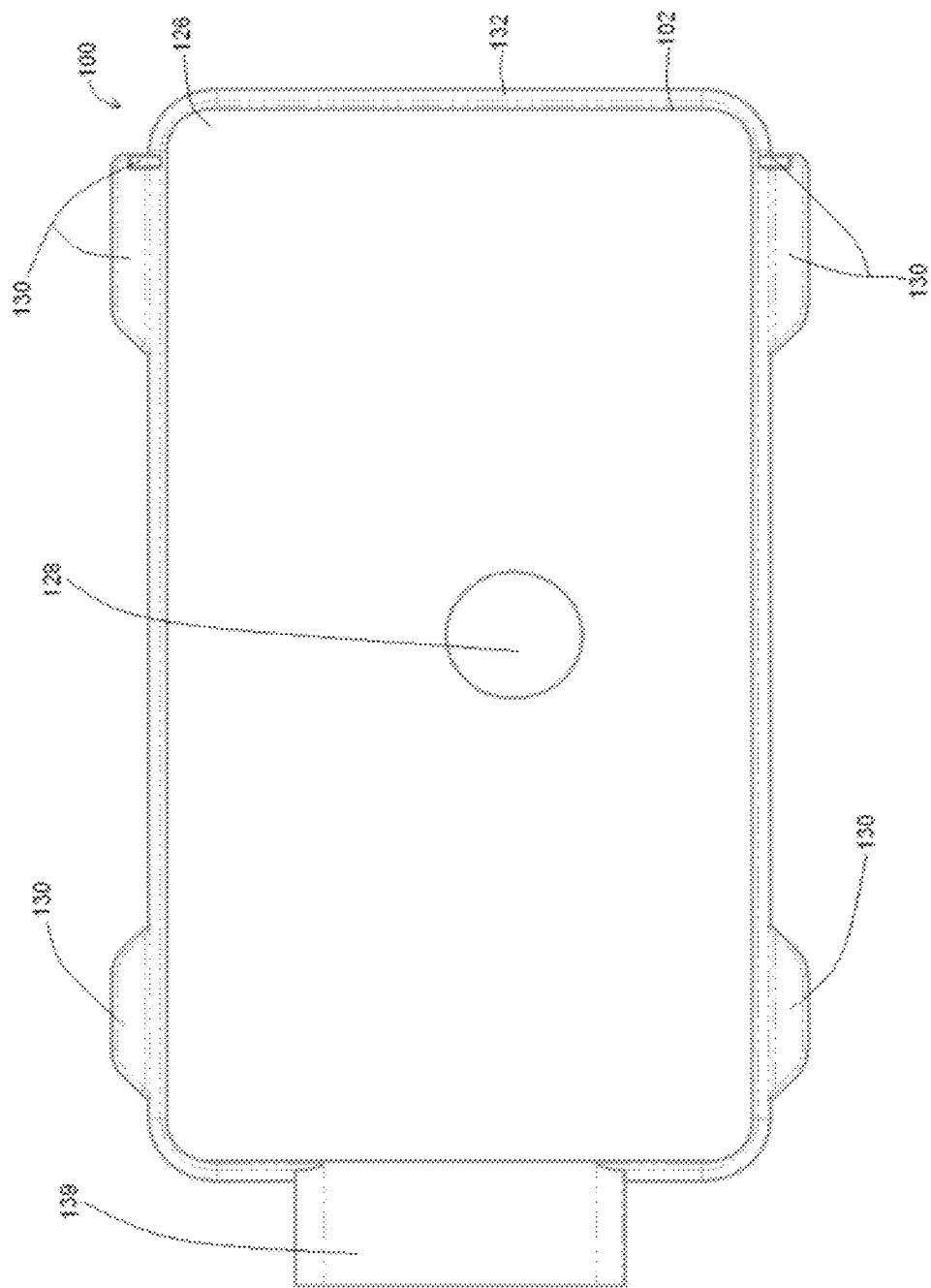

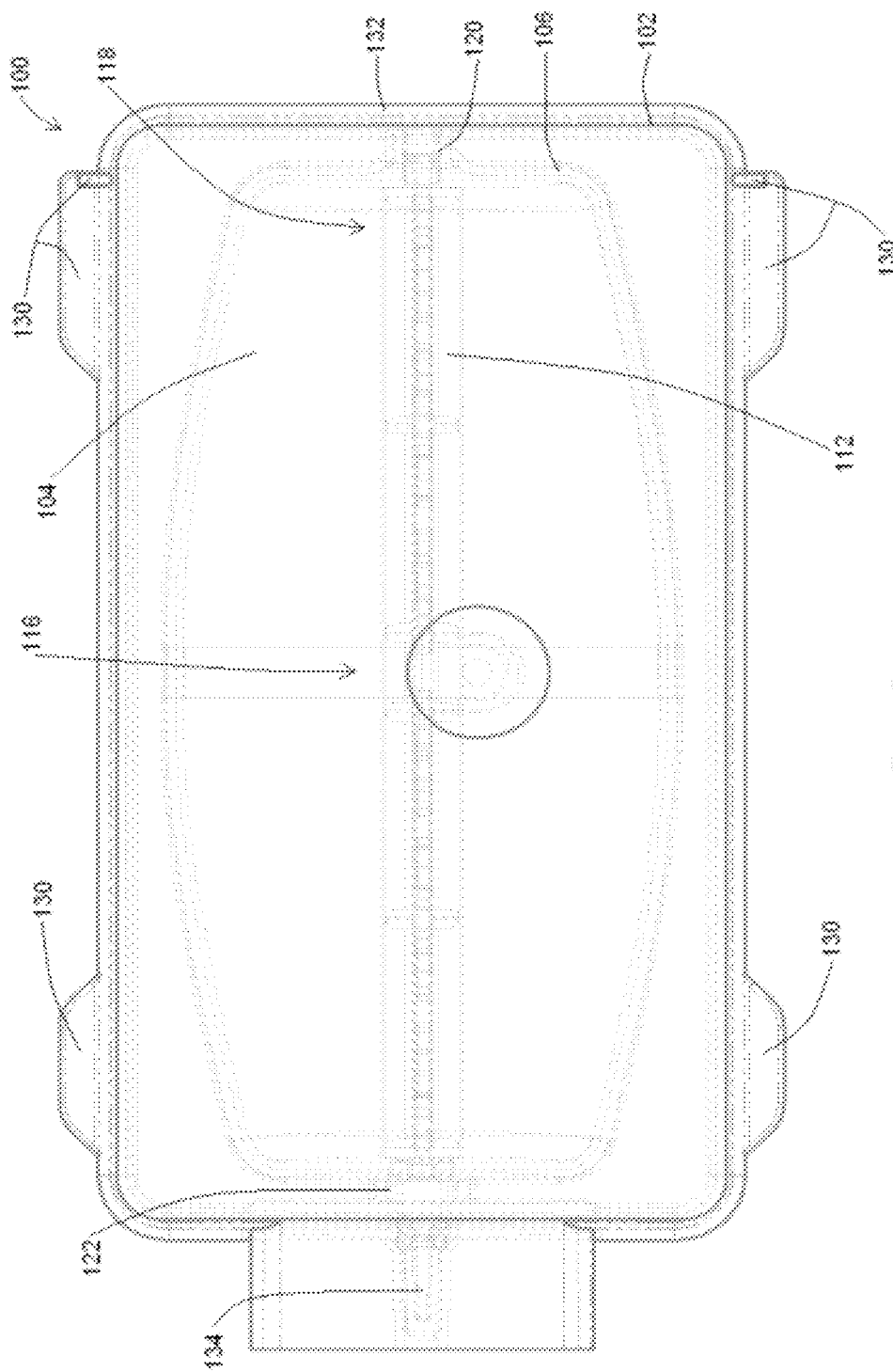

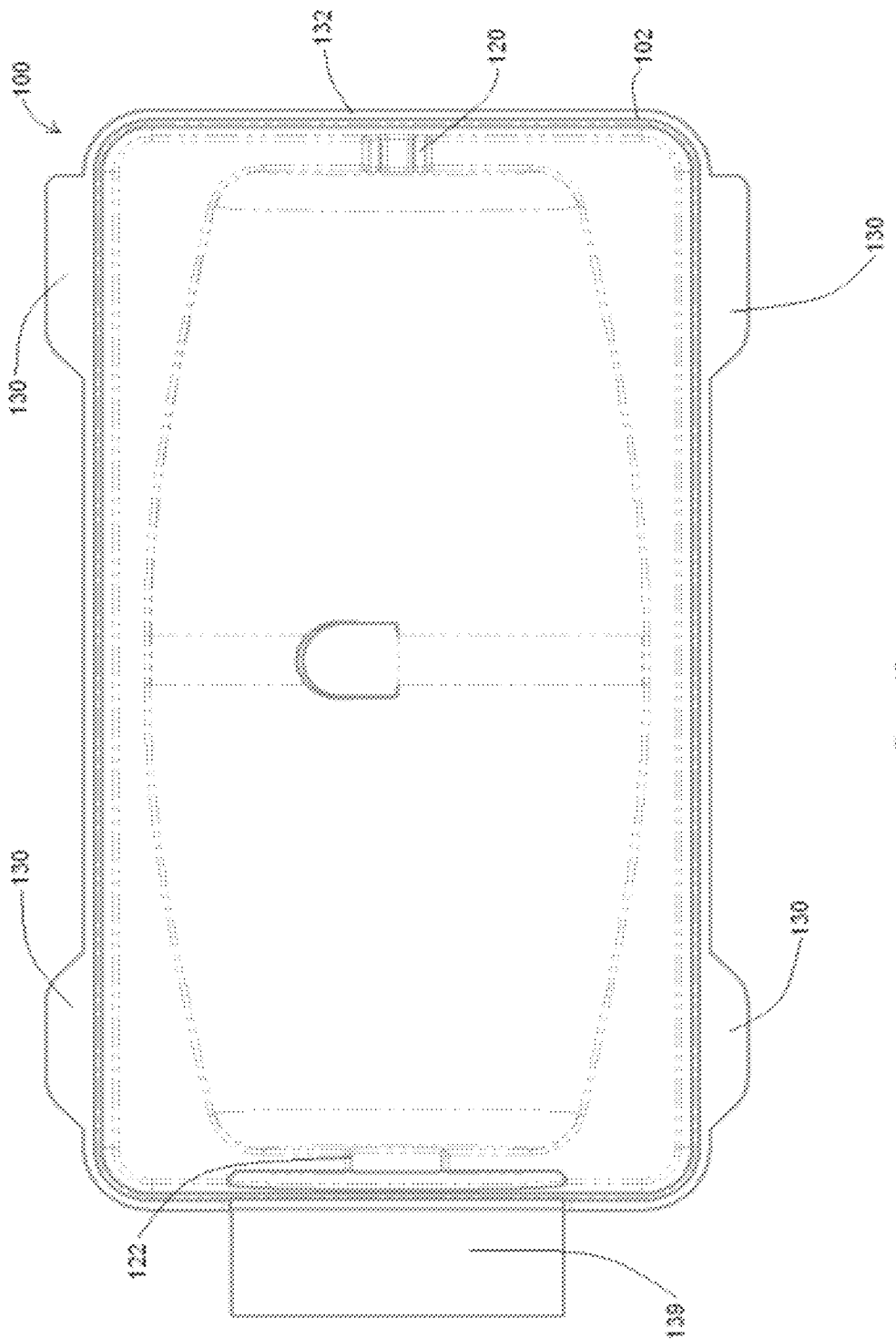

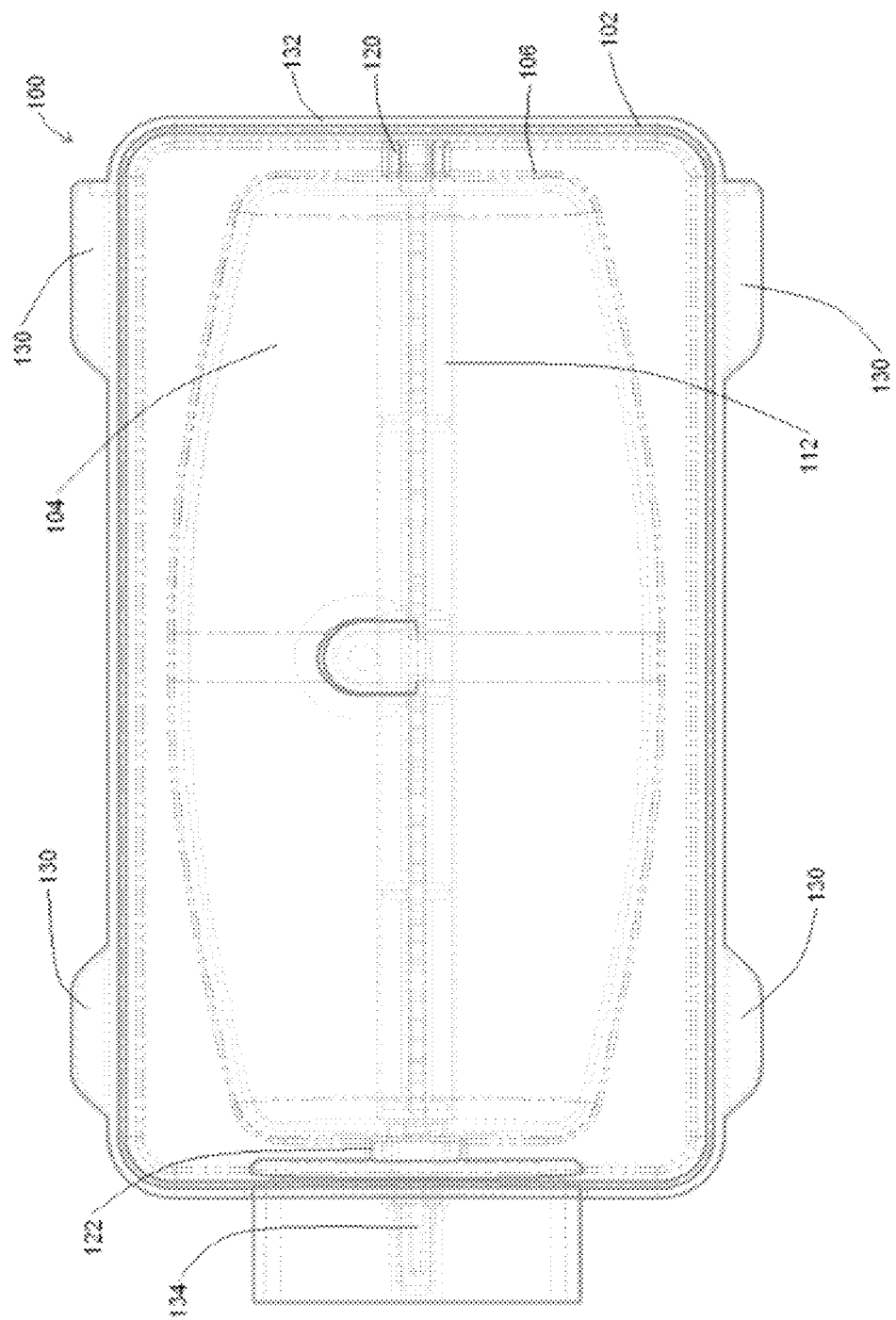

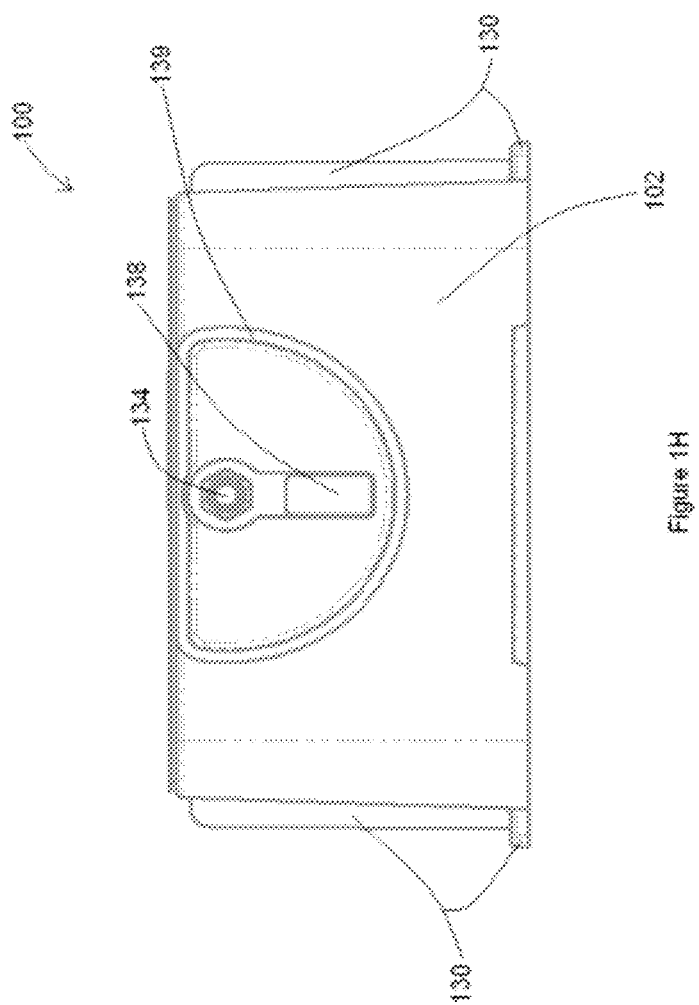

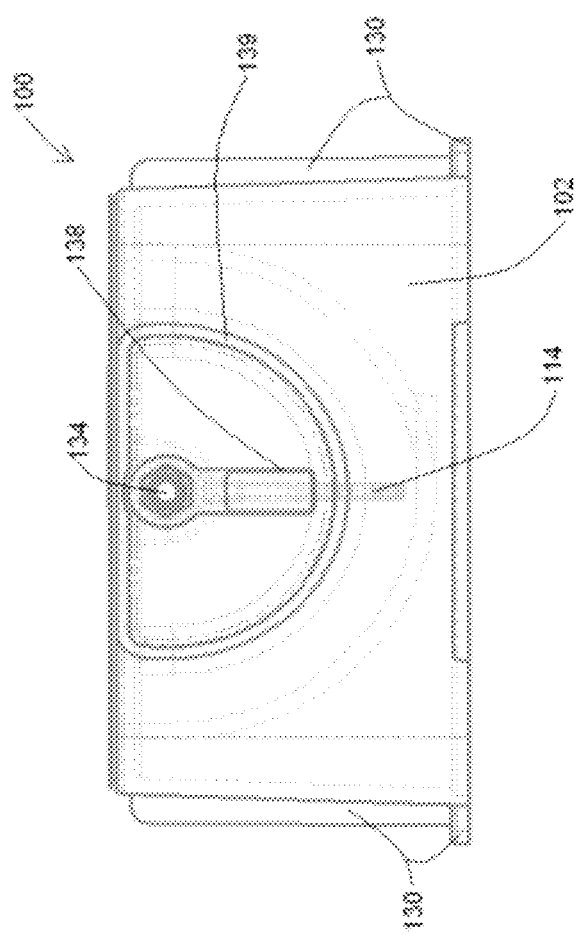

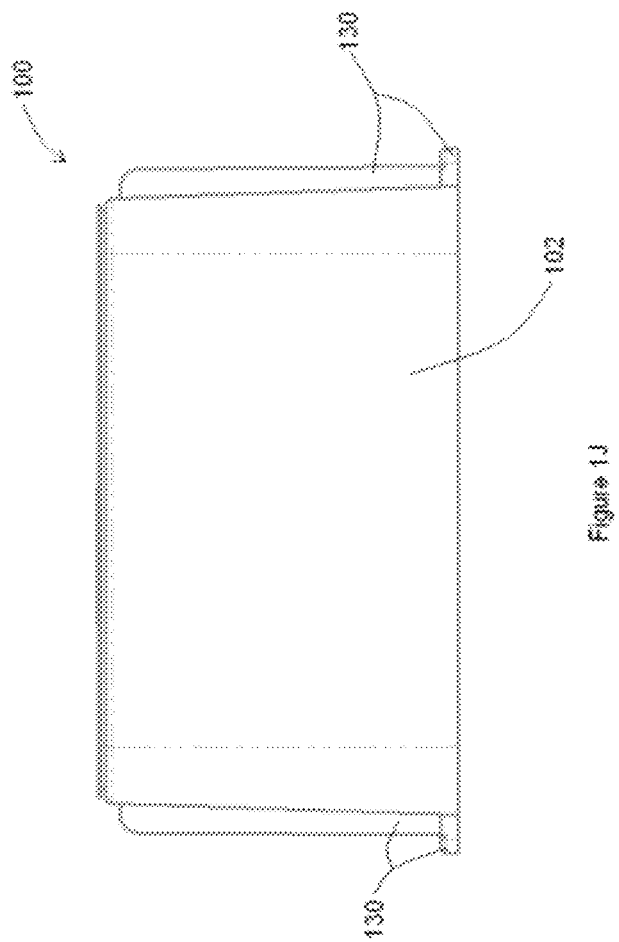

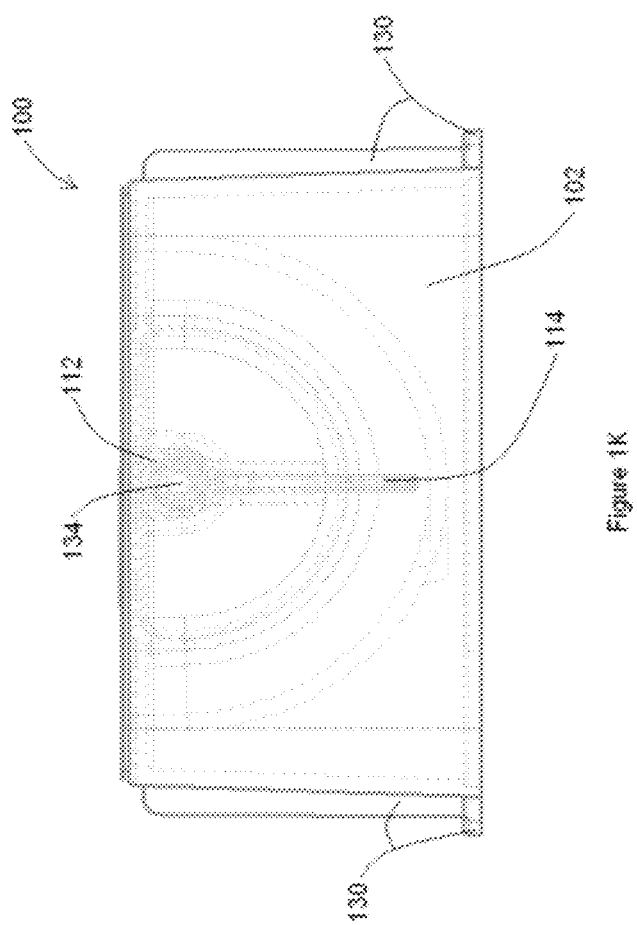

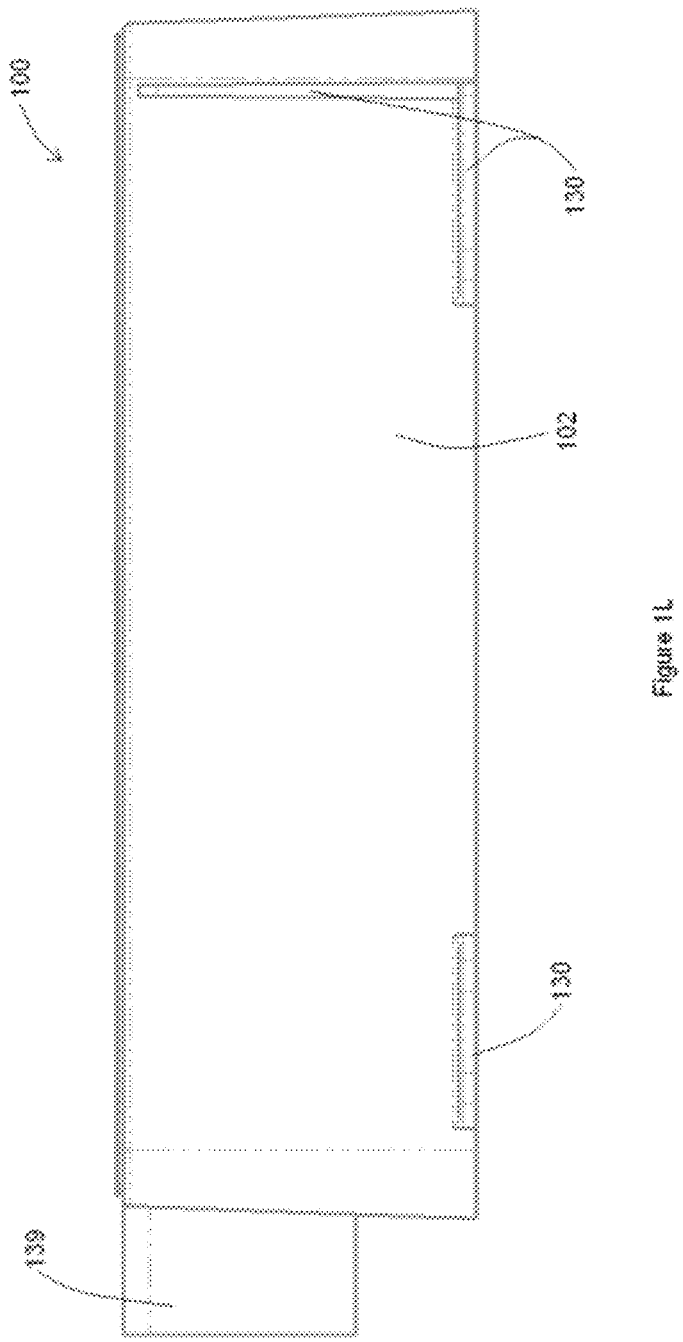

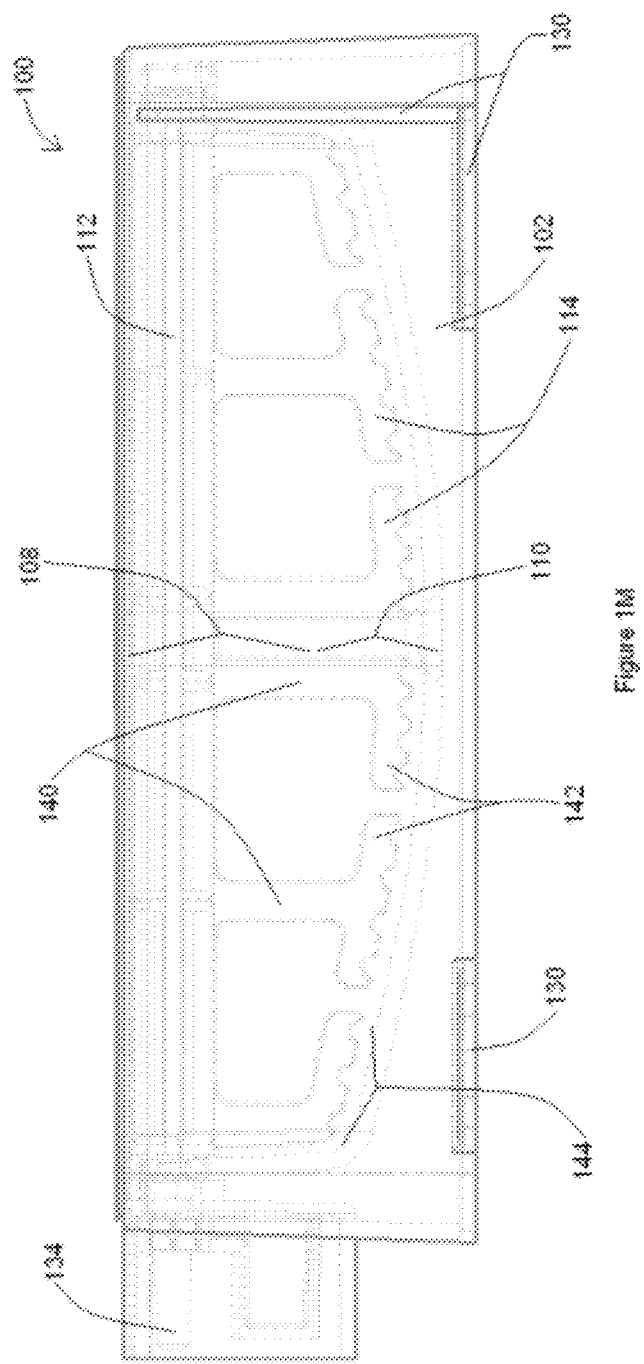

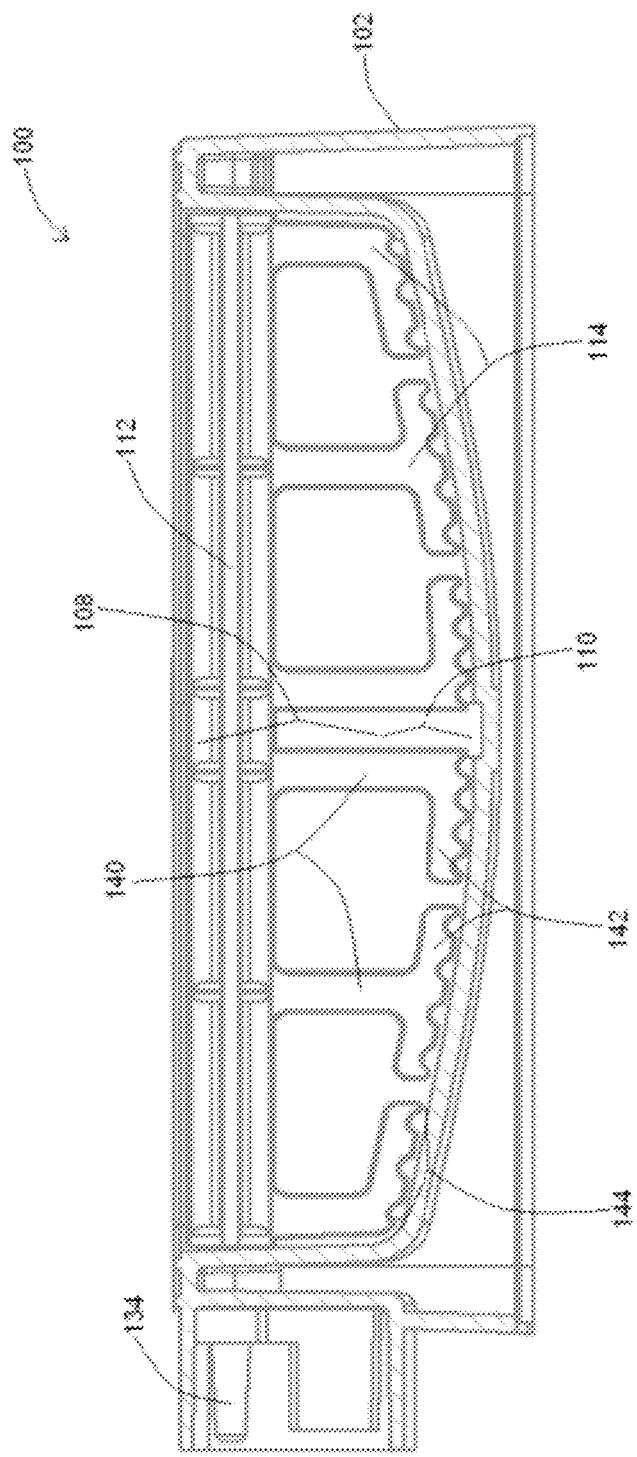

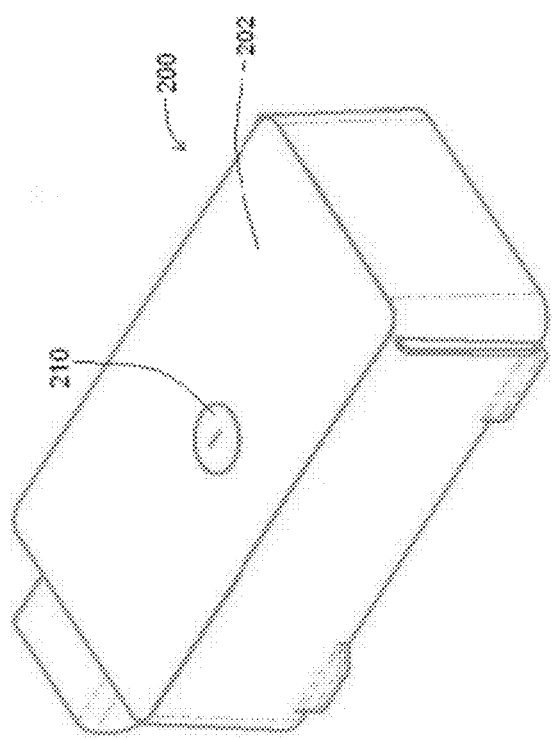

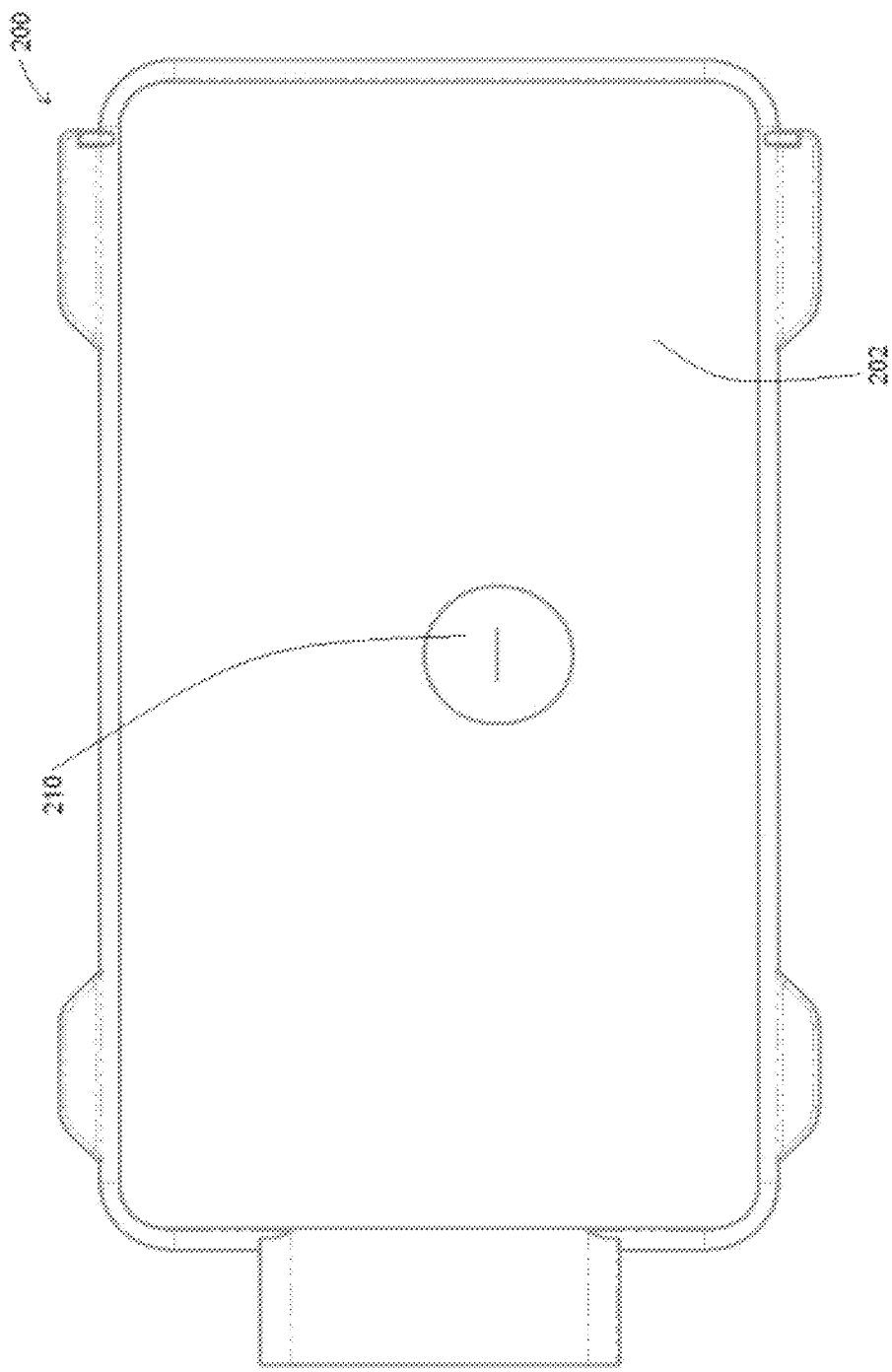

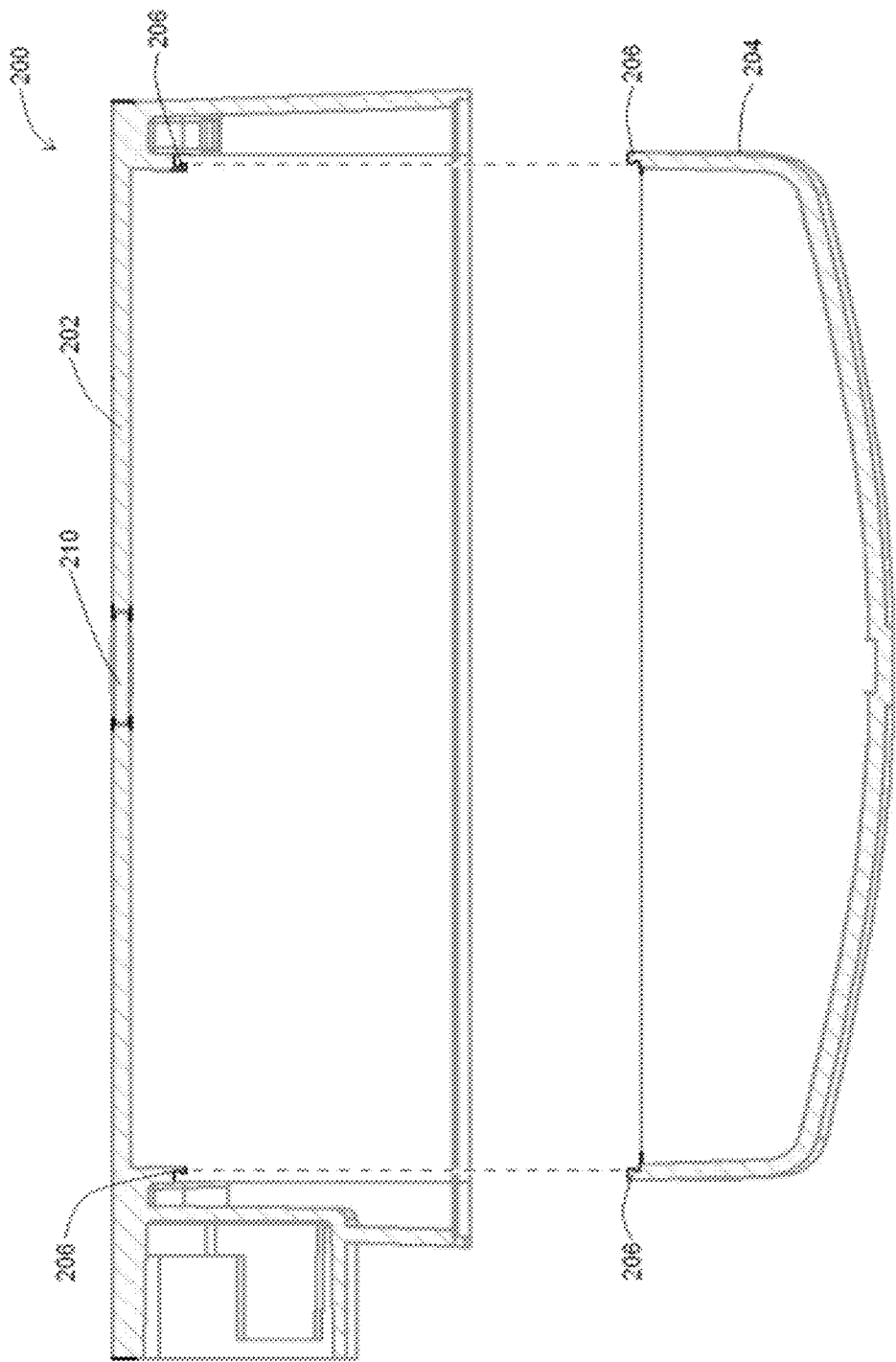

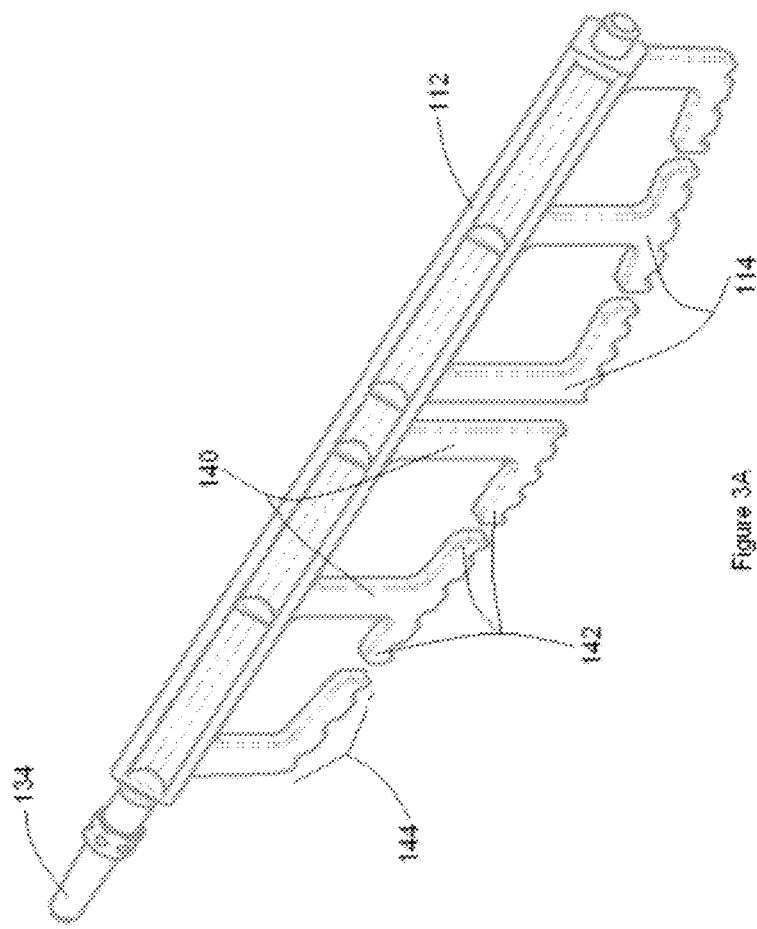

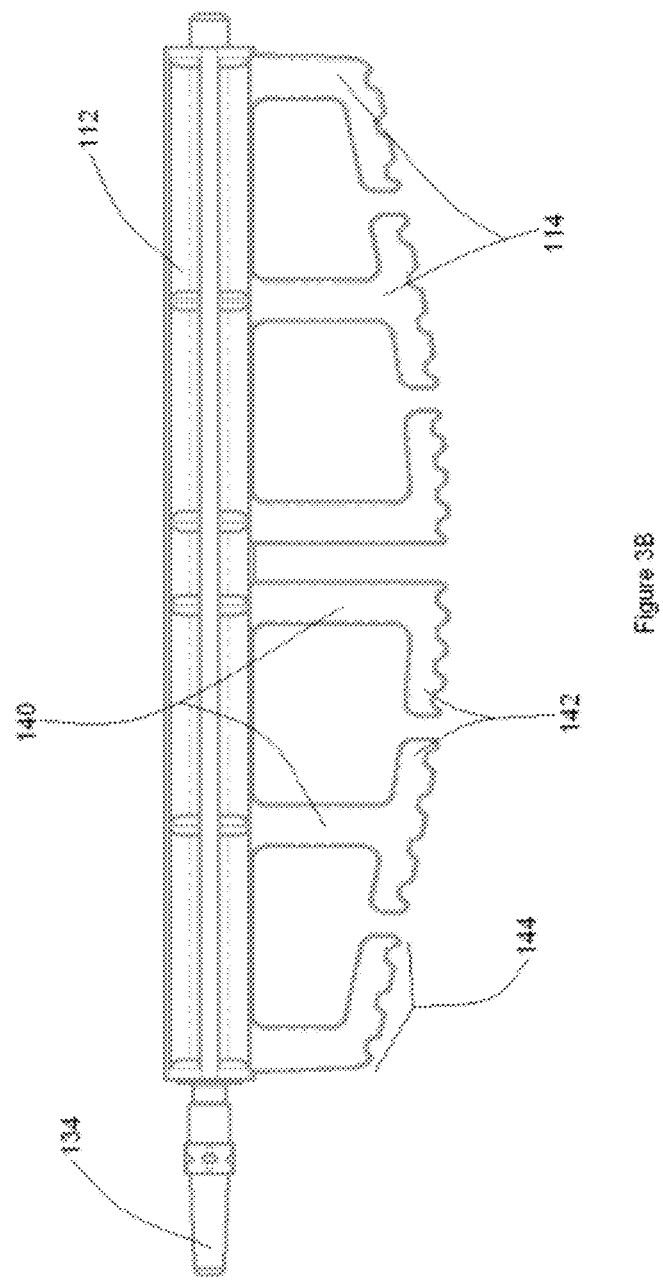

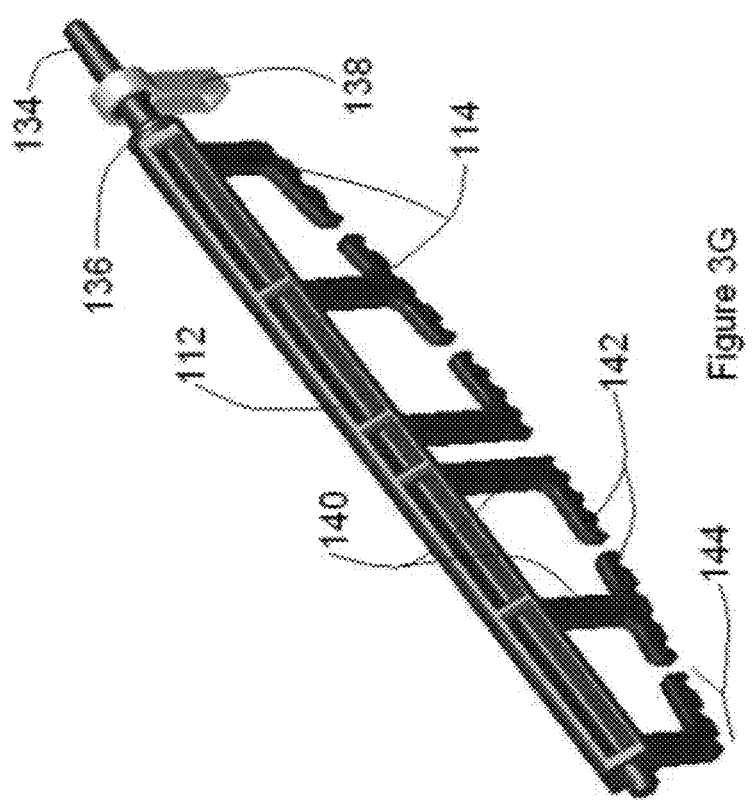

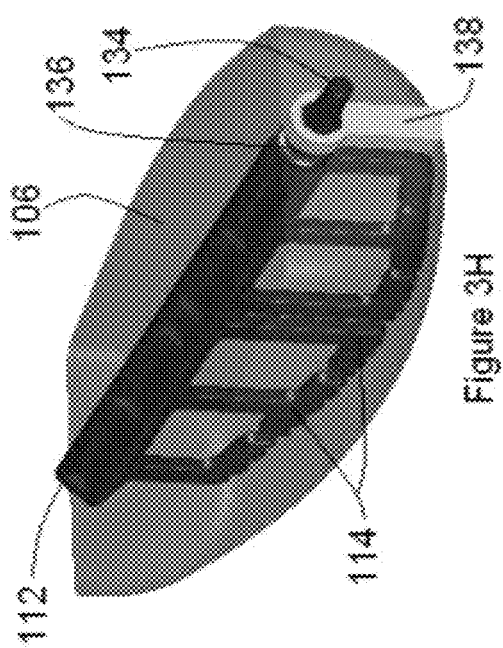

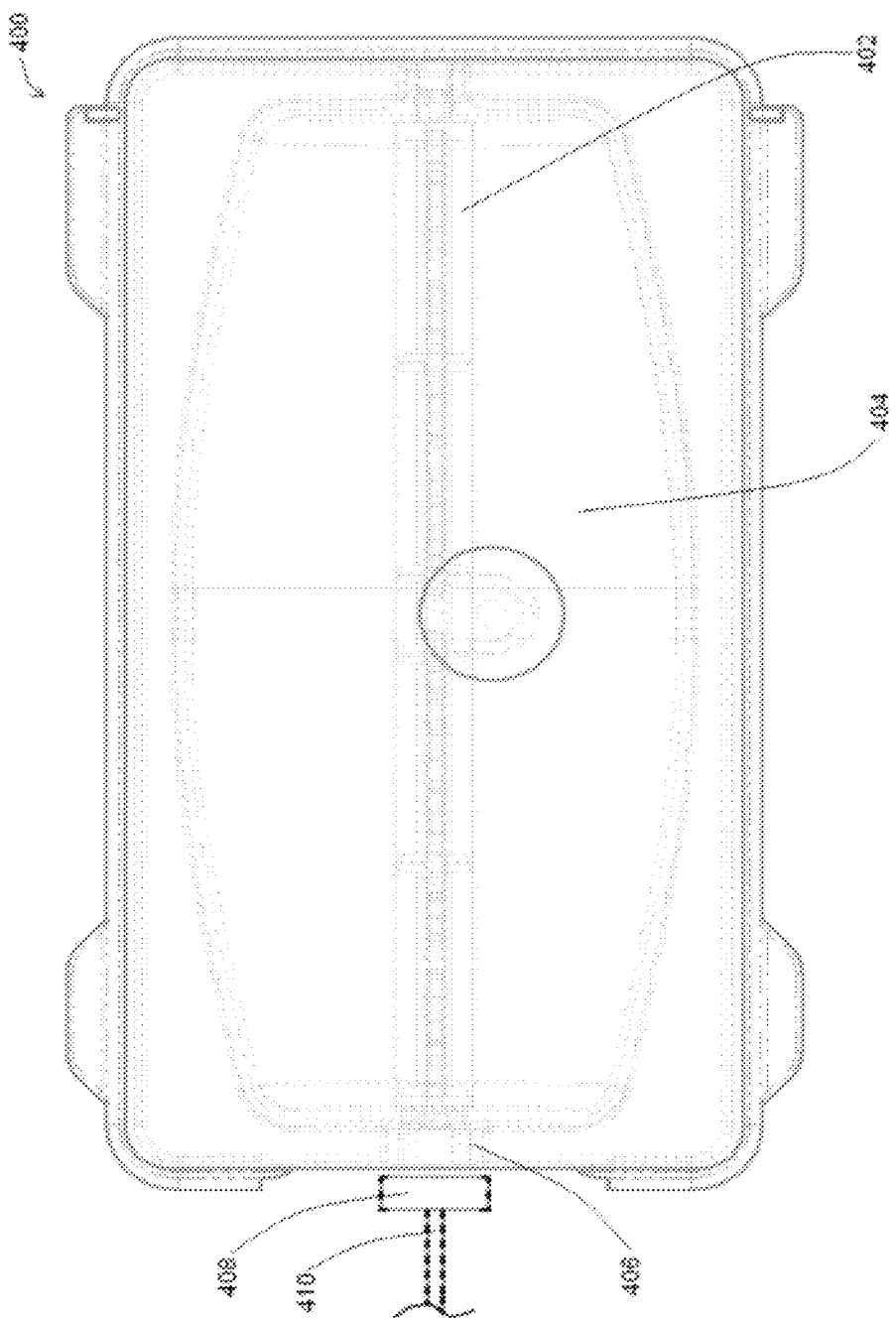

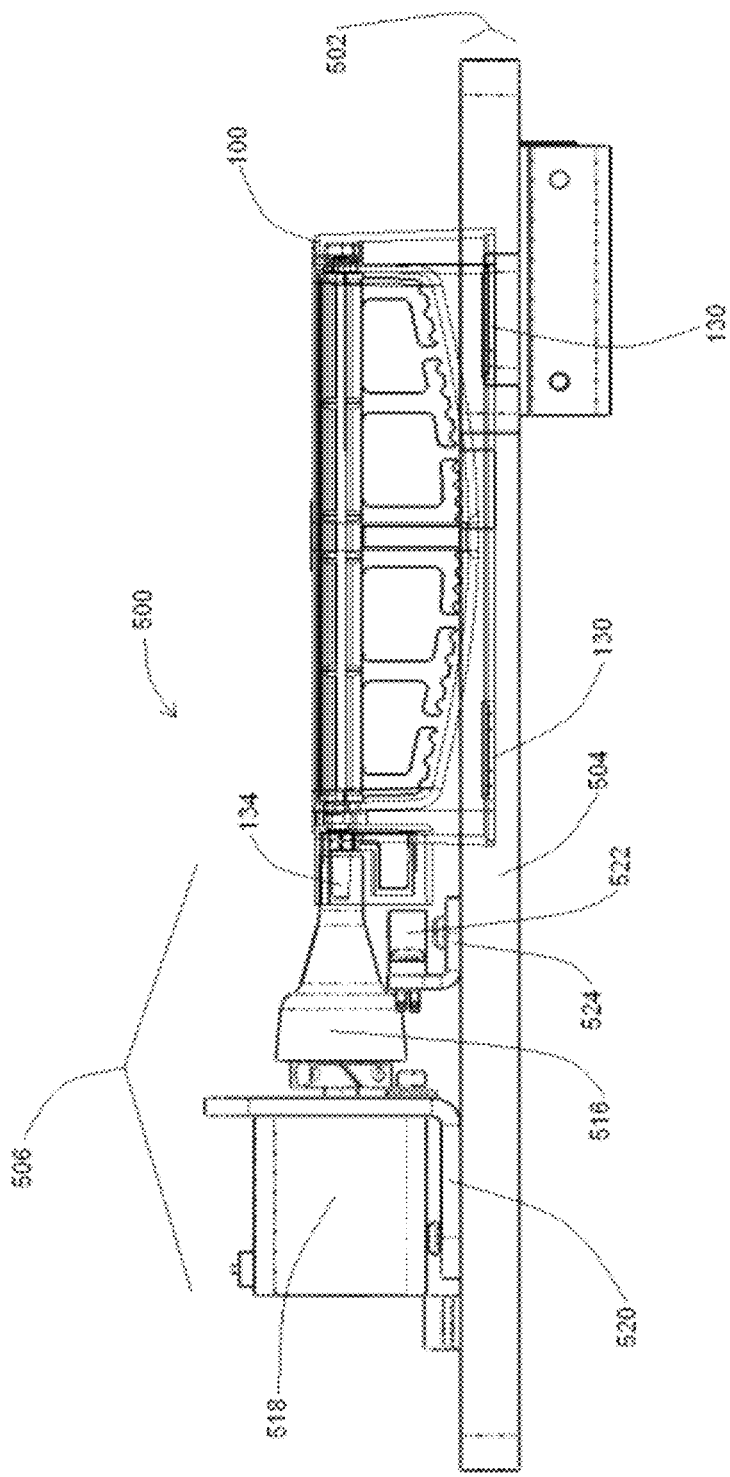

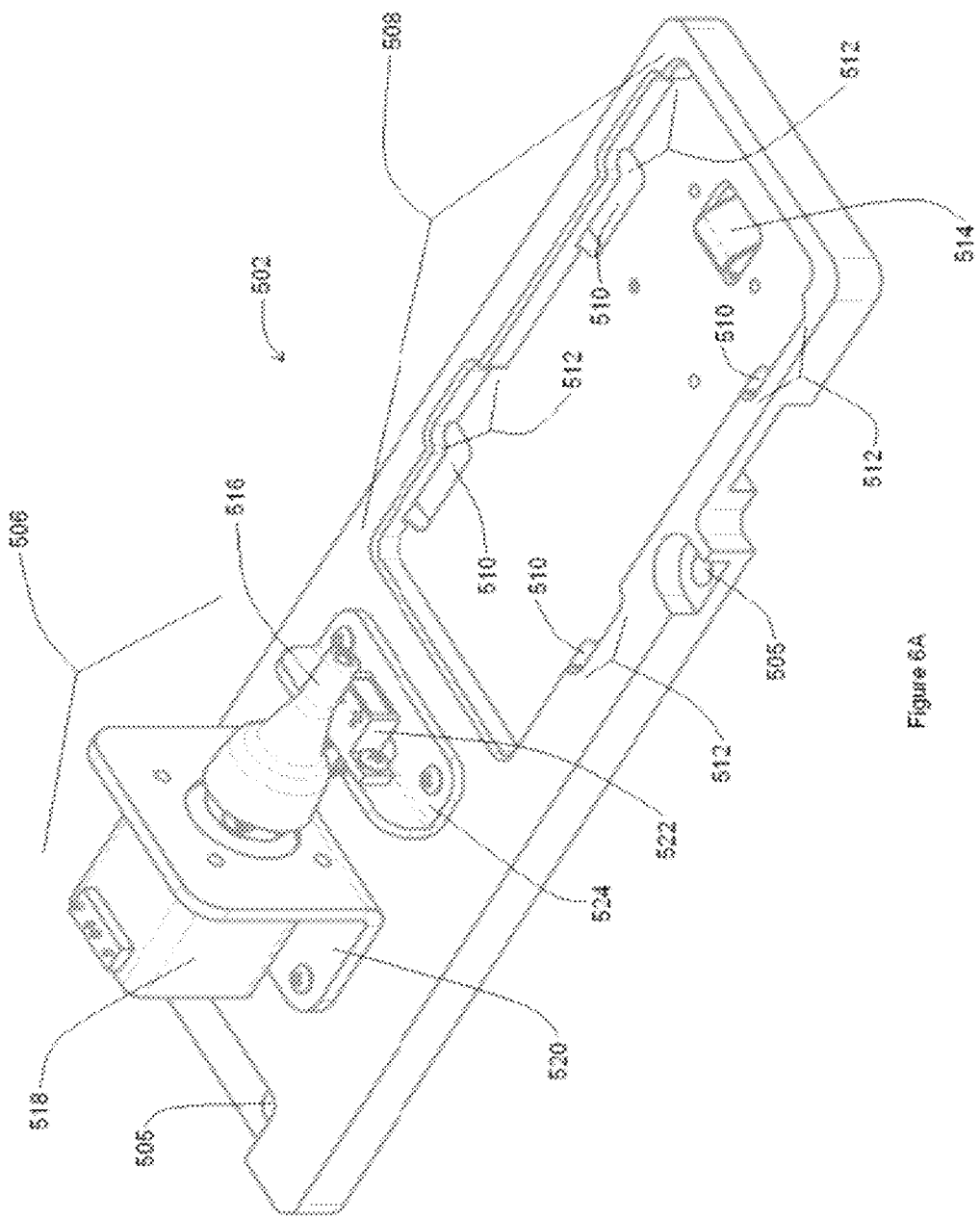

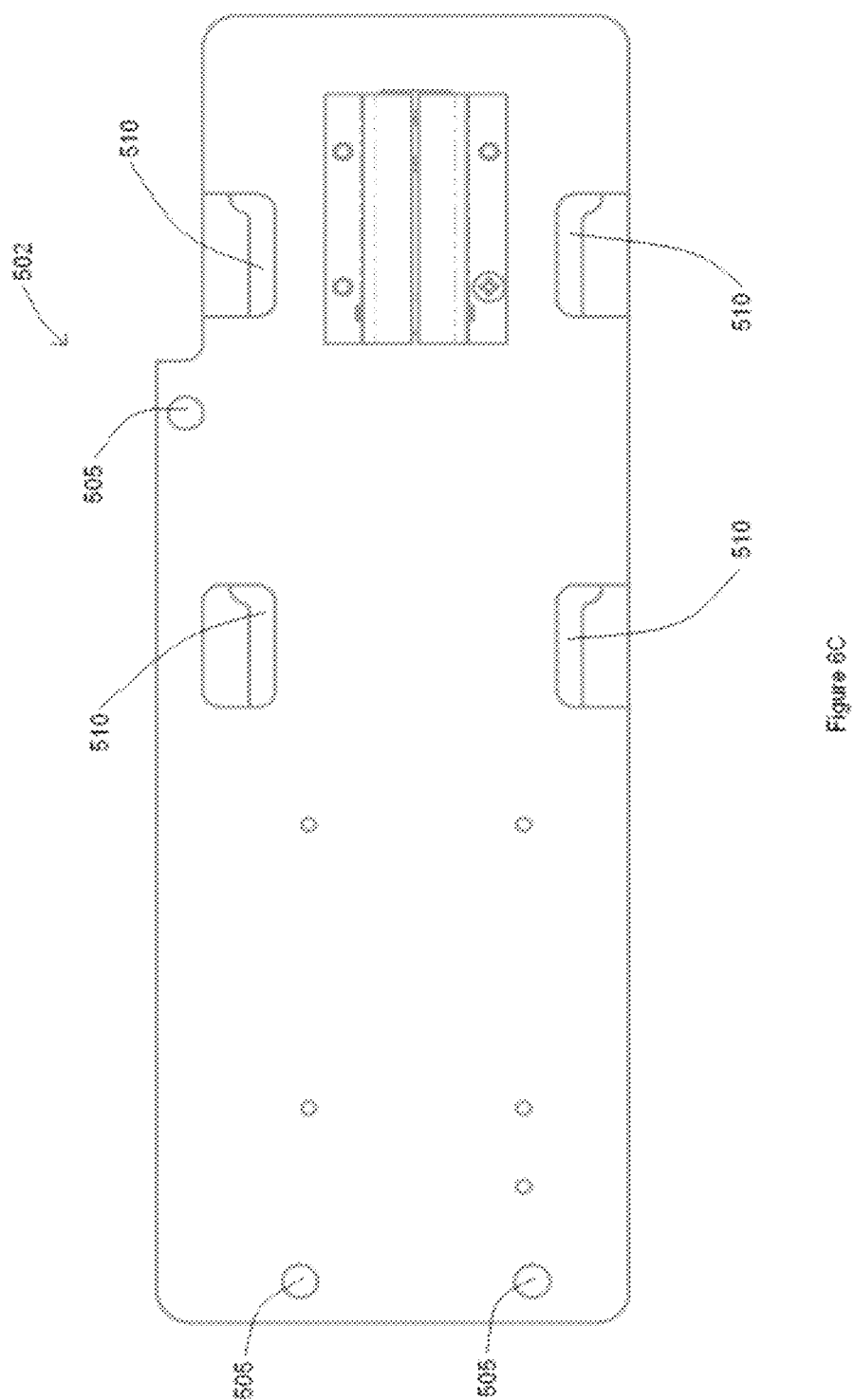

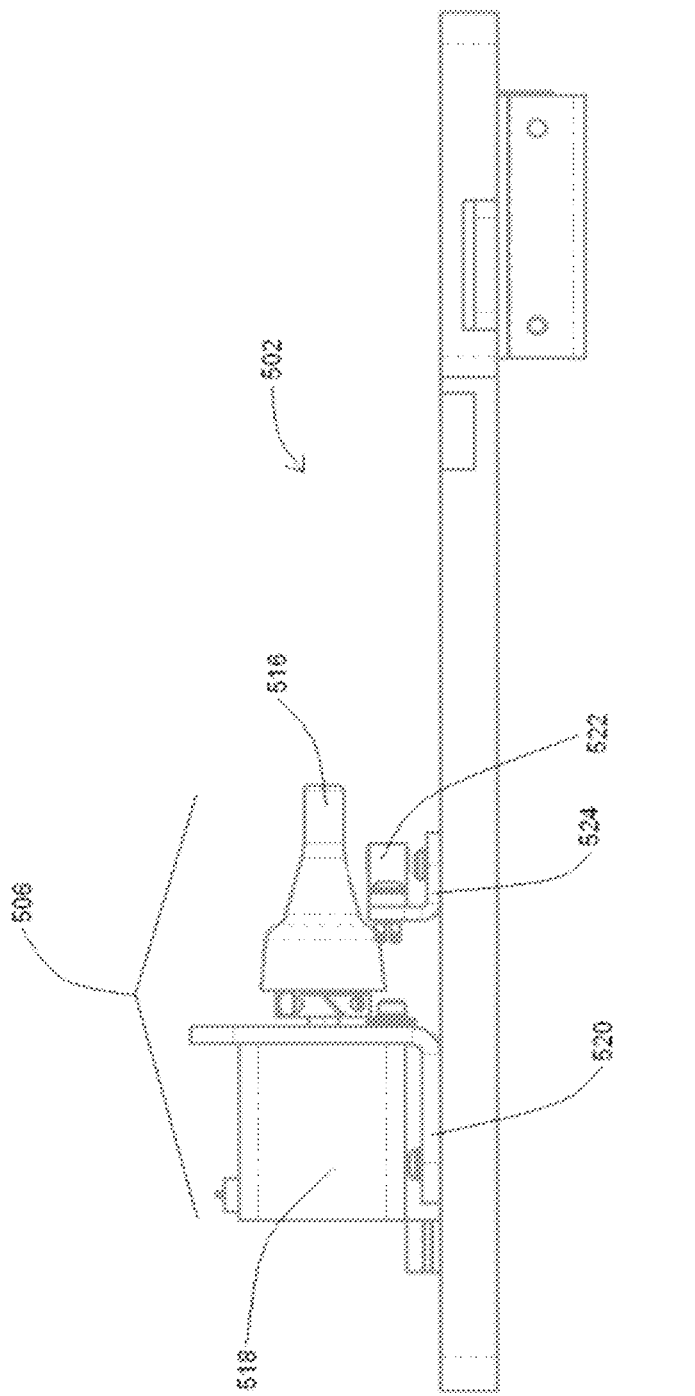

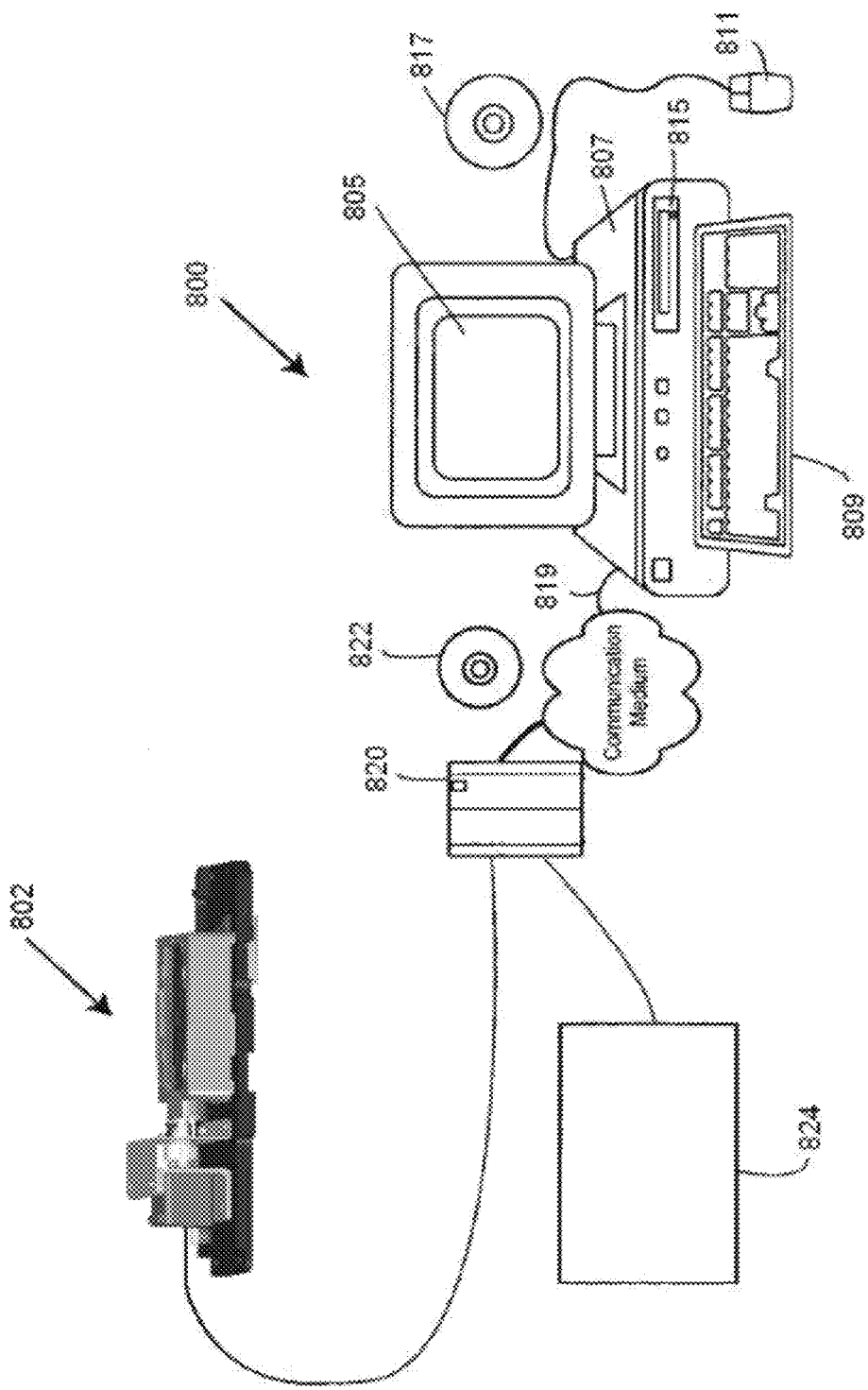

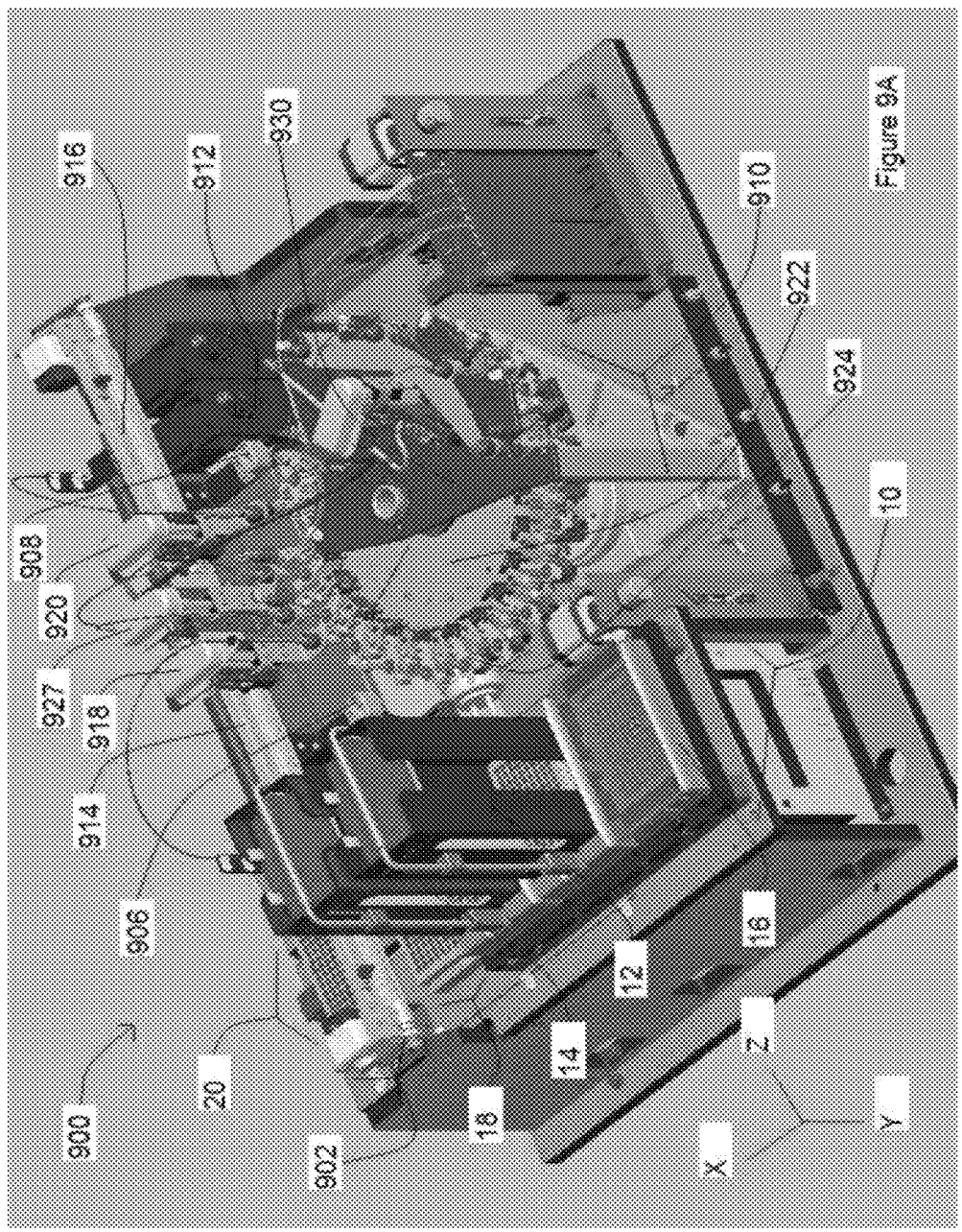

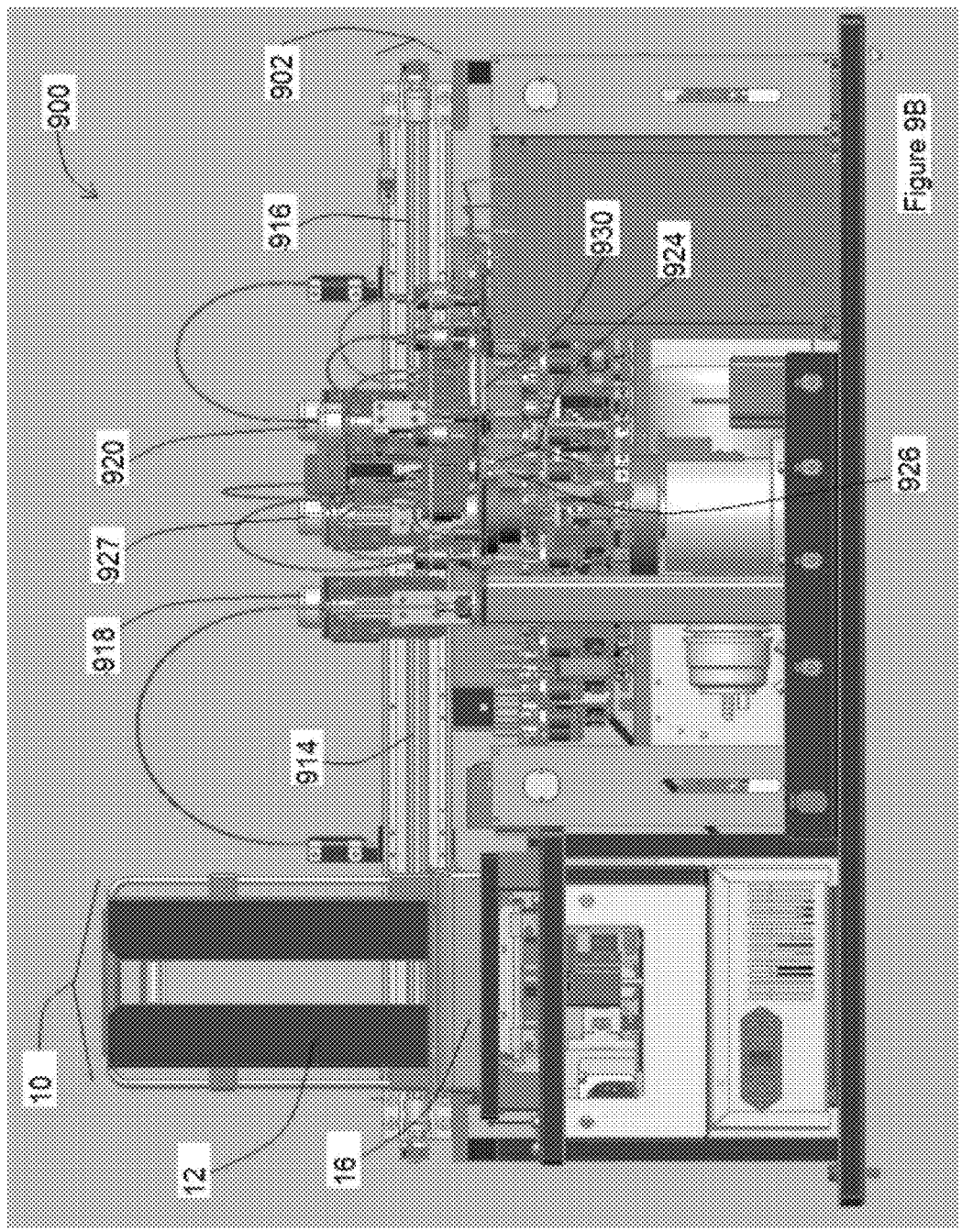

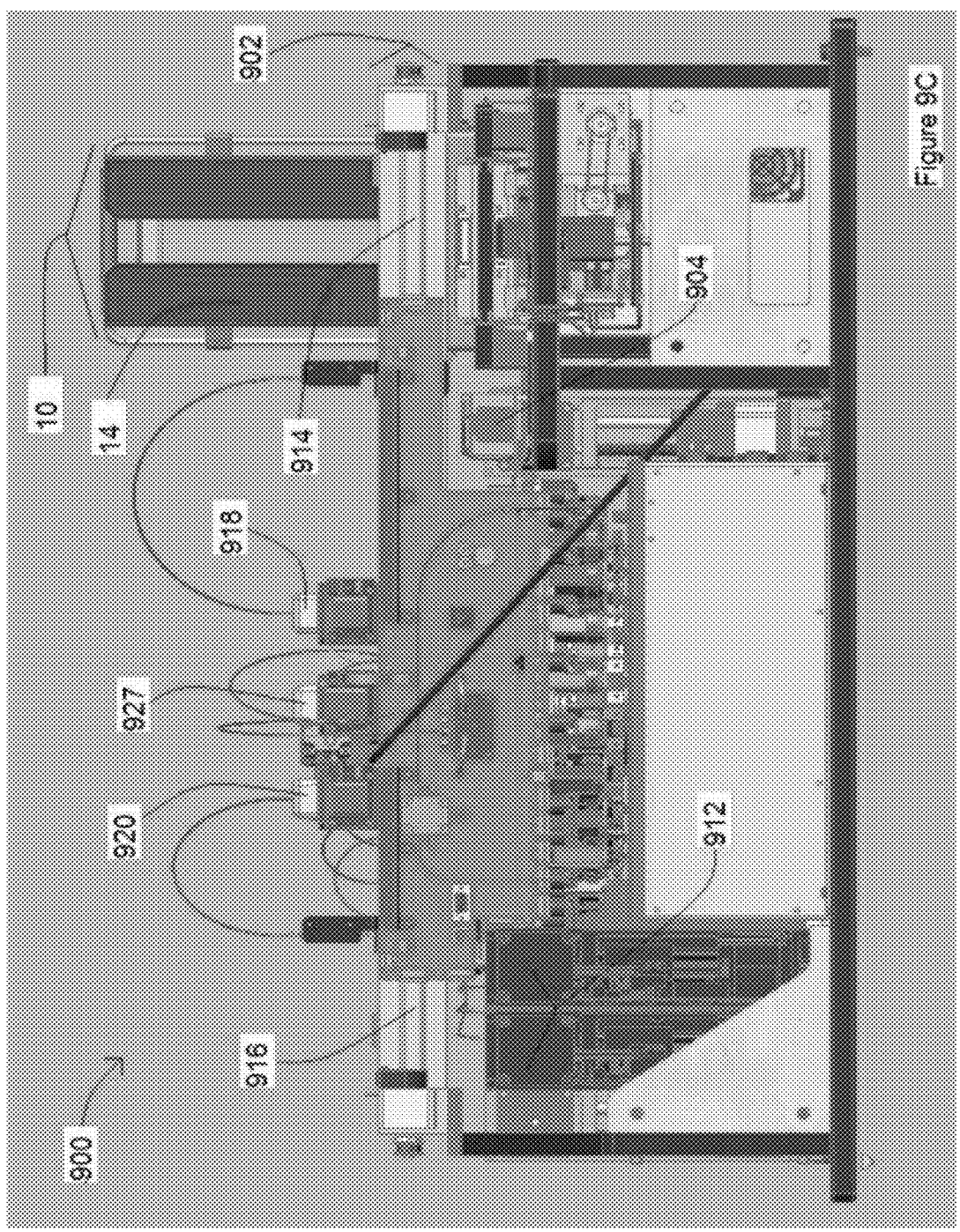

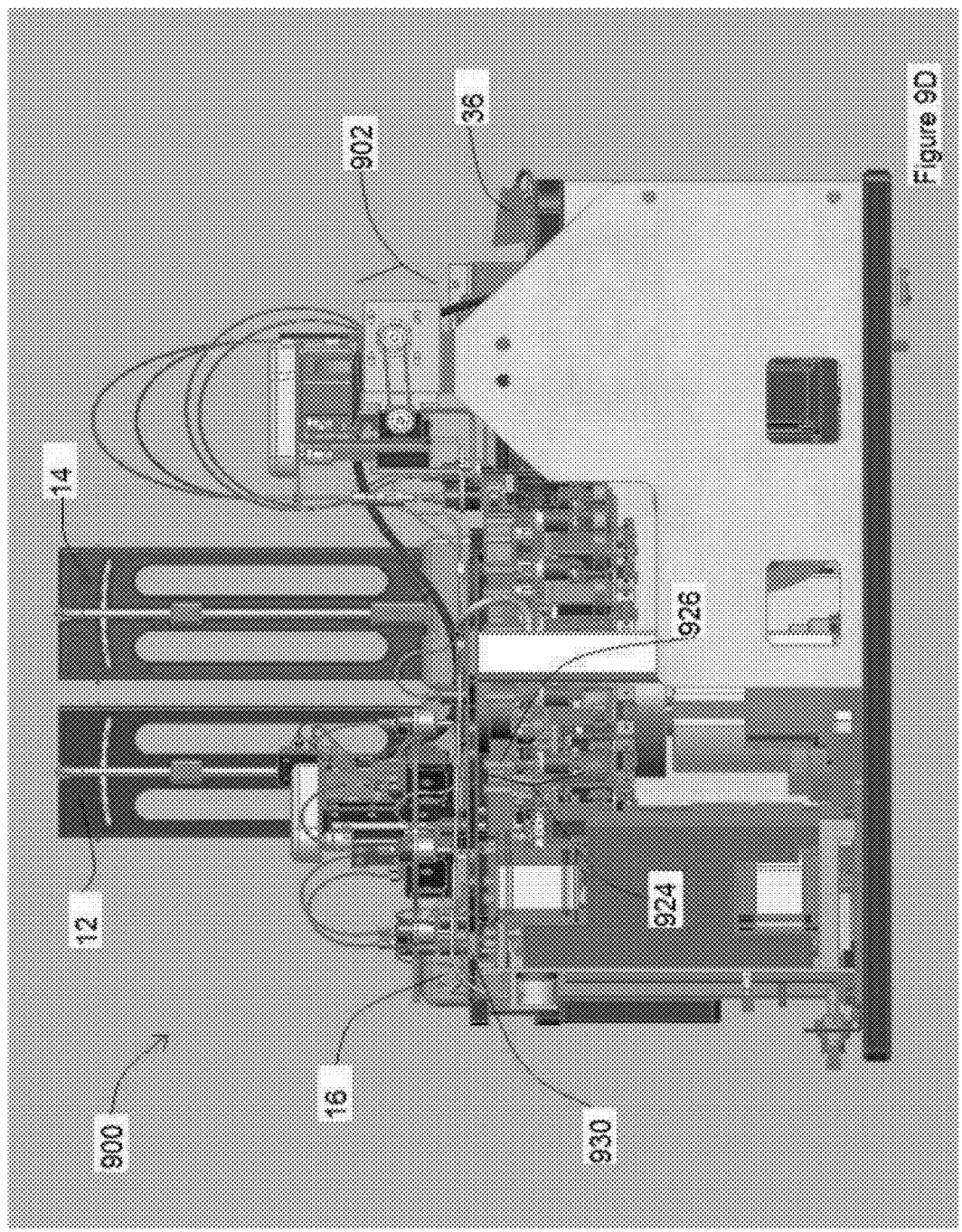

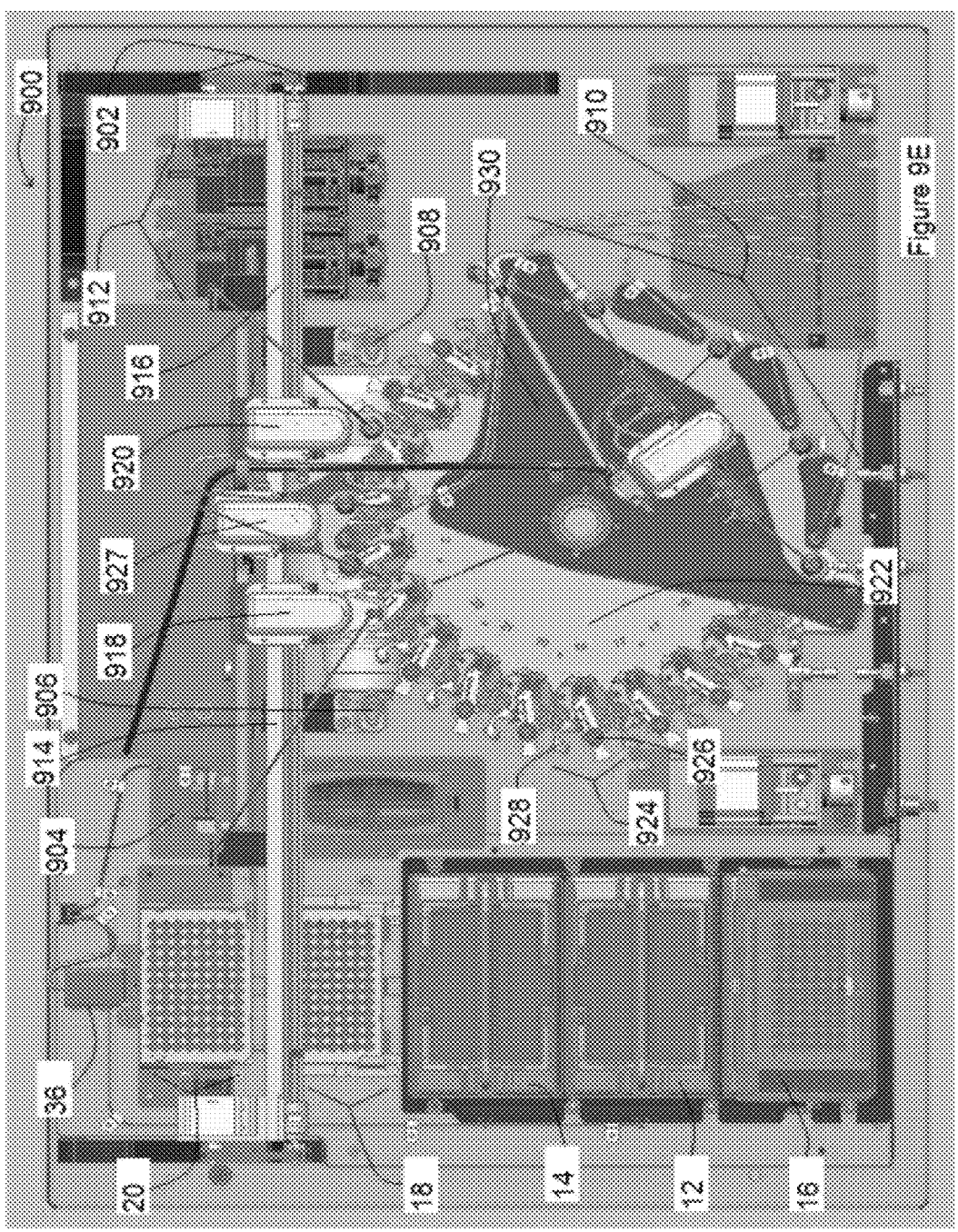

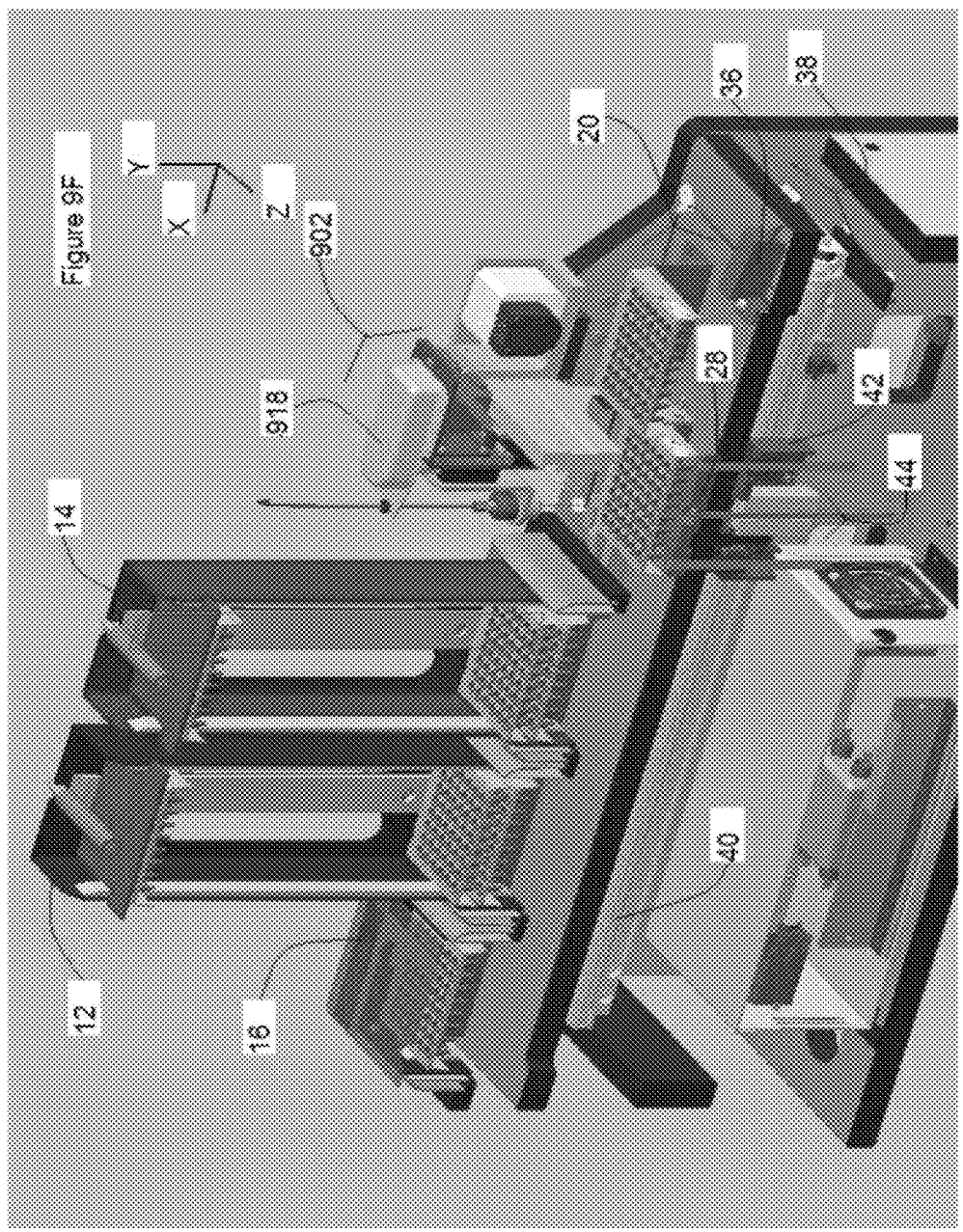

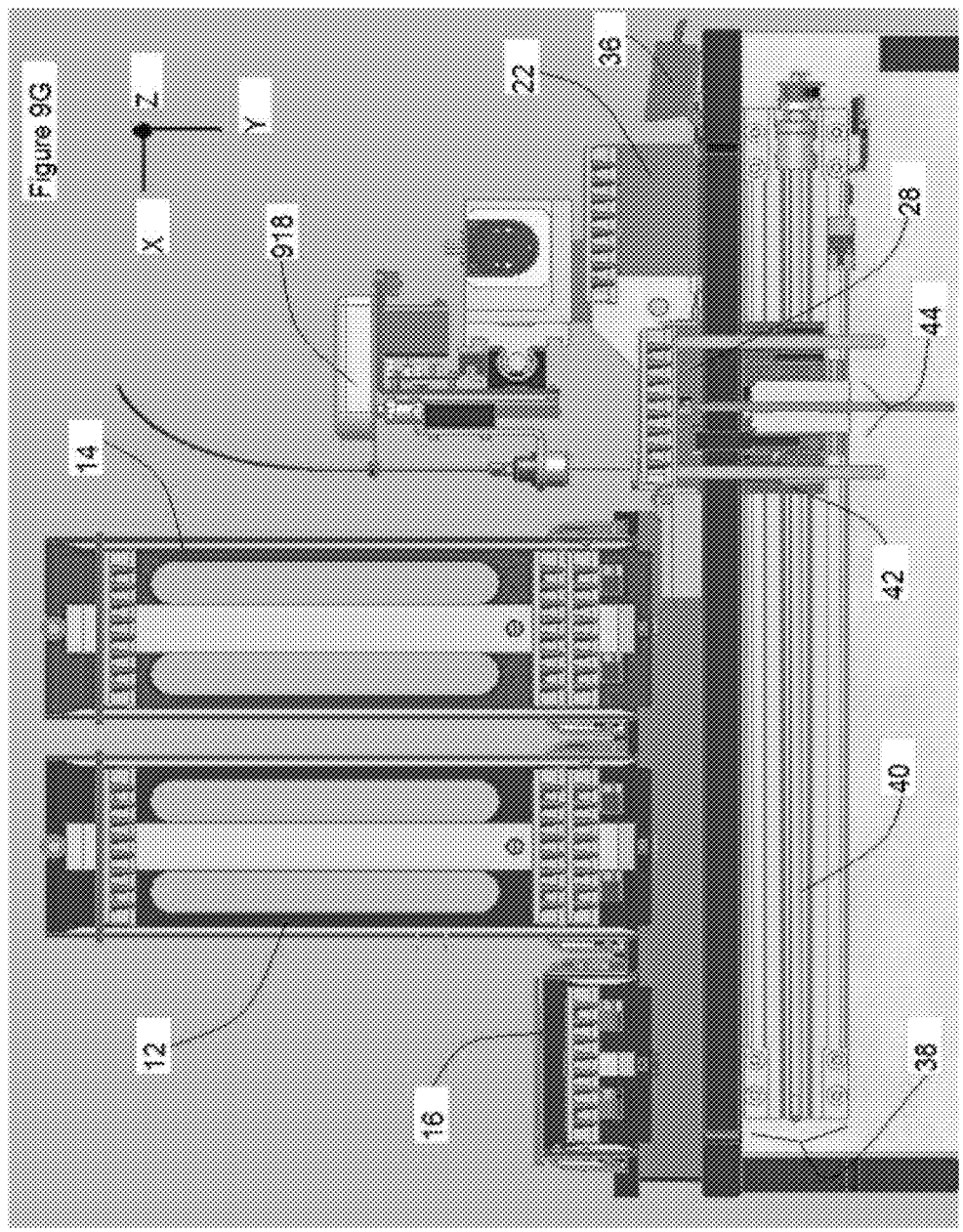

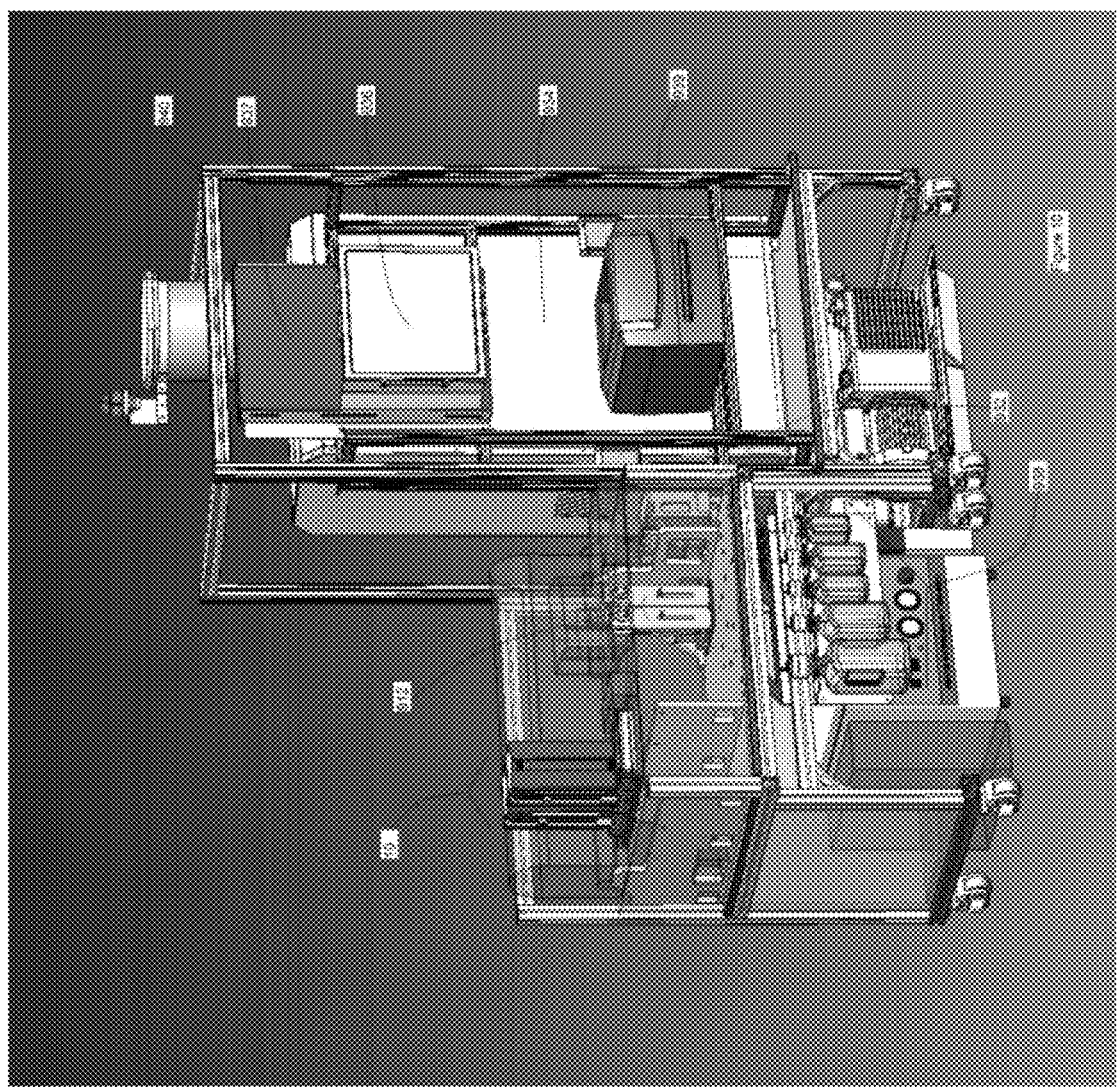

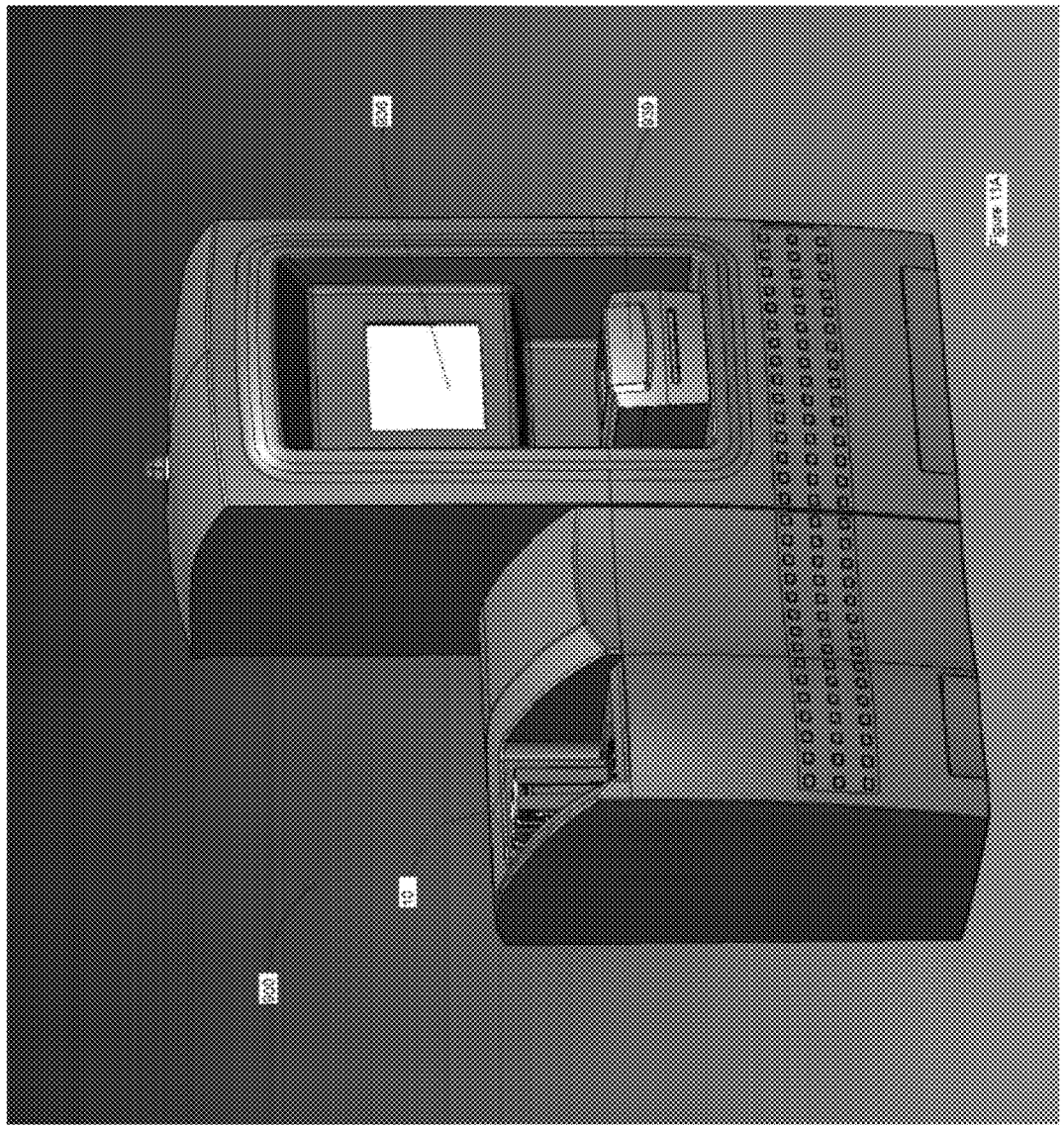

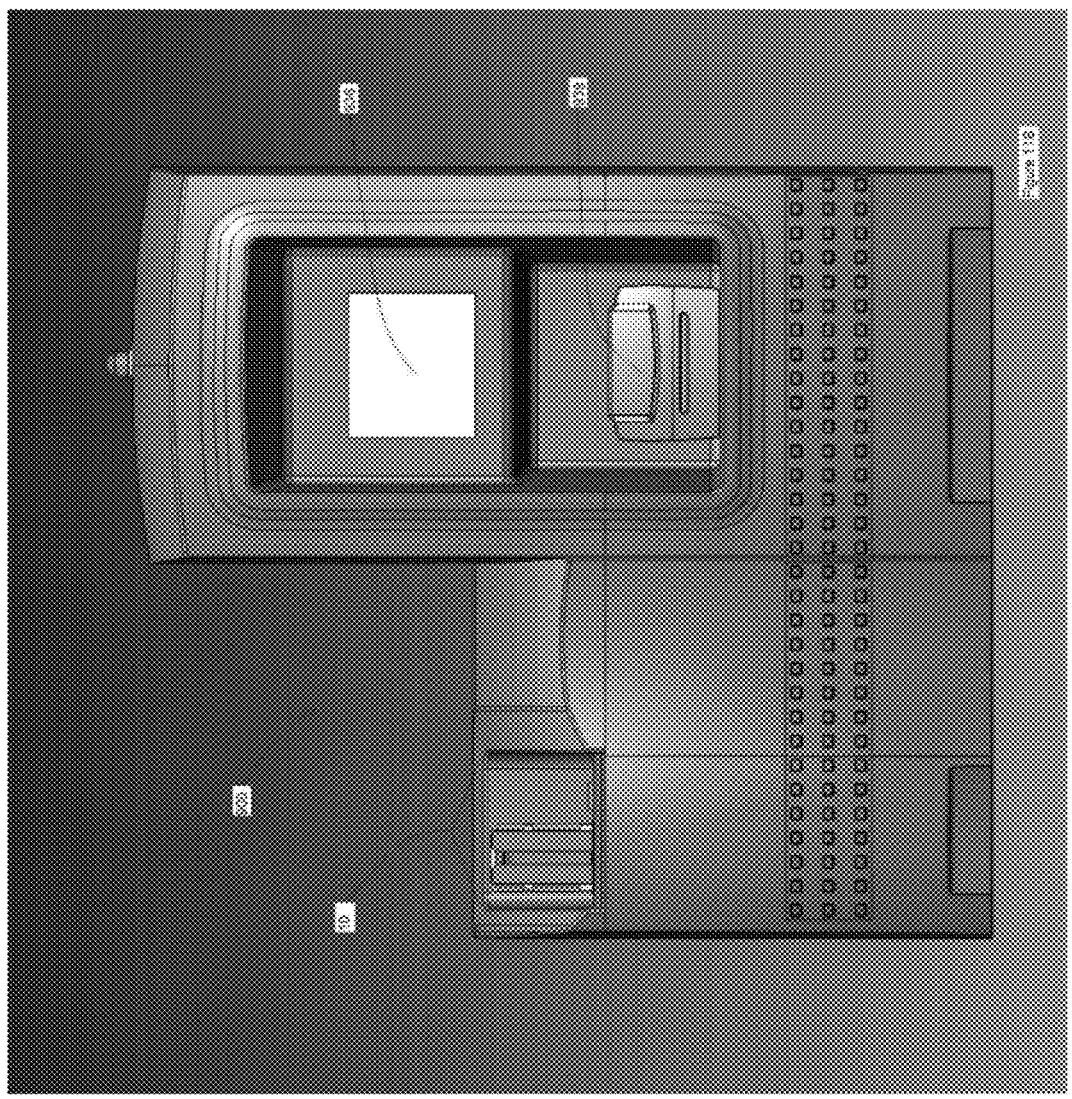

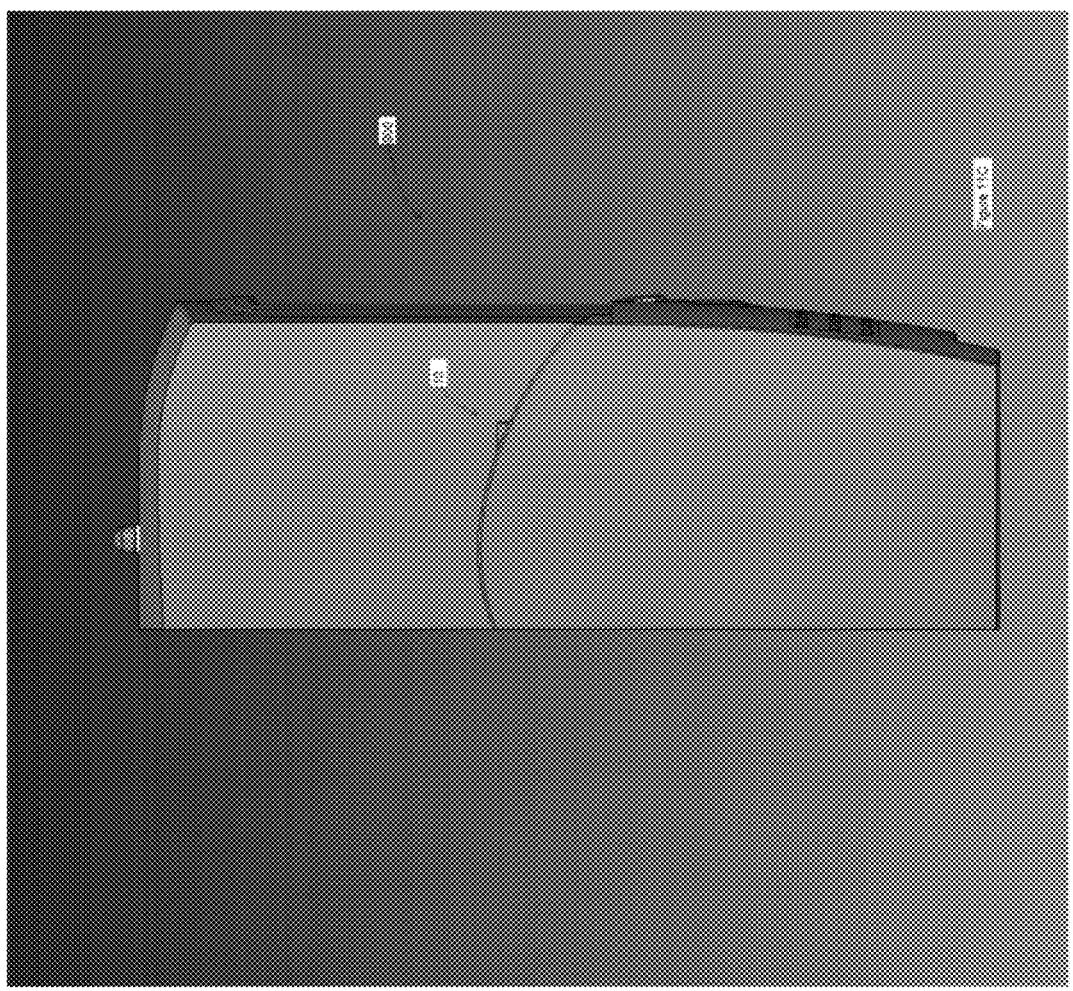

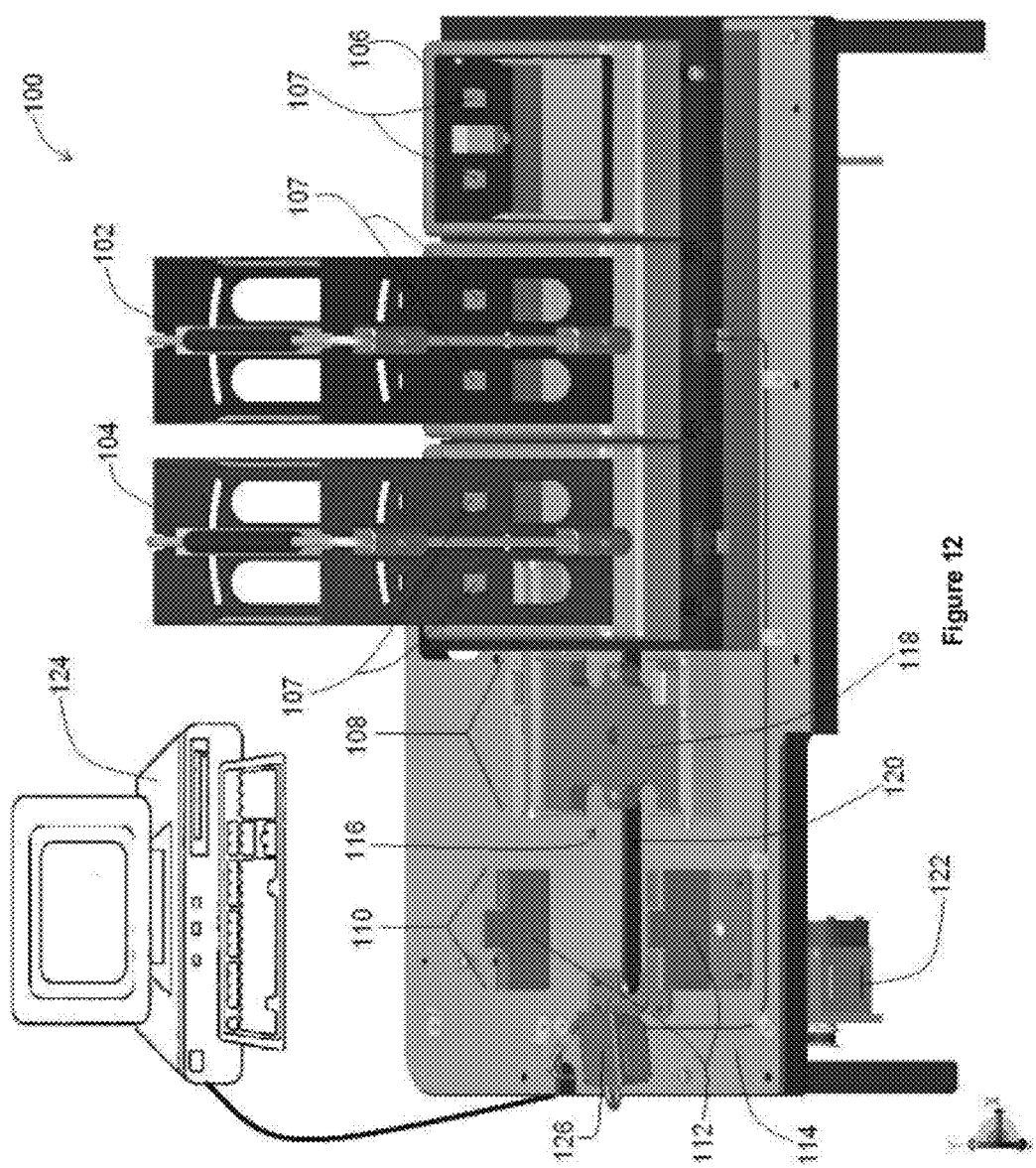

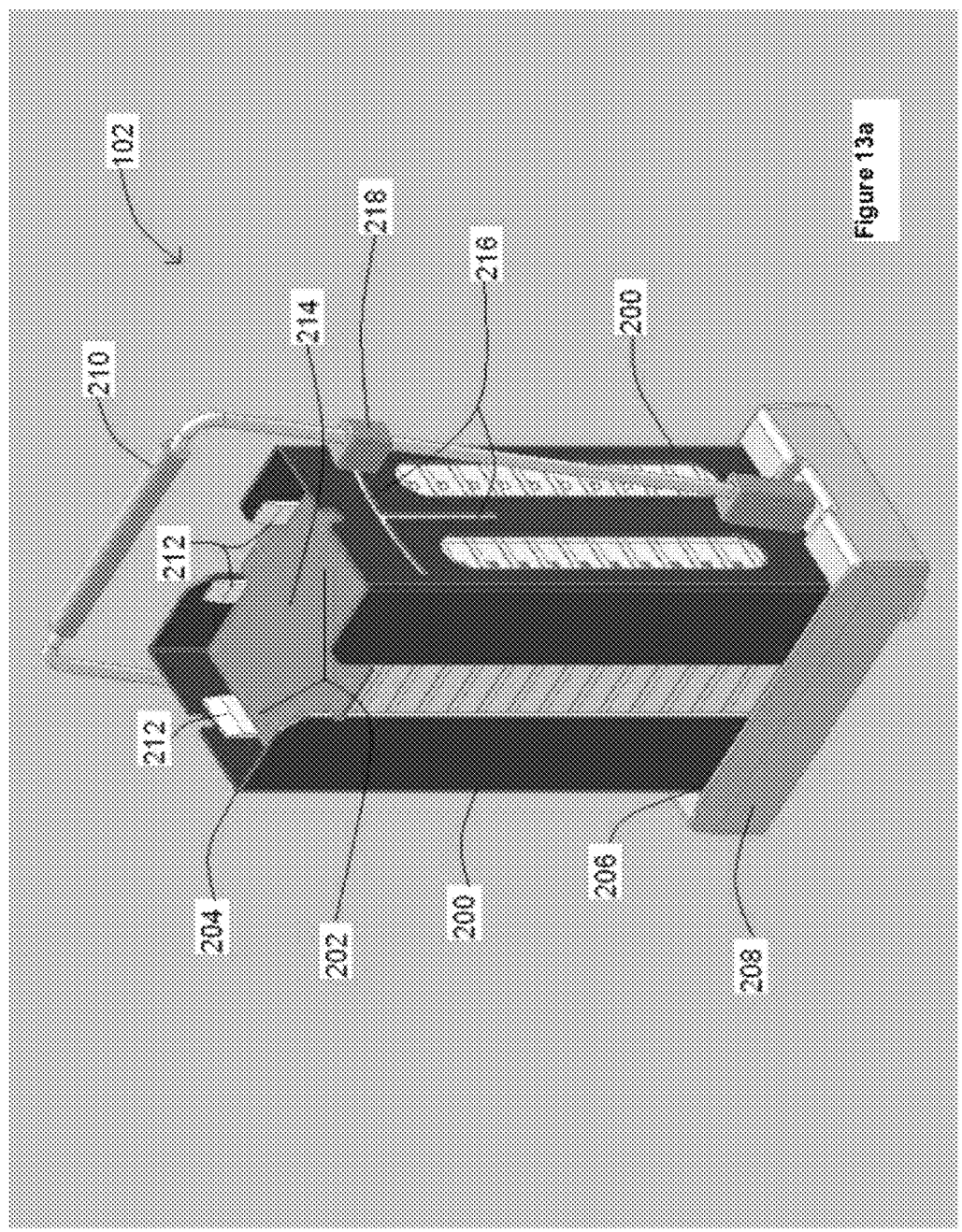

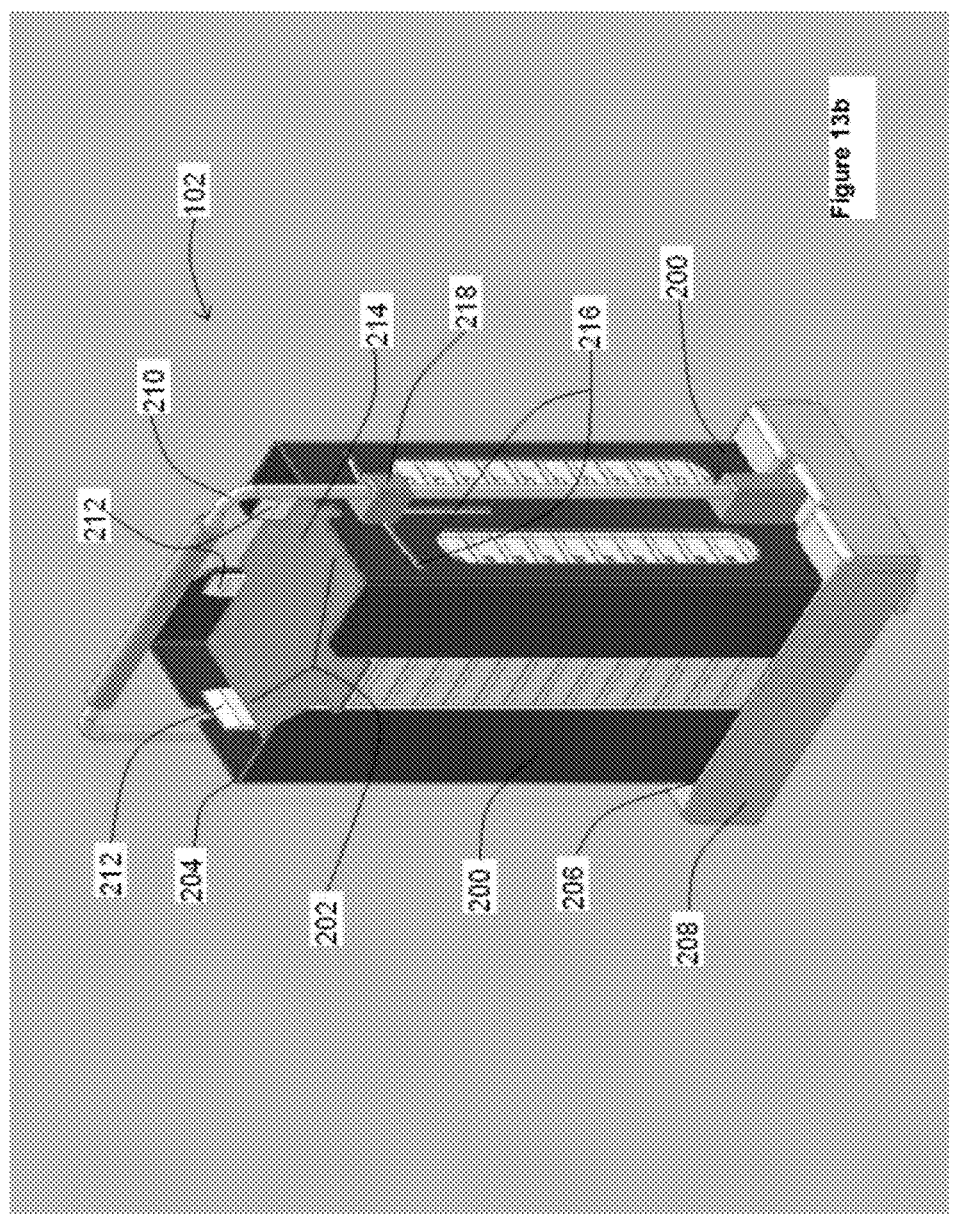

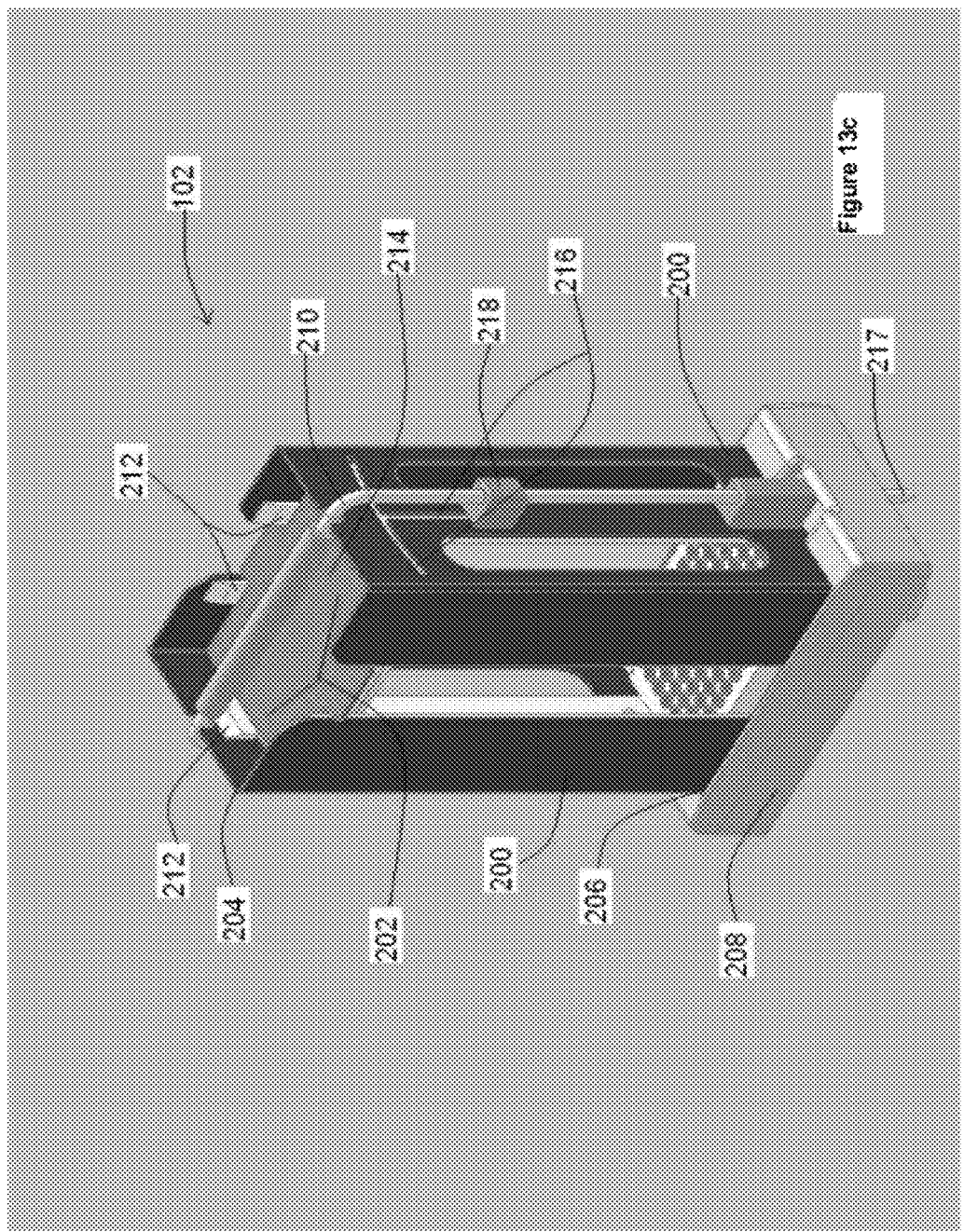

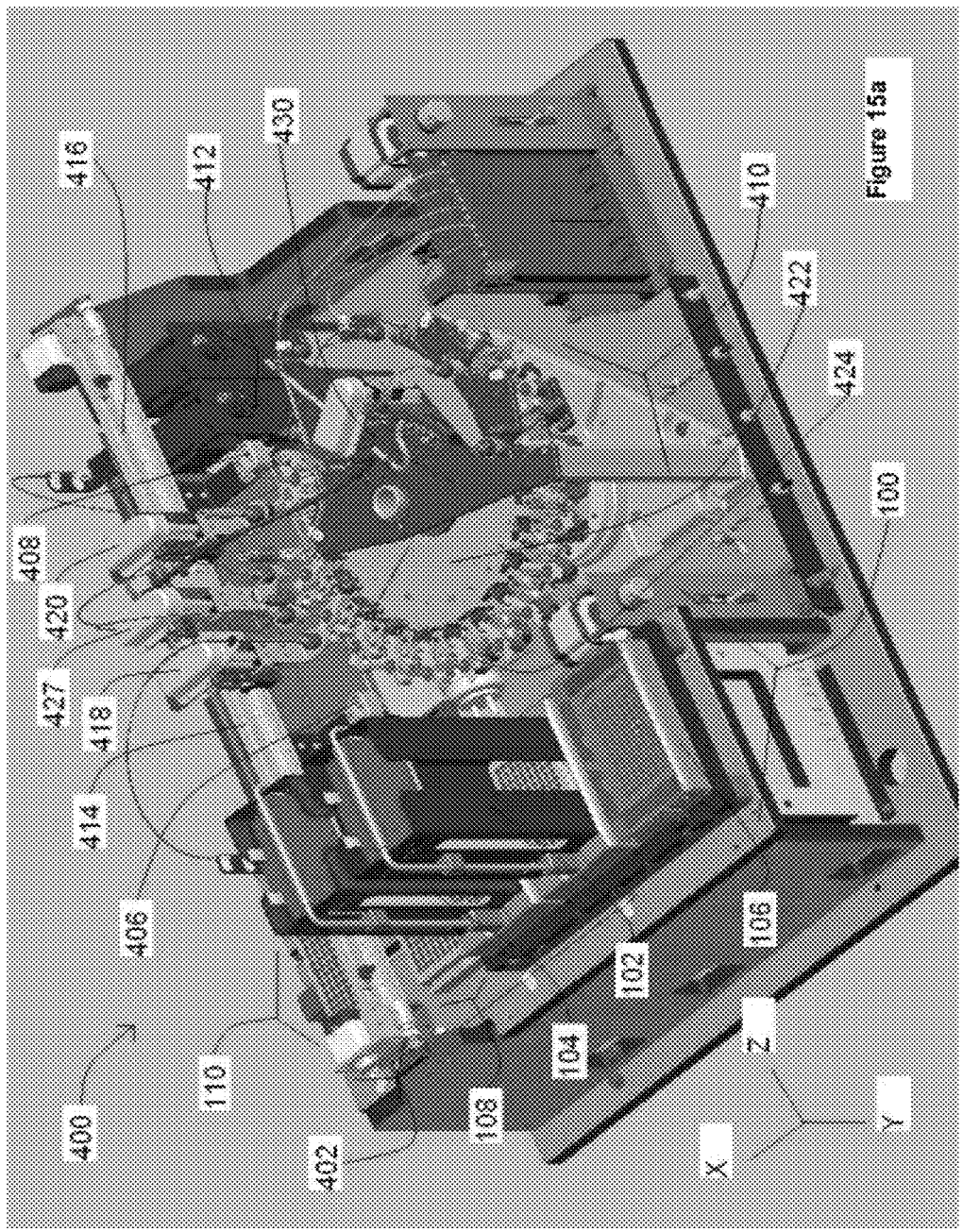

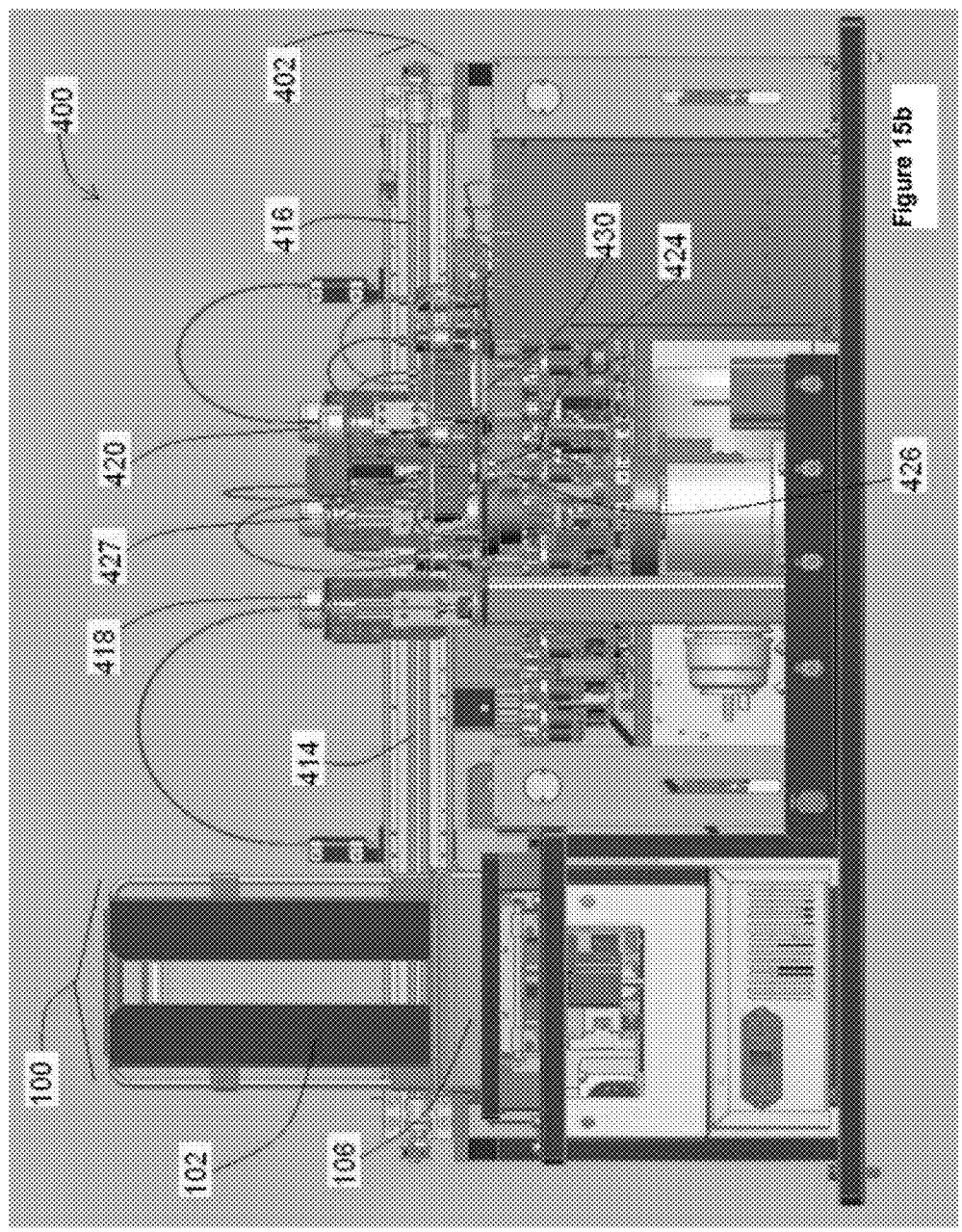

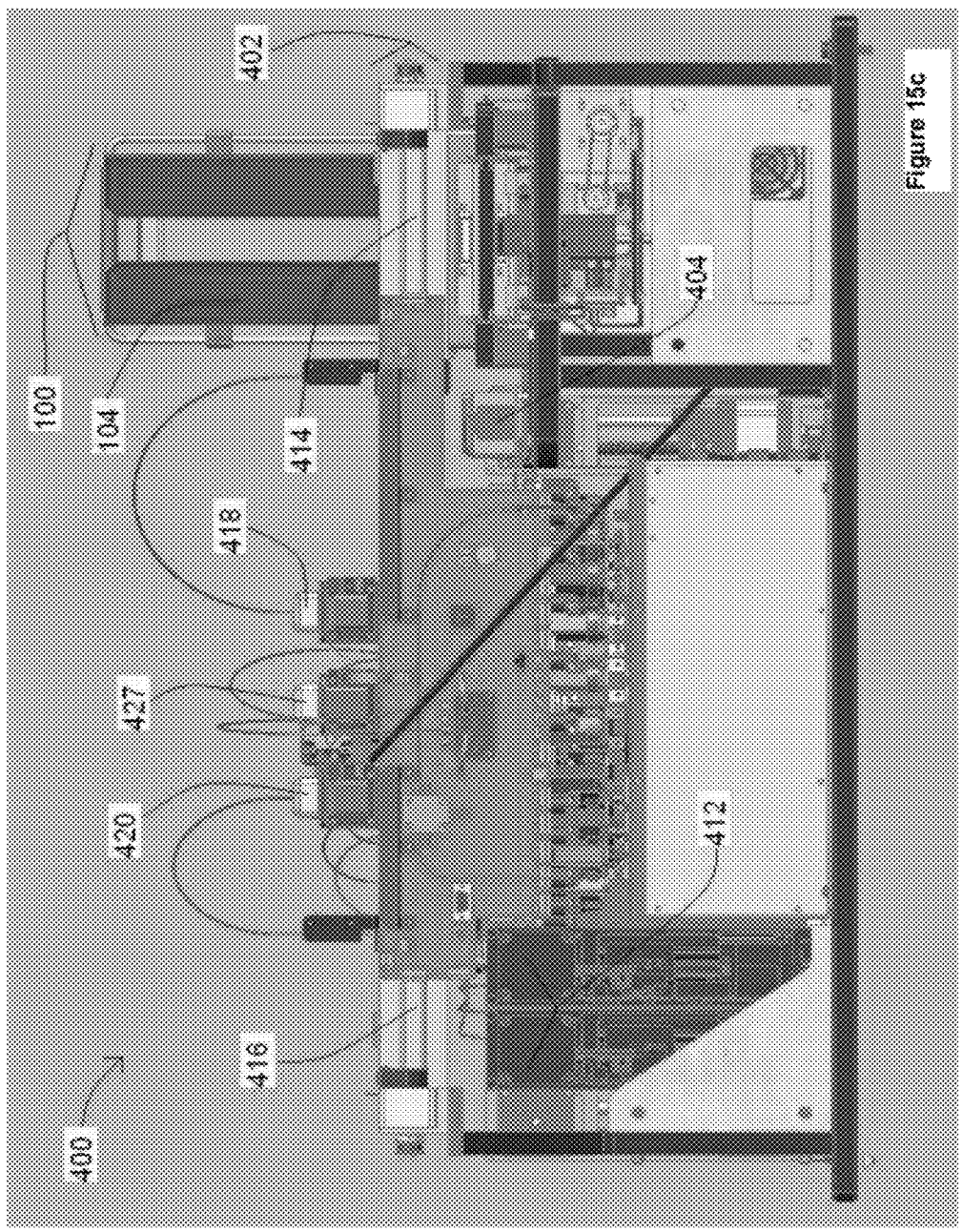

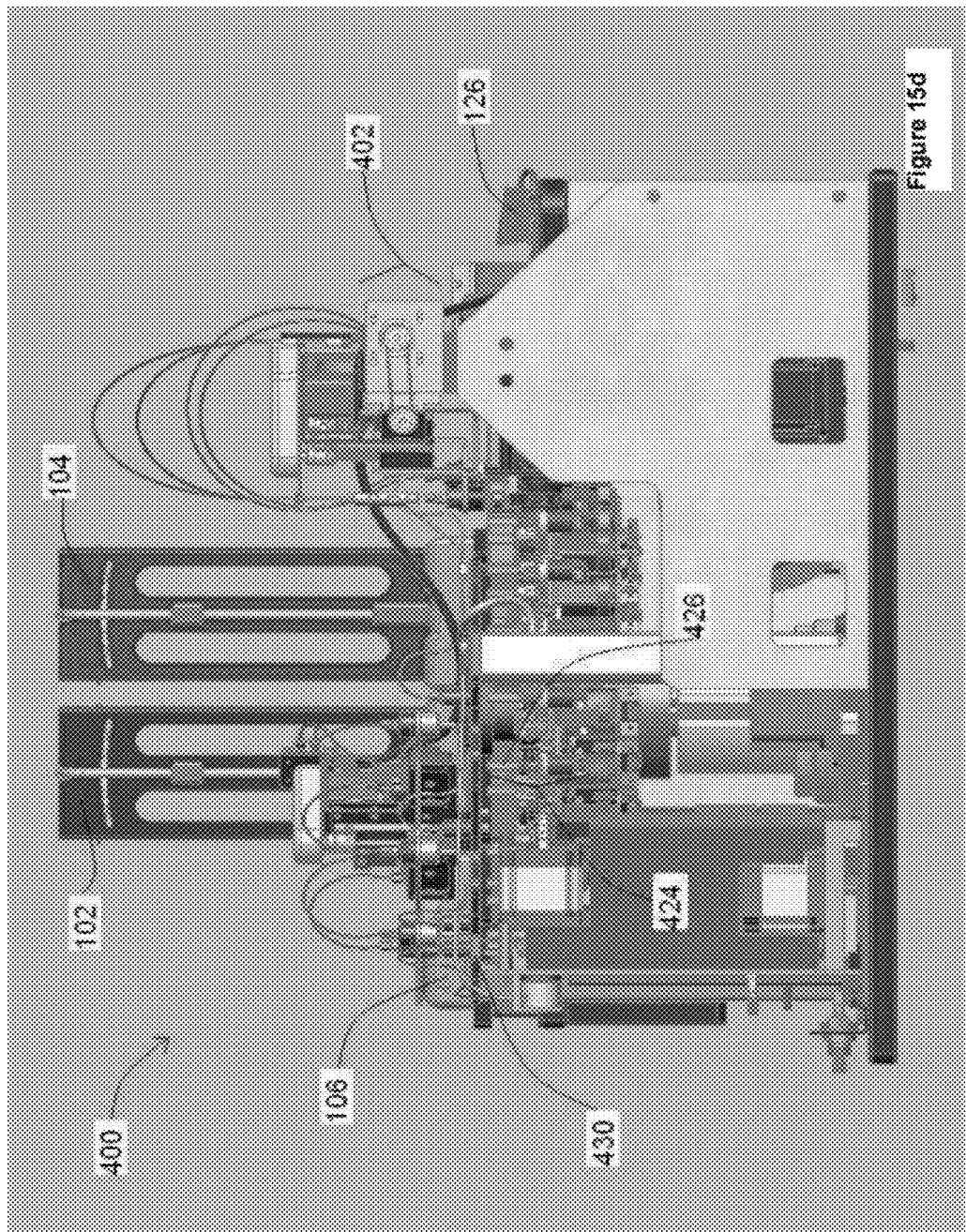

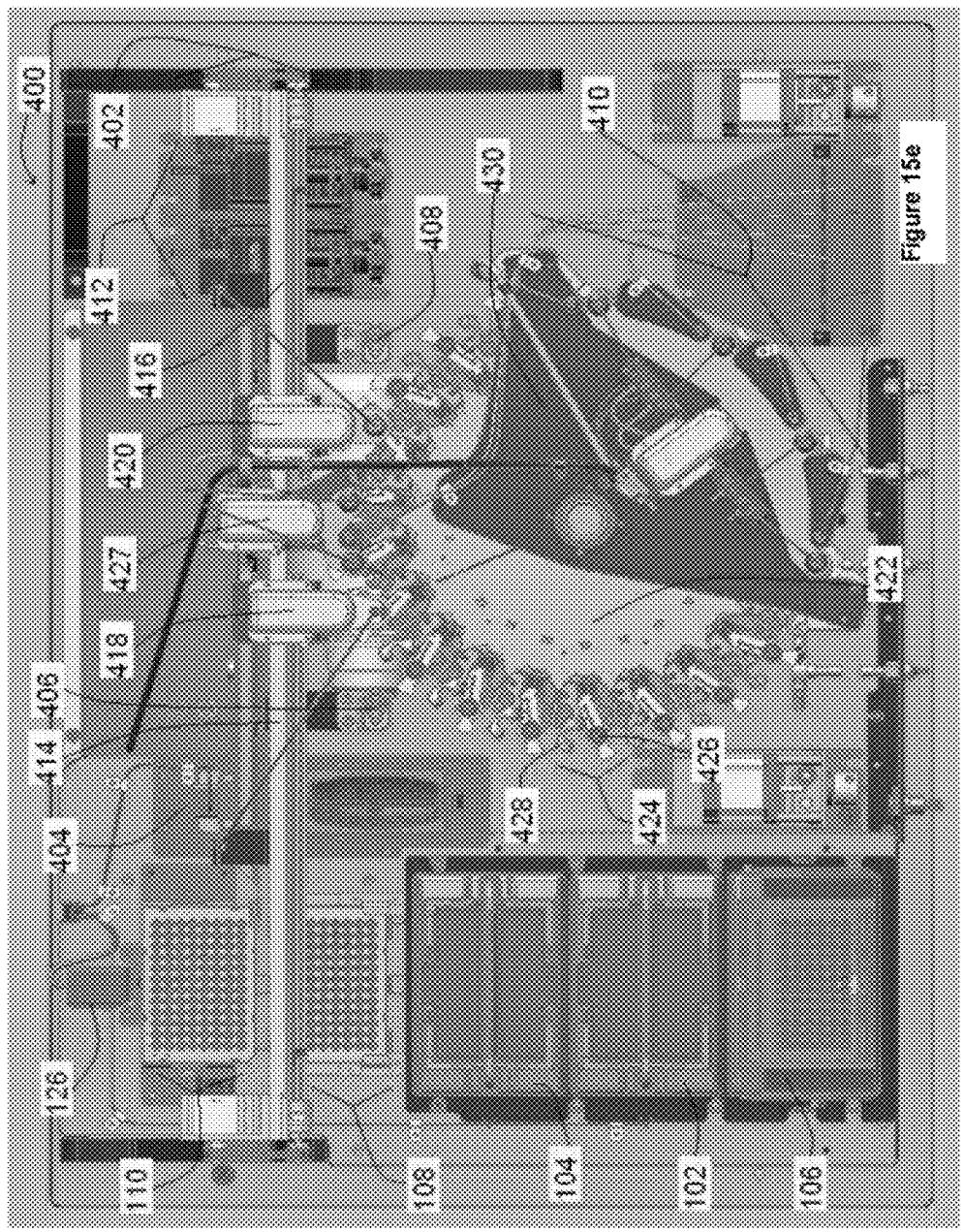

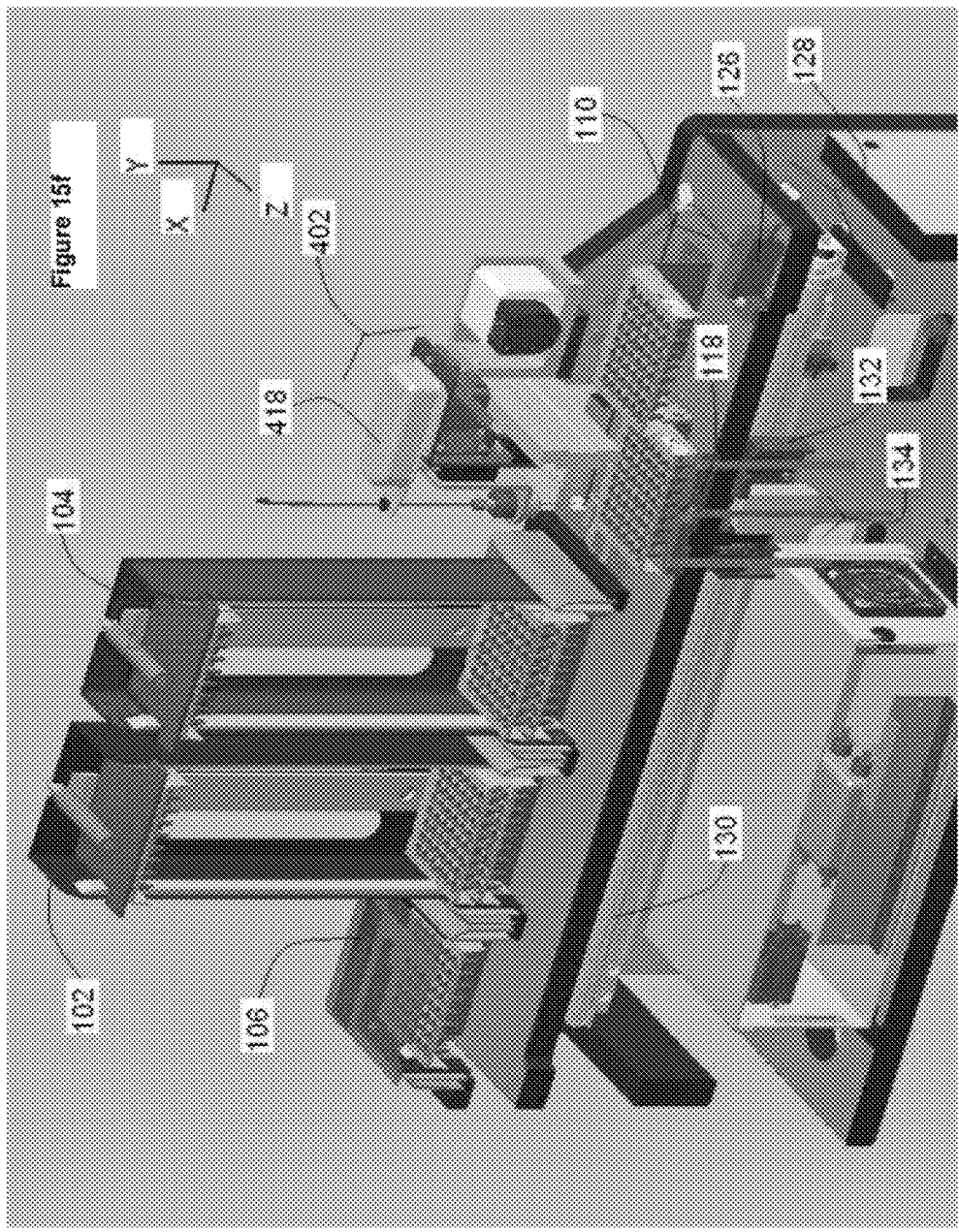

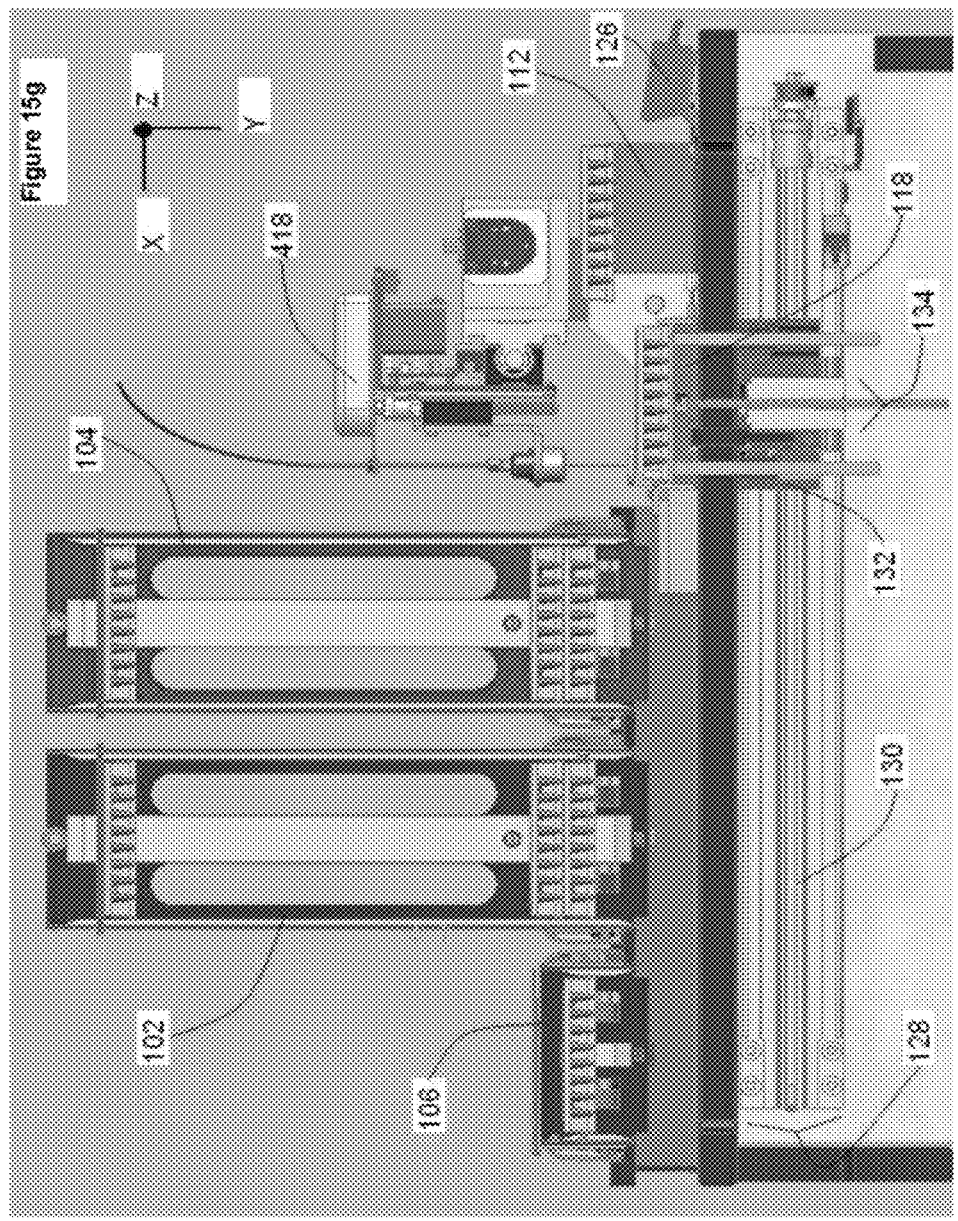

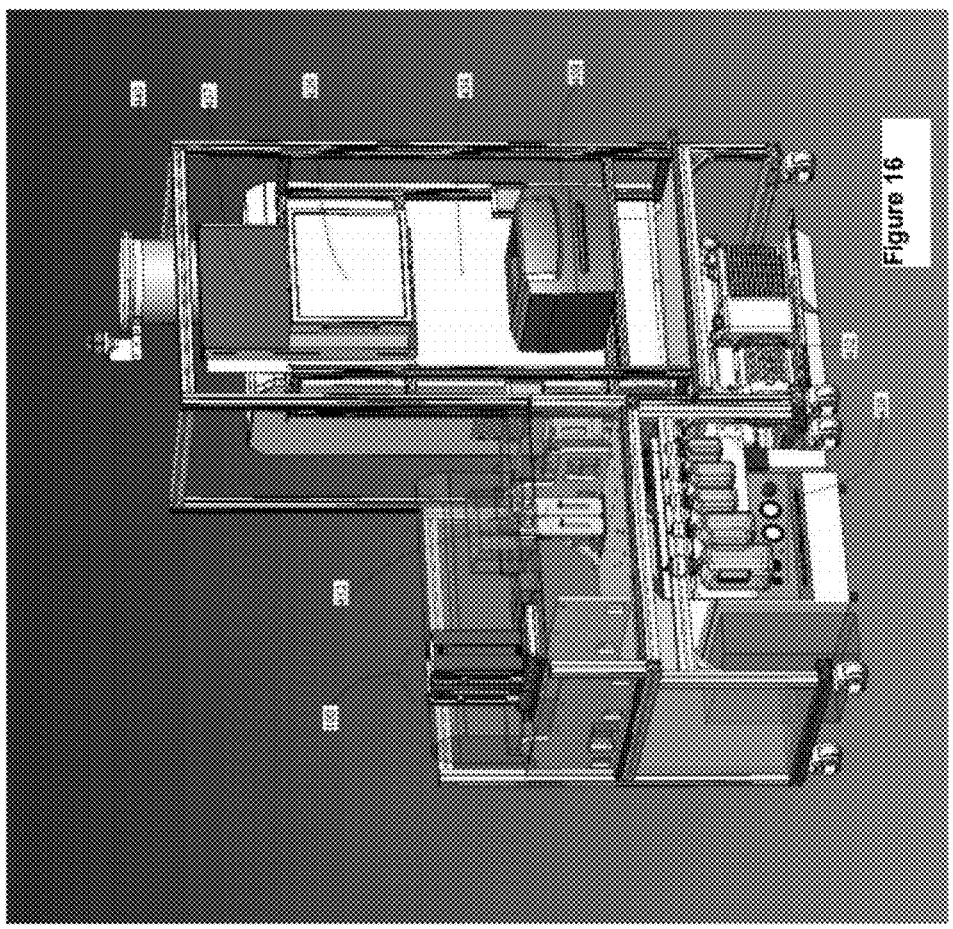

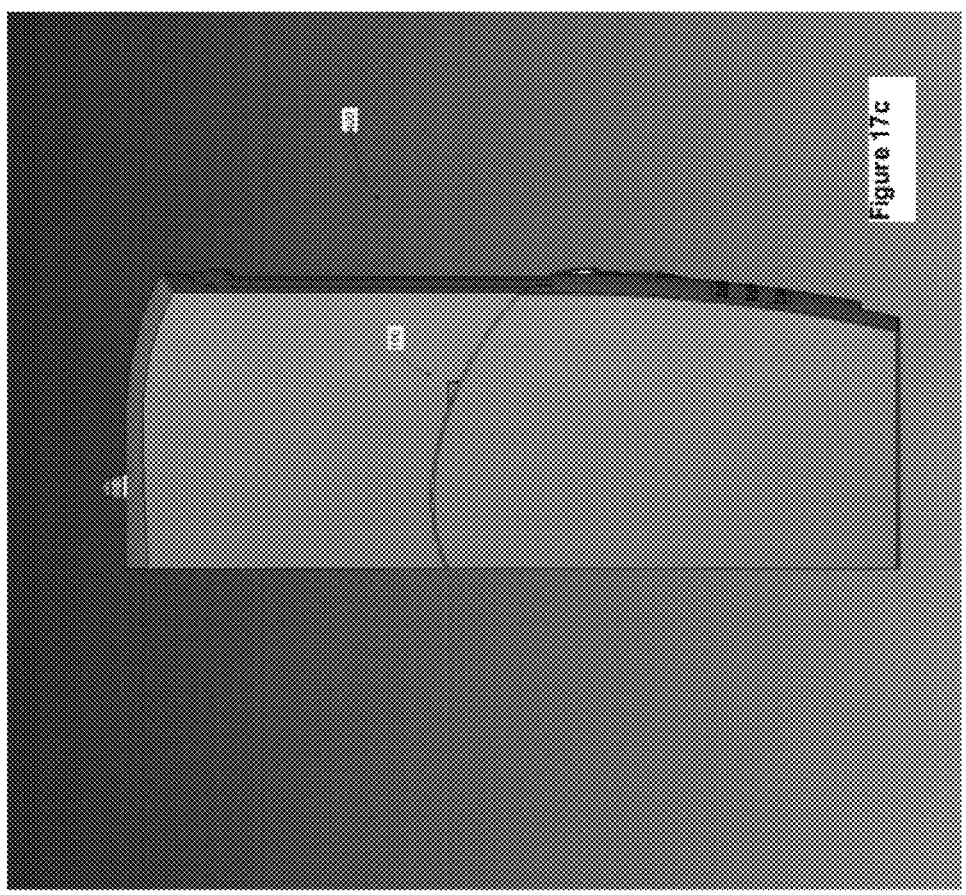

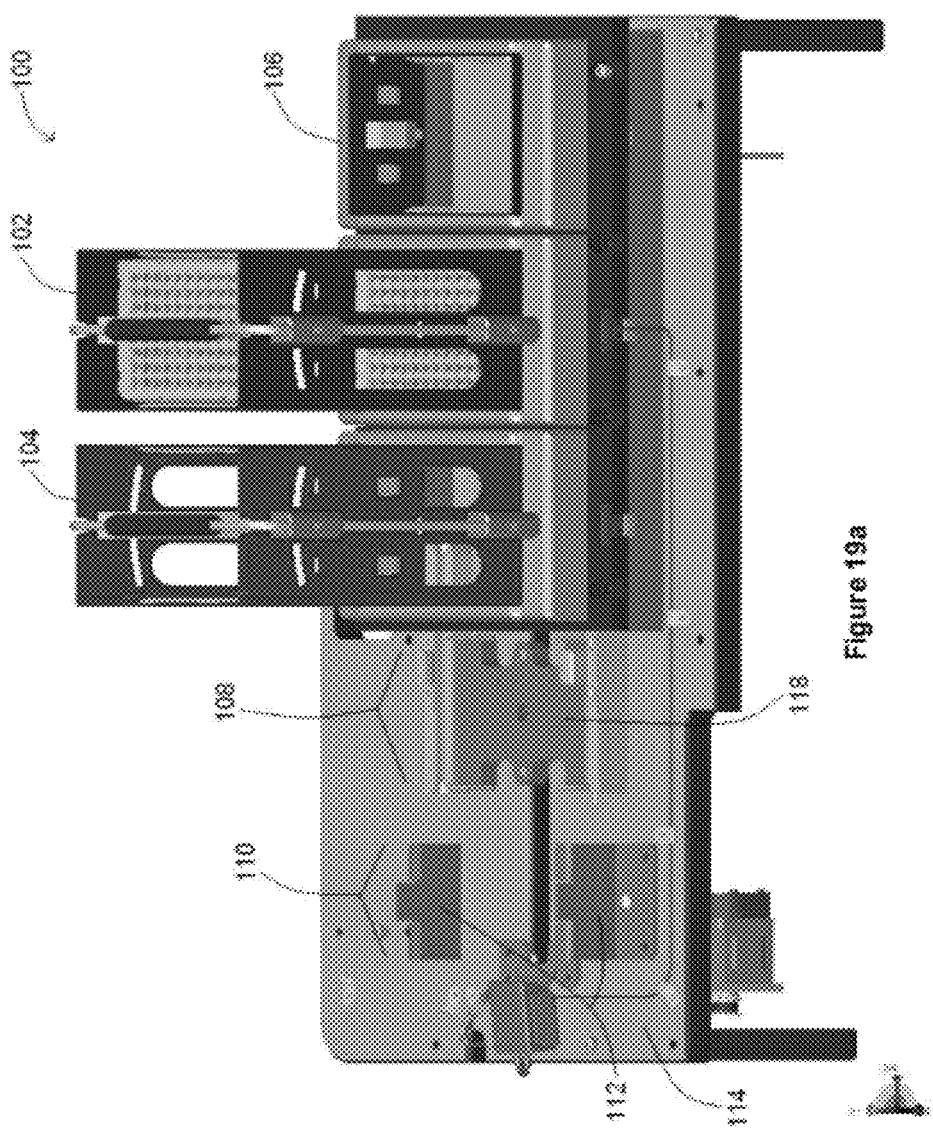

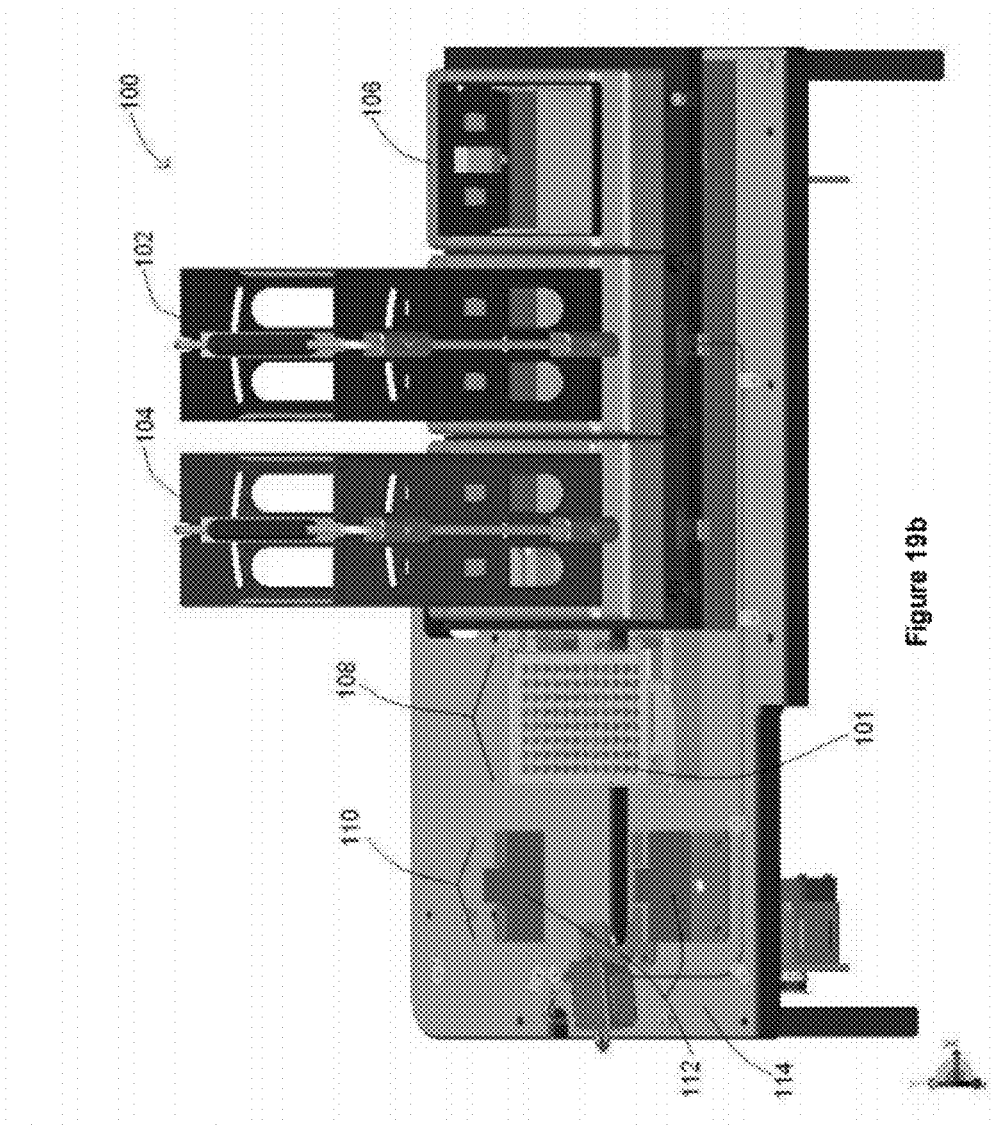

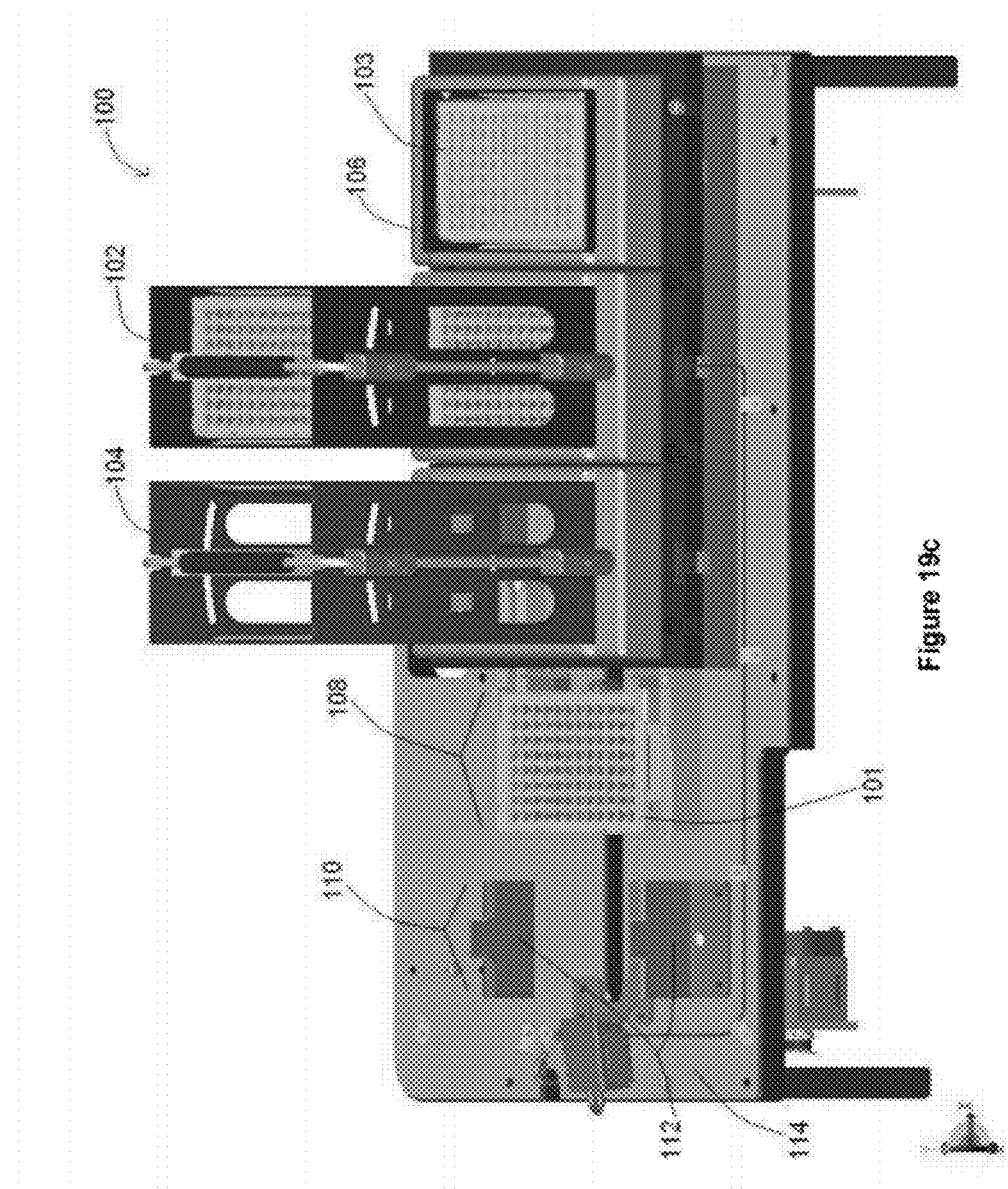

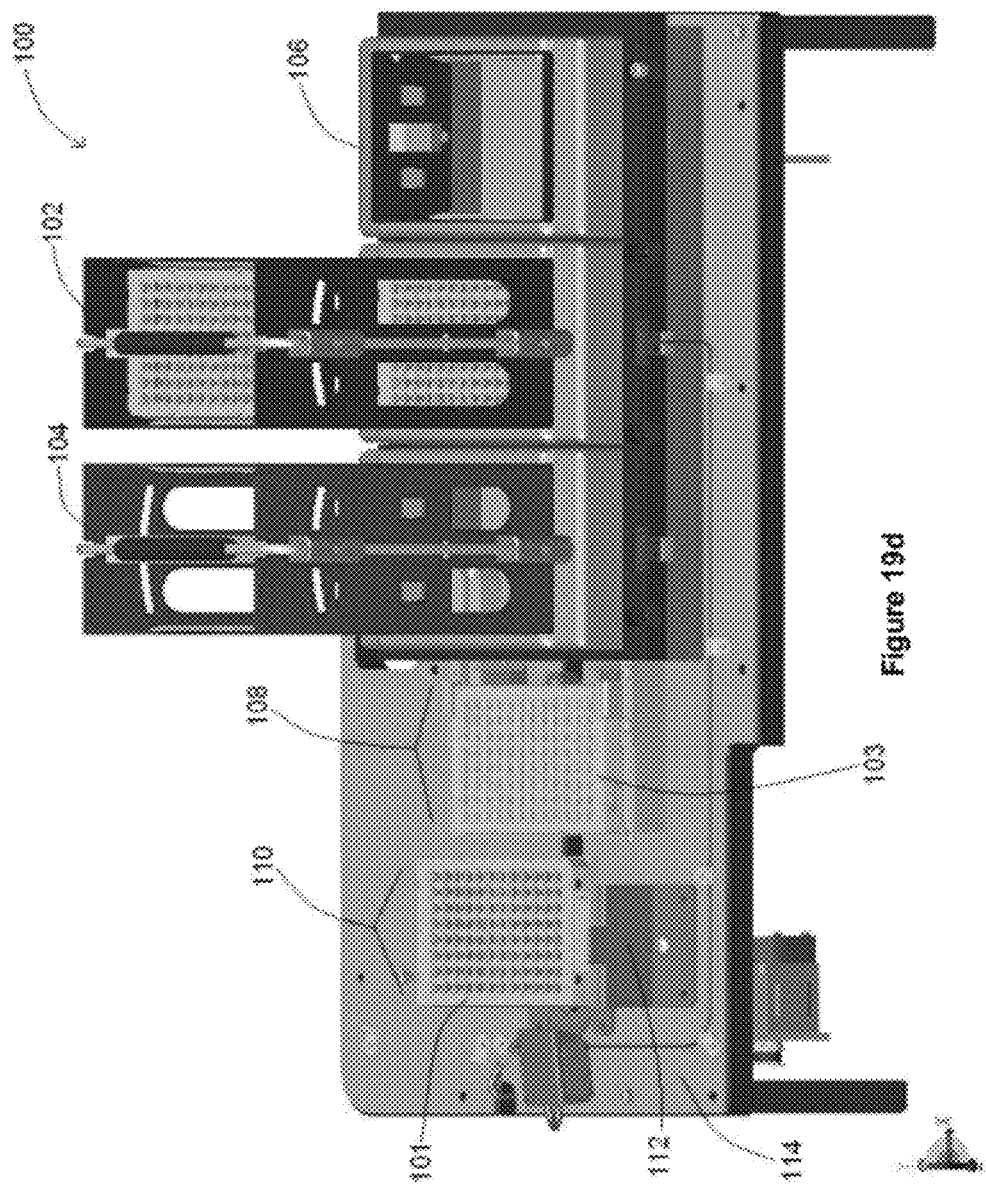

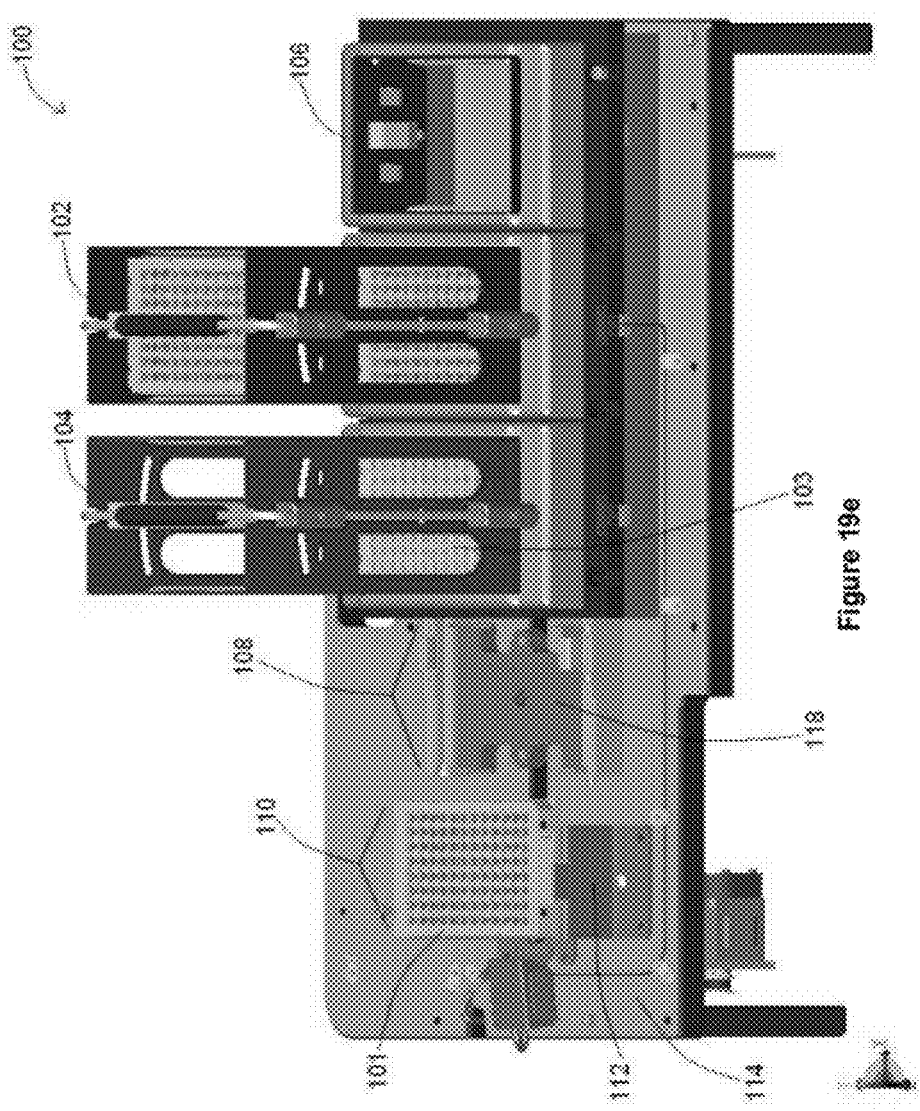

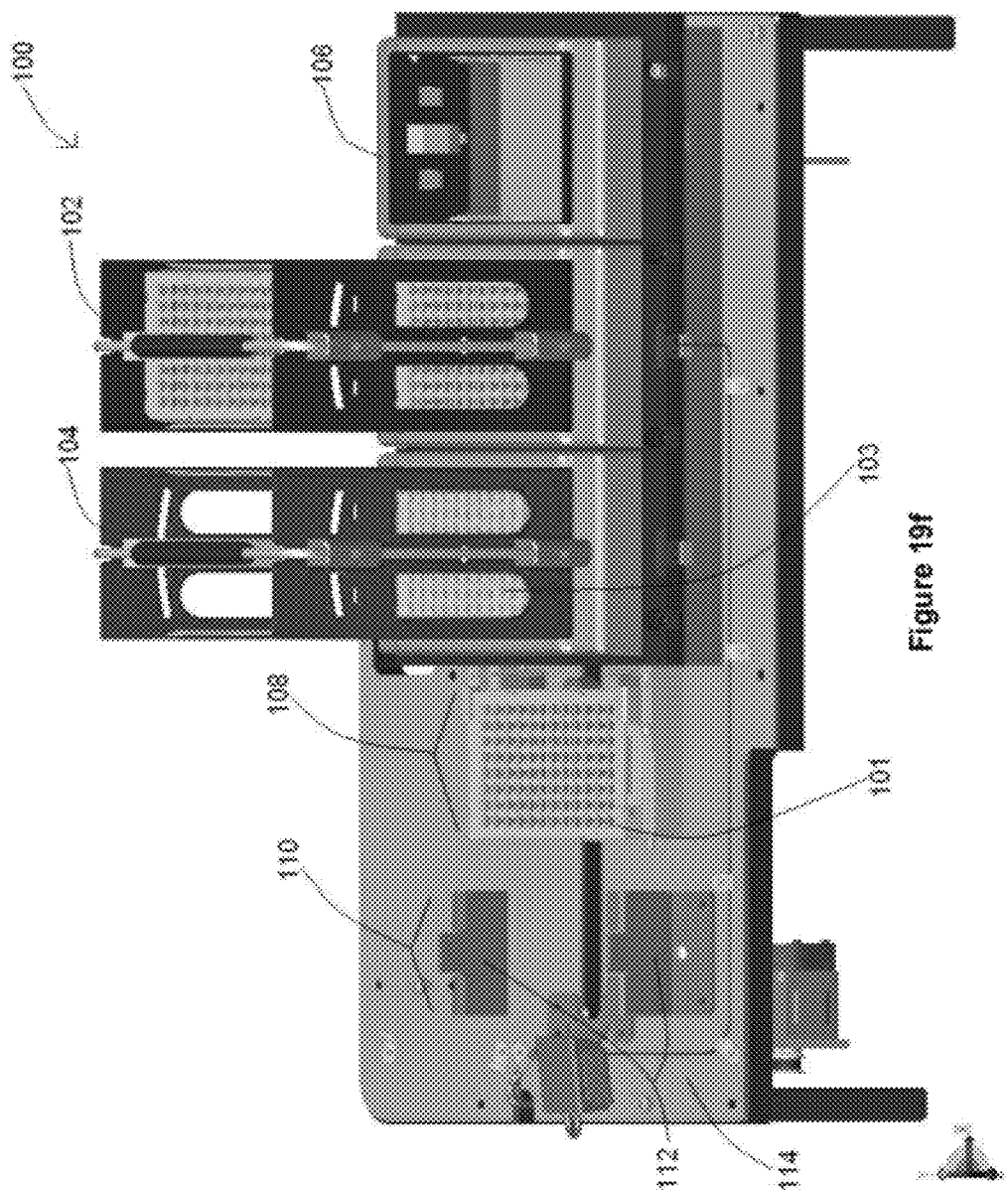

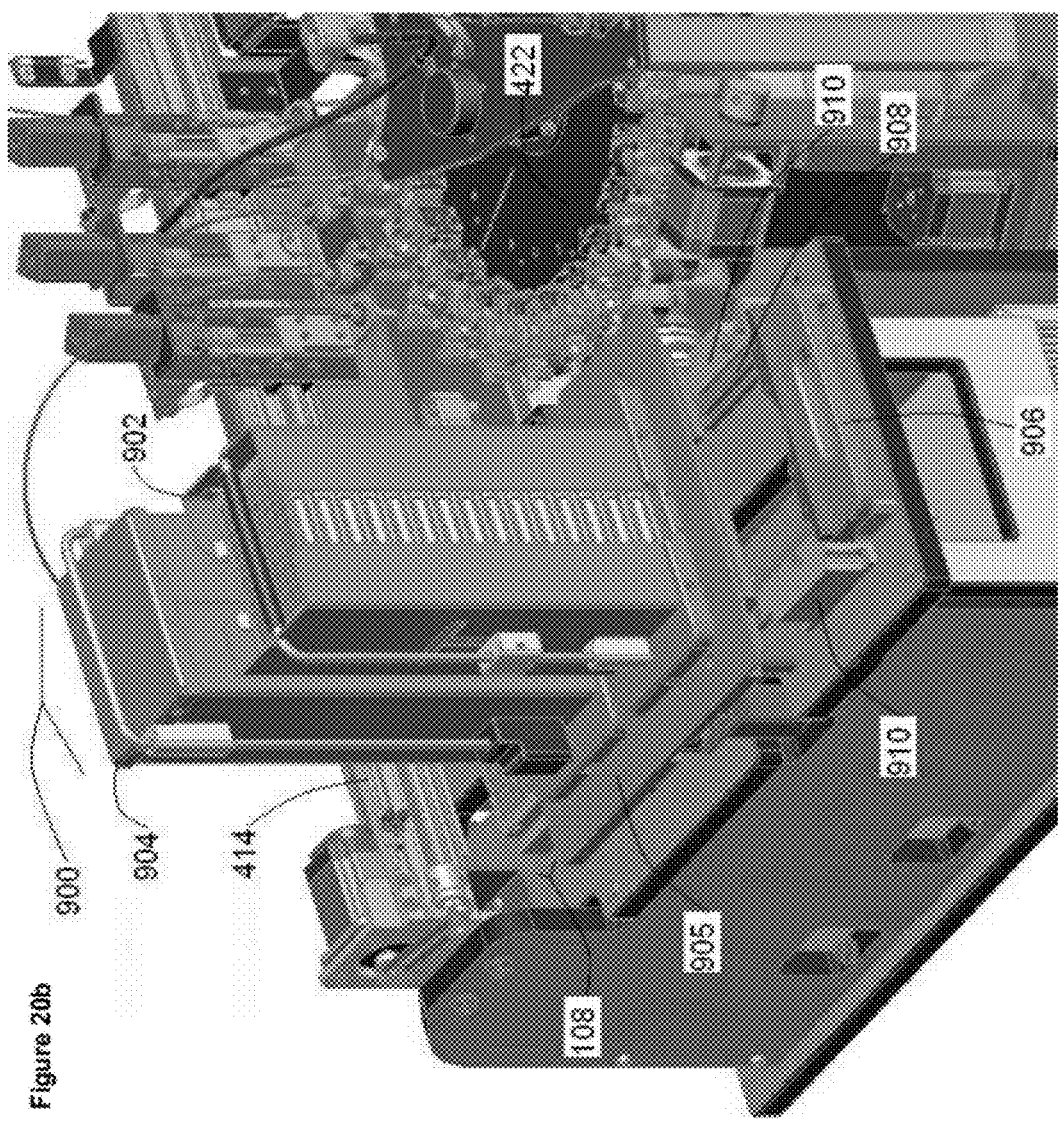

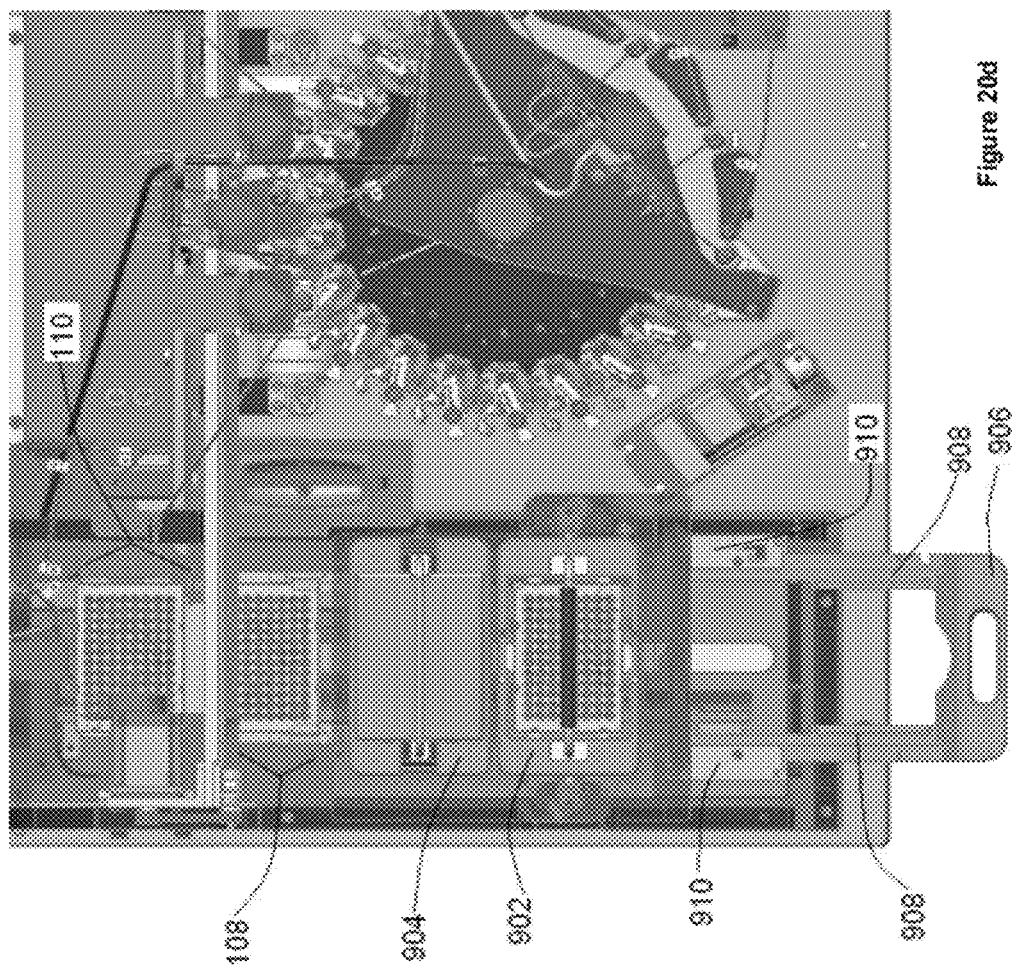

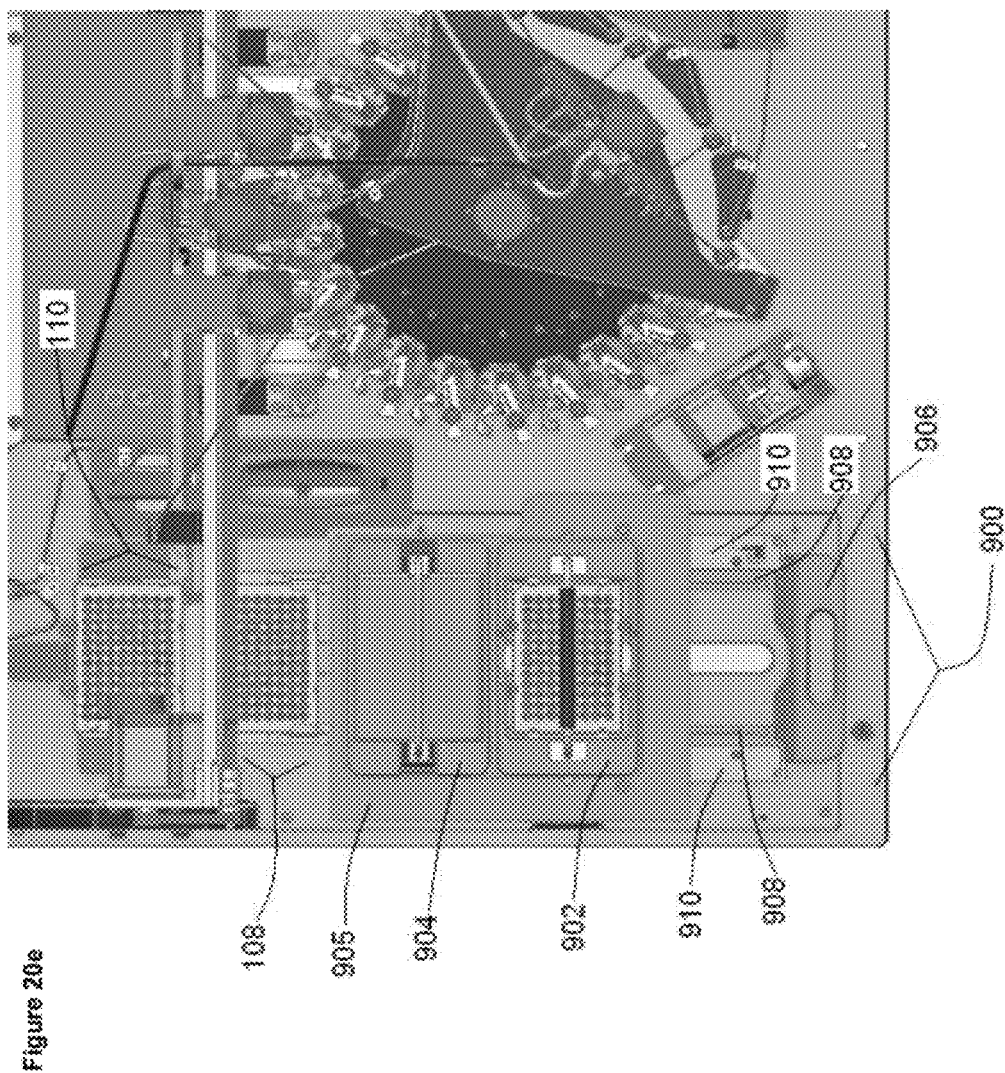

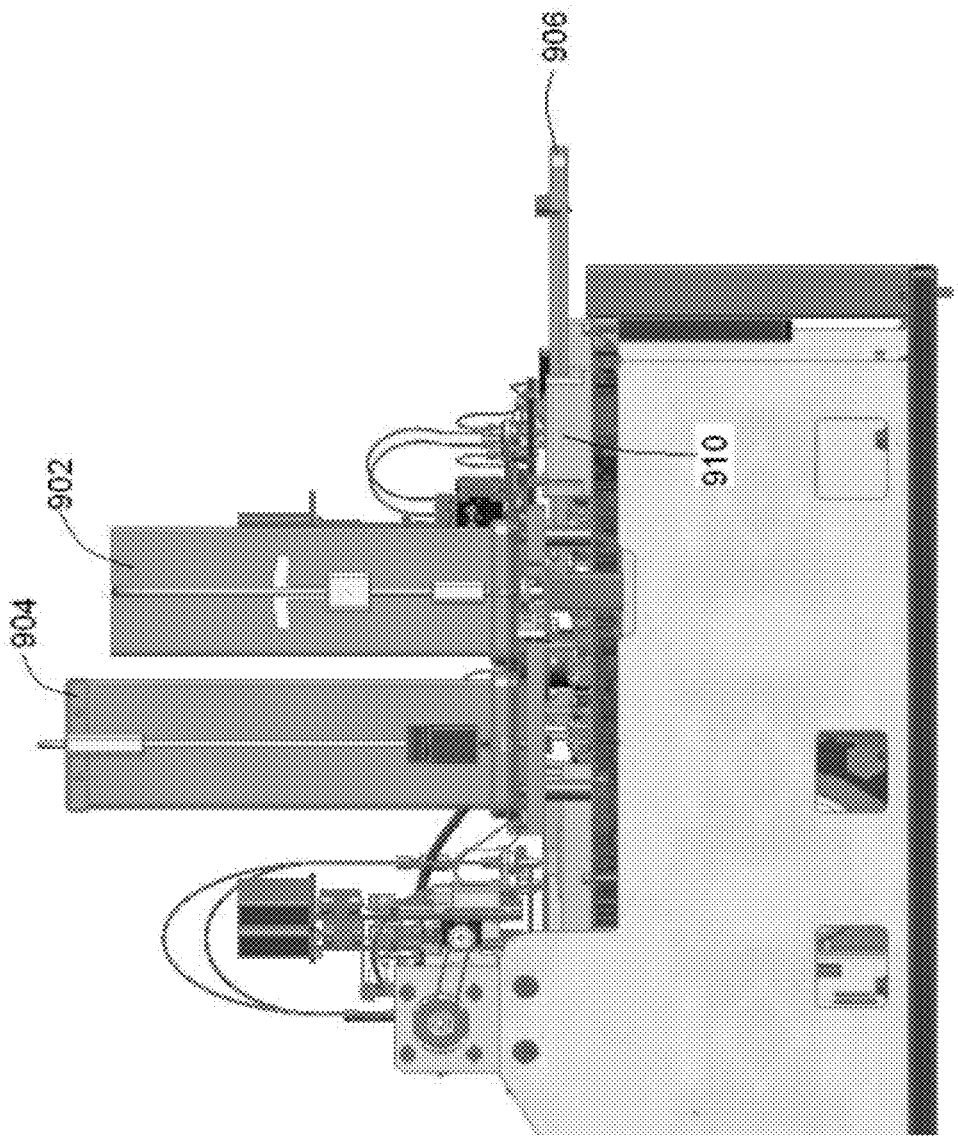

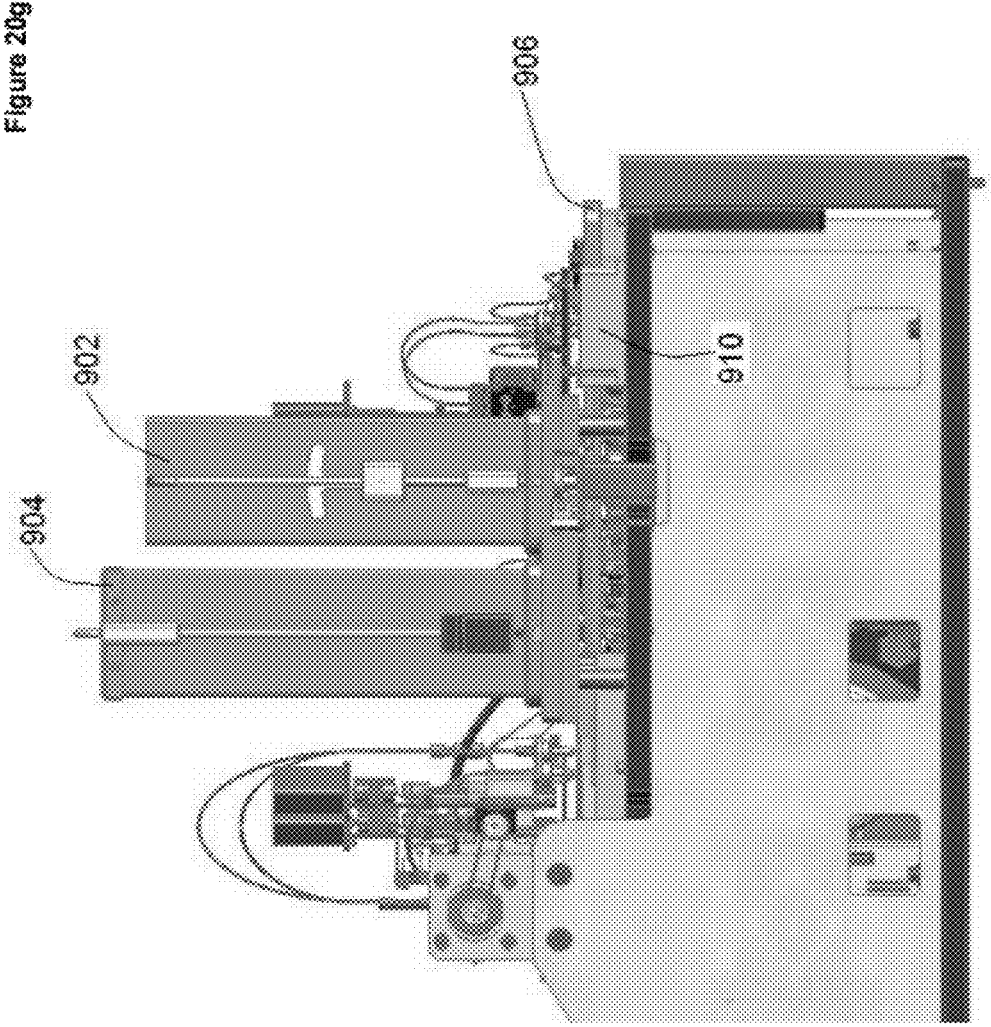

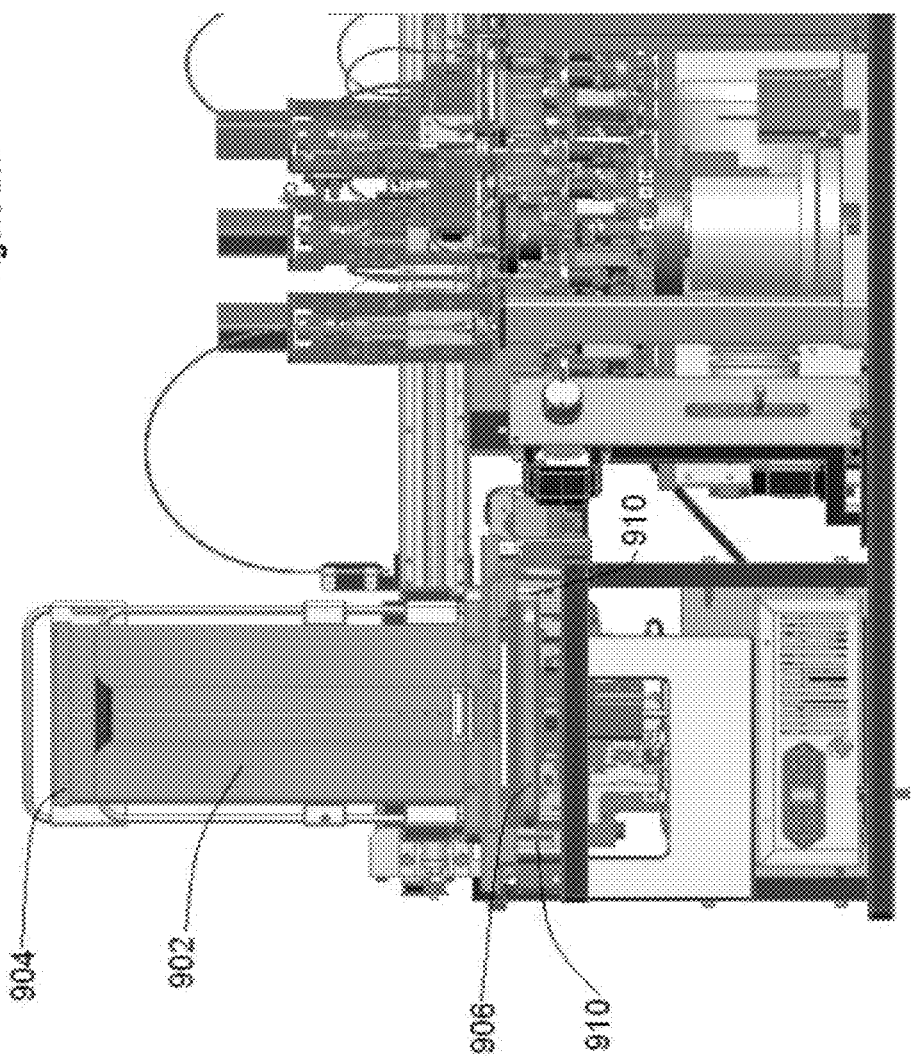

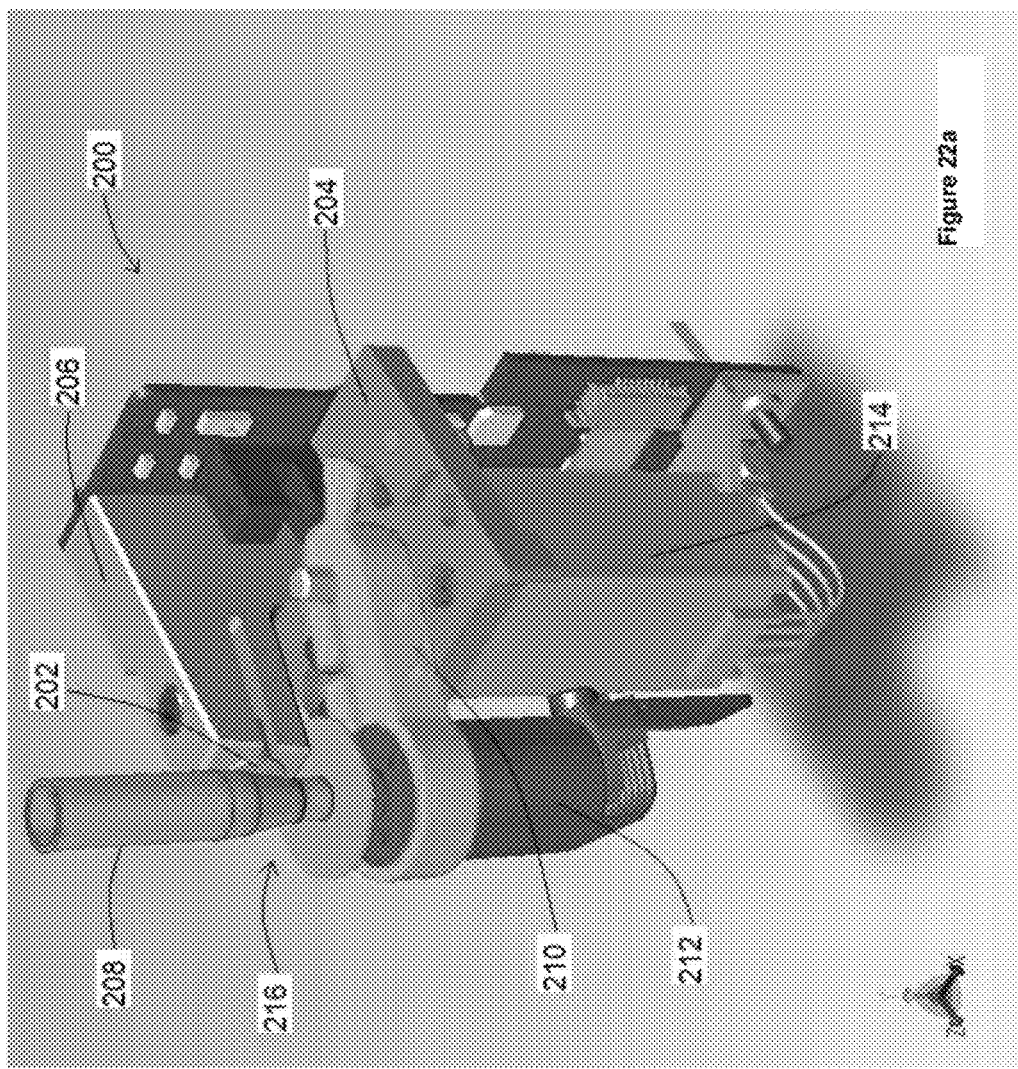

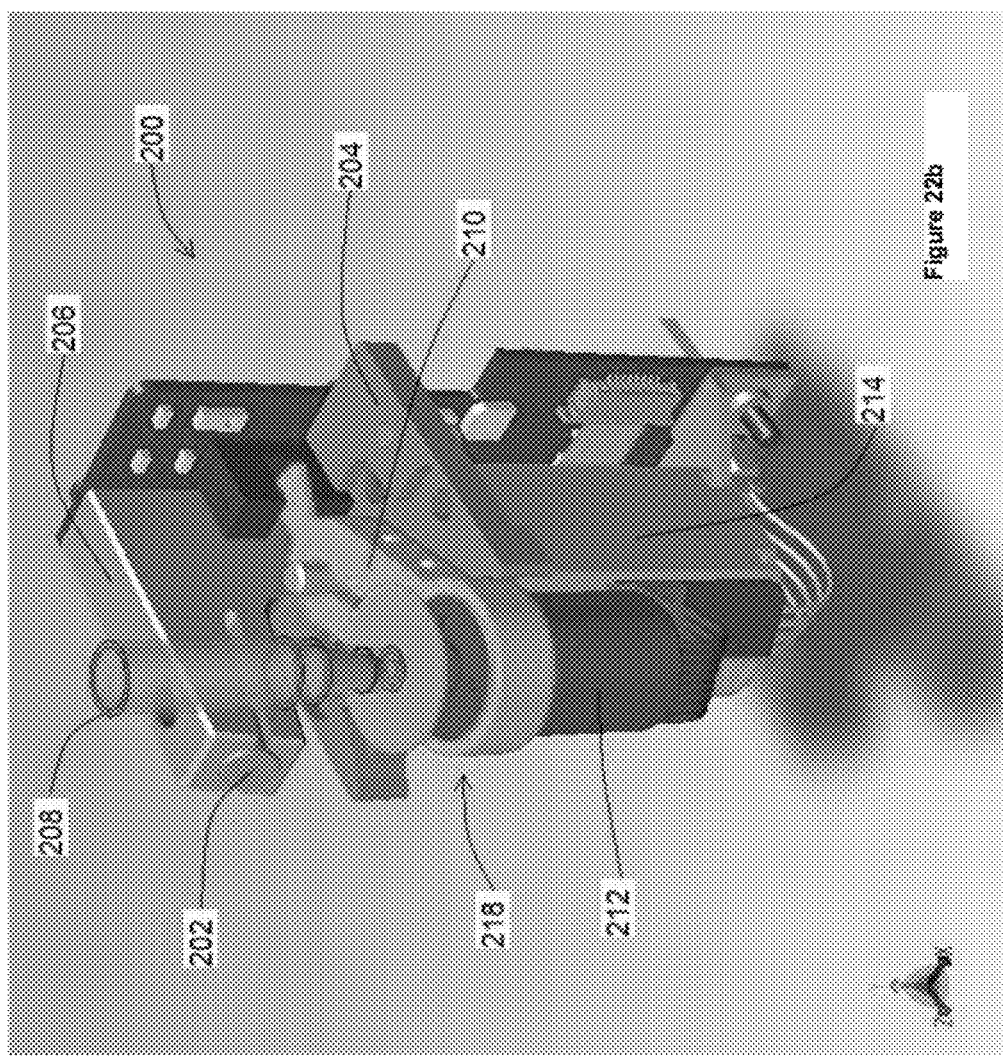

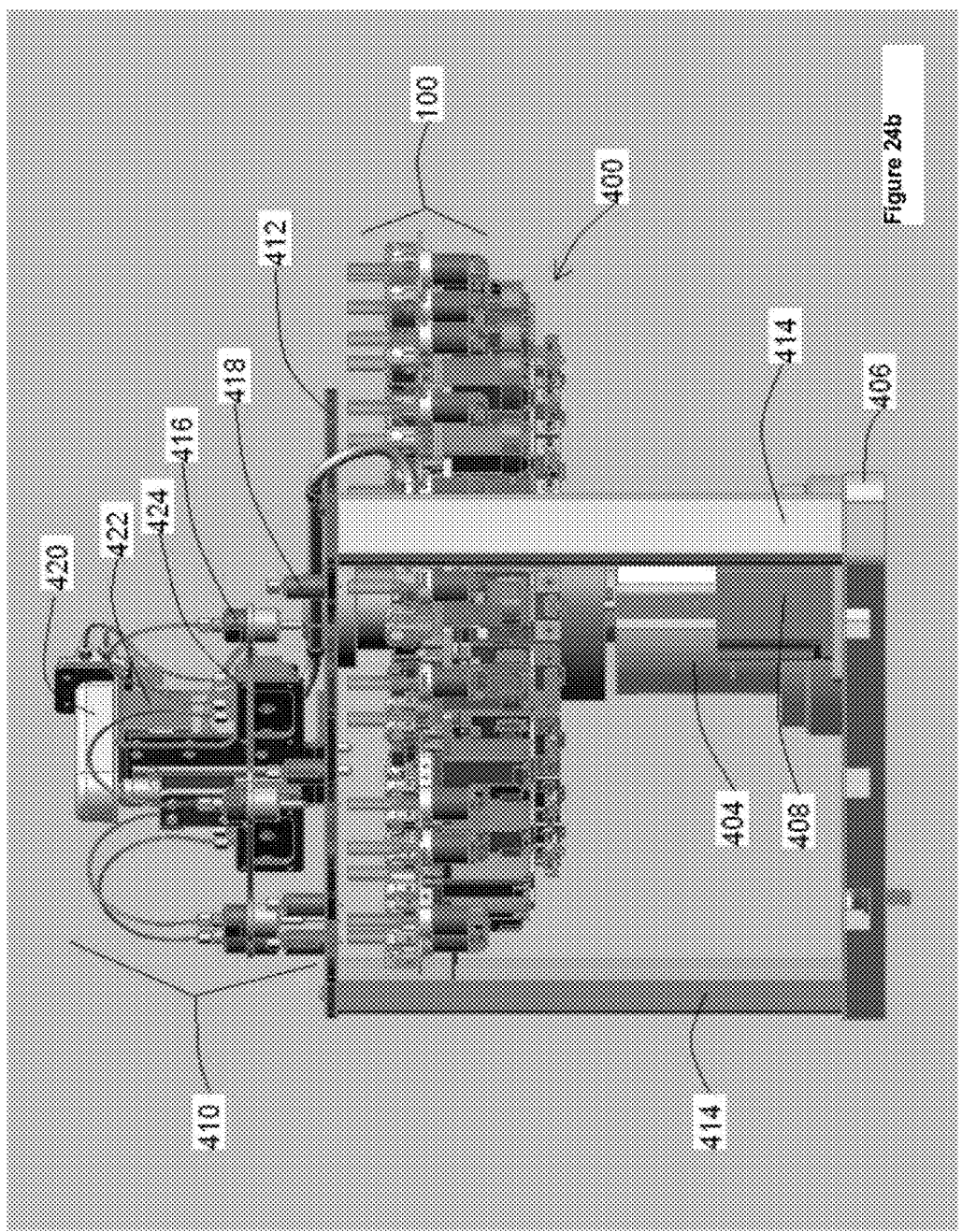

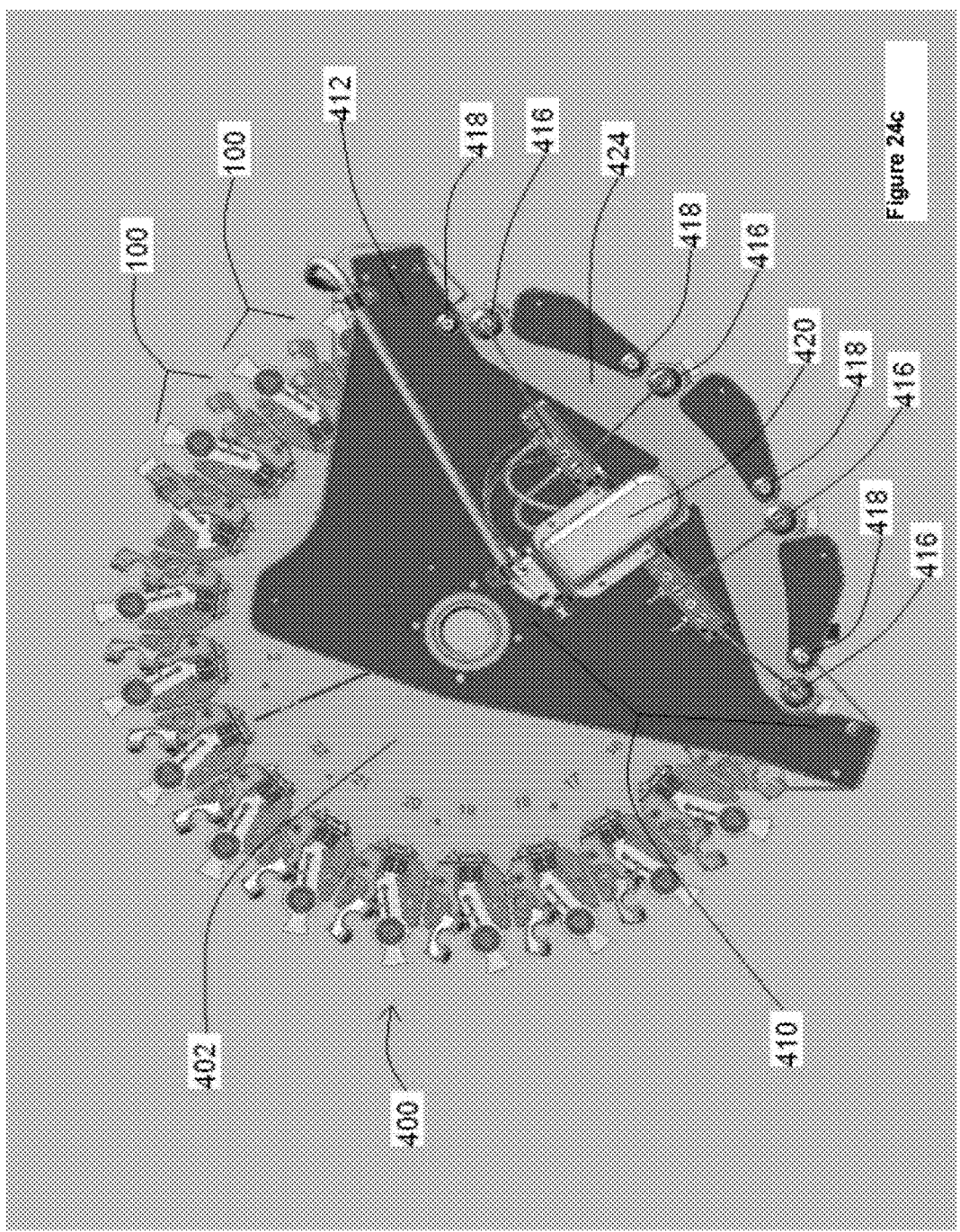

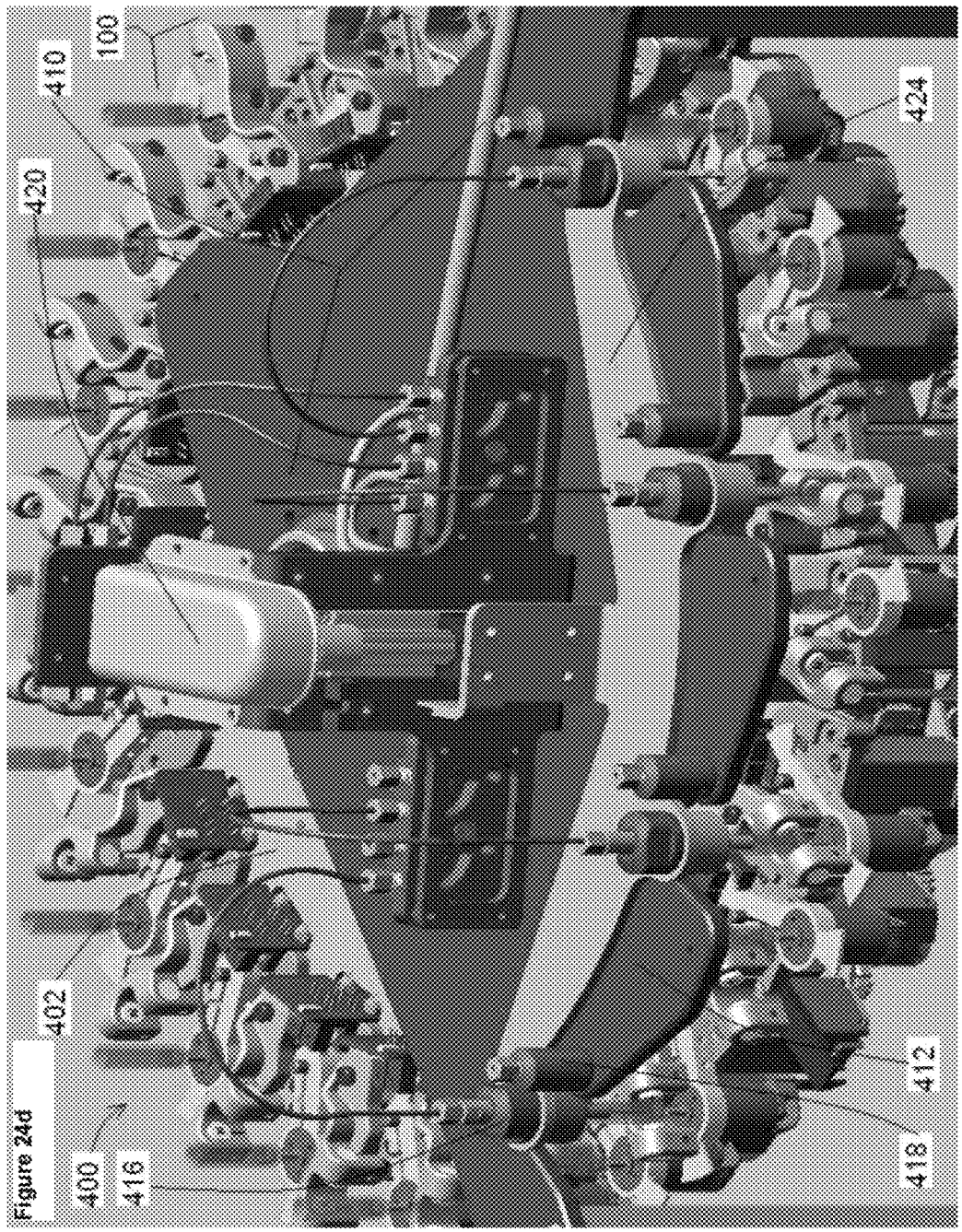

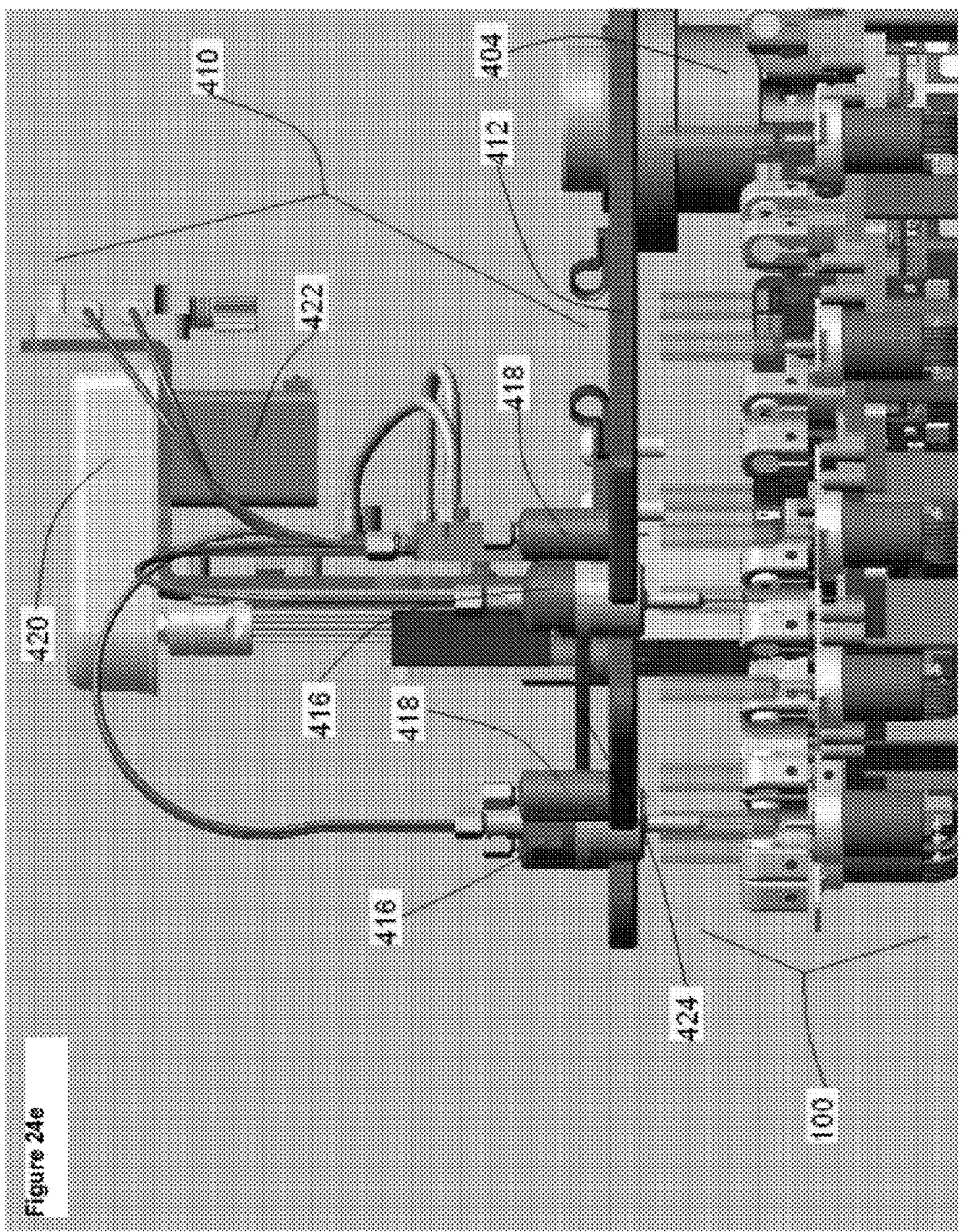

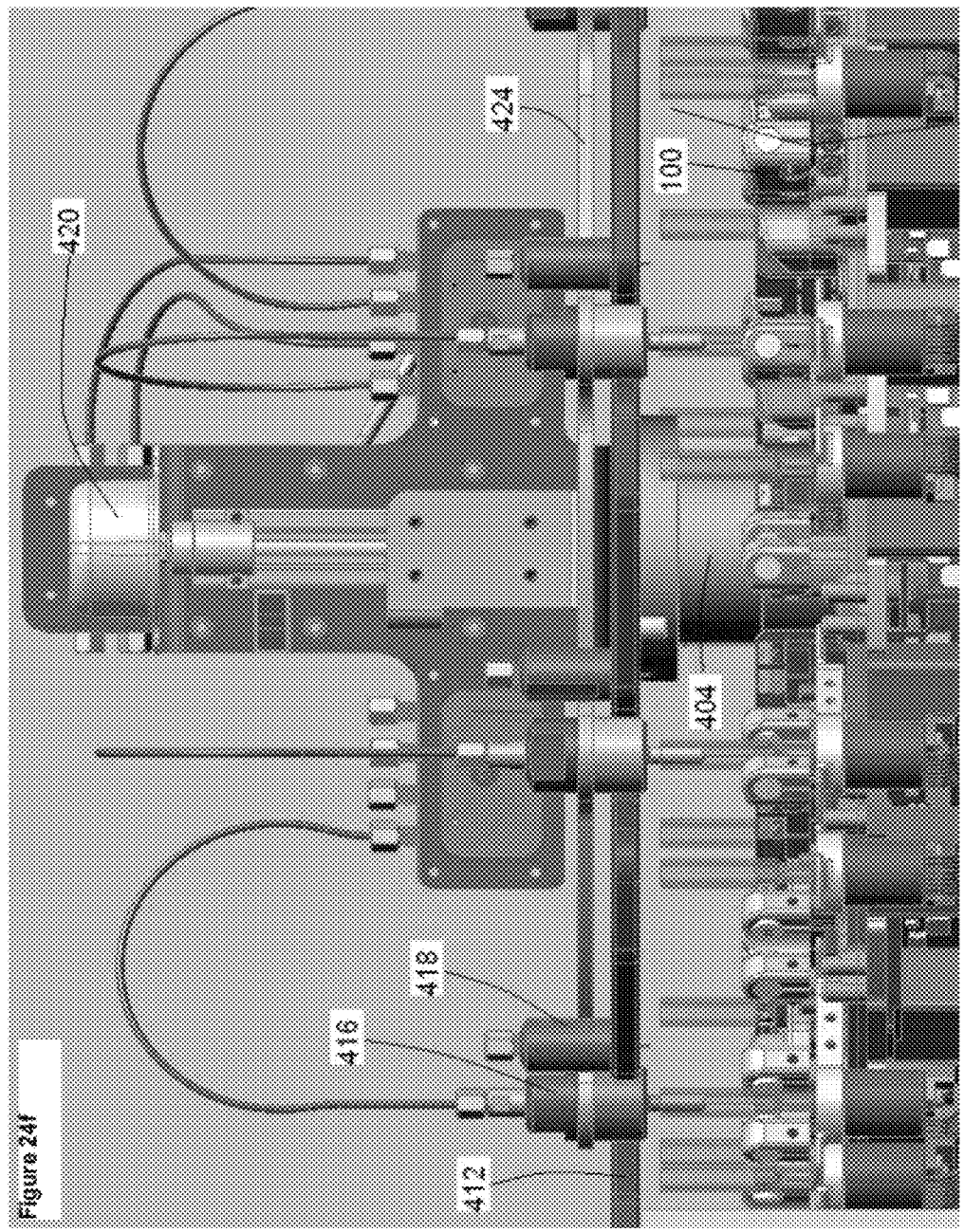

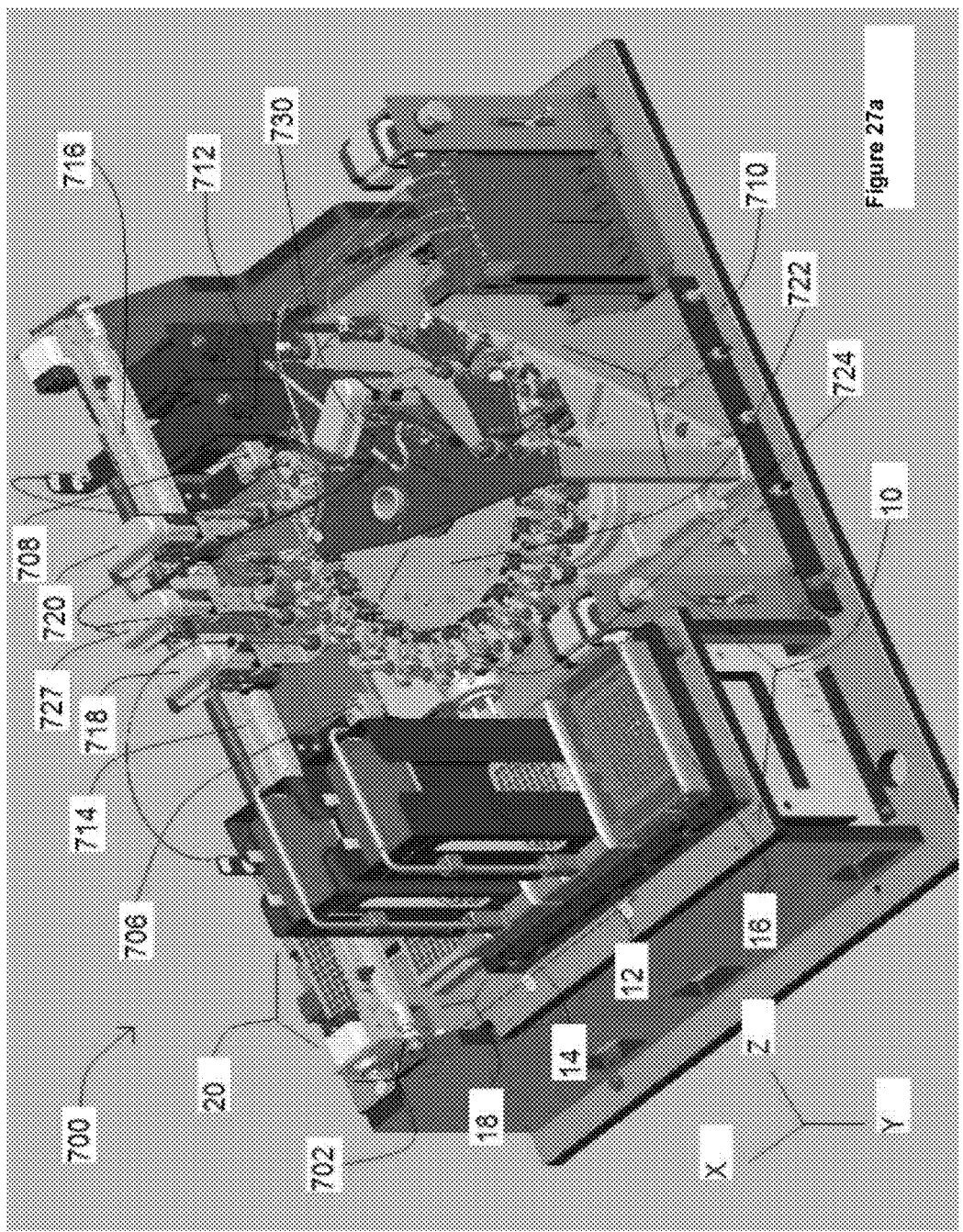

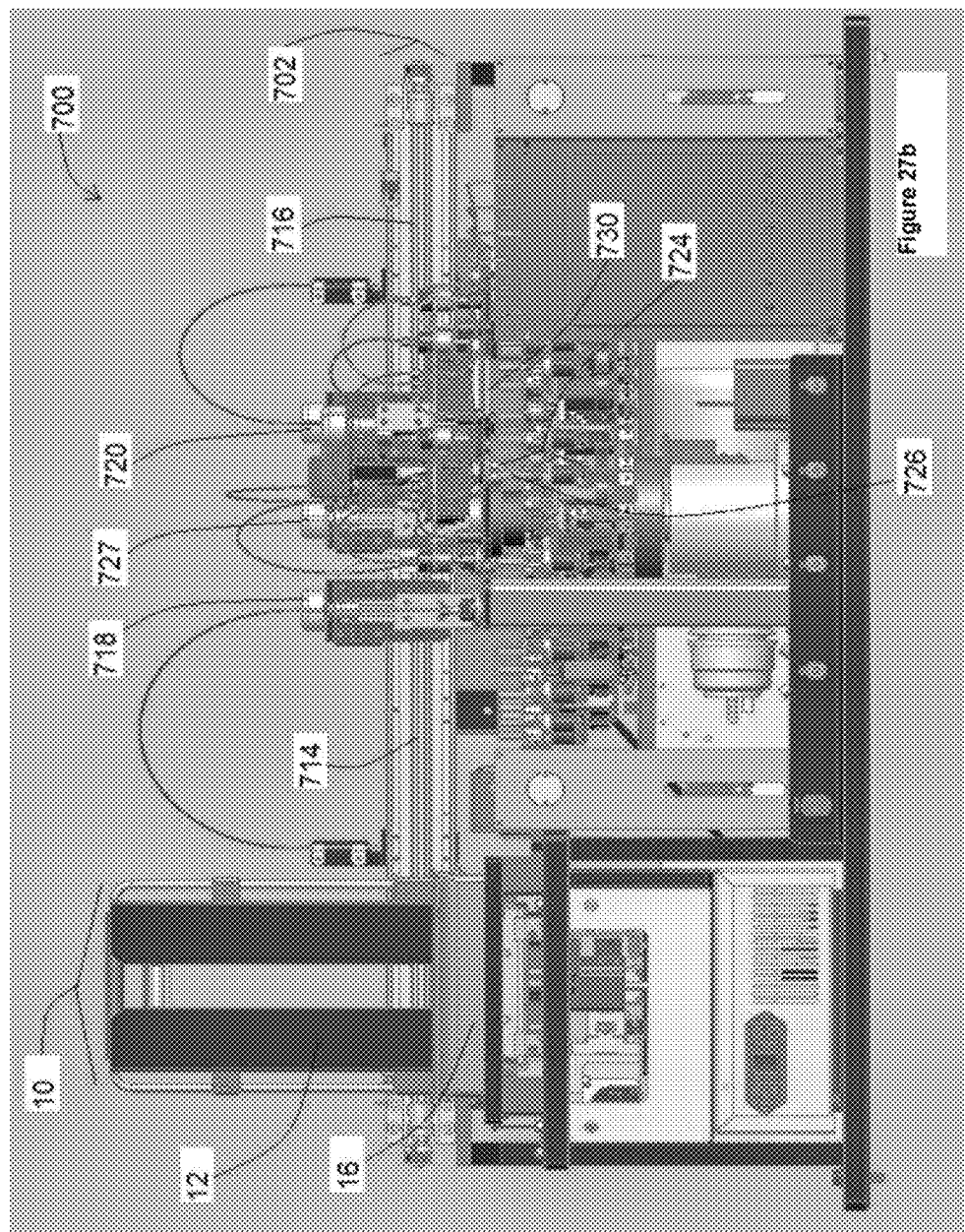

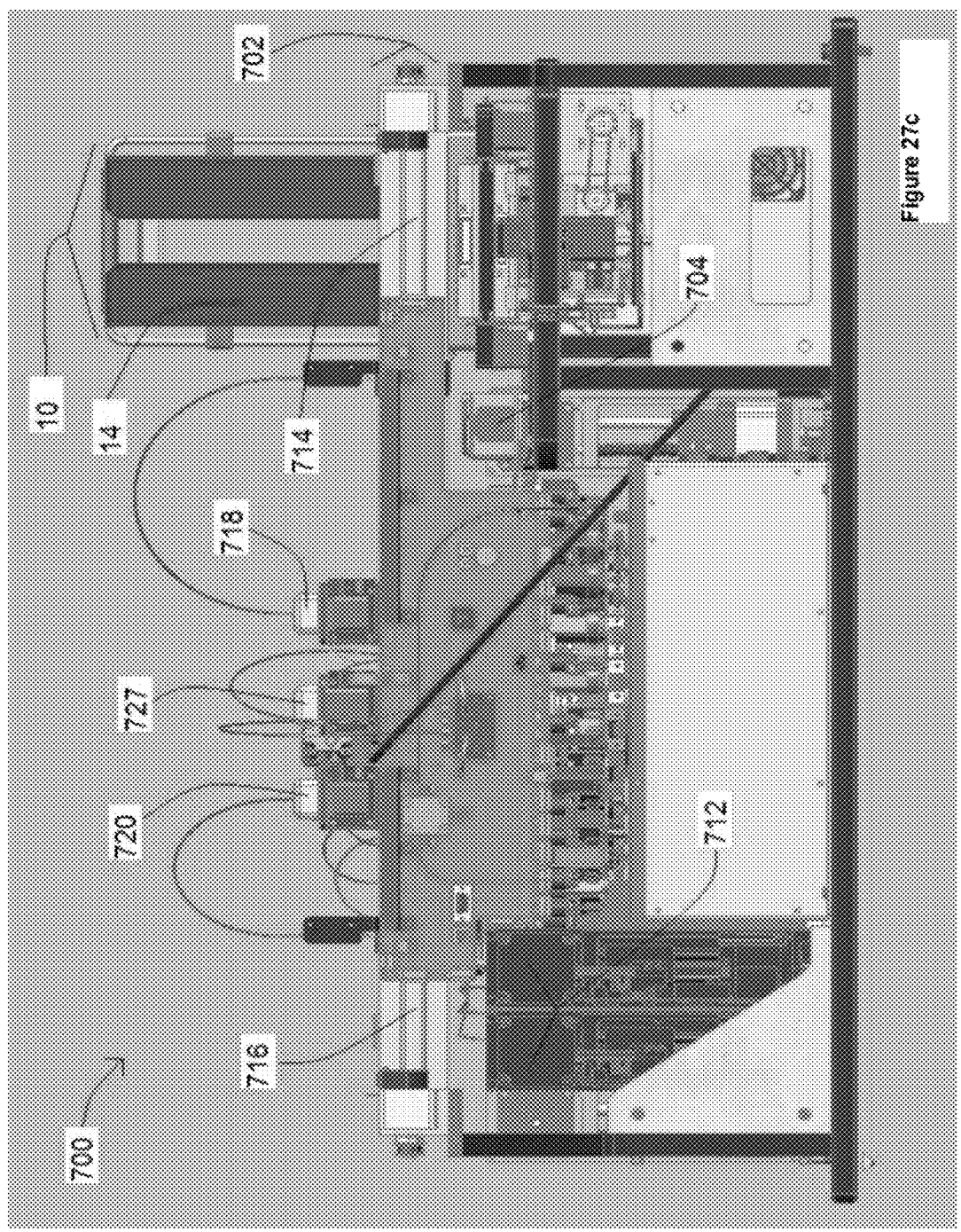

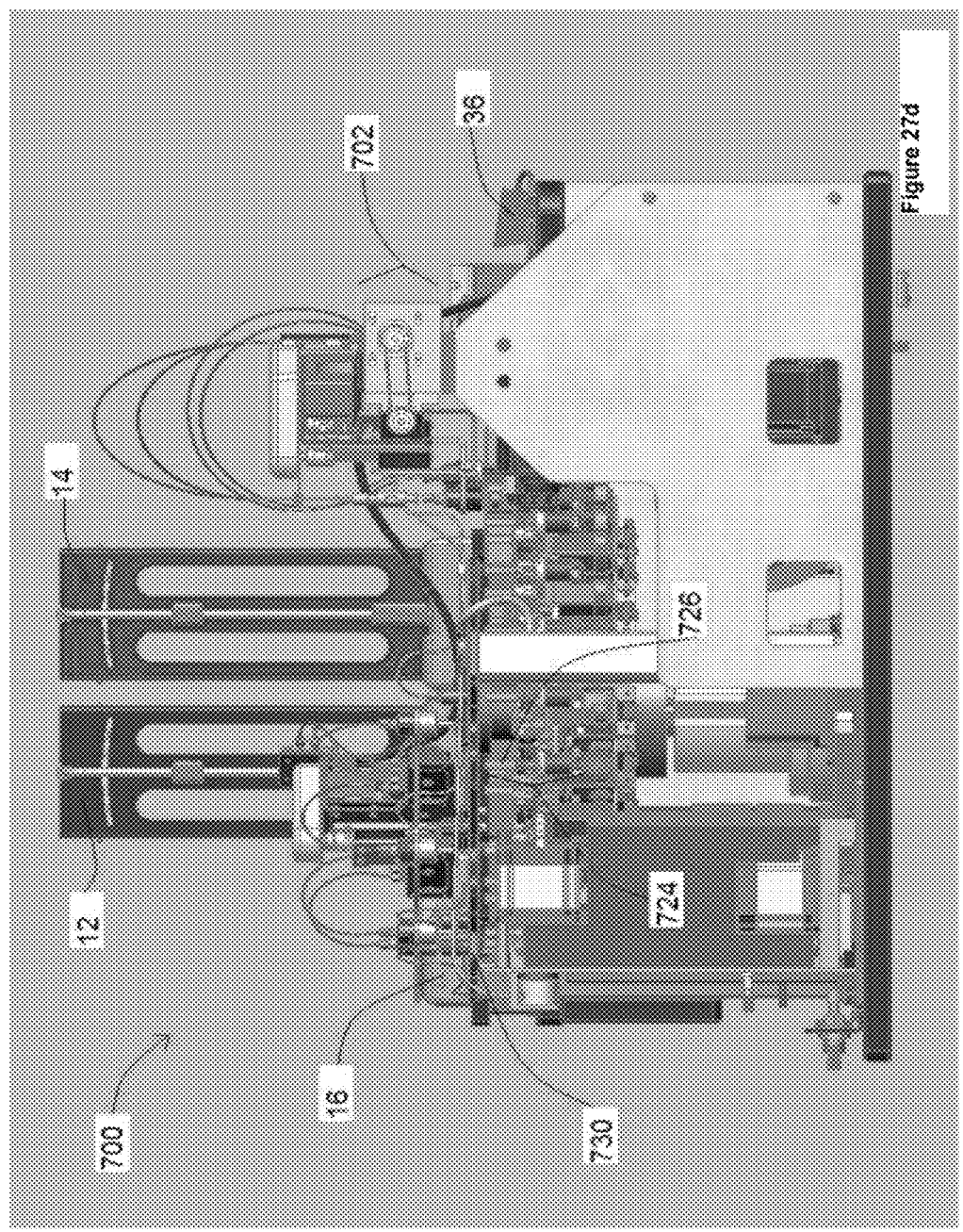

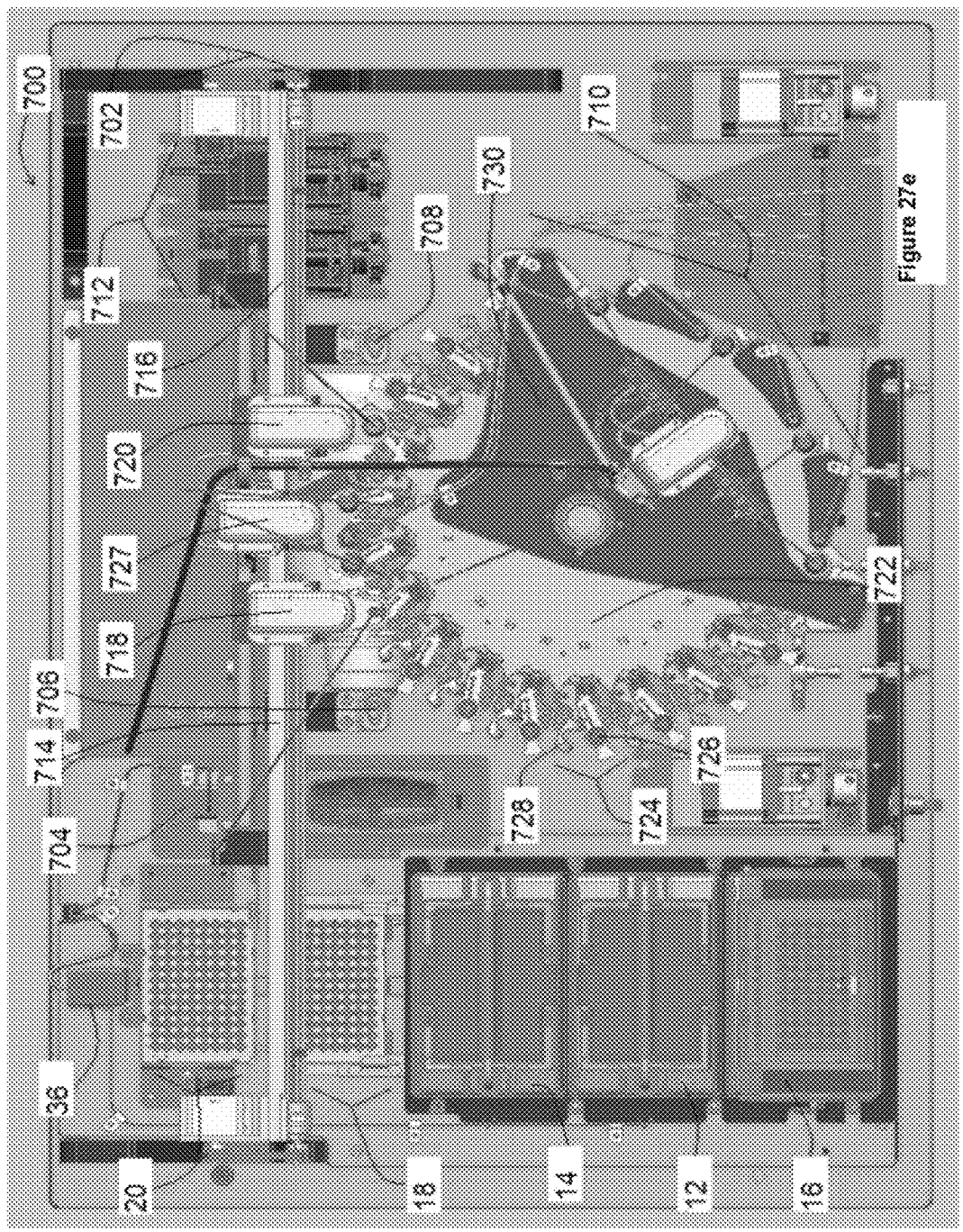

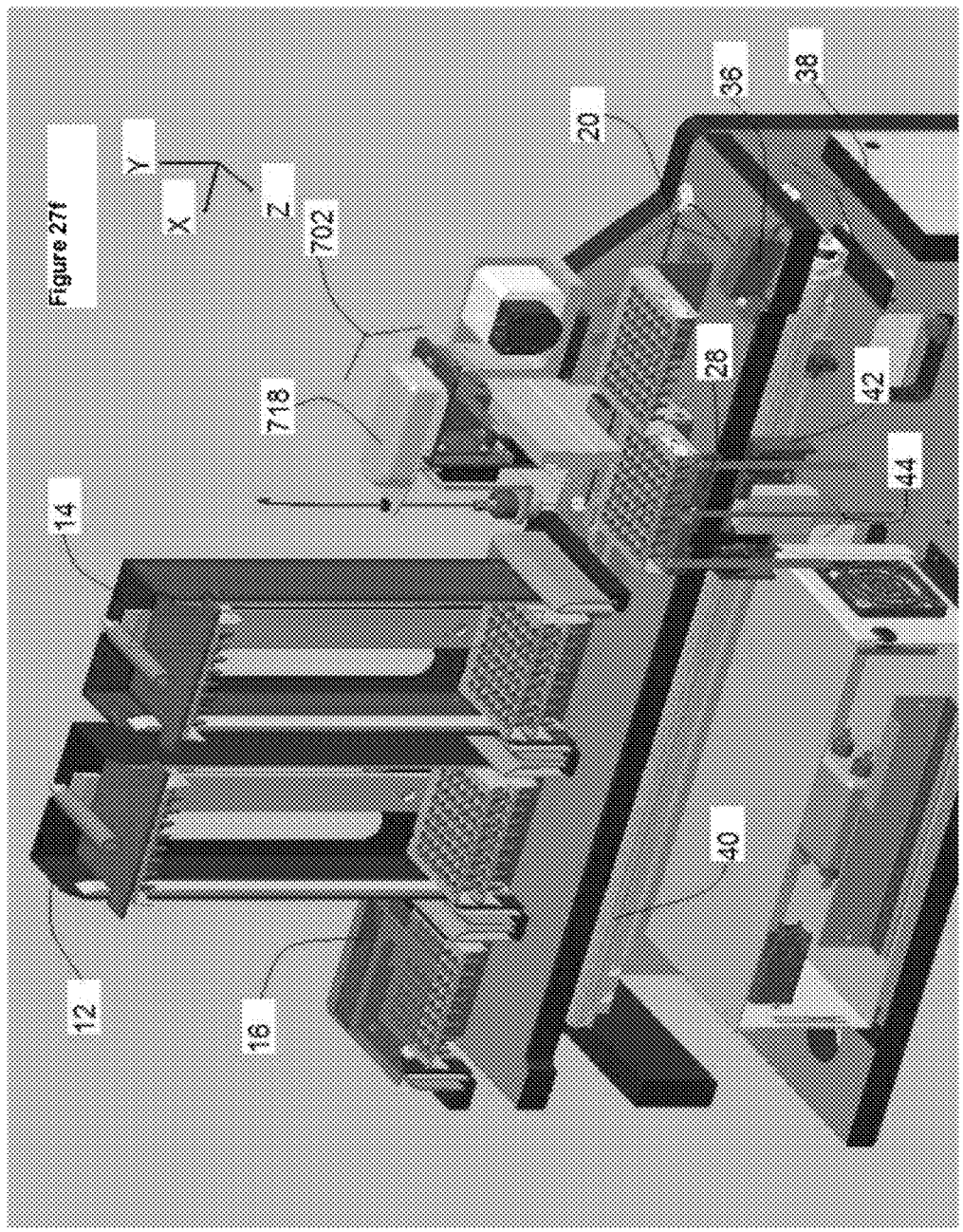

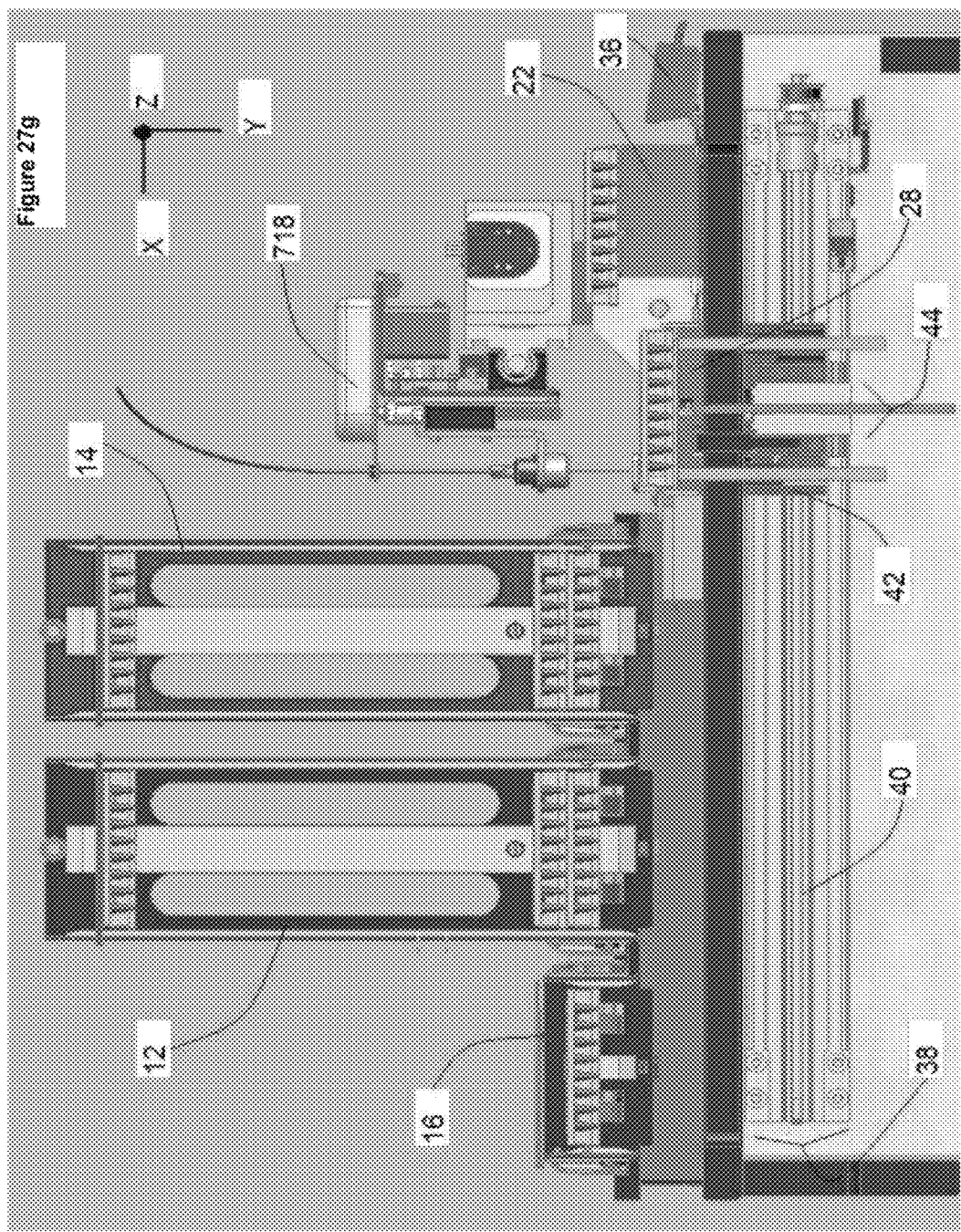

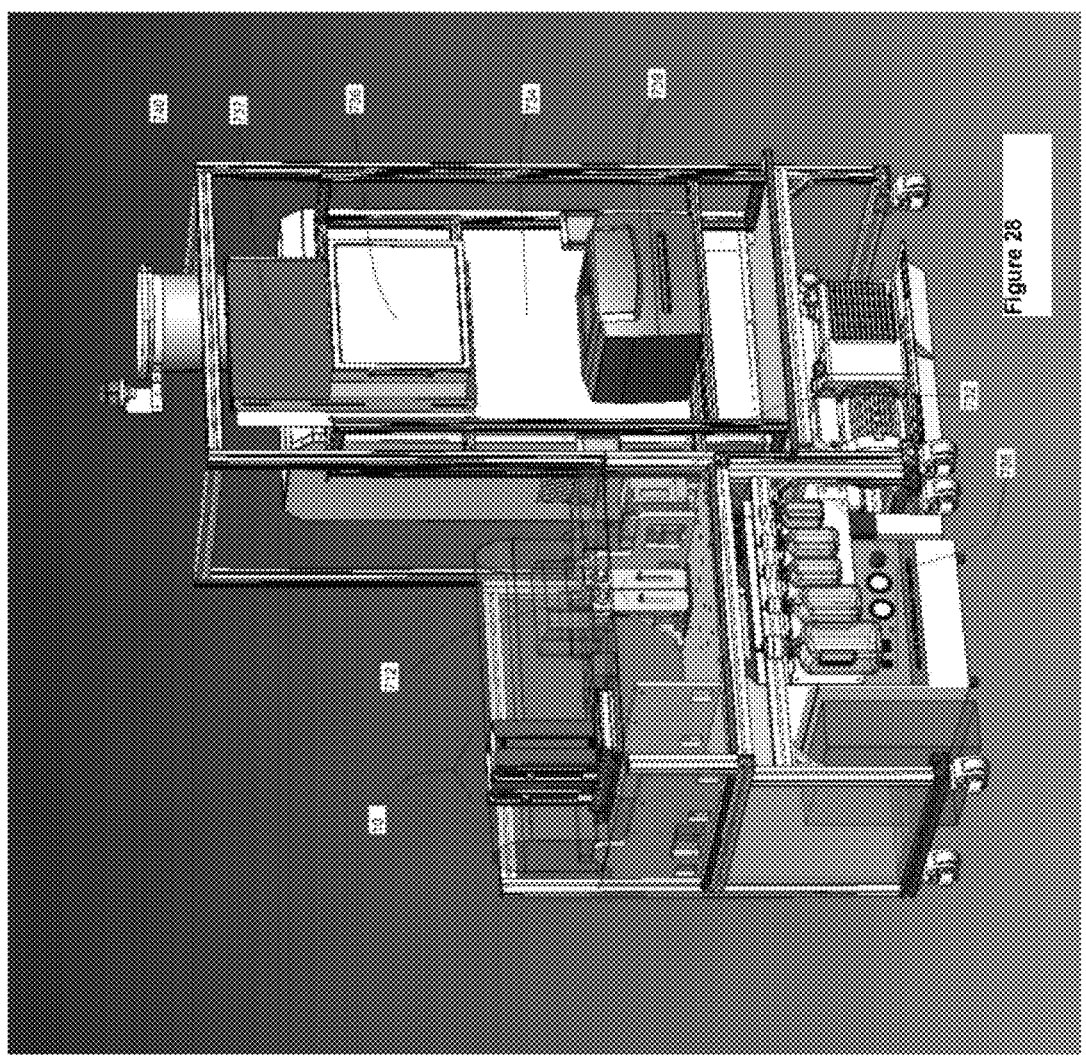

FIGURE 39
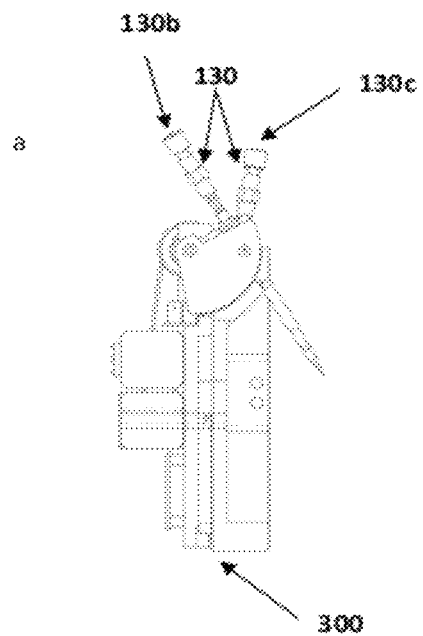
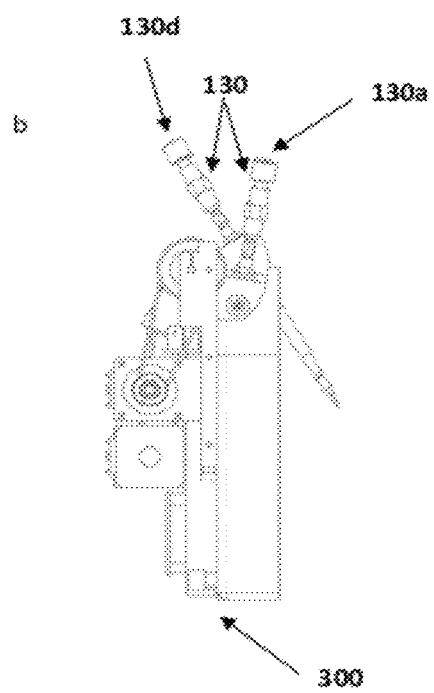

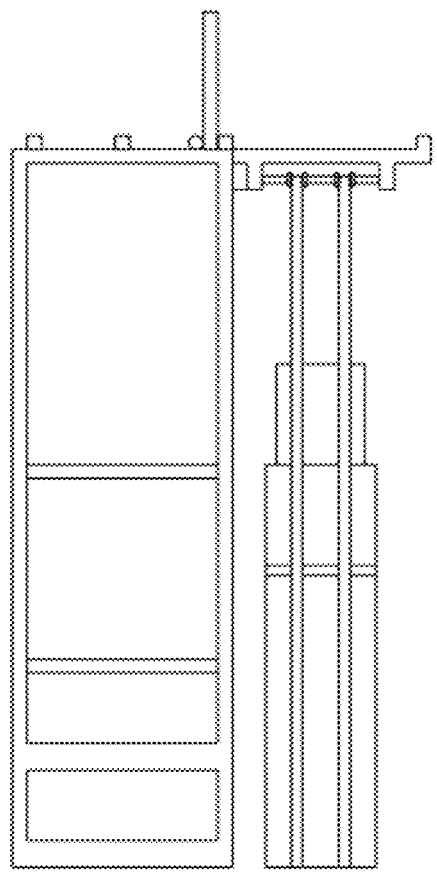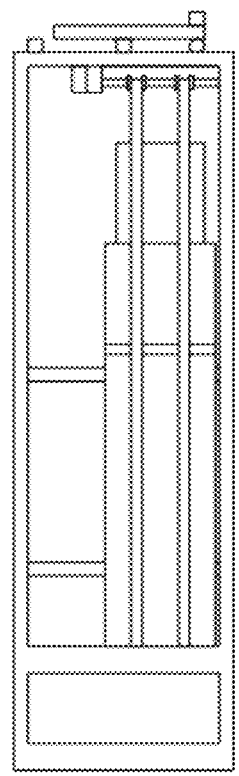
Figure 43a                    Figure 43b

FIGURE 54
A.
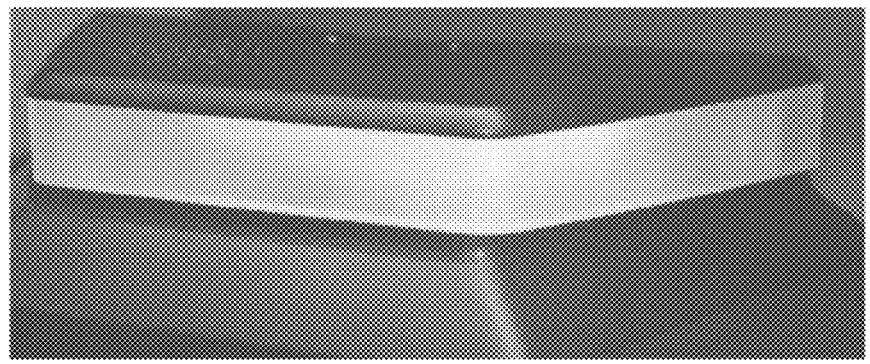
B.
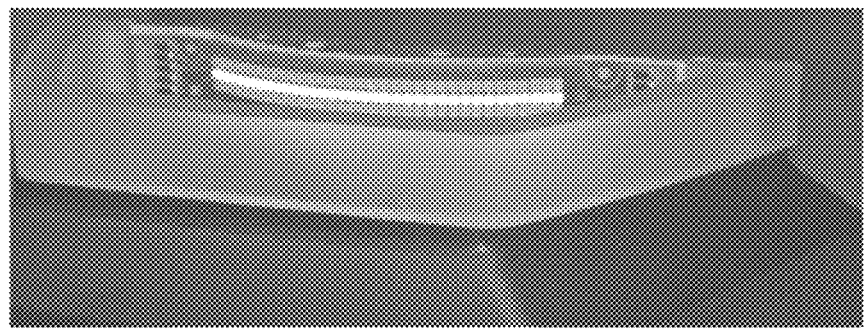
C.
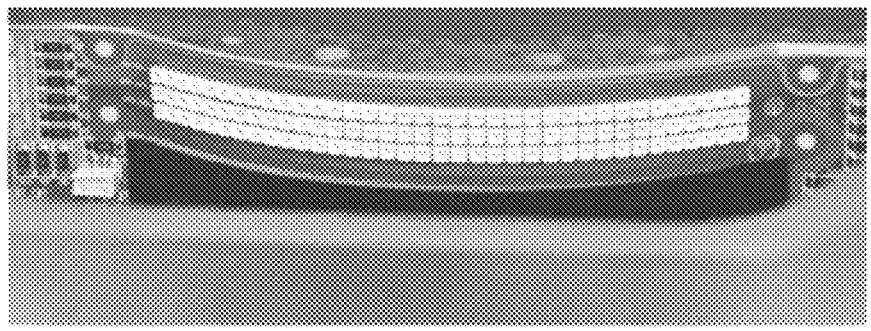

FIGURE 55
A.
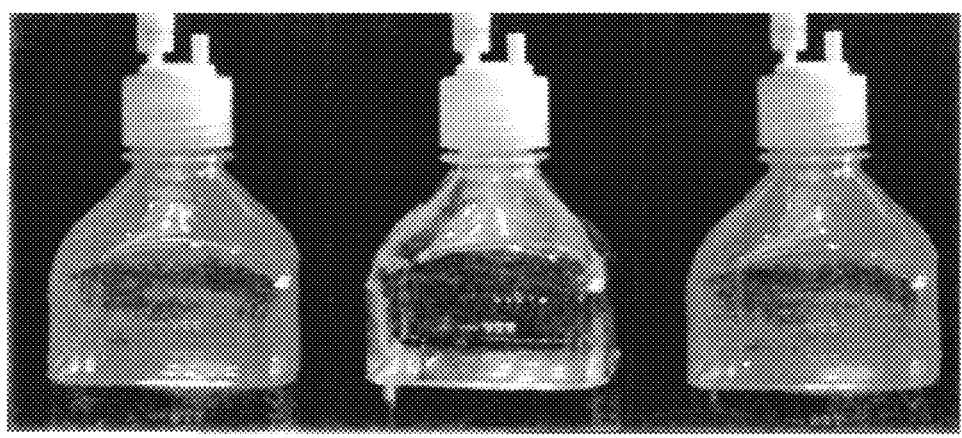
B.

SYSTEMS FOR BIOAGENT INDENTIFICATION

CROSS REFERENCE TO RELATED APPLICATIONS

The present Application claims priority to PCT Patent Application No. PCT/US2010/042159 filed Jul. 16, 2010 and U.S. Provisional Application Ser. No. 61/226,537 filed Jul. 17, 2009, the entirety of each of which is herein incorporated by reference.

FIELD OF THE INVENTION

The present invention provides systems and methods for analysis of samples, particularly biological and environmental sample to detect biomolecules of interest contained therein. A variety of system components are described herein, including, but not limited to, components for sample handling, mixing of materials, sample processing, transfer of materials, and analysis of materials. The invention further provides mechanisms for combining and integrating the different components and for housing, moving, and storing system components or the system as a whole. The systems may include any one or more or all of these components. The system finds particular use when employed for analysis of nucleic acid molecule using mass spectrometry, however, the invention is not limited such specific uses.

BACKGROUND OF THE INVENTION

Nucleic acid amplification techniques, such as the polymerase chain reaction (PCR) have widespread applications in many scientific disciplines, including microbiology, medical research, forensic analysis, and clinical diagnostics. In some of these applications, PCR products are "sized" using traditional biochemical techniques such as standard gel electrophoresis involving either intercalating dyes or fluorescently labeled primers. Other applications, such as 5'-nuclease or TaqMan® probe-based assays, which are widely used in a number of PCR-related diagnostic kits, confirm the presence (or absence) of a specific PCR product, but provide no direct information on the size of the particular amplicon. These methods typically have limited utility for relatively small amplicons (less than 150 base pairs), owing to the proportionately high fluorescence background, and do not provide any information with respect to amplicon heterogeneity or exact length.

Electrospray ionization mass spectrometry (ESI-MS) has become an important technique for the analysis of biopolymers, including nucleic acids. Compared to the more traditional nucleic acid analysis methods mentioned above, ESI-MS as a platform on which to characterize PCR products typically provides improved speed, sensitivity, and mass accuracy, among other attributes. Further, since the exact mass of each nucleotide or nucleobase is known with great accuracy, a high-precision mass measurement obtained via mass spectrometry can be used to derive a base composition within the experimentally obtained mass measurement uncertainty. In certain applications, the base compositions of PCR products are used to identify unknown bioagents, genotype nucleic acids, and provide drug resistance profiles as well as other information about the corresponding template nucleic acids or source organisms.

In the electrospray ionization process, large charged droplets are produced in the process of "pneumatic nebulization" where the analyte solution is forced through a needle at the end of which is applied a potential sufficient to disperse the emerging solution into a very fine spray of charged droplets all of which have the same polarity. The solvent evaporates, shrinking the droplet size and increasing the charge concentration at the droplet's surface. Eventually, at the Rayleigh limit, Coulombic repulsion overcomes the droplet's surface tension and the droplet explodes. This "Coulombic explosion" forms a series of smaller, lower charged droplets. The process of shrinking followed by explosion is repeated until individually charged analyte ions are formed. The charges are statistically distributed amongst the analyte's available charge sites, leading to the possible formation of multiply charged ions. Increasing the rate of solvent evaporation, by introducing a drying gas flow counter current to the sprayed ions, increases the extent of multiple-charging. Decreasing the capillary diameter and lowering the analyte solution flow rate, e.g., in nanospray ionization, typically creates ions with higher mass-to-charge (m/z) ratios (i.e., it is a softer ionization technique) than those produced by "conventional" ESI and are commonly used in the field of bioanalysis.

ESI generally requires relatively clean samples and is intolerable of cationic salts, detergents, and many buffering agents commonly used in biochemical laboratories. Buffer systems commonly employed in polymerase chain reactions, for example, typically include electrospray incompatible reagents such as KCl, $MgCl_2$, Tris-HCl, and each of the four deoxynucleotide triphosphates (dNTPs). Even the presence of relatively low concentrations of metal cations (e.g., less than 100 µM) can reduce MS sensitivity for oligonucleotides as the signal for each molecular ion is spread out over multiple salt adducts. Thus, in addition to removing detergents and dNTPs, effective ESI-MS of PCR products typically requires that the salt concentration be reduced by more than a factor of 1000 prior to analysis.

Ethanol precipitation has been used to desalt PCR products for subsequent MS analysis as short oligonucleotides and salts are removed while the sample is concentrated. In some of these methods, the PCR product can be precipitated from concentrated ammonium acetate solutions, either overnight at 5° C. or over the course of 10-15 minutes with cold (−20° C.) ethanol. Unfortunately, a precipitation step alone is generally insufficient to obtain PCR products which are adequately desalted to obtain high-quality ESI spectra; consequently, precipitation is generally followed by a dialysis step to further desalt the sample. While several approaches have successfully employed these methods to characterize a number of PCR products, there remains a need to apply these and related methods in a robust and fully automated high-throughput manner.

SUMMARY OF THE INVENTION

The present invention provides systems and methods for analysis of samples, particularly biological and environmental sample to detect biomolecules of interest contained therein. A variety of system components are described herein, including, but not limited to, components for sample handling, mixing of materials, sample processing, transfer of materials, and analysis of materials. The invention further provides mechanisms for combining and integrating the different components and for housing, moving, and storing system components or the system as a whole. The systems may include any one or more or all of these components. The system finds particular use when employed for analysis of nucleic acid molecule using mass spectrometry, however, the invention is not limited such specific uses.

The present invention provides cartridges that are useful in mixing materials, including fluidic materials. Typically, the fluidic materials include particles, such as magnetically responsive beads, cells, solid supports, or the like, which are maintained in suspension using the cartridges described herein. In some embodiments, the cartridges are consumable or disposable components of mixing stations. Optionally, fluid mixing stations are included as components of systems. To illustrate, in certain embodiments, the cartridges described herein are used to maintain substantially homogenous mixtures including magnetically responsive beads, which are utilized in systems that perform nucleic acid purification and detection. In addition, the invention also provides related kits and methods.

In one aspect, the invention provides a cartridge for mixing material (e.g., fluidic material, etc.). The cartridge includes at least one body structure comprising one or more surfaces that define a cavity having upper and lower portions. The cartridge also includes at least one rotatable member extending at least partially along an axis that is substantially horizontally disposed in the upper portion of the cavity. The rotatable member is configured to operably connect to a rotational mechanism. In addition, the cartridge also includes at least one protrusion extending outward from the rotatable member and into the lower portion of the cavity. The protrusion is configured to mix the material when the material is disposed in the cavity, the rotatable member is operably connected to the rotational mechanism, and the rotational mechanism at least partially rotates the rotatable member about the axis.

The cartridges described herein include various embodiments. In certain embodiments, for example, cartridges are included as components of the mixing stations, kits, and/or systems described herein.

Typically, the cavity lacks substantial dead zones, e.g., areas where particles tend to fall out of suspension. In some embodiments, the upper portion of the cavity comprises at least one hole or indentation that receives at least a section of the rotatable member. In certain embodiments, the cavity comprises a volume capacity of about 500 mL or less.

In some embodiments, the body structures of the cartridges of the invention comprise one or more dimensions selected from, e.g., a height of about 10 cm or less, a width of about 15 cm or less, and a length of about 20 cm or less. In certain embodiments, the body structure comprises a weight of about 1 kg or less. Typically, the body structure is dimensioned to be handheld. Also, in some embodiments, the body structure, the rotatable member, the protrusion, or any combination thereof are disposable. In certain embodiments, the body structure comprises at least one alignment feature configured to align the cartridge relative to a cartridge support structure of a cartridge receiver/rotation assembly, when the cartridge is positioned on the cartridge support structure of the cartridge receiver/rotation assembly. In addition, in some embodiments, the body structure comprises at least one retention component configured to engage at least one retention mechanism of a cartridge receiver/rotation assembly, when the cartridge is positioned on a cartridge support structure of the cartridge receiver/rotation assembly.

The rotatable members of the cartridges described herein are typically configured to rotate about 180 degrees or less within the cavities of the cartridges. In some embodiments, rotatable members are configured to operably connect to the rotational mechanism via a substantially vertically disposed side surface of the body structure. To further illustrate, the rotatable member optionally comprises at least a first magnetic coupler that is configured to interact with at least a second magnetic coupler of the rotational mechanism to effect rotation of the rotatable member when the first and second magnetic couplers are within magnetic communication with one another and the rotational mechanism effects rotation of the second magnetic coupler.

In some embodiments, the protrusion of the cartridges described herein comprises at least one paddle or at least on blade. Optionally, the protrusion is fabricated integral with the rotatable member. Typically, the rotatable member comprises a plurality of protrusions.

In some embodiments, the cavity is fully enclosed within the body structure. In some of these embodiments, an aperture is disposed through a top surface of the body structure. The aperture is generally configured to receive a fluid handling component that fluidly communicates with the cavity. Typically, the aperture is disposed through the top surface of the body structure relative to the rotatable member and to the protrusion such that the fluid handling component does not contact the rotatable member or the protrusion when the rotatable member rotates the protrusion and the aperture receives the fluid handling component. In certain embodiments, a closure is disposed in or over the aperture. In some embodiments, the closure comprises a septum. In certain embodiments, the closure is re-sealable.

In other embodiments, a top surface of the body structure comprises an opening that communicates with the cavity. In some of these embodiments, a sealing member is operably connected to the body structure. The sealing member is generally structured to substantially seal the opening. In some embodiments, the sealing member comprises a removable cover that is structured to engage at least one surface of the body structure. Optionally, the sealing member comprises a film that overlays the opening on the top surface of the body structure. In certain embodiments, the film comprises a heat sealed film. Optionally, the film comprises an adhesive. Typically, an aperture is disposed through the sealing member. The aperture is generally configured to receive a fluid handling component such that the fluid handling component can fluidly communicate with the cavity. In some embodiments, the aperture is disposed through the sealing member relative to the rotatable member and to the protrusion such that the fluid handling component does not contact the rotatable member or the protrusion when the rotatable member rotates the protrusion and the aperture receives the fluid handling component. In some embodiments, a closure is disposed in or over the aperture. In certain embodiments, the closure comprises a septum. In some embodiments, the closure is re-sealable.

In certain embodiments, a fluidic material is disposed in the cavity. In these embodiments, the fluidic material typically comprises particles. To further illustrate, the particles are optionally selected from, e.g., cells, biopolymers, and solid supports. In some embodiments, the particles are maintained in suspension within the fluidic material when the rotatable member is operably connected to the rotational mechanism and the rotational mechanism at least partially rotates the rotatable member about the axis. Optionally, the particles comprise magnetically responsive particles (e.g., magnetically responsive beads, etc.).

In some embodiments, at least a first surface of the body structure is substantially symmetrical about the axis of the cavity. In these embodiments, a distance between a lower portion of the protrusion and the first surface of the cavity is typically substantially identical at two or more positions about the axis of the cavity. In some embodiments, the first surface of the cavity is curved. For example, a radius of curvature of the first surface of the cavity optionally varies along the length of the cavity. In certain embodiments, a radius of curvature of the first surface of the cavity is larger at a central portion of the cavity than the radius of curvature near an end portion of the cavity.

In some embodiments, the rotatable member comprises a proximal end which extends through a hole or an indentation in a surface of the cavity. Typically, the proximal end is configured to operably connect to the rotational mechanism. In certain embodiments, at least one washer is disposed around the proximal end of the rotatable member to seal the hole or indentation in the surface of the cavity. In some embodiments, there is a projection that extends outward from the rotatable member. The projection is typically configured to activate a motion sensor when the motion sensor is in sensory communication with the projection and the rotatable member is rotated.

In certain embodiments, the protrusion comprises at least one substantially vertically disposed segment that extends downward from the rotatable member and at least one substantially laterally disposed segment that extends outward from the substantially vertically disposed segment. In some embodiments, the substantially laterally disposed segment comprises an edge having a textured surface that, for example, enhances the uniform mixing of materials in a cartridge cavity relative to a protrusion lacking such an edge.

In another aspect, the invention provides a mixing station that includes at least one cartridge that comprises at least one body structure comprising one or more surfaces that define a cavity having upper and lower portions. The cartridge also comprises at least one rotatable member extending at least partially along an axis that is substantially horizontally disposed in the upper portion of the cavity, and at least one protrusion extending outward from the rotatable member and into the lower portion of the cavity. In addition, the mixing station also includes a cartridge receiver/rotation assembly that comprises at least one cartridge support structure that supports the body structure of the cartridge, and a rotational mechanism operably connected to the rotatable member. In some embodiments, the mixing station includes a thermal modulating component within thermal communication of the cavity to modulate temperature of fluidic material when the fluidic material is disposed in the cavity. Typically, the cartridge is removable from the cartridge support structure. In some embodiments, the body structure comprises at least one retention component. In these embodiments, the cartridge receiver/rotation assembly typically comprises at least one retention mechanism that engages the retention component to retain the cartridge on the cartridge support structure of the cartridge receiver/rotation assembly. In certain embodiments, the rotatable member comprises at least a first magnetic coupler. In these embodiments, the rotational mechanism comprises at least a second magnetic coupler that magnetically communicates with the first magnetic coupler to effect rotation of the rotatable member when the rotational mechanism rotates the second magnetic coupler. In some embodiments, the rotational mechanism comprises a motor. Typically, the rotational mechanism is mounted on the cartridge support structure. In certain embodiments, the cartridge receiver/rotation assembly comprises at least one controller operably connected at least to the rotational mechanism. The controller is typically configured to selectively direct the rotational mechanism to rotate the rotatable member in an initiation mode or in a maintenance mode in which a rate of rotation of the rotatable member is greater in the initiation mode than in the maintenance mode.

In some embodiments, the cartridge receiver/rotation assembly comprises a motion sensor that is configured to sense motion of the rotatable member when the rotational mechanism rotates the rotatable member. In these embodiments, a projection typically extends outward from the rotatable member. The projection is generally configured to activate the motion sensor when the rotatable member is rotated.

In certain embodiments, the mixing station includes at least one detection component in sensory communication with the cavity. The detection component is typically configured to detect one or more parameters of a fluidic material when the fluidic material is disposed in the cavity. In some embodiments, for example, the parameters are selected from, e.g., pH, temperature, pressure, density, salinity, conductivity, fluid level, radioactivity, luminescence, fluorescence, phosphorescence, and the like.

Optionally, the cartridge support structure comprises a recessed region that receives at least part of the body structure. In some embodiments, the recessed region comprises at least one groove. In these embodiments, the body structure typically comprises at least one alignment feature that is received within the groove to align the cartridge relative to the cartridge support structure of the cartridge receiver/rotation assembly.

In another aspect, the invention provides a kit that includes at least one cartridge that comprises at least one body structure comprising one or more surfaces that define a cavity having upper and lower portions. The cartridge also includes at least one rotatable member extending at least partially along an axis that is substantially horizontally disposed in the upper portion of the cavity. In addition, the cartridge further includes at least one protrusion extending outward from the rotatable member and into the lower portion of the cavity. The kit also includes at least one fluidic material and/or at least one particle disposed in the cavity and/or in at least one separate container. The kit further includes instructions for mixing the fluidic material and/or the particle in the cartridge and/or loading the fluidic material and/or the particle into the cavity of the cartridge. Typically, the kit also includes packaging for containing the cartridge, the separate container, and/or the instructions. To illustrate, the fluidic material generally includes water, a buffer, a cell culture medium, or the like. In some embodiments, the particle comprises at least one magnetically responsive particle. In certain embodiments, the particle is a cell, a biopolymer, a solid support, or the like.

In another aspect, the invention provides a system that includes at least one mixing station that comprises a cartridge. The cartridge includes at least one body structure comprising one or more surfaces that define a cavity having upper and lower portions. The cartridge also includes at least one rotatable member extending at least partially along an axis disposed in the upper portion of the cavity. In addition, the cartridge also includes at least one protrusion extending outward from the rotatable member and into the lower portion of the cavity. The mixing station also includes at least one cartridge receiver/rotation assembly that comprises at least one cartridge support structure that supports the body structure of the cartridge, and a rotational mechanism operably connected to the rotatable member. The system also includes at least one additional system component selected from, e.g., at least one nucleic acid amplification component, at least one sample preparation component, at least one microplate handling component, at least one material transfer component, at least one sample processing component, at least one mass spectrometer, at least one controller, at least one database, and/or the like.

In another aspect, the invention provides a method of mixing a fluidic material. The method includes (a) providing a cartridge that comprises at least one body structure comprising one or more surfaces that define a cavity having upper and lower portions, at least one rotatable member extending at least partially along an axis that is substantially horizontally disposed in the upper portion of the cavity, at least one protrusion extending outward from the rotatable member and into the lower portion of the cavity, and the fluidic material disposed in the cavity. The method also includes (b) rotating the rotatable member to cause the protrusion to agitate the fluidic material to thereby mix the fluidic material. In some embodiments, (b) comprises rotating the rotatable member back-and-forth about 180 degrees or less within the cavity. Typically, the method includes adding and/or removing material to and/or from the cavity. In some embodiments, one or more particles are disposed within the fluidic material and (b) maintains the particles in suspension within the fluidic material. In certain embodiments, (b) includes (i) rotating the rotatable member in an initiation mode to suspend the particles within the fluidic material, and (ii) rotating the rotatable member in an maintenance mode to maintain the particles in suspension within the fluidic material in which a rate of rotation of the rotatable member is greater in the initiation mode than in the maintenance mode.

In another aspect, the invention provides a method of fabricating a cartridge. The method includes (a) forming at least one body structure comprising one or more surfaces that define a cavity having upper and lower portions and (b) forming at least one rotatable member comprising at least one outwardly extending protrusion, which rotatable member is configured to extend at least partially along an axis that is substantially horizontally disposed in the upper portion of the cavity. The method also includes (c) coupling the rotatable member to the body structure such that the protrusion extends into the lower portion of the cavity.

In another aspect, the invention provides a method that includes (a) receiving an order from a customer for at least one cartridge that comprises at least one body structure comprising one or more surfaces that define a cavity having upper and lower portions, at least one rotatable member extending at least partially along an axis that is substantially horizontally disposed in the upper portion of the cavity, and at least one protrusion extending outward from the rotatable member and into the lower portion of the cavity. The method also includes (b) supplying the cartridge to the customer in response to the order. Optionally, (a) comprises receiving the order via a personal appearance by the customer or an agent thereof, via a postal or other delivery service, via a telephonic communication, or via an email communication or another electronic medium. In some embodiments, (a) comprises receiving the order for a kit that comprises the cartridge. In certain embodiments, (b) comprises supplying the cartridge to the customer via a personal appearance by the customer or an agent thereof, or via a postal or other delivery service.

The present invention provides microplate handling systems that are useful in handling or managing microplates in essentially any microplate-based application. Typically, these systems include microplate storage units that store multiple stacked microplates. These storage units generally function as input and/or output points for microplates introduced into and/or taken out of the systems of the invention. In certain embodiments, for example, batches of microplates (e.g., non-priority microplates) are stored in input microplate storage units in a user-selected order or sequence. The microplate handling systems of the invention also provide mechanisms for readily introducing priority or stat samples for processing ahead of other samples. Typically, these samples are introduced into the systems of the invention at any point in a given processing application via priority microplate storage units of the systems. In addition to computer program products useful in managing microplate-based processes and hardware in the systems of the invention, and related methods are also provided.

In one aspect, the invention provides a microplate handling system. The system includes at least first and second non-priority microplate storage units that each store two or more microplates; at least one priority microplate storage unit that stores at least one microplate; and at least one microplate processing area. The system also includes at least one non-priority microplate holding area; at least one microplate transport mechanism configured to transport one or more microplates between the first and second non-priority microplate storage units, the priority microplate storage unit, the microplate processing area, and/or the non-priority microplate holding area; and at least one controller operably connected at least to the microplate transport mechanism. In some embodiments, the controller is configured to selectively direct the microplate transport mechanism to carry out one or more or all of: (a) transport a non-priority microplate from the first non-priority microplate storage unit to the microplate processing area; (b) position the non-priority microplate while in the microplate processing area; (c) transport the non-priority microplate from the microplate processing area to the non-priority microplate holding area when a priority microplate is stored in the priority microplate storage unit; (d) transport the priority microplate from the priority microplate storage unit to the microplate processing area; (e) position the priority microplate while in the microplate processing area; (f) transport the priority microplate from the microplate processing area to the second non-priority microplate storage unit or to the priority microplate storage unit; (g) transport the non-priority microplate from the non-priority microplate holding area to the microplate processing area; and (h) transport the non-priority microplate from the microplate processing area to the second non-priority microplate storage unit. Typically, the controller is configured to selectively direct the microplate transport mechanism to execute (c) prior to (d) and/or (f) prior to (g).

The first and second non-priority microplate storage units each typically store two or more stacked microplates (e.g., in vertically stacked orientations). In some embodiments, for example, the first and second non-priority microplate storage units each comprise a support structure that defines a cavity that is configured to store two or more stacked microplates. In these embodiments, at least a lower surface of the support structure generally comprises an opening that communicates with the cavity in which dimensions of the opening are sufficient to accommodate microplates moving into or out of the cavity. Typically, at least one retaining mechanism is operably connected to the support structure. The retaining mechanism is generally configured to reversibly retain at least one microplate in the cavity.

In some embodiments, the priority microplate storage unit comprises a support structure that defines a cavity that is configured to store the microplate. In certain of these embodiments, at least a lower surface of the support structure comprises an opening that communicates with the cavity in which dimensions of the opening accommodate microplates moving into or out of the cavity. Typically, at least one retaining mechanism is operably connected to the support structure. The retaining mechanism is generally configured to reversibly retain at least one microplate in the cavity. In some embodiments, at least one movement mechanism (e.g., a sliding mechanism or the like) is operably connected to the support structure. In these embodiments, the movement mechanism is typically configured to move the support structure relative to the first and second non-priority microplate storage units.

In certain embodiments, a microplate handling system includes a support base on which the first and second non-priority microplate storage units, the priority microplate storage unit, the microplate processing area, and the non-priority microplate holding area are disposed. The non-priority microplate holding area typically comprises at least one non-priority microplate holding component that is structured to hold one or more non-priority microplates above the support base. To further illustrate, in certain embodiments, at least the first and second non-priority microplate storage units are detachable from the support base. In these embodiments, the first and/or second non-priority microplate storage unit typically comprises a handle, e.g., to facilitate transport of the unit to and from the system.

The microplate transport mechanism of a microplate handling system includes various embodiments. In some embodiments, for example, the microplate transport mechanism comprises at least one platform (e.g., a nest or the like) that is structured to support one or more microplates; at least a first linear motion component operably connected to the platform, which first linear motion component selectively moves the platform along a first axis; and at least a second linear motion component operably connected to the platform, which second linear motion component selectively moves the platform along a second axis. Typically, the first linear motion component is configured to selectively raise and lower the platform. In certain embodiments, the first linear motion component comprises a stepper motor. Typically, the second linear motion component is configured to selectively move the platform between the first non-priority microplate storage unit, the second non-priority microplate storage unit, the priority microplate storage unit, the microplate processing area, and/or the non-priority microplate holding area. In some embodiments, for example, the second linear motion component is configured to move the platform beneath the first non-priority microplate storage unit, the second non-priority microplate storage unit, and the priority microplate storage unit. In certain embodiments, the second linear motion component comprises at least one gantry. In some embodiments, the second linear motion component comprises at least one encoder and at least one stepper motor.

Typically, the microplate handling systems of the invention include additional system components, or themselves are included as components or sub-systems of other systems. In some embodiments, for example, microplate handling systems include at least one barcode reader or radio frequency identification (RFID) reader configured to read barcodes or radio frequency tags disposed on microplates when the microplates are disposed in or proximal to the first non-priority microplate storage unit, the second non-priority microplate storage unit, the priority microplate storage unit, the microplate processing area, and/or the non-priority microplate holding area. Other automatic identification and data capture (AIDC) technologies are also optionally utilized. To further illustrate, in certain embodiments, microplate handling systems include at least one material transfer component configured to transfer material to and/or from selected wells disposed in at least one microplate when the microplate is disposed in the microplate processing area. In these embodiments, the material transfer component is typically configured to transfer fluidic material. Typically, the material transfer component includes at least one gantry, and in certain embodiments, the material transfer component comprises at least one gantry head (e.g., includes one or more needles). In some of these embodiments, microplate handling systems include at least one magnetically responsive particle source. The material transfer component is generally configured to aspirate an aliquot of magnetically responsive particles from the magnetically responsive particle source prior to or after aspirating an aliquot of material from a selected well of the microplate when the microplate is disposed in the microplate processing area. In addition, in some of these embodiments, microplate handling systems include at least one wash station configured to wash the material transfer component or a portion thereof. In certain of these embodiments, microplate handling systems include at least one sample processing component (e.g., a desalting station or the like) in which the material transfer component is configured to transfer the material from the selected wells disposed in the microplate to the sample processing component.

In another aspect, the invention provides a microplate storage unit that includes a support structure that defines a cavity that is configured to store two or more stacked microplates. The support structure comprises a top end and a bottom end. The microplate storage unit also includes a base structure operably connected to the bottom end of the support structure. An opening is disposed through the base structure and communicates with the cavity and dimensions of the opening are sufficient to accommodate microplates moving into or out of the cavity. Further, the base structure is configured to detachably engage a support base of a microplate handling system. The microplate storage unit also includes at least one retaining mechanism operably connected to the support structure and/or to the base structure. The retaining mechanism is configured to reversibly retain at least one microplate in the opening and/or in the cavity. In addition, the microplate storage unit also includes at least one handle that is pivotally attached to the support structure and/or to the base structure. The handle pivots between an open position and a closed position in which the top end of the support structure accommodates microplates moving into or out of the cavity when the handle is in the open position. In certain embodiments, at least one alignment member operably connected to at least one surface of the support structure. The alignment member is configured to align microplates when the microplates are disposed in the cavity. Optionally, the microplate storage unit includes a cover member that is configured to cover microplates when the microplates are disposed in the cavity.

In certain embodiments, the handle comprises a swing arm having ends that are pivotally attached to the base structure. In some of these embodiments, the ends of the swing arm extend through the base structure and are configured to align the base structure relative to the support base of the microplate handling system, when the handle is in the closed position and the support structure engages the support base of the microplate handling system. In other exemplary embodiments, one or more slots are disposed in or through the support structure and wherein the swing arm comprises one or more sliding members that slide in the slots.

In another aspect, the invention relates to a computer program product that includes a computer readable medium having one or more logic instructions for directing a microplate transport mechanism of a microplate handling system to carry out one or more or all of: (a) transport a non-priority microplate from a first non-priority microplate storage unit of the microplate handling system to a microplate processing area of the microplate handling system; (b) position the non-priority microplate while in the microplate processing area; (c) transport the non-priority microplate from the microplate processing area to a non-priority microplate holding area of the microplate handling system when a priority microplate is stored in a priority microplate storage unit of the microplate handling system; (d) transport the priority microplate from the priority microplate storage unit to the microplate processing area; (e) position the priority microplate while in the microplate processing area; (f) transport the priority microplate from the microplate processing area to a second non-priority microplate storage unit of the microplate handling system or to the priority microplate storage unit; (g) transport the non-priority microplate from the non-priority microplate holding area to the microplate processing area of the microplate handling system; and (h) transport the non-priority microplate from the microplate processing area to the second non-priority microplate storage unit. In some embodiments, the computer readable medium comprises one or more logic instructions for directing a material transfer component to transfer material to and/or from selected wells disposed in at least one microplate when the microplate is positioned in the microplate processing area. Optionally, the computer readable medium comprises one or more logic instructions for directing a barcode reader or radio frequency identification (RFID) reader of the microplate handling system to read barcodes or radio frequency tags disposed on microplates when the microplates are disposed in or proximal to the first non-priority microplate storage unit, the second non-priority microplate storage unit, the priority microplate storage unit, the microplate processing area, and/or the non-priority microplate holding area. Typically, the logic instructions are configured to direct the microplate transport mechanism to execute (c) prior to (d) and/or (f) prior to (g). In some embodiments, a controller of the microplate handling system comprises the logic instructions. In certain of these embodiments, the controller comprises or is operably connected to a database comprising one or more microplate descriptors.

In another aspect, the invention provides a method of handling a priority microplate in a microplate handling system. The method includes one or more or all of the steps of: (a) placing the priority microplate in a priority microplate storage unit of the microplate handling system; (b) transporting a first non-priority microplate from a microplate processing area of the microplate handling system to a non-priority microplate holding area of the microplate handling system using a microplate transport mechanism of the microplate handling system; and (c) placing the first non-priority microplate onto a non-priority microplate holding component disposed in the non-priority microplate holding area using the microplate transport mechanism. In addition, the method also includes (d) transporting the priority microplate from the priority microplate storage unit to the microplate processing area using the microplate transport mechanism; (e) transferring material to and/or from one or more selected wells of the priority microplate using a material transfer component of the microplate handling system, and (f) transporting the priority microplate from the microplate processing area to a second non-priority microplate storage unit of the microplate handling system or to the priority microplate storage unit using the microplate transport mechanism, thereby handling the priority microplate in the microplate handling system. In some embodiments, one or more wells of the priority microplate comprise nucleic acid molecules. In these embodiments, the method typically comprises amplifying one or more target regions of the nucleic acid molecules prior to (a). Typically, the method includes transporting the first non-priority microplate from a first non-priority microplate storage unit of the microplate handling system to the microplate processing area using the microplate transport mechanism prior to (b). In some embodiments, the method includes removing material from one or more selected wells of the first non-priority microplate using the material transfer component prior to (b).

In certain embodiments, the method includes loading a plurality of non-priority microplates in a selected order into the first non-priority microplate storage unit. In some of these embodiments, one or more wells of the plurality of non-priority microplates comprise nucleic acids and the method comprises amplifying one or more target regions of the nucleic acids prior to loading the plurality of non-priority microplates into the first non-priority microplate storage unit.

In some embodiments, the method includes transporting the first non-priority microplate from the non-priority microplate holding area to the microplate processing area using the microplate transport mechanism. Typically, the method includes transferring material to and/or from one or more selected wells of the first non-priority microplate using the material transfer component. In some of these embodiments, the method includes transporting the first non-priority microplate from the microplate processing area to the second non-priority microplate storage unit using the microplate transport mechanism. In certain embodiments, the method includes transporting a second non-priority microplate from the first non-priority microplate storage unit to the microplate processing area using the microplate transport mechanism. To further illustrate, in some embodiments, the material transfer component comprises one or more needles and the method comprises aspirating one or more aliquots of magnetically responsive particles into the needles from a magnetically responsive particle source prior to or after transferring the material from the selected wells of the first non-priority microplate. In these embodiments, the material typically comprises a fluidic material and the method comprises aspirating one or more aliquots of the fluidic material into the needles from the selected wells of the first non-priority microplate. In some of these embodiments, the method includes transferring the aliquots of magnetically responsive particles and fluidic material to a container of a sample processing station to form a mixture in which the magnetically responsive particles capture at least a first component of the mixture. These embodiments typically also include moving and/or retaining the magnetically responsive particles proximal to a surface of the container using a magnetic field and removing at least a second component of the mixture from the container. Typically, the method includes eluting the captured first component from the magnetically responsive particles and detecting a molecular mass of the first component. In certain of these embodiments, the first component comprises a nucleic acid molecule and the method comprises determining a base composition of the nucleic acid molecule from the molecular mass of the nucleic acid molecule.

The material transfer component typically comprises one or more needles and the method comprises aspirating one or more aliquots of magnetically responsive particles into the needles from a magnetically responsive particle source prior to (e). In some of these embodiments, the material comprises a fluidic material and (e) comprises aspirating one or more aliquots of the fluidic material into the needles from the selected wells of the priority microplate. In certain of these embodiments, the method includes transferring the aliquots of magnetically responsive particles and fluidic material to a container of a sample processing station to form a mixture in which the magnetically responsive particles capture at least a first component of the mixture. In these embodiments, the method typically includes moving and/or retaining the magnetically responsive particles proximal to a surface of the container using a magnetic field and removing at least a second component of the mixture from the container. Typically, in these embodiments, the method includes eluting the captured first component from the magnetically responsive particles and detecting a molecular mass of the first component. In some of these embodiments, the first component comprises a nucleic acid molecule and the method comprises determining a base composition of the nucleic acid molecule from the molecular mass of the nucleic acid molecule.

The present invention provides sample processing units that are useful in various purification processes. In certain embodiments, for example, the sample processing units are used to perform solution capture methods of purifying nucleic acids, which are subsequently analyzed using any suitable approach, including electrospray mass spectrometric-based analysis. Some of these embodiments include adding an anion exchange resin to the solution and mixing these materials in a sample processing unit to yield a suspension of the anion exchange resin in the solution in which the nucleic acids bind to the anion exchange resin. Additional processing steps performed using the sample processing units described herein typically include isolating the anion exchange resin from the solution, washing the anion exchange resin to remove one or more contaminants with one or more wash buffers while retaining the nucleic acids bound to the resin, and eluting the nucleic acids from the anion exchange resin with an elution buffer, thereby yielding purified nucleic acids that are suitable for further analysis. In addition to sample processing units and stations, the invention also provides related systems and methods.

In one aspect, the invention provides a sample processing unit that includes at least one container (e.g., a cuvette or the like) configured to contain at least one sample comprising at least one magnetically responsive particle (e.g., a magnetically responsive bead coated with a selected capture reagent, etc.), and at least one magnet (e.g., a permanent magnet, an electromagnet, etc.) that generates, or is configured to generate, at least one magnetic field, which magnet is in a substantially fixed position relative to the container. The sample processing unit also includes at least one conveyance mechanism configured to convey the container between at least first and second positions in which at least the first position is within magnetic communication with the magnet when the magnet generates the magnetic field, and at least one rotational mechanism operably connected to the container, which rotational mechanism is configured to rotate the container when the container is in at least the second position. Typically, the sample processing unit includes at least one mounting bracket that is operably connected to one or more of: the container, the magnet, the conveyance mechanism, or the rotational mechanism. In some embodiments, a sample processing station includes the sample processing unit. In certain embodiments, a carrier mechanism includes the sample processing unit. In some of these embodiments, a system includes the carrier mechanism.

In some embodiments, the conveyance mechanism comprises at least one motor. The conveyance mechanism is configured to rotate the container between the first and second positions in certain embodiments. In other exemplary embodiments, the conveyance mechanism is configured to slide the container between the first and second positions. To further illustrate, in some embodiments, the conveyance mechanism comprises at least one support member operably connected to the container and/or to the rotational mechanism. In some of these embodiments, the support member is configured to slide between the first and second positions, whereas in other exemplary embodiments, the support member is configured to rotate between the first and second positions.

In certain embodiments, the rotational mechanism is configured to rotate the container in at least one pulsed mode, during which a substantial portion of the time of rotation, a rate of rotation of the container exceeds a rate of rotation of the sample when the container contains the sample such that the sample is sheared away from a surface of the container. In some embodiments, the rotational mechanism is configured to rotate the container in at least one oscillating motion.

In another aspect, the invention provides a sample processing unit that includes at least one cuvette configured to contain at least one sample comprising at least one magnetically responsive particle, and at least one magnet (e.g., a permanent magnet, an electromagnet, etc.) that generates, or is configured to generate, at least one magnetic field, which magnet is in a substantially fixed position. In some embodiments, two or more magnets are disposed proximal to a receiving space in which the cuvette is located at least partially within the receiving space when the cuvette is in the first position. The sample processing unit also includes at least a first motor operably connected to the cuvette. The first motor is configured to rotate the cuvette around a central longitudinal axis of the cuvette. In addition, the sample processing unit also includes at least one support member (e.g., a swing arm or the like) operably connected to the first motor, and at least a second motor operably connected to the support member. The second motor is configured to rotate the cuvette between at least first and second positions in which at least the first position is within magnetic communication with the magnet when the magnet generates the magnetic field. In certain embodiments, a sample processing station includes the sample processing unit. Optionally, a carrier mechanism (e.g., a carousel, a conveyor track, etc.) includes the sample processing unit. In some of these embodiments, a system includes the carrier mechanism.

In some embodiments, the first motor (e.g., a stepper motor, a servo motor, etc.) is configured to rotate the cuvette in at least one pulsed mode, during which a substantial portion of the time of rotation, a rate of rotation of the cuvette exceeds a rate of rotation of the sample when the cuvette contains the sample such that the sample is sheared away from a surface of the cuvette, e.g., to effect thorough mixing of the sample and other materials that may be present in the cuvette. To further illustrate, the first motor is optionally configured to rotate the cuvette in at least one oscillating motion. In certain embodiments, the second motor comprises a brushless direct current motor or the like. The sample processing unit generally includes circuitry configured to control the first and second motors.

In certain embodiments, the support member comprises a first end and a second end in which the cuvette is retained at or proximal to the first end of the support member, and in which the second motor is operably connected to the support member at or proximal to the second end of the support member. In some of these embodiments, the support member is configured to rotate at least partially around a rotational axis extending through the second end of the support member. As a further illustrate, in some embodiments, a pin is fixedly coupled to the second end of the support member and aligned with the rotational axis in which the pin is operably coupled to the second motor.

In some embodiments, the sample processing unit includes a mounting bracket in which the support member is operably connected to the mounting bracket. In certain of these embodiments, the magnet is operably connected to the mounting bracket.

In another aspect, the invention provides a sample processing system. The system includes at least one sample processing unit that comprises: at least one cuvette configured to contain at least one sample comprising at least one magnetically responsive particle; at least one magnet that generates, or is configured to generate, at least one magnetic field, which magnet is in a substantially fixed position; at least a first motor operably connected to the cuvette, which first motor is configured to rotate the cuvette around a central longitudinal axis of the cuvette; at least one support member operably connected to the first motor; and at least a second motor operably connected to the support member, which second motor is configured to rotate the cuvette between at least first and second positions in which at least the first position is within magnetic communication with the magnet when the magnet generates the magnetic field. The system also includes at least one carrier mechanism operably connected to the sample processing unit. The carrier mechanism is configured to move the sample processing unit to one or more locations. The system further includes at least one material transfer component configured to transfer material to and/or from the cuvette, and at least one controller operably connected to the sample processing unit, the carrier mechanism, and/or the material transfer component. The controller is configured to effect one or more of: the magnet to generate the magnetic field, the first motor to rotate the cuvette, the second motor to rotate the cuvette between the first and second positions, the carrier mechanism to move the sample processing unit to the one or more locations, or the material transfer component to transfer the material to and/or from the cuvette.

The carrier mechanism includes various embodiments. In one embodiment, for example, the carrier mechanism comprises a carousel that is configured to rotate the sample processing unit to the one or more locations. In another exemplary embodiment, the carrier mechanism comprises a conveyor track that is configured to convey the sample processing unit to the one or more locations. Typically, the carrier mechanism comprises a plurality of sample processing units. In some of these embodiments, the material transfer component comprises a manifold that is configured to transfer material to and/or from the cuvettes of at least two sample processing units substantially simultaneously.

In some embodiments, the material transfer component comprises one or more of: a sample input gantry head, a sample wash station, a sample output gantry head, or a cuvette wash station. Typically, the material transfer component is configured to transfer fluidic material. In certain embodiments, the material transfer component comprises one or more needles.

In certain embodiments, the controller is configured to effect the first motor to rotate the cuvette in one or more selectable modes. In some embodiments, for example, the controller is configured to effect the first motor to rotate the cuvette in at least one pulsed mode, during which a substantial portion of the time of rotation, a rate of rotation of the cuvette exceeds a rate of rotation of the sample when the cuvette contains the sample such that the sample is sheared away from a surface of the cuvette. In other exemplary embodiment, the controller is configured to effect the first motor to rotate the cuvette in at least one oscillating motion.

In some embodiments, the sample processing system includes at least one detector configured to detect one or more detectable signals of or from one or more sample components. In certain embodiments, the detector is within sensory communication with the cuvette when the carrier mechanism moves the sample processing unit to at least one of the locations. Optionally, the material transfer component is configured to transfer the material from the cuvette to the detector. In some embodiments, the controller is operably connected to the detector. In these embodiments, the controller is configured to effect the detector to detect the detectable signals of or from the sample components. To further illustrate, in certain embodiments, the detector comprises a mass spectrometer. In some of these embodiments, the mass spectrometer comprises an electrospray ionization time-of-flight mass spectrometer.

In another aspect, the invention relates to a method of processing a sample. The method includes (a) providing at least one sample processing unit that comprises: at least one cuvette that contains at least one sample comprising at least one magnetically responsive particle comprising at least one captured first component (e.g., a biopolymer, such as a polynucleotide, a polypeptide, or the like); at least one magnet that is in a substantially fixed position; at least a first motor operably connected to the cuvette, which first motor is configured to rotate the cuvette around a central longitudinal axis of the cuvette; at least one support member operably connected to the first motor; and at least a second motor operably connected to the support member, which second motor is configured to rotate the cuvette between at least first and second positions in which the magnet is capable of magnetically communicating with the cuvette when the cuvette is at least in the first position. The method also includes (b) moving the cuvette into the first position using the second motor such that a magnetic field generated by the magnet causes the magnetically responsive particle to move and/or be retained proximal to a surface of the cuvette. In addition, the method also includes (c) removing at least a second component from the cuvette to thereby process the sample. In some embodiments, the method includes adding the sample and/or the magnetically responsive particle to the cuvette prior to (a) when the cuvette is in the second position. Optionally, the method includes adding at least one wash reagent to the cuvette. In certain embodiments, the magnet comprises a permanent magnet. In other exemplary embodiments, the magnet comprises an electromagnet. In these embodiments, the method typically comprises generating the magnetic field prior to or during (b). Typically, a carrier mechanism comprises the sample processing unit and the method comprises moving the sample processing unit to one or more locations.

The magnetically responsive particle includes various embodiments. In some embodiments, for example, the magnetically responsive particle comprises an anion exchange resin. Typically, the magnetically responsive particle comprises at least one biopolymer capture reagent. In certain embodiments, the biopolymer capture reagent comprises at least one anion exchange functional group. The anion exchange functional group typically comprises a pKa value of 9.0 or greater. To further illustrate, exemplary anion exchange functional groups are selected from, e.g., a primary amine, a second amine, a tertiary amine, a quaternary amine, a polyethyleneimine, a charged aromatic amine, a diethylaminomethyl, a diethylaminoethyl.

The method typically includes rotating the cuvette using the first motor such that sample components mix with one another. In some embodiments, the method includes rotating the cuvette when the cuvette is in the second position. In certain embodiments, the method includes rotating the cuvette in at least one pulsed mode, during which a substantial portion of the time of rotation, a rate of rotation of the cuvette exceeds a rate of rotation of the sample such that the sample is sheared away from a surface of the cuvette. Optionally, the method includes rotating the cuvette in at least one oscillating motion.

In certain embodiments, the method includes detecting at least one detectable signal of or from the sample. For example, the method optionally includes detecting a molecular mass of the first component. In these embodiments, the molecular mass is generally detected using a mass spectrometer. In some of these embodiments, the first component comprises a nucleic acid and the method comprises correlating the molecular mass of the nucleic acid with a base composition and/or an identity of the nucleic acid.

The present invention provides ionization probe assemblies that are useful in spraying and ionizing sample materials. Typically, the ionization probe assemblies are configured to substantially continuously introduce sample materials into ion source housings of molecular mass measurement systems via multiple probes that are individually configured to discontinuously spray or otherwise introduce sample materials into the ion source housings. In some embodiments, for example, probes of the ionization probe assemblies are configured to duty cycle between spray and rinse positions that are substantially electrically isolated from one another. In addition to ionization probe assemblies, the invention also provides related molecular mass measurement systems, computer program products, and methods.

In one aspect, the invention provides an ionization probe assembly that includes at least one probe mounting structure and at least one probe that is movably coupled to the probe mounting structure. The probe is configured to discontinuously introduce sample aliquots into an ion source housing. In addition, the ionization probe assembly also includes at least one probe conveyance mechanism operably connected to the probe. The probe conveyance mechanism is configured to convey the probe between at least a first position and at least a second position. The first position is substantially electrically isolated from the second position. In some embodiments, an electrospray ion source housing includes the ionization probe assembly. In these embodiments, a mass spectrometer typically includes the electrospray ion source housing. In certain embodiments, at least one cavity is disposed in or proximal to the probe mounting structure. The cavity typically comprises the second position. In some of these embodiments, the cavity fluidly communicates with at least one outlet. Typically, the ionization probe assembly includes at least two probes that are each movably coupled to the probe mounting structure. In these embodiments, the probes are generally independently movably coupled to the probe mounting structure.

The probe mounting structures include various embodiments. In certain embodiments, for example, the probe mounting structure includes at least one view port. In some embodiments, at least one cover operably connected to the probe mounting structure. In certain embodiments, the probe mounting structure comprises an ion source housing back plate that is configured to operably connect to an ion source housing. In these embodiments, the ion source housing back plate typically comprises at least one alignment feature that is structured to align the ion source housing back plate relative to the ion source housing when the ion source housing back plate operably connects to the ion source housing. In some embodiments, at least a first mounting component is operably connected to the probe mounting structure. The first mounting component is configured to engage at least a second mounting component that is operably connected to an ion source housing when the probe mounting structure is mounted on the ion source housing. Typically, the first and second mounting components comprise hinge and/or latch components. In certain embodiments, the probe mounting structure comprises an ion source housing. In some of these embodiments, the ion source housing comprises at least one view port.

Typically, at least one channel is disposed through a length of the probe. In addition, the probe generally comprises at least one sprayer needle that fluidly communicates with the channel. In some embodiments, at least one nebulizer gas source and/or nebulizer gas sheath fluidly communicates with the channel.

In some embodiments, the ionization probe assembly includes at least one thermal modulator operably connected to the probe. The thermal modulator is typically configured to modulate a temperature of the probe. In certain embodiments, for example, the thermal modulator comprises a nebulizer gas heater. Typically, at least one controller circuit board operably connected to the thermal modulator.

In certain embodiments, the ionization probe assembly includes at least two probes independently that are movably coupled to the probe mounting structure. Typically, each probe is movably coupled to the probe mounting structure via a pivot mechanism. In some embodiments, the probe conveyance mechanism comprises at least one motor operably connected to at least one of the pivot mechanisms via a pulley and belt drive assembly. Optionally, each probe is configured to move between a spray position and a rinse position in which the spray position is substantially electrically isolated from the rinse position. In certain embodiments, at least one cavity is disposed in or proximal to the probe mounting structure. The cavity generally comprises at least one of the rinse positions. In these embodiments, the cavity typically fluidly communicates with at least one outlet.

In some embodiments, the probe is movably coupled to the probe mounting structure via a slide mechanism. Typically, the slide mechanism comprises at least two probes. In some of these embodiments, the probes are substantially fixedly coupled to the slide mechanism. In certain embodiments, the first position comprises a spray position and the second position comprises at least first and second rinse positions that are each substantially electrically isolated from the spray position. Typically, when a first probe is in the spray position, a second probe is in the second rinse position, and when the second probe is in the spray position, the first probe is in the first rinse position. In some of these embodiments, the slide mechanism comprises a probe support plate coupled to the probe mounting structure via a linear slide, and the probe is mounted on the probe support plate. In certain embodiments, the probe conveyance mechanism comprises a dual acting pneumatic cylinder operably connected to the probe mounting structure and to the probe support plate.

In another aspect, the invention provides an ionization probe assembly that includes at least one ion source housing back plate that comprises one or more surfaces that define at least one spray orifice. The ion source housing back plate is configured to operably connect to an ion source housing. The ionization probe assembly also includes at least one rinse cavity that is at least partially disposed within the ion source housing back plate in which the rinse cavity communicates with the spray orifice via at least one opening. Typically, the rinse cavity fluidly communicates with at least one outlet. In addition, the ionization probe assembly also includes at least one probe support structure coupled to the ion source housing back plate via at least one linear slide, and at least one probe substantially fixedly mounted on the probe support structure. The ionization probe assembly also includes at least one probe conveyance mechanism operably connected to the probe support structure. The probe conveyance mechanism is configured to selectively convey the probe support structure such that the probe slides between the spray orifice and the rinse cavity through the opening.

In another aspect, the invention provides an ionization probe assembly that includes at least one ion source housing back plate that comprises one or more surfaces that define at least one spray orifice. The ion source housing back plate is configured to operably connect to an ion source housing. The ionization probe assembly also includes at least one rinse cavity that is at least partially disposed within the ion source housing back plate in which the rinse cavity communicates with the spray orifice via at least one opening, and at least one probe movably coupled to the ion source housing back plate via at least one pivot mechanism. In addition, the ionization probe assembly also includes at least one probe conveyance mechanism that comprises at least one motor operably connected to the pivot mechanism via a pulley and belt drive assembly. The probe conveyance mechanism is configured to selectively convey the probe between the spray orifice and the rinse cavity through the opening.

In another aspect, the invention provides a molecular mass measurement system. The system includes at least one mass spectrometer that comprises at least one ion source housing, and at least one ionization probe assembly operably connected to the ion source housing. The ionization probe assembly comprises: at least one probe mounting structure; at least one probe that comprises at least one inlet and at least one outlet in which the inlet fluidly communicates with the outlet, the probe is movably coupled to the probe mounting structure, which probe is configured to discontinuously introduce sample aliquots into the ion source housing; and at least one probe conveyance mechanism operably connected to the probe, which probe conveyance mechanism is configured to convey the probe between a spray position and a rinse position in which the spray position is substantially electrically isolated from the rinse position. The system also includes at least one sample source in fluid communication with the inlet of the probe, and at least one rinse fluid source in fluid communication with the inlet of the probe. In addition, the system also includes at least one controller operably connected at least to the ionization probe assembly. The controller is configured to selectively direct the ionization probe assembly to: (a) convey the probe from the rinse position to the spray position; (b) spray at least one sample aliquot into the ion source housing from the sample source when the probe is in the spray position; (c) convey the probe from the spray position to the rinse position; and (d) rinse the probe with rinse fluid from the rinse fluid source when the probe is in the rinse position. In some embodiments, the system includes at least one additional system component selected from, e.g., at least one nucleic acid amplification component; at least one sample preparation component; at least one microplate handling component; at least one mixing station; at least one material transfer component; at least one sample processing component; at least one database; and the like.

In another aspect, the invention provides a computer program product that includes a computer readable medium having one or more logic instructions for directing an ionization probe assembly of a molecular mass measurement system to: (a) convey a first probe from a first rinse position to a first spray position of the molecular mass measurement system, wherein the first rinse position and the first spray position are substantially electrically isolated from one another; (b) convey a second probe from a second spray position to a second rinse position of the molecular mass measurement system, wherein the second spray position and the second rinse position are substantially electrically isolated from one another; (c) spray at least a first sample aliquot into an ion source housing of the molecular mass measurement system via the first probe when the first probe is in the first spray position; (d) rinse the second probe when the second probe is in the second rinse position; (e) convey the first probe from the first spray position to the first rinse position; (f) convey the second probe from the second rinse position to the second spray position; (g) spray at least a second sample aliquot into the ion source housing of the molecular mass measurement system via the second probe when the second probe is in the second spray position; and, (h) rinse the first probe when the first probe is in the first rinse position. In some embodiments, the computer program product includes at least one logic instruction for directing the ionization probe assembly of the molecular mass measurement system to modulate a temperature of the first probe and/or second probe using at least one thermal modulator operably connected to the first probe and/or second probe. In certain embodiments, the logic instructions are configured to direct the ionization probe assembly to execute (a) substantially simultaneously with (b), (c) substantially simultaneously with (d), (e) substantially simultaneously with (f), and/or (g) substantially simultaneously with (h). Typically, a controller of the molecular mass measurement system comprises the logic instructions.

In another aspect, the invention provides a method of spraying sample aliquots into an ion source housing of a molecular mass measurement system. The method includes (a) conveying a first probe from a first rinse position to a first spray position of the molecular mass measurement system in which the first rinse position and the first spray position are substantially electrically isolated from one another and wherein the first spray position is in fluid communication with the ion source housing; and (b) conveying a second probe from a second spray position to a second rinse position of the molecular mass measurement system, wherein the second spray position and the second rinse position are substantially electrically isolated from one another. The method also includes (c) spraying at least a first sample aliquot into the ion source housing via the first probe when the first probe is in the first spray position; (d) rinsing the second probe when the second probe is in the second rinse position; and (e) conveying the first probe from the first spray position to the first rinse position. In addition, the method also includes (f) conveying the second probe from the second rinse position to the second spray position in which the second spray position is in fluid communication with the ion source housing; (g) spraying at least a second sample aliquot into the ion source housing of the molecular mass measurement system via the second probe when the second probe is in the second spray position; and (h) rinsing the first probe when the first probe is in the first rinse position, thereby spraying the sample aliquots into the ion source housing of the molecular mass measurement system. In certain embodiments, the method includes performing (a) substantially simultaneously with (b), (c) substantially simultaneously with (d), (e) substantially simultaneously with (f), and/or (g) substantially simultaneously with (h).

In some embodiments, the method includes modulating a temperature of the first probe and/or second probe using at least one thermal modulator operably connected to the first probe and/or second probe. Typically, the method includes ionizing the first sample aliquot and the second sample aliquot when the first sample aliquot and the second sample aliquot are sprayed into the ion source housing. The method also generally includes measuring a molecular mass of at least one component of the first sample aliquot and/or the second sample aliquot using the molecular mass measurement system. In some embodiments, the component of the first sample aliquot and/or the second sample aliquot comprises at least one nucleic acid molecule. In these embodiments, the method generally comprises determining a base composition of the nucleic acid molecule from the molecular mass of the nucleic acid molecule. In certain of these embodiments, the method includes correlating the base composition of the nucleic acid molecule with an identity or property of the nucleic acid molecule.

The present invention provides devices, apparatuses, and systems for lifting and mounting of clinical- and research-related equipment. In certain exemplary embodiments, the present invention provides a lift and mount system for mass spectrometers (e.g., for time of flight (TOF) mass spectrometers (MS) of TOF-MS) (see e.g., those devices and components of such devices described in U.S. patent application. Ser. Nos. 61/152,214, 29/328,150, 29/328,151, 29/330,905, and 29,330,904, herein incorporated by reference in their entireties; see also T5000 device of Ibis Biosciences, Inc.). In some embodiments, the devices, apparatuses, and systems provide a safe and secure scaffold for moving, positioning, mounting, and using a large and/or heave analytical machine.

In some embodiments, the present invention provides a system comprising: (a) an device, wherein the device comprises a biomedical, biophysical, or biochemical device, and (b) an apparatus, wherein the apparatus comprises (i) a mounting assembly and (ii) a structural assembly, wherein the structural assembly comprises a platform member, wherein the mounting assembly is configured to lift the device to a height higher than the height of the platform member, wherein the mounting assembly is configured to retract the device into a position directly above the platform member, wherein the mounting assembly is configured to lower the device onto the platform member, and wherein the structural assembly and the platform member are configured to stably support the device. In some embodiments, the mounting assembly is supported by the structural assembly. In some embodiments, the mounting assembly is located atop the structural assembly. In some embodiments, the mounting assembly comprises a lifting assembly and a retracting assembly.

In some embodiments, the retracting assembly is configured to extend the lifting assembly beyond the front of the structural assembly, and the retracting assembly is configured retract the lifting assembly within the structural assembly and above the platform member. In some embodiments, the lifting assembly comprises one or more device engagement members, wherein the device engagement members extend from the lifting assembly to the device, and wherein the device engagement members are configured to stably engage and support the device. In some embodiments, the device engagement members are configured to retract toward the top of the system, thereby lifting the device. In some embodiments, the lifting assembly is configured to lift the device to a height which is higher than the height of the platform member. In some embodiments, the retracting assembly is configured retract the lifting assembly and the device within the structural assembly and directly above the platform member. In some embodiments, the lifting assembly is configured to extend the device engagement members, thereby setting the device onto the platform member. In some embodiments, the present invention comprises an accessory assembly, wherein the accessory assembly is configured to support one or more accessory devices, wherein the accessory devices are configured to function in conjunction with the device (e.g., in fluid, electronic, or mechanical communication with the device). In some embodiments, the accessory assembly is attached to the structural assembly. In some embodiments, the device comprises a mass spectrometer.

The present invention further provides apparatuses, as described above, lacking the device (e.g., but configured for moving, mounting, or using such a device). In some embodiments, the present invention provides an apparatus comprising: (a) a structural assembly and (b) a mounting assembly, wherein the mounting assembly is located atop the structural assembly and the mounting assembly is supported by the structural assembly, wherein the structural assembly comprises a platform member, wherein the mounting assembly comprises a lifting assembly and a retracting assembly, wherein the lifting assembly is configured to lift the device to a height higher than the height of the platform member, wherein the retracting assembly is configured to retract the lifting assembly and the device into a position directly above the platform member, wherein the lifting assembly is configured to lower the device onto the platform member, and wherein the structural assembly and the platform member are configured to stably support the device. In some embodiments, the device comprises a mass spectrometer. In some embodiments, the lifting assembly comprises a device engagement member.

The present invention further provides methods of moving, positioning, mounting, and using devices. For example, in some embodiments, the present invention provides a method comprising: (a) providing: (i) an apparatus as described in any of the embodiments herein, and (ii) a device, (b) engaging of the device with the device engagement member of the lifting assembly of the apparatus, (c) lifting the device by the lifting assembly of the apparatus, wherein lifting comprises lifting the device to a height wherein the bottom of the device reaches a height higher than the platform member of the apparatus, (d) retracting the device and the lifting assembly by the retracting assembly, wherein retracting results in the device being positioned above the platform member, and (e) lowering the device by the lifting assembly of the apparatus, wherein lowering results in the device being positioned onto the platform member. In some embodiments, the present invention further comprises using the device for its designated purpose. In some embodiments, the device comprises a mass spectrometer.

In some embodiments, the present invention provides a system, comprising one or more of: a) at least one sample container handling component that comprises at least one non-priority sample container storage unit and at least one priority sample container storage unit that each store at least one sample container that is configured to contain one or more samples; b) at least one mixing station that comprises at least one mixing container and at least one mixing mechanism that is configured to mix at least one composition comprising magnetically responsive particles disposed in the mixing container; c) at least one sample processing component that comprises one or more of: i) at least one sample processing unit that comprises: at least one sample processing vessel that is configured to contain at least one sample comprising at least one magnetically responsive particle; at least one magnet that generates, or is configured to generate, at least one magnetic field at least proximal to the sample processing vessel; and ii) at least one carrier mechanism operably connected to the sample processing unit, which carrier mechanism is configured to move the sample processing unit to one or more locations; d) at least one detection component that is configured to detect at least one detectable property of at least one sample component; e) at least one material transfer component that is configured to transfer material to and/or from the sample container handling component, the mixing station, the sample processing component, and/or the detection component; and, f) at least one controller operably connected to, and configured to effect operation of, the sample container handling component, the mixing station, the sample processing component, and/or the detection component.

In some embodiments, the non-priority sample container storage unit and the priority sample container storage unit are each configured to store at least one microplate.

In some embodiments, the sample processing vessel comprises at least one cuvette.

In some embodiments, the magnet is in a substantially fixed position.

In some embodiments, the detection component comprises at least one mass spectrometer.

In some embodiments, the detection component comprises at least one biopolymer sequencing component.

In some embodiments, the system comprises at least one sample preparation component and/or at least one nucleic acid amplification component.

In some embodiments, the system comprises at least one database.

In some embodiments, the system comprising: at least one sample container processing area; at least one non-priority sample container holding area; and, at least one sample container transport mechanism that is configured to transport one or more sample containers between the non-priority sample container storage unit, the priority sample container storage unit, the priority sample container storage unit, the sample container processing area, and/or the non-priority sample container holding area. In some embodiments, the controller is configured to selectively direct the sample container transport mechanism to carry out one or more of: transport a non-priority sample container from the non-priority sample container storage unit to the sample container processing area; position the non-priority sample container while in the sample container processing area; transport the non-priority sample container from the sample container processing area to the non-priority sample container holding area when a priority sample container is stored in the priority sample container storage unit; transport the priority sample container from the priority sample container storage unit to the sample container processing area; position the priority sample container while in the sample container processing area; transport the priority sample container from the sample container processing area to the non-priority sample container storage unit or to the priority sample container storage unit; transport the non-priority sample container from the non-priority sample container holding area to the sample container processing area; and transport the non-priority sample container from the sample container processing area to the non-priority sample container storage unit.

In some embodiments, the mixing container comprises a cartridge that comprises: at least one body structure comprising one or more surfaces that define a cavity having upper and lower portions; at least one rotatable member extending at least partially along an axis that is substantially horizontally disposed in the upper portion of the cavity; and at least one protrusion extending outward from the rotatable member and into the lower portion of the cavity.

In some embodiments, the mixing mechanism comprises at least one cartridge receiver/rotation assembly that comprises: at least one cartridge support structure that supports the body structure of the cartridge; and a rotational mechanism operably connected to the rotatable member.

In some embodiments, the controller is configured to selectively direct the rotational mechanism to rotate the rotatable member in an initiation mode or in a maintenance mode, wherein a rate of rotation of the rotatable member is greater in the initiation mode than in the maintenance mode.

In some embodiments, the sample processing unit comprises: at least a first motor operably connected to the sample processing vessel, which first motor is configured to rotate the sample processing vessel around a central longitudinal axis of the sample processing vessel; at least one support member operably connected to the first motor; and, at least a second motor operably connected to the support member, which second motor is configured to rotate the sample processing vessel between at least first and second positions, wherein at least the first position is within magnetic communication with the magnet when the magnet generates the magnetic field. In some embodiments, the controller is configured to effect one or more of: the magnet to generate the magnetic field, the first motor to rotate the sample processing vessel, the second motor to rotate the sample processing vessel between the first and second positions, the carrier mechanism to move the sample processing unit to the one or more locations, or the material transfer component to transfer the material to and/or from the sample processing vessel. In some embodiments, the controller is configured to effect the first motor to rotate the sample processing vessel in one or more selectable modes.

The present invention further provides a system, comprising: a) a sample processing unit comprising a magnet; b) a container for containing a reagent housed in said sample processing unit; and c) a sample transfer component for transferring reagent from said container to a different region of said sample processing unit; wherein said sample transfer component comprises a channel configured to withdraw reagent from said container, said channel comprising a metal base and a non-metal tip. In some embodiments, the non-metal tip is a plastic or ceramic tip. In some embodiments, the container houses said reagent. In some embodiments, the reagent comprises magnetic particles.

The present invention further provides a system, comprising: a) a reagent housing component configured to house a plurality of reagent containers, said reagent housing component having a capacitive level sensor that measures the level of reagent in said reagent containers, said reagent housing component having an alarm system, said alarm system configured to generate a signal identifying one or more of said reagent containers falling above or below a predetermined threshold level of reagent, said level identify by said capacitive level sensor; b) a sample processing unit configured to process a biological sample using said reagents; c) a reagent transfer mechanism for transferring reagents from one or more of said plurality of reagent containers to said sample processing unit; and d) a housing covering said sample processing unit and at least part of said reagent housing component and said reagent transfer mechanism; said housing having an alarm display that displays a signal on the visible from the outer surface of said housing, said alarm display being triggered if any one or more of said reagent housing components falls above or below said predetermined threshold level. In some embodiments, the alarm system comprises a light located under each of said reagent containers, wherein said lights are configured to identify individual members of said plurality of containers that fall above or below said predetermined threshold level. In some embodiments, alarm display comprises one or more colored lights. In some embodiments, the reagent housing component is removably contained within said housing.

The present invention further provides methods for using any of the system disclosed herein. In some embodiments, such methods comprise: a) providing a system disclosed herein; b) introducing a sample into the system; c) processing the sample using the system to generate data; and d) displaying the data. In some embodiments, the sample is a biological or environmental sample. In some embodiments, the sample comprises one or more pathogenic organisms. In some embodiments, the sample comprises nucleic acid from one or more pathogenic organisms. In some embodiments, the processing comprises amplifying a portion the nucleic acid to generate an amplicon. In some embodiments, the data comprises a mass of said amplicon. In some embodiments, the data comprises a base composition of said amplicon. In some embodiments, the data comprises an identity of an organism associated with said nucleic acid.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 1C schematically shows the cartridge of FIG. 1A further including a sealing member from a perspective view.

FIG. 1D schematically illustrates the cartridge of FIG. 1C from a top view.

FIG. 1E schematically depicts the cartridge of FIG. 1C from a transparent top view.

FIG. 1F schematically shows the cartridge of FIG. 1C from a bottom view.

FIG. 1G schematically illustrates the cartridge of FIG. 1C from a transparent bottom view.

FIG. 1H schematically illustrates the cartridge of FIG. 1C from a front elevation view.

FIG. 1I schematically depicts the cartridge of FIG. 1C from a transparent front elevation view.

FIG. 1J schematically illustrates the cartridge of FIG. 1C from a back elevation view.

FIG. 1K schematically shows the cartridge of FIG. 1C from a transparent back elevation view.

FIG. 1L schematically illustrates the cartridge of FIG. 1C from a side elevation view.

FIG. 1M schematically depicts the cartridge of FIG. 1C from a transparent side elevation view.

FIG. 1N schematically shows the cartridge of FIG. 1C from a cross-sectional side elevation view.

FIG. 2A schematically illustrates a cartridge from a perspective view according to one embodiment of the invention.

FIG. 2B schematically shows the cartridge of FIG. 2A from a top view.

FIG. 2C schematically shows components of the cartridge of FIG. 2A from a partially exploded, cross-sectional side elevation view.

FIG. 2D schematically depicts the cartridge of FIG. 2A from a cross-sectional side elevation view.

FIG. 3A schematically shows the rotatable member and protrusions from the cartridge of FIG. 1A from a perspective view.

FIG. 3B schematically shows the rotatable member and protrusions of FIG. 3A from a side elevation view.

FIG. 3G schematically shows the rotatable member and protrusions of FIG. 3A with a projection attached to the rotatable member from a perspective view.

FIG. 3H schematically illustrates the rotatable member and protrusions of FIG. 3A disposed in a cartridge cavity from a perspective view.

FIG. 4 schematically illustrates a cartridge having magnetic coupler from a partially transparent bottom view according to one embodiment of the invention.

FIG. 5B schematically shows the mixing station of FIG. 5A from a side elevation view.

FIG. 6A schematically shows the cartridge receiver/rotation assembly of the mixing station of FIG. 5A from a perspective view.

FIG. 6C schematically illustrates the cartridge receiver/rotation assembly of the mixing station of FIG. 5A from a bottom view.

FIG. 6D schematically depicts the cartridge receiver/rotation assembly of the mixing station of FIG. 5A from a side elevation view.

FIG. 8 is a block diagram showing a representative logic device in which various aspects of the present invention may be embodied.

FIG. 9A schematically illustrates selected components of a representative system that includes a mixing station as a subsystem component from a perspective view according to one embodiment of the invention.

FIG. 9B schematically shows the representative system of FIG. 9A from a front elevation view.

FIG. 9C schematically depicts the representative system of FIG. 9A from a rear elevation view.

FIG. 9D schematically shows the representative system of FIG. 9A from a side elevation view.

FIG. 9E schematically illustrates the representative system of FIG. 9A from a top elevation view.

FIG. 9F schematically depicts the representative system of FIG. 9A from a cross-sectional view.

FIG. 9G schematically illustrates the representative system of FIG. 9A from a cross-sectional view.

FIG. 10 schematically shows additional components of the representative system of FIG. 9A from a perspective view.

FIG. 11A schematically illustrates the representative system of FIG. 9A with an external covering from a perspective view.

FIG. 11B schematically illustrates the representative system of FIG. 9A with an external covering from a front elevation view.

FIG. 11C schematically shows the representative system of FIG. 9A with an external covering from a side view.

FIG. 12 schematically shows a microplate handling system from a perspective view according to one embodiment of the invention.

FIG. 13A schematically illustrates a microplate storage unit with a handle in an open position from a perspective view according to one embodiment of the invention.

FIG. 13B schematically depicts the microplate storage unit of FIG. 2A with the handle in a partially closed and unlocked position.

FIG. 13C schematically shows the microplate storage unit of FIG. 2A with the handle in a closed and locked position.

FIG. 15A schematically illustrates selected components of a representative system that includes a microplate handling system as a sub-system component from a perspective view according to one embodiment of the invention.

FIG. 15B schematically shows the representative system of FIG. 4A from a front elevation view.

FIG. 15C schematically depicts the representative system of FIG. 4A from a rear elevation view.

FIG. 15D schematically shows the representative system of FIG. 4A from a side elevation view.

FIG. 15E schematically illustrates the representative system of FIG. 4A from a top elevation view.

FIG. 15F schematically depicts the representative system of FIG. 4A from a cross-sectional view.

FIG. 15G schematically illustrates the representative system of FIG. 4A from a cross-sectional view.

FIG. 16 schematically shows additional components of the representative system of FIG. 4A from a perspective view.

FIG. 17C schematically shows the representative system of FIG. 4A with an external covering from a side view.

FIG. 19A schematically illustrates non-priority microplates stored in an input non-priority microplate storage unit of a microplate handling system from a perspective view according to one embodiment of the invention.

FIG. 19B schematically shows a non-priority microplate positioned in microplate processing area of the microplate handling system of FIG. 8A after being transported from an input non-priority microplate storage unit.

FIG. 19C schematically illustrates a priority microplate stored in a priority microplate storage unit of the microplate handling system of FIG. 8A, while a non-priority microplate is positioned in a microplate processing area of the microplate handling system.

FIG. 19D schematically shows a priority microplate positioned in a microplate processing area of the microplate handling system of FIG. 8A after a non-priority microplate has been transported and positioned in a non-priority microplate holding area of the microplate handling system.

FIG. 19E schematically shows a platform of a microplate transport mechanism in a microplate processing area of the microplate handling system of FIG. 8A after the microplate transport mechanism transported a priority microplate to an output non-priority microplate storage unit.

FIG. 19F schematically depicts a non-priority microplate positioned in a microplate processing area of the microplate handling system of FIG. 8A after a microplate transport mechanism of the microplate handling system transported the non-priority microplate from a non-priority microplate holding area of the microplate handling system.

FIG. 22A schematically shows a sample processing unit with a cuvette in a first position from a perspective view according to one embodiment of the invention.

FIG. 22B schematically depicts the sample processing unit of FIG. 2A with the cuvette in a second position from a perspective view.

FIG. 24B schematically shows the carrier mechanism and manifold of FIG. 4A from a side elevation view.

FIG. 24C schematically shows the carrier mechanism and manifold of FIG. 4A from a top view.

FIG. 24D schematically illustrates a detailed perspective view of the carrier mechanism and manifold of FIG. 4A.

FIG. 24E schematically depicts a detailed side elevation view of the carrier mechanism and manifold of FIG. 4A.

FIG. 24F schematically depicts a detailed front elevation view of the carrier mechanism and manifold of FIG. 4A.

FIG. 27A schematically illustrates selected components of a representative system that includes a sample processing station as a sub-system component from a perspective view according to one embodiment of the invention.

FIG. 27B schematically shows the representative system of FIG. 7A from a front elevation view.

FIG. 27C schematically depicts the representative system of FIG. 7A from a rear elevation view.

FIG. 27D schematically shows the representative system of FIG. 7A from a side elevation view.

FIG. 27E schematically illustrates the representative system of FIG. 7A from a top elevation view.

FIG. 27F schematically depicts the representative system of FIG. 7A from a cross-sectional view.

FIG. 27G schematically illustrates the representative system of FIG. 7A from a cross-sectional view.

FIG. 28 schematically shows additional components of the representative system of FIG. 7A from a perspective view.

Figure 37:
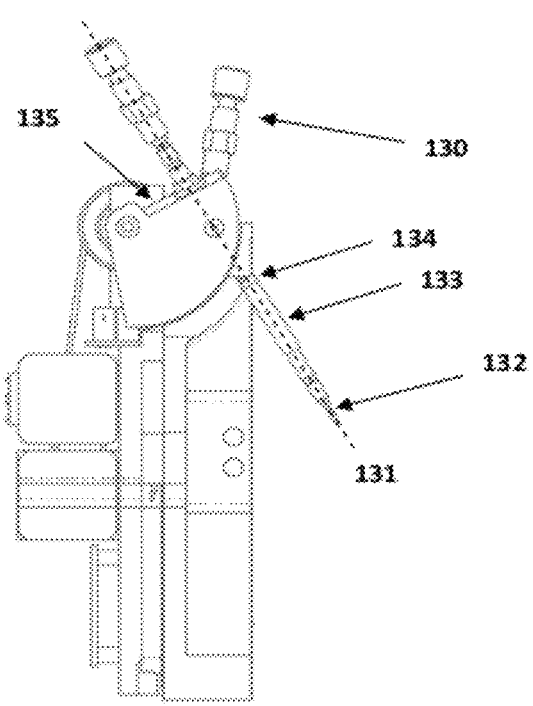

FIG. 37 schematically shows a dual sprayer probe mounted on a dual sprayer.

Figure 38:
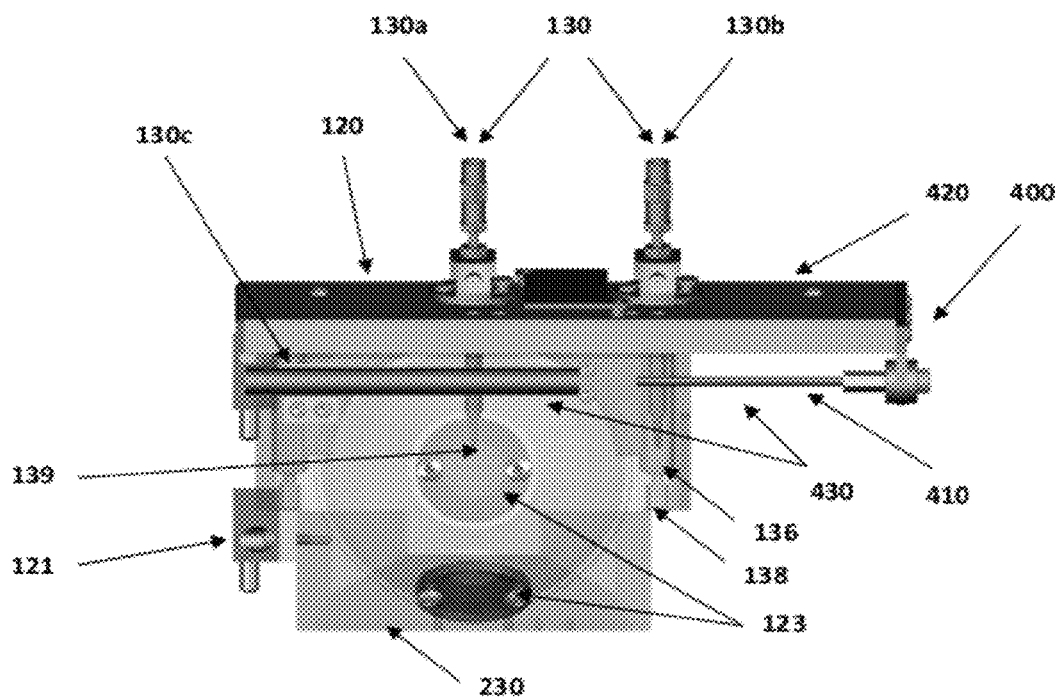

FIG. 38 schematically shows a dual sprayer with two probes mounted on a sliding mechanism.

FIG. 39a schematically shows a dual sprayer having a first probe in a first position and a second probe in a second position.

FIG. 39b schematically shows a dual sprayer having a first probe in a second position and a second probe in a first position.

Figure 40:
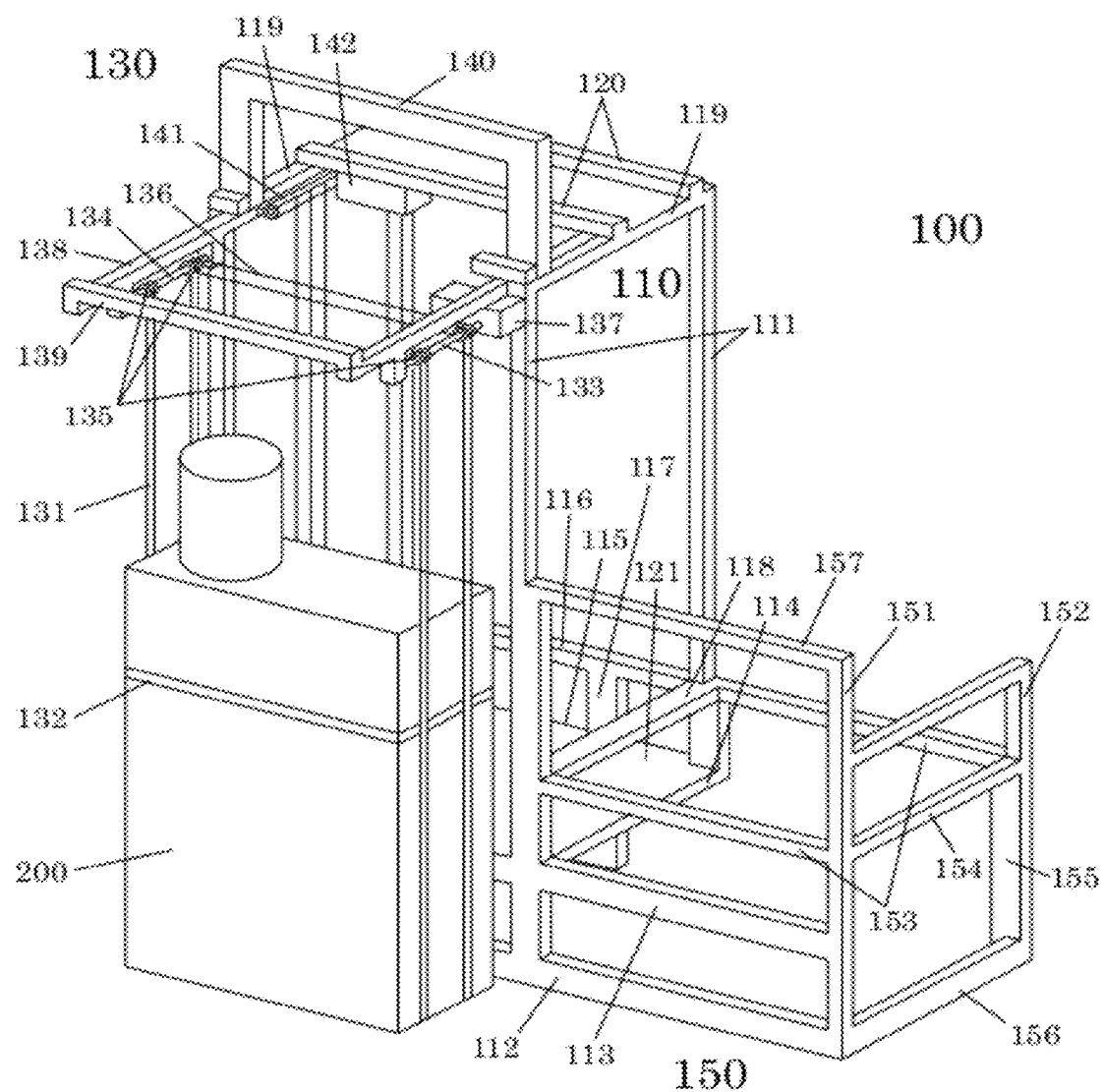

FIG. 40 shows a schematic of an exemplary apparatus in the unmounted conformation.

Figure 41:
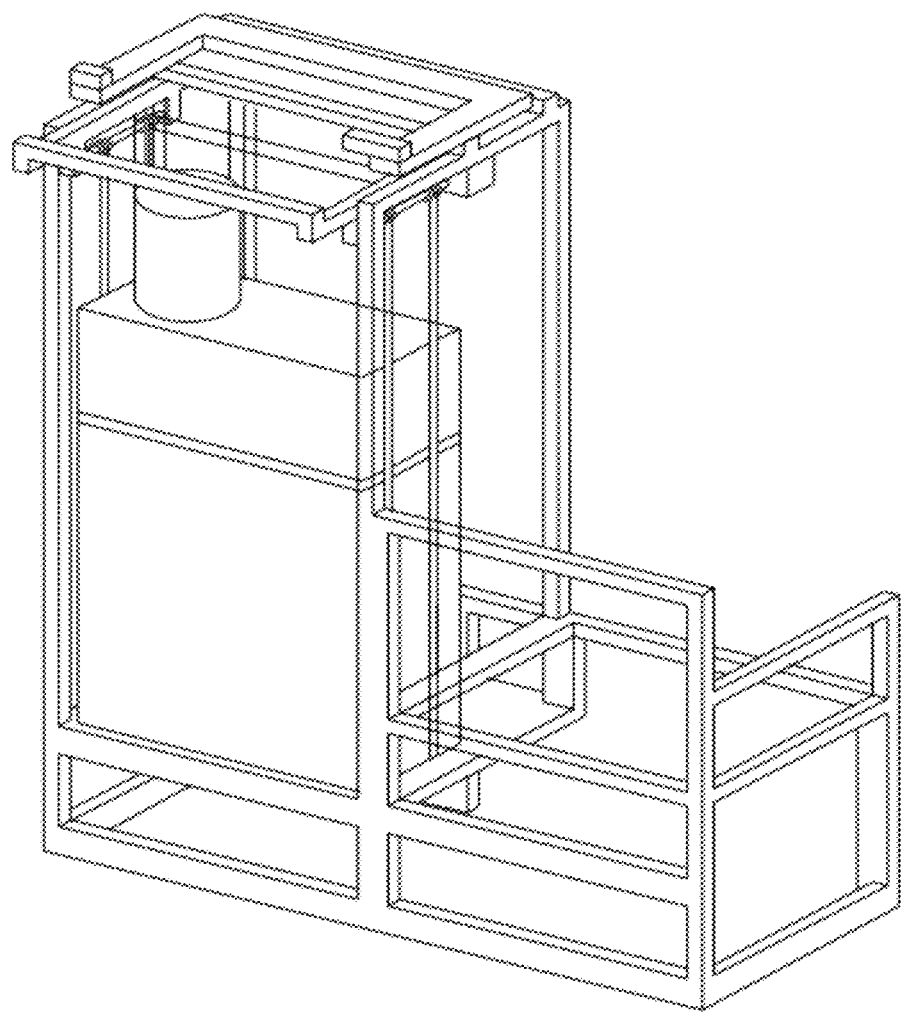

FIG. 41 shows a schematic of an exemplary apparatus with a mounted TOF-MS.

Figure 42A:
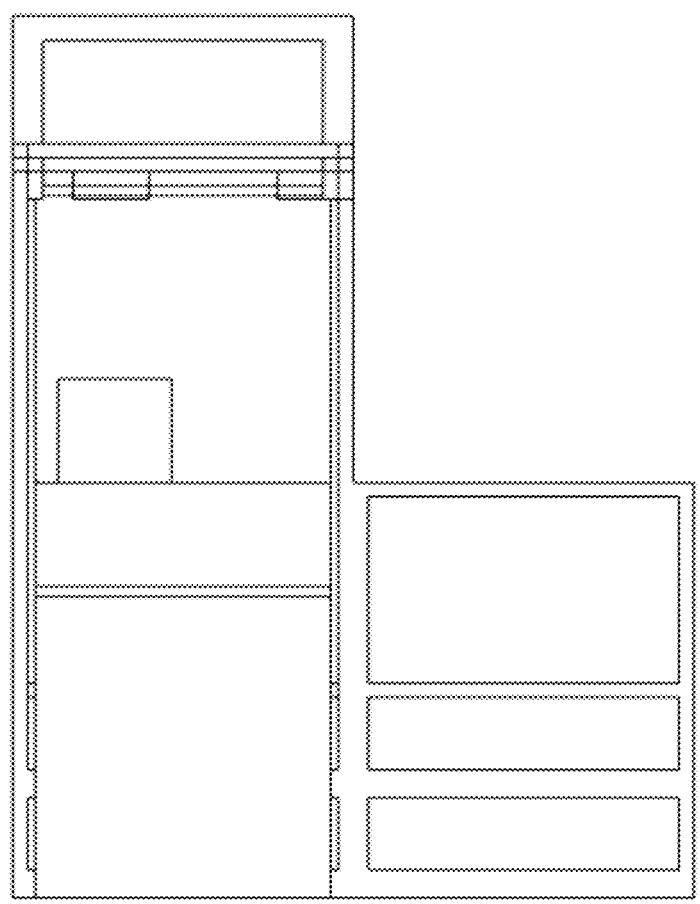
Figure 42B:
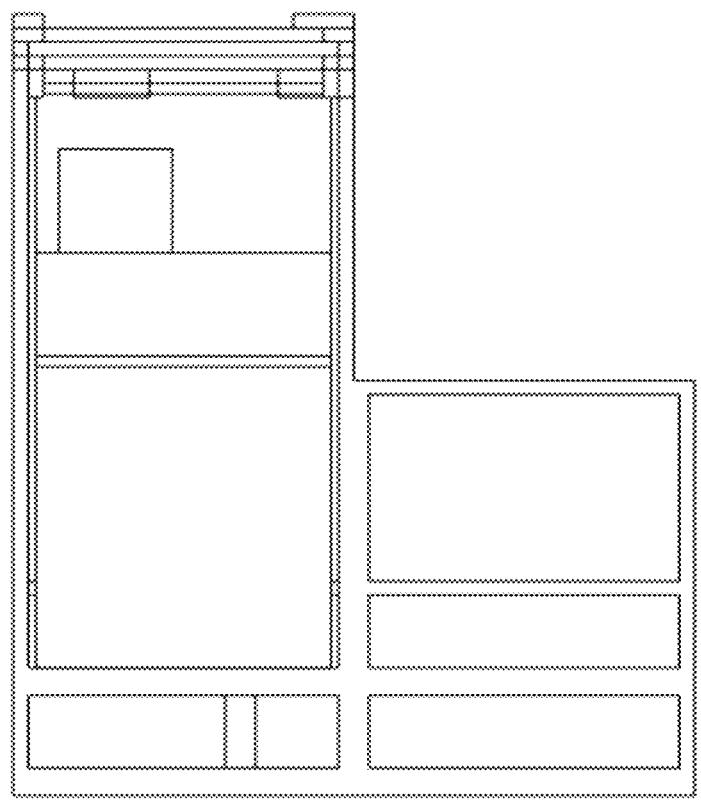

FIG. 42 shows a schematic of an exemplary apparatus: A) prior to mounting a TOF-MS, and B) with a mounted TOF-MS.

FIG. 43 shows a schematic of the right view of an exemplary apparatus: A) prior to mounting a TOF-MS, and B) with a mounted TOF-MS.

Figure 44A:
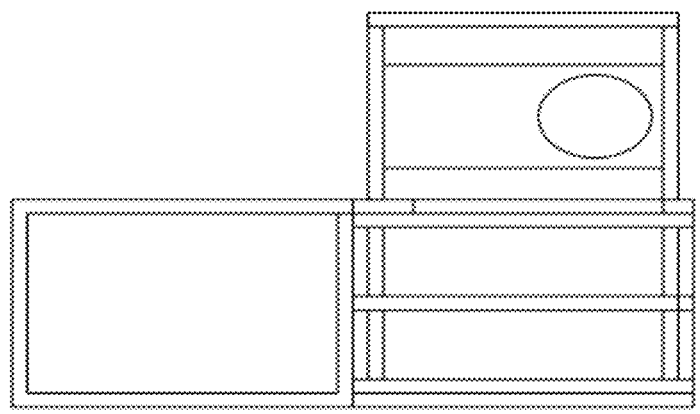
Figure 44B:
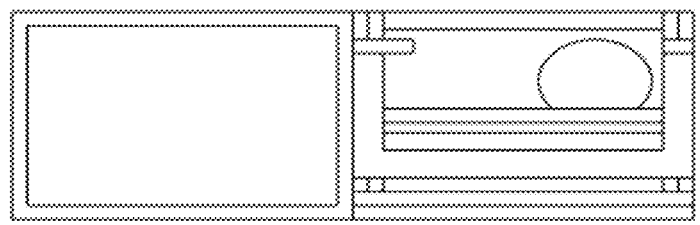

FIG. 44 shows a schematic of the top view of an exemplary apparatus: A) prior to mounting a TOF-MS, and B) with a mounted TOF.

Figure 45:
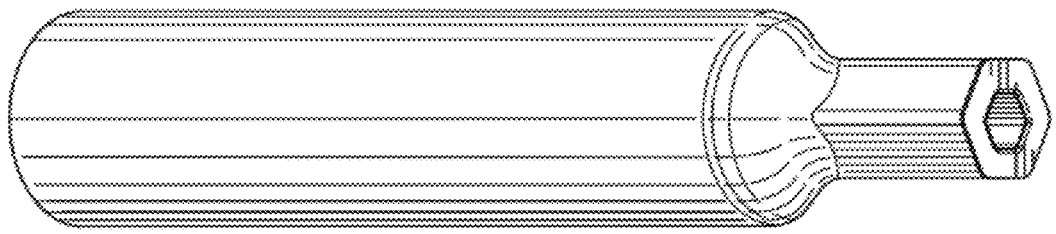

FIG. 45 shows a top perspective view of an exemplary spin cuvette.

Figure 46:
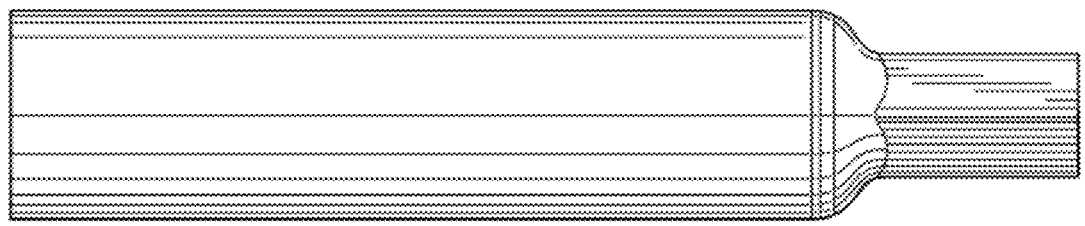

FIG. 46 shows a top plan view of an exemplary spin cuvette.

Figure 47:
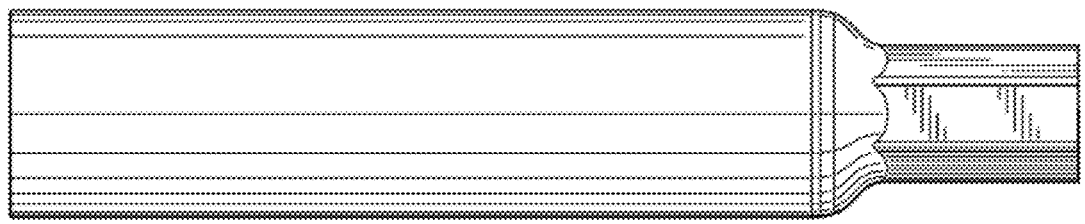

FIG. 47 shows a left side elevational view of an exemplary spin cuvette.

Figure 48:
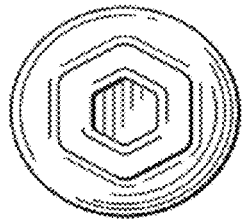

FIG. 48 shows a front elevational view of an exemplary spin cuvette.

Figure 49:
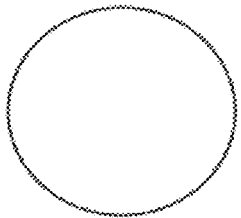

FIG. 49 shows a rear elevational view of an exemplary spin cuvette.

Figure 50:
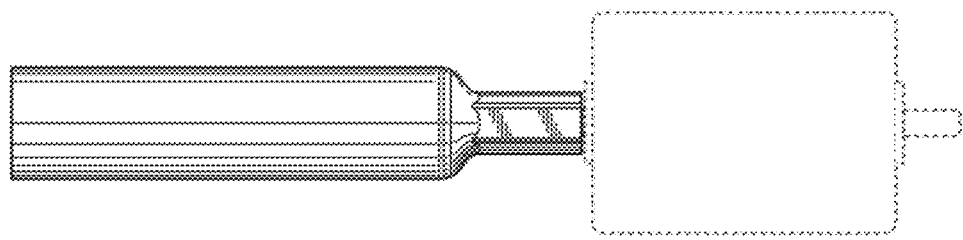

FIG. 50 shows an alternate left side elevational view of an exemplary spin cuvette.

Figure 51:
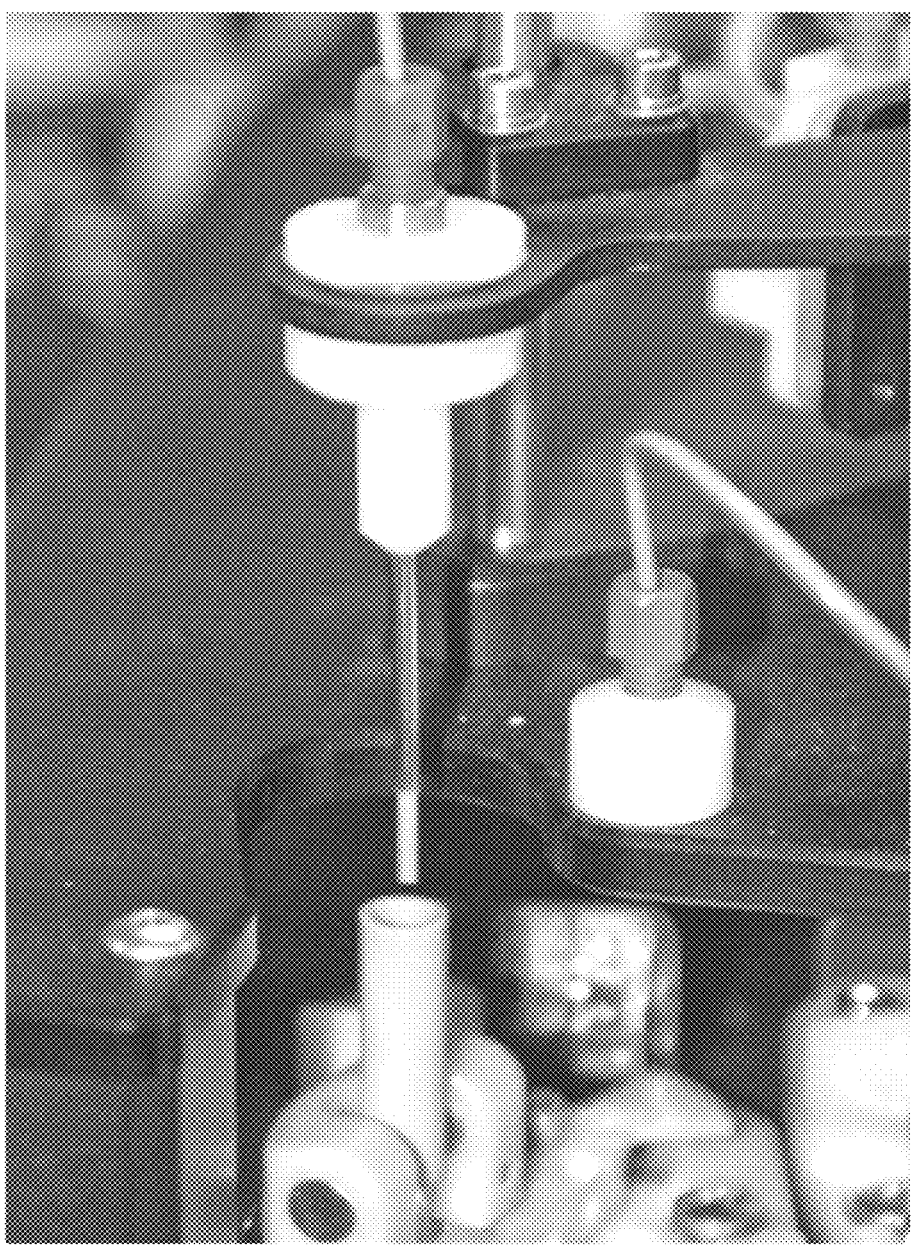

FIG. 51 shows one embodiment of an aspirate needle of the present invention.

Figure 52:
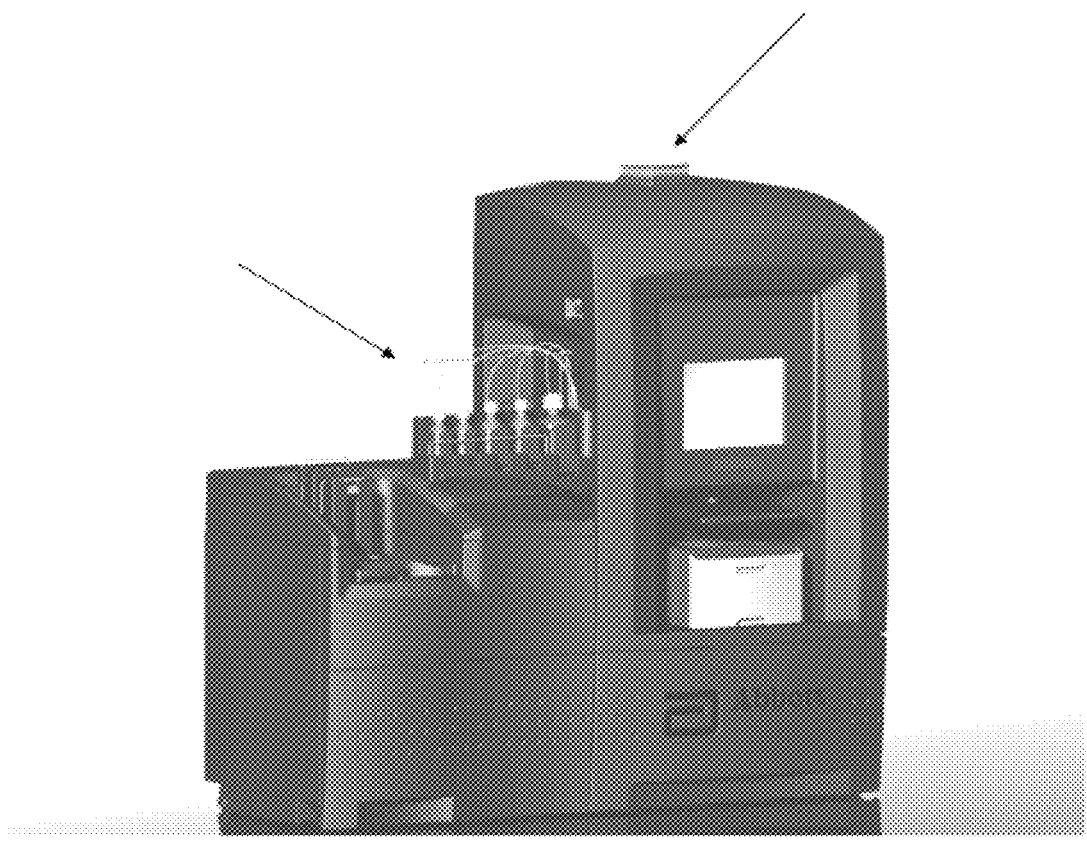

FIG. 52 shows one embodiment of an integrated bioagent detection system of the present invention. FIG. 52 shows the reagent rack swung forward into a loading position.

Figure 53:
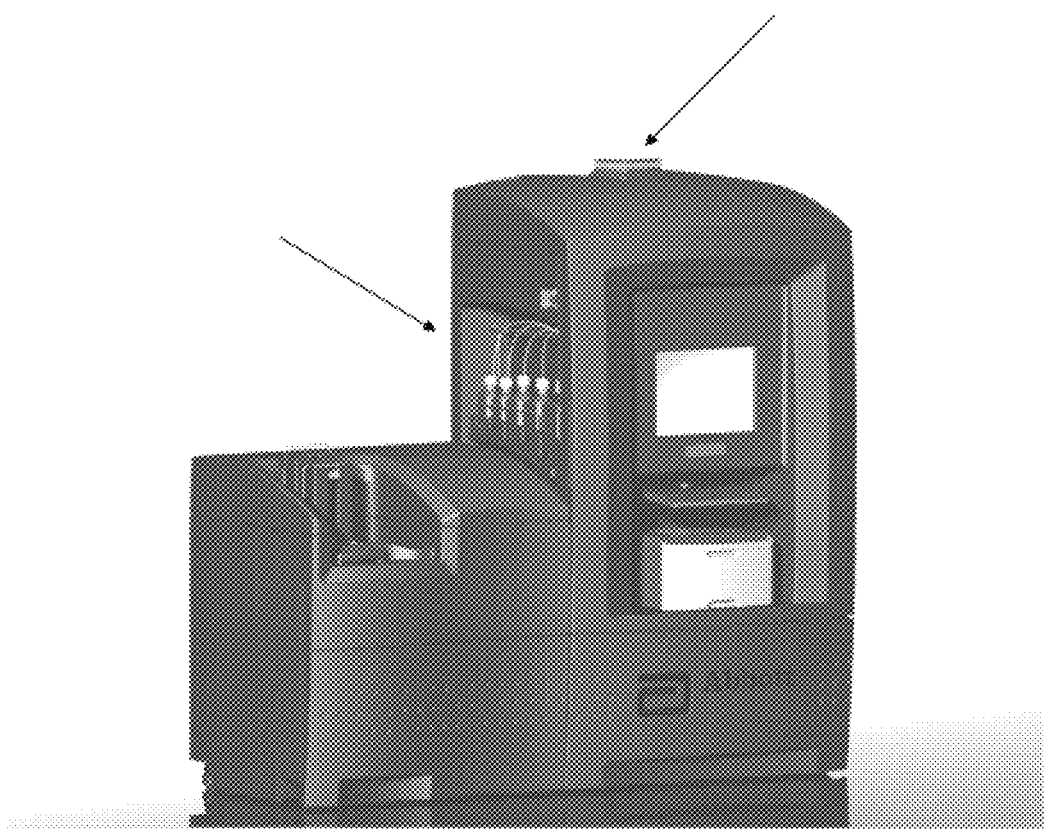

FIG. 53 shows one embodiment of an integrated bioagent detection system of the present invention. FIG. 53 shows the reagent rack swung back into a run position.

FIG. 54 shows one embodiments of the signal light of the present invention. FIG. 54A shows the signal light with the translucent cover covering LED lights. FIG. 54B shows the cover removed from the light, showing the internal LED light system. FIG. 54C shows a close up view of the LED light system, which is composed of 3 roes of 120 degree angle LED's (blue, red, and amber) which has variable intensity for each.

FIG. 55A shows three bottles, with two of the bottle (left and right) being one color to indicate an acceptable reagent level, and the middle bottle being a different color indicating a low level of reagent in this bottle. FIG. 55B shows a light emitting diodes (LEDs) underneath a reagent bottle such that the color of the reagent bottle can be illuminated to indicate liquid level in the reagent bottle.

DEFINITIONS

Before describing the invention in detail, it is to be understood that this invention is not limited to particular cartridges, mixing stations, systems, kits, or methods, which can vary. As used in this specification and the appended claims, the singular forms "a," "an," and "the" also include plural referents unless the context clearly provides otherwise. Thus, for example, reference to "a cartridge" includes a combination of two or more cartridge. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

The term "base composition" refers to the number of each residue comprised in an amplicon or other nucleic acid, without consideration for the linear arrangement of these residues in the strand(s) of the amplicon. The amplicon residues comprise, adenosine (A), guanosine (G), cytidine, (C), (deoxy)thymidine (T), uracil (U), inosine (I), nitroindoles such as 5-nitroindole or 3-nitropyrrole, dP or dK (Hill F et al. (1998) "Polymerase recognition of synthetic oligodeoxyribonucleotides incorporating degenerate pyrimidine and purine bases" *Proc Natl Acad Sci U.S.A.* 95(8):4258-63), an acyclic nucleoside analog containing 5-nitroindazole (Van Aerschot et al., Nucleosides and Nucleotides, 1995, 14, 1053-1056), the purine analog 1-(2-deoxy-beta-D-ribofuranosyl)-imidazole-4-carboxamide, 2,6-diaminopurine, 5-propynyluracil, 5-propynylcytosine, phenoxazines, including G-clamp, 5-propynyl deoxy-cytidine, deoxy-thymidine nucleotides, 5-propynylcytidine, 5-propynyluridine and mass tag modified versions thereof, including 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, $O^6$-methyl-2'-deoxyguanosine-5'-triphosphate, $N^2$-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$. In some embodiments, the non-natural nucleosides used herein include 5-propynyluracil, 5-propynylcytosine and inosine. Herein the base composition for an unmodified DNA amplicon is notated as $A_w G_x C_y T_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon. Base compositions are calculated from a molecular mass measurement of an amplicon, as described below. The calculated base composition for any given amplicon is then compared to a database of base compositions. A match between the calculated base composition and a single database entry reveals the identity of the bioagent.

The term "communicate" refers to the direct or indirect transfer or transmission, and/or capability of directly or indirectly transferring or transmitting, something at least from one thing to another thing. Objects "fluidly communicate" with one another when fluidic material is, or is capable of being, transferred from one object to another. In some embodiments, for example, an aperture is disposed through a top surface of a cartridge body structure. In these embodiments, the aperture is typically configured to receive a fluid handling component that fluidly communicates with the cavity (e.g., adds and/or removes material to and/or from the cavity). Objects are in "thermal communication" with one another when thermal energy is or can be transferred from one object to another. In certain embodiments, for example, a mixing station includes a thermal modulating component that can transfer thermal energy to and/or receive thermal energy from a cartridge cavity to modulate (e.g., raise and/or lower) temperature of fluidic materials disposed in the cavity. Objects are in "magnetic communication" with one another when one object exerts or can exert a magnetic field of sufficient strength on another object to effect a change (e.g., a change in position or other movement) in the other object. In some embodiments, for example, a rotational mechanism magnetically communicates with a rotatable member of a cartridge via magnetic couplers that effect the rotation of the rotatable member. Objects are in "sensory communication" when a characteristic or property of one object is or can be sense, perceived, or otherwise detected by another object. In certain embodiments, for example, a projection that extends outward from a rotatable member is configured to activate a motion sensor such that movement of the rotatable member can be monitored when the motion sensor is in sensory communication with the projection. To further illustrate, in some embodiments, a detection component is positioned in sensory communication with a cartridge cavity so as to detect one or more parameters (e.g., temperature, pH, or the like) of a fluidic material disposed in the cavity. It is to be noted that there may be overlap among the various exemplary types of communication referred to above.

The phrase "dead zone" in the context of cartridge cavities refers to an area of a cavity in which particles tend to fall out of suspension or otherwise settle even when a fluidic material comprising the particles is agitated or otherwise mixed within the cavity, or to an area of a cavity in which materials are mixed less uniformly or thoroughly than in others within the cavity.

The phrase "horizontally disposed" refers to something that is positioned, and/or operates, in a plane that is parallel to the horizon or to a baseline. In some embodiments, for example, a rotatable member extends at least partially along an axis that is substantially horizontally disposed in the cavity of a cartridge during typical or intended use of the cartridge. An axis is "substantially horizontally disposed" in a cavity when it is either exactly parallel to the horizon or to a baseline, or forms an angle with the horizon or a baseline that is less than 45° (e.g., 40° or less, 35° or less, 30° or less, 25° or less, 20° or less, 15° or less, 10° or less, 5° or less, etc.).

The term "kit" is used in reference to a combination of articles that facilitate a process, method, assay, analysis or manipulation of a sample. Kits can contain instructions describing how to use the kit (e.g., instructions describing the methods of the invention), cartridges, mixing stations, magnetically responsive particles or other particles, chemical reagents, as well as other components. Kit components may be packaged together in one container (e.g., box, wrapping, and the like) for shipment, storage, or use, or may be packaged in two or more containers.

The phrase "laterally disposed" refers to something that extends outward from at least one side of the same or another thing. In some embodiments, for example, a protrusion includes a substantially vertically disposed segment that extends downward from a rotatable member and a substantially laterally disposed segment that extends outward from the substantially vertically disposed segment.

The phrase "lower portion" in the context of a mixing cartridge cavity refers to an area or region of the cavity having a maximum height that is not more than 50% of the maximum height of the entire cavity and which is disposed below another area or region of the cavity during intended operation of the cartridge.

The term "material" refers to something comprising or consisting of matter. The term "fluidic material" refers to material (such as, a liquid or a gas) that tends to flow or conform to the outline of its container.

The term "microplate" refers to a plate or other support structure that includes multiple cavities or wells that are structured to contain materials, such as fluidic materials. The wells typically have volume capacities of less than about 1.5 mL (e.g., about 1000 µL, about 800 µL, about 600 µL, about 400 µL, or less), although certain microplates (e.g., deep-well plates, etc.) have larger volume capacities, such as about 4 mL per well. Microplates can include various numbers of wells, for example, 6, 12, 24, 48, 96, 384, 1536, 3456, 9600, or more wells. In addition, the wells of a microplate are typically arrayed in a rectangular matrix. Microplates generally conform to the standards published by the American National Standards Institute (ANSI) on behalf of the Society for Biomolecular Screening (SBS), namely, ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions, and ANSI/SBS 4-2004: Microplates—Well Positions, which are each incorporated by reference. Microplates are available from a various manufacturers including, e.g., Greiner America Corp. (Lake Mary, Fla., U.S.A.) and Nalge Nunc International (Rochester, N.Y., U.S.A.), among many others. Microplates are also commonly referred to by various synonyms, such as "microtiter plates," "micro-well plates," "multi-well containers," and the like The term "molecular mass" refers to the mass of a compound as determined using mass spectrometry, for example, ESI-MS. Herein, the compound is preferably a nucleic acid. In some embodiments, the nucleic acid is a double stranded nucleic acid (e.g., a double stranded DNA nucleic acid). In some embodiments, the nucleic acid is an amplicon. When the nucleic acid is double stranded the molecular mass is determined for both strands. In one embodiment, the strands may be separated before introduction into the mass spectrometer, or the strands may be separated by the mass spectrometer (for example, electro-spray ionization will separate the hybridized strands). The molecular mass of each strand is measured by the mass spectrometer.

The term "non-priority microplate" refers to a microplate that is processed or otherwise handled after at least one other microplate, or whose processing or handling is interrupted or deferred in order to process or otherwise handle at least one other microplate, in a given microplate handling system of the invention. That is, the order, schedule, or timing of processing or handling a non-priority microplate is subject to interruption or delay when a higher priority microplate is presented, such as a microplate including stat samples. In some embodiments, non-priority microplates are introduced into a given system via non-priority microplate storage units.

The term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-$N^6$-methyladenosine, aziridinylcytosine, pseudoisocytosine, 5-(carboxyhydroxyl-methyl)-uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, $N^6$-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "priority microplate" refers to a microplate that is processed or otherwise handled before the processing or handling of a non-priority microplate is commenced or completed in a given microplate handling system of the invention. In some embodiments, one or more wells of priority microplates comprise stat or urgent samples. In certain embodiments, priority microplates are introduced into a given system via priority microplate storage units.

The term "system" refers a group of objects and/or devices that form a network for performing a desired objective. In some embodiments, for example, mixing stations with cartridges having fluidic materials with magnetically responsive particles are included as part of systems in which nucleic acids are purified using the magnetically responsive particles such that the molecular masses of the nucleic acids can be more readily detected by mass spectrometers of these systems.

The phrase "upper portion" in the context of a mixing cartridge cavity refers to an area or region of the cavity having a maximum height that is not more than about 65% of the maximum height of the entire cavity and which is disposed above another area or region of the cavity during intended operation of the cartridge.

The phrase "vertically disposed" refers to something that is positioned, and/or operates, in a plane that is perpendicular to the horizon or to a baseline. In certain embodiments, for example, the body structure of a cartridge includes a substantially vertically disposed side surface during typical or intended use of the cartridge. As side surface is "substantially vertically disposed" when it is either exactly perpendicular to the horizon or to a baseline, or forms an angle with the horizon or a baseline that is more than 45° and less than 90° (e.g., between about 50° and about 85°, between about 55° and about 80°, between about 60° and about 75°, between about 65° and about 70°, etc.).

DETAILED DESCRIPTION

The present invention provides systems and methods for analysis of samples, particularly biological and environmental sample to detect biomolecules of interest contained therein. A variety of system components are described herein, including, but not limited to, components for sample handling, mixing of materials, sample processing, transfer of materials, and analysis of materials. The invention further provides mechanisms for combining and integrating the different components and for housing, moving, and storing system components or the system as a whole. The systems may include any one or more or all of these components. The system finds particular use when employed for analysis of nucleic acid molecule using mass spectrometry, however, the invention is not limited such specific uses. Exemplary embodiments of certain of these components is described in more detail below. The invention is not limited to these specific embodiments.

I. Mixing Cartridges

The invention relates to material mixing, and in various embodiments provides cartridges, mixing stations, systems, kits, and related methods that are useful for this purpose. In some applications, for example, fluidic materials are mixed such that particles (e.g., magnetically responsive particles or other solid supports, cells, and the like) are maintained in suspension and uniformly distributed within the fluidic material. In other exemplary applications, different particles are mixed with one another, solid materials are dissolved in liquids, different liquids are mixed with one another or emulsified, and gases are distributed within liquid phases. Homogeneous mixtures of materials are commonly used in a host of scientific and industrial processes, including biopolymer purification procedures, compound screening methods, and chemical synthesis schemes, among many others. The cartridges, mixing stations, and other aspects described herein can be used, or readily adapted for use, in these as well as essentially any other application that involves mixtures of materials. These and many other attributes will be apparent upon reviewing the description provided herein.

A. Example Cartridges

Figure 1A:
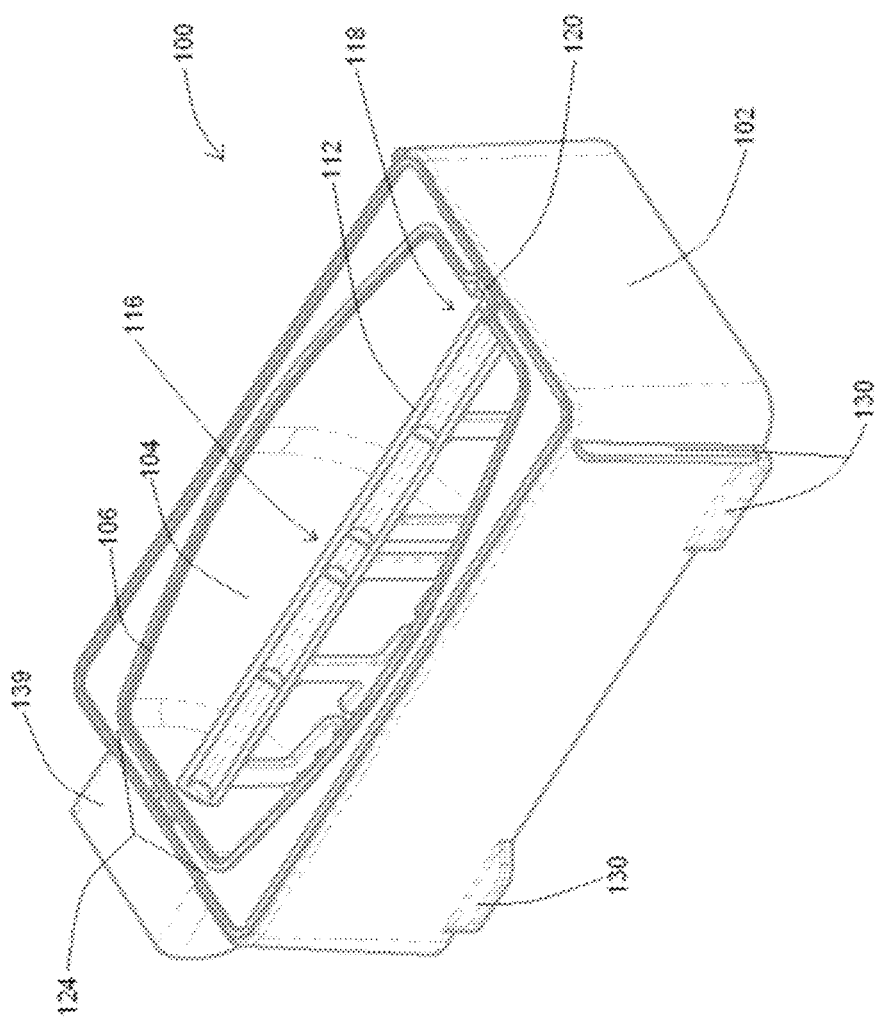
FIG. 1A schematically illustrates a cartridge from a perspective view according to one embodiment of the invention.

FIGS. 1 A-N schematically illustrate a representative mixing cartridge of the invention. As shown, cartridge 100 includes body structure 102, which includes curved surface 104 that partially defines cavity 106 having upper portion 108 and lower portion 110. As further shown, cartridge 100 also includes rotatable member 112 extending along an axis that is substantially horizontally disposed in upper portion 108 of the cavity 106. In addition, protrusions 114 extend outward from rotatable member 112 and into lower portion 110 of cavity 106, e.g., when rotatable member 112 is not being rotated. Protrusions 114 (shown as a blade or paddle) are configured to mix material when the material (e.g., a fluidic material, etc.) is disposed in cavity 106 and a rotational mechanism rotates rotatable member 112 about the substantially horizontally disposed axis. Suitable rotational mechanisms are described further herein.

Body structures are generally dimensioned to be handheld, although other sizes are also optionally utilized. Handheld cartridges are typically readily transportable (e.g., manually or robotically), e.g., to and from cartridge receiver/rotation assemblies in a given mixing station or system, via a carrier service (e.g., the postal service or the like) as a kit component, or the like. In some embodiments, for example, cartridge body structures have heights of about 10 cm or less (e.g., about 9.5 cm, about 9 cm, about 8.5 cm, about 8 cm, about 7.5 cm, about 7 cm, about 6.5 cm, about 6 cm, about 5.5 cm, about 5 cm, about 4.5 cm, about 4 cm, about 3.5 cm, about 3 cm, about 2.5 cm, etc.). In certain embodiments, cartridge body structures have widths of about 15 cm or less (e.g., about 14.5 cm, about 14 cm, about 13.5 cm, about 13 cm, about 12.5 cm, about 12 cm, about 11.5 cm, about 11 cm, about 10.5 cm, about 10 cm, about 9.5 cm, about 9 cm, about 8.5 cm, about 8 cm, about 7.5 cm, about 7 cm, about 6.5 cm, about 6 cm, about 5.5 cm, about 5 cm, about 4.5 cm, about 4 cm, about 3.5 cm, about 3 cm, about 2.5 cm, etc.). In some embodiments, cartridge body structures have lengths of about 20 cm or less (e.g., about 19.5 cm, about 19 cm, about 18.5 cm, about 18 cm, about 17.5 cm, about 17 cm, about 16.5 cm, about 16 cm, about 15.5 cm, about 15 cm, about 14.5 cm, about 14 cm, about 13.5 cm, about 13 cm, about 12.5 cm, about 12 cm, about 11.5 cm, about 11 cm, about 10.5 cm, about 10 cm, about 9.5 cm, about 9 cm, about 8.5 cm, about 8 cm, about 7.5 cm, about 7 cm, about 6.5 cm, about 6 cm, about 5.5 cm, about 5 cm, about 4.5 cm, about 4 cm, about 3.5 cm, about 3 cm, about 2.5 cm, etc.). In some exemplary embodiments, mixing cartridge body structures include a height of about 3.0 cm (e.g., 3.3 cm, 3.2 cm, 3.1 cm, 3.0 cm, 2.9 cm, 2.8 cm, 2.7 cm, etc.), a width of about 5.5 cm (e.g., 5.8 cm, 5.7 cm, 5.6 cm, 5.5 cm, 5.4 cm, 5.3 cm, 5.2 cm, etc.), and a length of about 12.0 cm (e.g., 12.3 cm, 12.2 cm, 12.1 cm, 12.0 cm, 12.9 cm, 12.8 cm, 12.7 cm, etc.). To further illustrate, mixing cartridge body structures can also include a variety of shapes. In some embodiments, for example, body structures include substantially rectangular-shaped, substantially square-shaped, substantially oval-shaped, and/or substantially circular-shaped cross-sections. In addition, mixing cartridges, or body structures thereof, generally include weights of about 1 kg or less (e.g., about 750 grams, 500 grams, 250 grams, 200 grams, 150 grams, 100 grams, 50 grams, etc.). Cartridge fabrication materials and techniques are described further herein.

The cavities of the mixing cartridges include numerous embodiments. For example, they can include various shapes and volume capacities. A mixing cartridge cavity generally has a shape that lacks substantial dead zones (e.g., areas where particles tend to settle or otherwise not be mixed) when a given rotatable member mixes materials in the cavity. In some embodiments, for example, one or more surfaces of a body structure that define its cavity are substantially symmetrical about a substantially horizontally disposed axis (e.g., an axis about which a rotatable member rotates) of the cavity. Curved surface 104 of cavity 106 illustrate one of these embodiments. Further, a radius of curvature of a surface of a given cavity optionally varies along the length of the cavity in some embodiments. As shown, for example, in FIGS. 1B and K, the radius of curvature of curved surface 104 of cavity 106 is larger at central portion 116 of cavity 106 than the radius of curvature near end portion 118 of cavity 106. To further illustrate, a distance between a lower portion of a protrusion of a rotatable member and a surface of the cavity is substantially identical at two or more positions about the axis of the cavity in some embodiments. Protrusions 104 and curved surface 104 of cartridge 100 show one of these embodiments. Typically, the upper portions of cavities include holes, indentations, or the like that receive sections of rotatable members, e.g., to position the rotatable members within the cavities. As an example, cavity 106 of cartridge 100 include indentation 120 and hole 122 that receive sections of rotatable member 112. Although mixing cartridge cavities optionally include other volume capacities, they include volume capacities of about 500 mL or less (e.g., about 450 mL, about 400 mL, about 350 mL, about 300 mL, about 250 mL, about 200 mL, about 150 mL, about 100 mL, about 50 mL, etc.).

In certain embodiments, a top surface of the body structure comprises an opening that communicates with the cavity. As shown, for example, in FIGS. 1A and B, body structure 102 includes opening 124 that communicates with cavity 106. In these embodiments, a mixing cartridge typically includes a sealing member that operably connects to the body structure, e.g., to seal the cavity during operation, transport, or the like. In some embodiments, the sealing member includes a removable cover that is structured to engage one or more surfaces of the body structure. To illustrate, the sealing member optionally includes a film (e.g., a heat sealed or otherwise adhered film) that overlays the opening on the top surface of the body structure. To facilitate communication with the cavity, one or more apertures are generally disposed through the sealing member. In some embodiments, for example, apertures are configured to receive one or more fluid handling components such that the fluid handling components can fluidly communicate with the cavity (e.g., add and/or remove fluidic material to/from the cavity). Fluid handling components are described further below. Typically, an aperture is disposed through the sealing member relative to the rotatable member and to protrusions extending from the rotatable member such that the fluid handling component does not contact the rotatable member or the protrusions when the rotatable member rotates the protrusion and the aperture receives the fluid handling component, e.g., to minimize the chance of damaging these components during operation of a given process. In some embodiments, a closure (e.g., a re-sealable label, a septum, or the like) is disposed in or over the aperture, e.g., to reduce the possibility of contaminating the contents of the cavity, to prevent spillage during transport, to minimize evaporation of fluidic materials in the cavity, etc. In certain embodiments, a closure, such as a sealing label or the like is removed from a cartridge during operation, whereas in other embodiments, a closure such as a self-sealing septum remains positioned in or over an aperture, e.g., when a fluid handling component fluidly communicates with the cavity of the cartridge. To further illustrate, in FIGS. 1 C and D, for example, cartridge 100 includes sealing member 126 (shown as a foil/laminate cover) overlaying opening 124 of cavity 106. Although not within view, for example, in FIGS. 1 C and D, an aperture or fill port is disposed through sealing member 126, but has been covered and sealed by closure 128 (shown as a round seal label).

Figure 1B:
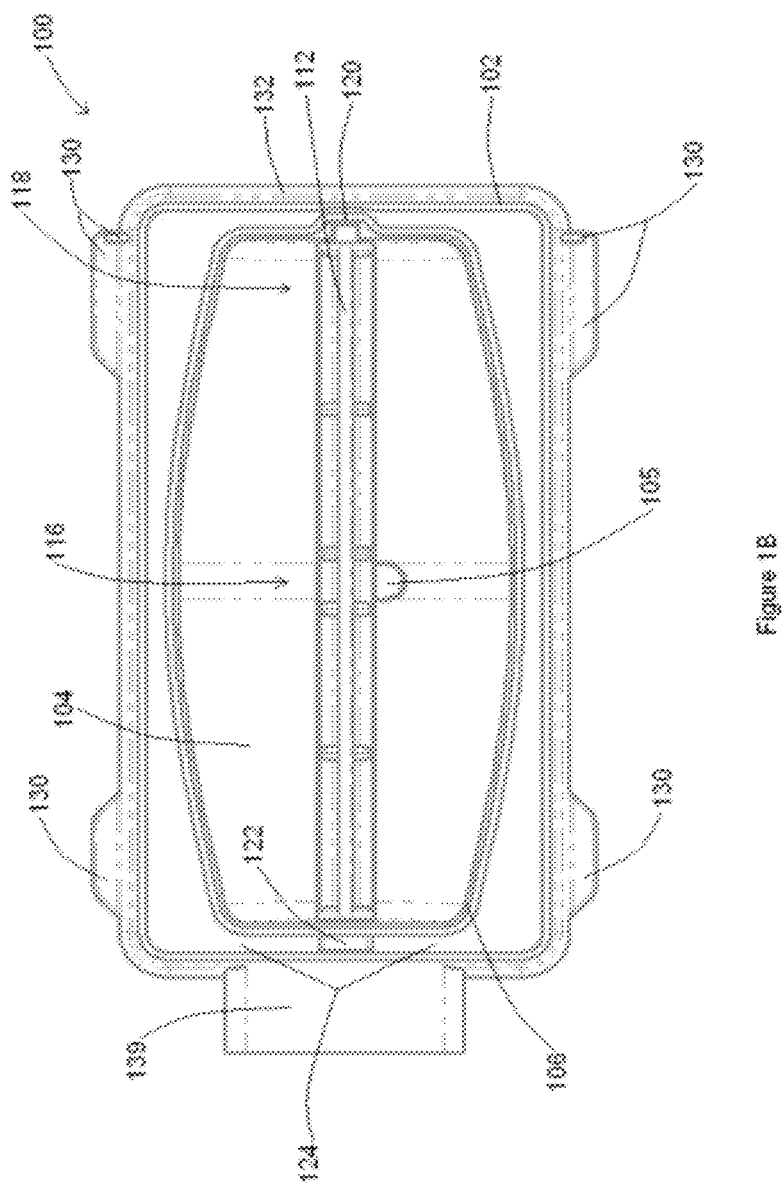
FIG. 1B schematically shows the cartridge of FIG. 1A from a top view.

As also shown, for example, in FIG. 1B, curved surface 104 of cartridge 100 also includes flattened area 105, which aligns with the aperture disposed through sealing member 126 and with closure 128. Flattened areas, such as flattened area 105 are included in certain embodiments to reduce the possibility of a fluid handling component (e.g., a pipette tip or needle) contacting curved surface 104 and causing damage to the fluid handling component and/or cartridge 100, when the fluid handling component fluidly communicates with cavity 106.

In other exemplary embodiments, a cavity is fully enclosed within a mixing cartridge body structure. That is, the body structure does not include an opening comparable to opening 124 in these embodiments. One or more apertures, however, are typically disposed through a top surface of the body structure. In some of these embodiments, for example, the top surface is fabricated integral with the body structure or otherwise attached during assembly. Suitable fabrication techniques and materials are described further herein. The aperture is generally configured to receive a fluid handling component that fluidly communicates with the cavity. In these embodiments, the aperture is typically disposed through the top surface of the body structure relative to the rotatable member and to protrusions extending from the rotatable member such that the fluid handling component does not contact the rotatable member or the protrusions when the rotatable member rotates the protrusions and the aperture receives the fluid handling component. A closure (such as, a re-sealable label, a septum, or the like) is typically disposed in or over the aperture, e.g., at least prior to use. To further illustrate these embodiments, FIGS. 2 A-D schematically show a representative mixing cartridge having a cavity that is fully enclosed. As shown, cartridge 200 includes top surface 202 fabricated integral (e.g., injection molded, machined, or the like) with other portions of the cartridge's body structure. In this exemplary embodiment, cavity portion 204 is fabricated separate from other components of the cartridge (FIG. 2C) and attached to the remaining portion of the body structure (via attachment components 206 (shown as corresponding male and female elements that are structured to engage one another) during device assembly to form cavity 208. As further shown, cartridge 200 includes pre-pierced septum 210 positioned in an aperture disposed through top surface 202. During operation, a fluid handling component (e.g., a manually or robotically operated pipetting apparatus) typically fluidly communicates with cavity 208 via septum 210.

In some embodiments, mixing cartridge body structures include alignment features that align the cartridges relative to other components, such as the cartridge support structure of a cartridge receiver/rotation assembly. To illustrate, cartridge 100 includes alignment features 130, which align cartridge 100 relative to a cartridge support structure when cartridge 100 is positioned on a cartridge receiver/rotation assembly (not shown in FIGS. 1 A-N). In addition, in certain embodiments, body structures also include retention components that engage retention mechanisms of cartridge receiver/rotation assemblies. As shown, cartridge 100 includes retention component 132 (shown as a lip at the base of body structure 102) that engages a retention mechanism of a cartridge receiver/rotation assembly (not shown in FIGS. 1 A-N) to hold cartridge 100 in place when body structure 102 is positioned on the assembly and, e.g., when a rotational mechanism of the assembly rotates rotatable member 112 of cartridge 100. Exemplary cartridge receiver/rotation assemblies are described further herein.

The rotatable members and protrusions of the mixing cartridges of the invention also include a wide variety of embodiments. To further illustrate one exemplary embodiment, FIGS. 3 A-H show additional views of rotatable member 112 and protrusions 114 of cartridge 100. Rotatable members are typically configured to rotate about 180 degrees or less (e.g., about 135 degrees, about 90 degrees, about 45 degrees, etc.) within the cavities of the cartridges described herein. Although rotatable member 112 of cartridge 100 extends along an entire length of a substantially horizontally disposed axis in upper portion 108 of the cavity 106, other configurations are also optionally utilized. In some embodiments, for example, rotatable members extend less than the entire length of a substantially horizontally disposed rotational axis. As an additional option, multiple rotatable members are used in certain embodiments.

Rotatable members are generally configured to operably connect to rotational mechanisms. Rotational mechanisms, which are described further herein, effect the rotation of the rotatable members. In some embodiments, rotatable members operably connect to rotational mechanisms via substantially vertically disposed side surfaces of cartridge body structures. For example, rotatable member 112 includes proximal end 134 that extends through hole 122 in a substantially vertical surface of cavity 106. As also shown, washer 136 is disposed around proximal end 134 of rotatable member 112, e.g., to seal in the surface of cavity 106. Proximal end 134 is configured to operably connect to a rotational mechanism that mechanically effects the rotation of rotatable member 112. Rotatable member rotation can also effected using other approaches. In some embodiments, for example, rotatable members include magnetic couplers that are configured to interact with magnetic couplers of the rotational mechanisms to effect rotation of the rotatable members when the magnetic couplers are within magnetic communication with one another. To illustrate, FIG. 4 schematically shows one embodiment of a cartridge that includes a magnetic coupler from a partially transparent bottom view. As shown, cartridge 400 includes rotatable member 402 disposed within cavity 404. In addition, magnetic coupler 406 is attached to rotatable member 402 and magnetic coupler 408 is rotatably connected to a rotational mechanism (not shown) via shaft 410. During operation, magnetic coupler 406 and magnetic coupler 408 are positioned within magnetic communication with one another such that when the rotational mechanism effects the rotation of magnetic coupler 408, magnetic coupler 408, in turn, effects the rotation of magnetic coupler 406 and rotatable member 402. Magnetic coupling mechanisms that are optionally adapted for use with the cartridges of the invention are also described in, e.g., U.S. Pat. No. 6,461,034, entitled "USE OF A BUBBLE PADDLE TUMBLE STIRRER TO MIX THE CONTENTS OF A VESSEL WHILE THE CONTENTS ARE BEING REMOVED," which issued Oct. 8, 2002 to Cleveland, which is incorporated by reference in its entirety. Rotational mechanisms and related cartridge receiver/rotation assemblies are described further herein.

Typically, mixing cartridges include mechanisms that facilitate the monitoring and regulation of mixing processes performed using the cartridges. In certain embodiments, for example, there is a projection that extends outward from the rotatable member. In these embodiments, the projection is generally configured to activate a motion sensor when the motion sensor is in sensory communication with the projection and the rotatable member is rotated. As an illustration, projection 138 is positioned in housing 139 near proximal end 134 of rotatable member 112. During operation, the rate of rotatable member 112 is typically tracked and adjusted when a motion sensor detects the motion of projection 138. Motion sensors are typically included as components of cartridge receiver/rotation assemblies, which are described further herein.

The protrusion or protrusions that extend from a given rotatable member also include a number of different embodiments. Essentially any number and configuration of protrusions that can effect the mixing of materials in the cartridges of the invention can be utilized. Typically, protrusions are configured (e.g., in conjunction with cavity surface shapes and/or textures) to minimize dead zones within cavities and to facilitate fluid communication with cartridge cavities concurrent with the rotation of rotatable members. In some embodiments, for example, a protrusion includes at least one substantially vertically disposed segment (e.g., substantially vertically disposed segment 140) that extends downward from the rotatable member (e.g., rotatable member 112) and at least one substantially laterally disposed segment (e.g., substantially laterally disposed segment 142) that extends outward from the substantially vertically disposed segment. In some embodiments, protrusions typically include one or more edges having textured surfaces (e.g., edge 144 of substantially laterally disposed segment 142). The use of textured surfaces typically enhances the uniformity of mixing materials within cartridge cavities. Protrusions are optionally fabricated as separate components and attached to rotatable members during cartridge assembly processes. In other embodiments, protrusions fabricated integral with rotatable members (e.g., as an integrated molded part, etc.). Cartridge fabrication is described further herein.

B. Example Mixing Stations

Figure 5A:
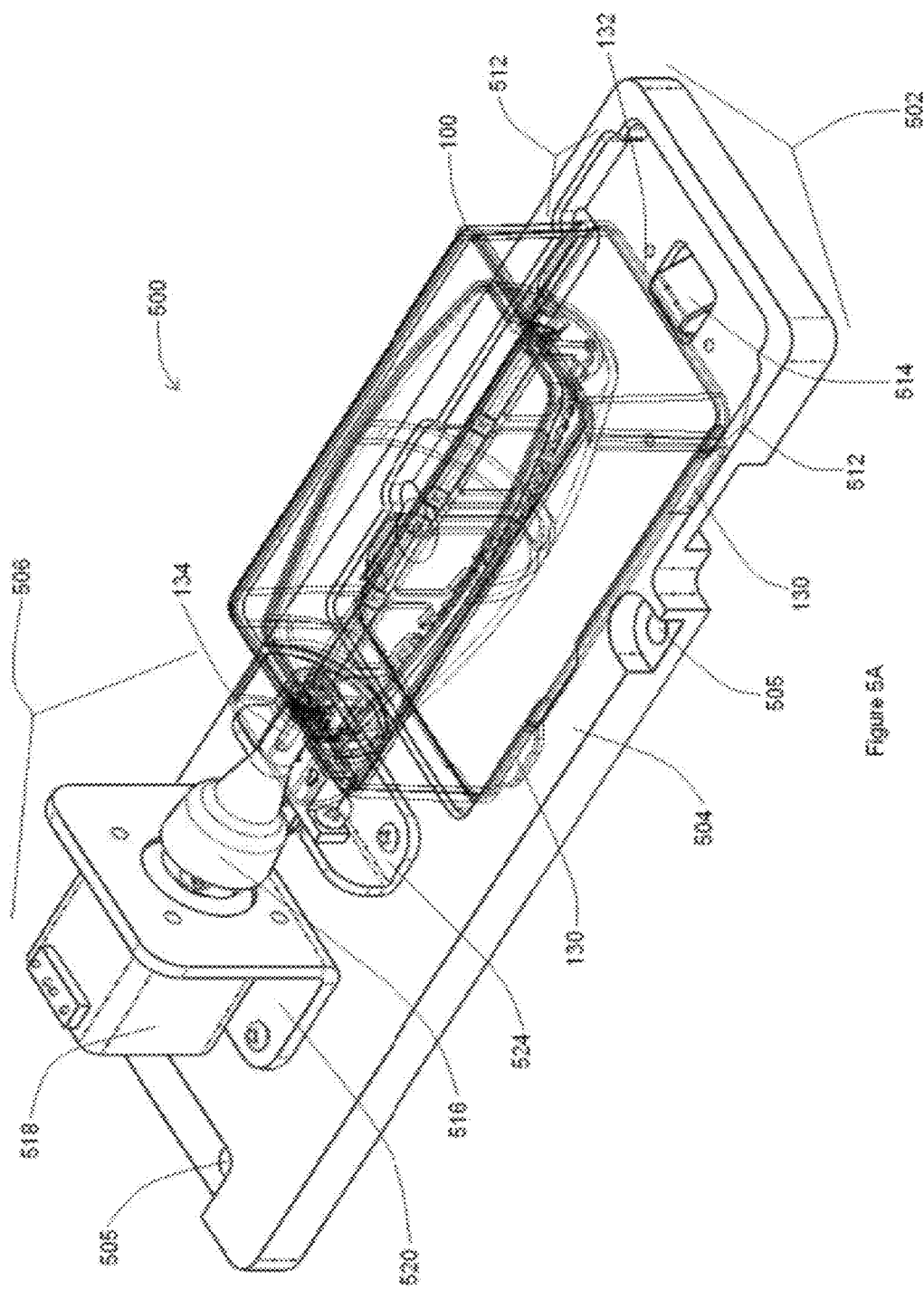
FIG. 5A schematically illustrates a mixing station from a perspective view according to one embodiment of the invention.
Figure 5C:
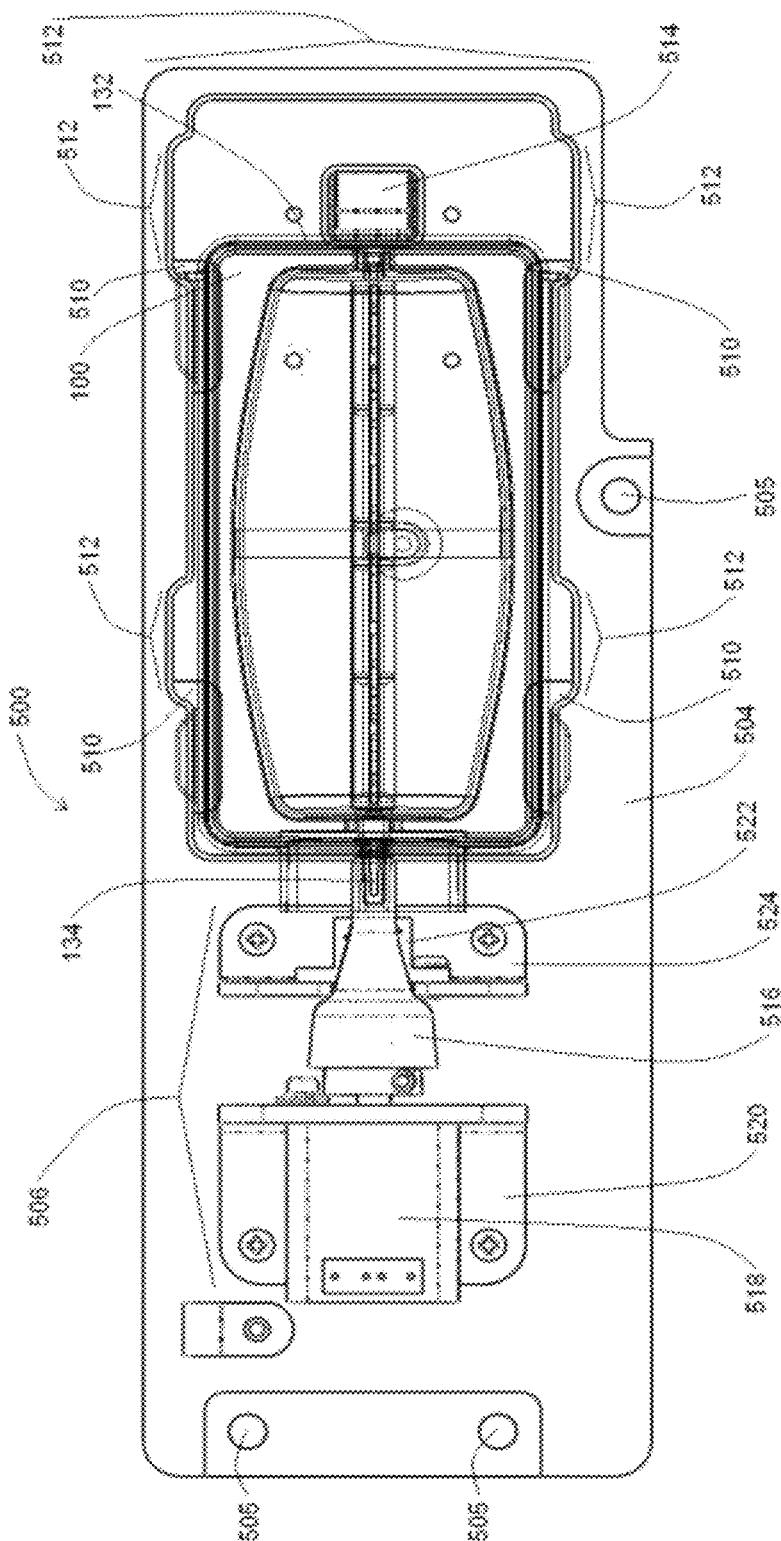
FIG. 5C schematically depicts the mixing station of FIG. 5A from a top view.
Figure 6B:
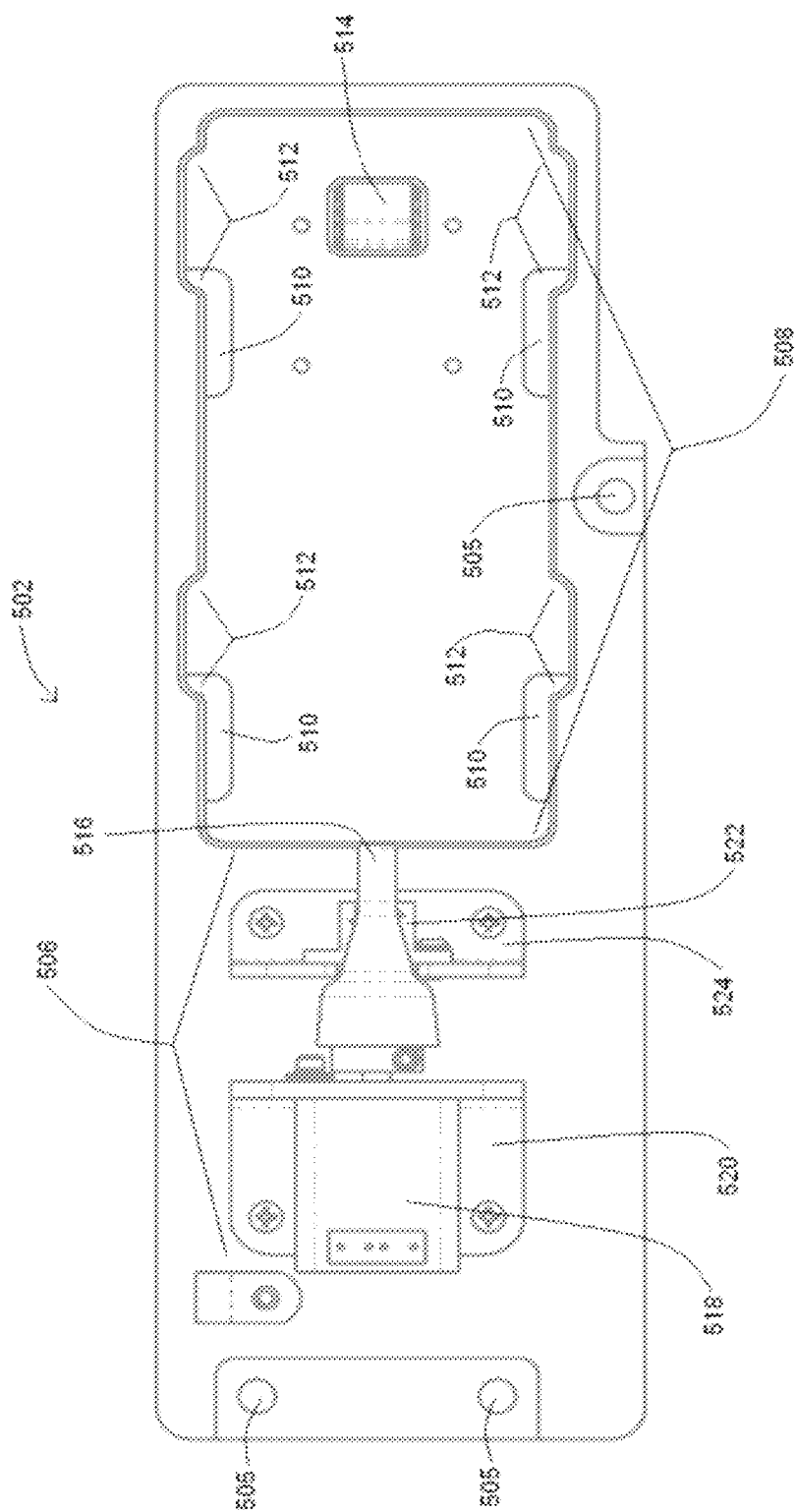
FIG. 6B schematically depicts the cartridge receiver/rotation assembly of the mixing station of FIG. 5A from a top view.
Figure 6E:
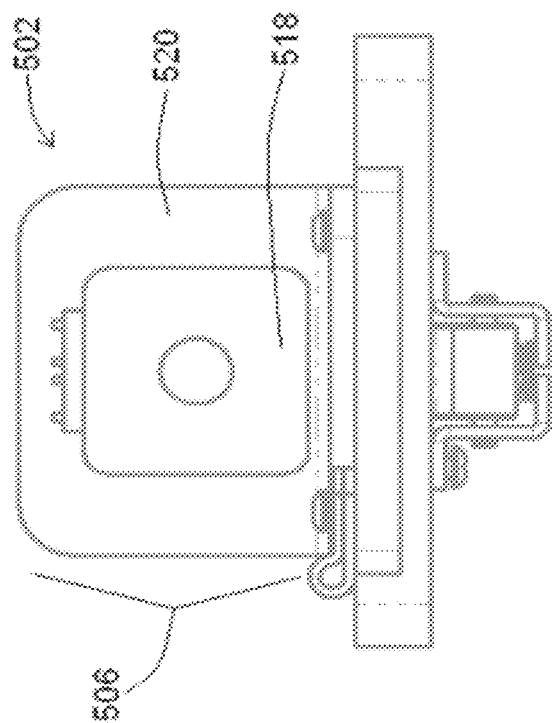
FIG. 6E schematically illustrates the cartridge receiver/rotation assembly of the mixing station of FIG. 5A from a front view.
Figure 6F:
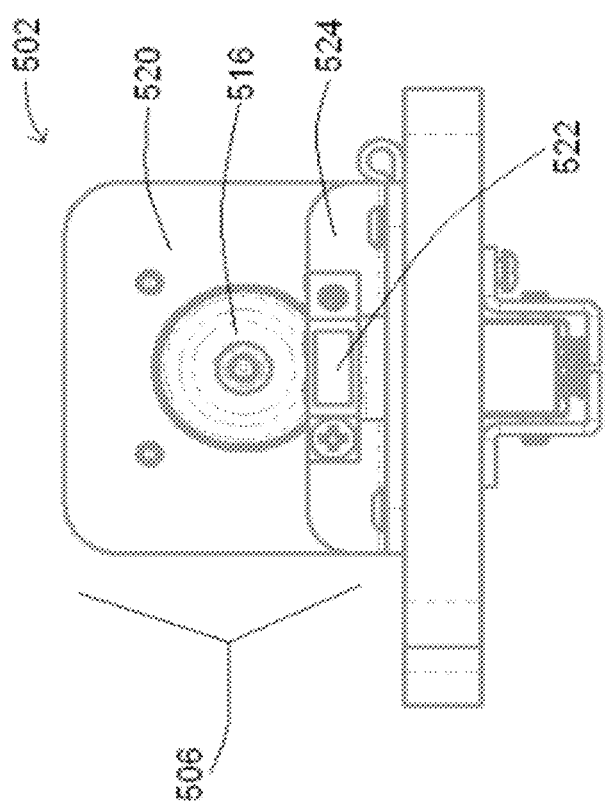
FIG. 6F schematically shows the cartridge receiver/rotation assembly of the mixing station of FIG. 5A from a back view.

FIGS. 5 A-C schematically illustrate a mixing station according to one embodiment of the invention. As shown, mixing station 500 includes cartridge 100 (depicted in various transparent views) and cartridge receiver/rotation assembly 502 (shown in various partially transparent views). To further illustrate, FIGS. 6 A-F schematically show cartridge receiver/rotation assembly 502 without cartridge 100. Cartridge receiver/rotation assembly 502 includes cartridge support structure 504 and rotational mechanism 506. Cartridge support structure 504 is structured to position and support cartridge 100, which is removable from cartridge receiver/rotation assembly 502. In some embodiments, cartridges are not removable components of mixing stations, e.g., are fabricated integral with cartridge receiver/rotation assemblies. In certain embodiments, cartridge support structure 504 is attached to or mounted on another support surface via mounting holes 505. As shown, cartridge support structure 504 includes recessed region 508 that receives body structure 102 of cartridge 100. Recessed region 508 includes grooves 510 that receive alignment features 130 of cartridge 100 via notched regions 512 of cartridge receiver/rotation assembly 502 to align cartridge 100 relative to cartridge support structure 504 and rotational mechanism 506 of cartridge receiver/rotation assembly 502. As mentioned above, cartridge 100 includes retention component 132 (shown as a lip at the base of the body structure of cartridge 100). When alignment features 130 of cartridge 100 are received within grooves 510 of cartridge support structure 504, retention component 132 engages retention mechanism 514 (shown as a spring loaded clamp) of cartridge receiver/rotation assembly 502 to reversibly hold cartridge 100 in place within recessed region 508, e.g., to secure cartridge 100 when rotational mechanism 506 rotates rotatable member 112.

As also shown, proximal end 134 of rotatable member 112 of cartridge 100 operably connects to rotational mechanism 506 via rotatable shaft 516. Rotatable shaft 516 is operably connected to motor 518 (shown as a stepper motor), which is mounted on cartridge support structure 504 via motor mounting bracket 520. Motor 518 effects the rotation of rotatable shaft 516 and rotational mechanism 506. As described herein, in other exemplary embodiments, rotatable shaft rotation and material mixing is effected by magnetic coupling mechanisms. For example, as described above with respect to FIG. 4, rotatable members and rotational mechanisms include magnetic couplers that magnetically communicate with one another to effect rotation in some of these embodiments.

As referred to above, mixing stations optionally include mechanisms for monitoring and regulating mixing processes performed using the cartridges described herein. To illustrate, cartridge receiver/rotation assembly 502 of mixing station 500 includes motion sensor 522 (shown as a reflective solder terminal phototransistor) mounted on cartridge support structure 504 via motion sensor mounting bracket 524. Suitable motion sensors are available from a variety of commercial supplier including, e.g., Omron Electronics LLC (Schaumburg, Ill., U.S.A.). During operation, the rotation of rotatable member 112 of cartridge 100 is typically monitored when motion sensor 522 detects the motion of projection 138 within housing 139 of cartridge 100.

Figure 7:
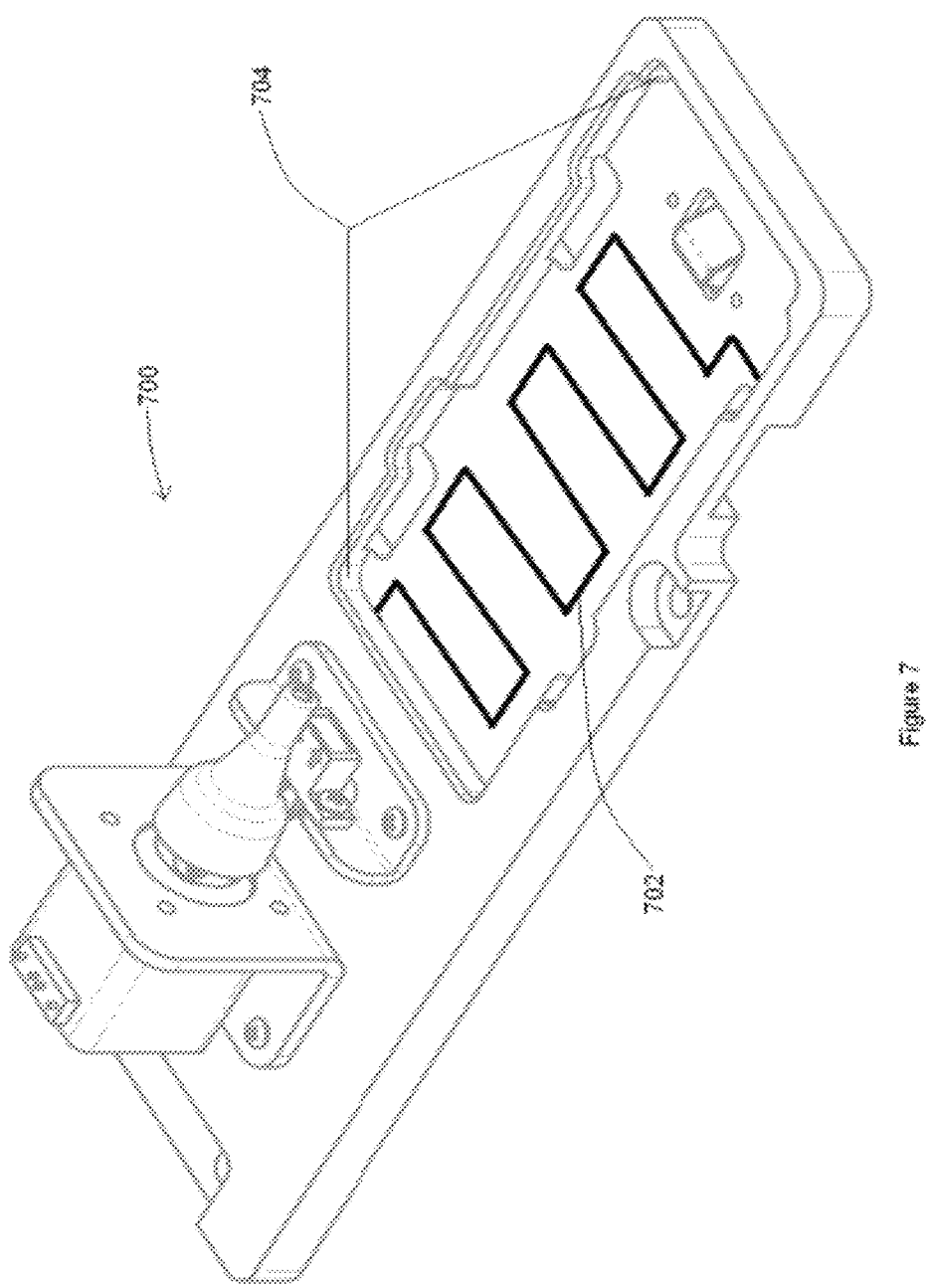
FIG. 7 schematically illustrates a cartridge receiver/rotation assembly of a mixing station that includes a thermal modulating component from a perspective view according to one embodiment of the invention.

In some embodiments, mixing stations include thermal modulating components (e.g., resistive heating coils, or the like) that modulate the temperature of materials disposed in the cavities of mixing cartridges during a given mixing process. For example, FIG. 7 schematically depicts cartridge receiver/rotation assembly 700, which includes heating element 702 disposed in recessed region 704. Heating element 702 is configured to thermally communicate with the cavity of a mixing cartridge to regulate the temperature of materials (e.g., a cell culture suspension, viscous fluidic materials, etc.) within the cavity when the cartridge is positioned within recessed region 704. Although not shown in FIG. 7, heating element 702 operably connects to a power source. Typically, thermal modulating components are operably connected to controllers (described below), e.g., via such power sources.

The controllers of the mixing stations and systems described herein are generally configured to effect, e.g. the rotation of rotatable members to mix materials disposed within the cavities of mixing cartridges, the monitoring of rotatable member rotation, the detection of one or more parameters of materials disposed in mixing cartridge cavities, and the like. Controllers are typically operably connected to one or more system components, such as motors (e.g., via motor drives), thermal modulating components, detectors, motion sensors, fluidic handling components, robotic translocation devices, or the like, to control operation of these components. More specifically, controllers are generally included either as separate or integral system components that are utilized to effect, e.g., the rotation of rotatable members in mixing cartridges according to one or more selectable rotational modes, the transport of mixing cartridges between system areas or components, the transfer of materials to and/or from mixing cartridges, the detection and/or analysis of detectable signals received from sample materials by detectors, etc. Controllers and/or other system components is/are generally coupled to an appropriately programmed processor, computer, digital device, or other logic device or information appliance (e.g., including an analog to digital or digital to analog converter as needed), which functions to instruct the operation of these instruments in accordance with preprogrammed or user input instructions (e.g., mixing mode selection, mixing cartridge cavity temperature, fluid volumes to be conveyed, etc.), receive data and information from these instruments, and interpret, manipulate and report this information to the user.

A controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. An exemplary system comprising a computer is schematically illustrated in FIG. 8.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., rotating a rotatable member of a mixing cartridge, aspirating fluidic materials from a mixing cartridge, dispensing materials into a cavity of a mixing cartridge, or the like. The computer then receives the data from, e.g., sensors/detectors included within the system, and interprets the data, either provides it in a user understood format, or uses that data to initiate further controller instructions, in accordance with the programming, e.g., such as in monitoring detectable signal intensity, mixing cartridge cavity temperature, or the like.

More specifically, the software utilized to control the operation of the mixing stations of the invention typically includes logic instructions that selectively direct, e.g., the rotational mechanism to rotate the rotatable member in an initiation mode or in a maintenance mode in which a rate of rotation of the rotatable member is greater in the initiation mode than in the maintenance mode. The logic instructions of the software are typically embodied on a computer readable medium, such as a CD-ROM, a floppy disk, a tape, a flash memory device or component, a system memory device or component, a hard drive, a data signal embodied in a carrier wave, and/or the like. Other computer readable media are known to persons of skill in the art. In some embodiments, the logic instructions are embodied in read-only memory (ROM) in a computer chip present in one or more system components, without the use of personal computers.

The computer can be, e.g., a PC (Intel x86 or Pentium chip-compatible DOS™, OS2™, WINDOWS™, WINDOWS NT™, WINDOWS98™, WINDOWS2000™, WINDOWS XP™, WINDOWS Vista™, LINUX-based machine, a MACINTOSH™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., rotatable member rotation, material conveyance to and/or from mixing cartridges, mixing process monitoring, assay detection, and data deconvolution is optionally constructed by one of skill using a standard programming language such as Visual basic, C, C++, Fortran, Basic, Java, or the like.

The mixing stations and related systems of the invention optionally include detection components configured to detect one or more detectable signals or parameters from a given mixing process, e.g., from materials disposed within mixing cartridge cavities. In some embodiments, systems are configured to detect detectable signals or parameters that are upstream and/or downstream of a given mixing process involving the mixing cartridges and mixing stations described herein. Suitable signal detectors that are optionally utilized in these systems detect, e.g., pH, temperature, pressure, density, salinity, conductivity, fluid level, radioactivity, luminescence, fluorescence, phosphorescence, molecular mass, emission, transmission, absorbance, and/or the like. In some embodiments, the detector monitors a plurality of signals, which correspond in position to "real time" results. Example detectors or sensors include PMTs, CCDs, intensified CCDs, photodiodes, avalanche photodiodes, optical sensors, scanning detectors, or the like. Each of these as well as other types of sensors is optionally readily incorporated into the mixing stations and systems described herein. The detector optionally moves relative to mixing cartridges or stations, sample containers or other assay components, or alternatively, mixing cartridges or stations, sample containers or other assay components move relative to the detector. Optionally, the mixing stations and systems of the invention include multiple detectors. In these stations and systems, such detectors are typically placed either in or adjacent to, e.g., a mixing cartridge cavity or other vessel, such that the detector is in sensory communication with the mixing cartridge cavity or other vessel (i.e., the detector is capable of detecting the property of the cavity or vessel or portion thereof, the contents of a portion of the cavity or vessel, or the like, for which that detector is intended).

The detector optionally includes or is operably linked to a computer, e.g., which has system software for converting detector signal information into assay result information or the like. For example, detectors optionally exist as separate units, or are integrated with controllers into a single instrument. Integration of these functions into a single unit facilitates connection of these instruments with the computer, by permitting the use of a few or even a single communication port for transmitting information between system components. Detection components that are optionally included in the systems of the invention are described further in, e.g., Skoog et al., Principles of Instrumental Analysis, $6^{th}$ Ed., Brooks Cole (2006) and Currell, Analytical Instrumentation: Performance Characteristics and Quality, John Wiley & Sons, Inc. (2000), which are both incorporated by reference.

The stations and systems of the invention optionally also include at least one robotic translocation or gripping component that is structured to grip and translocate mixing cartridges or other containers between components of the stations or systems and/or between the stations or systems and other locations (e.g., other work stations, etc.). In certain embodiments, for example, systems further include gripping components that move mixing cartridges between cartridge receiver/rotation assemblies, incubation or storage components, and the like. A variety of available robotic elements (robotic arms, movable platforms, etc.) can be used or modified for use with these systems, which robotic elements are typically operably connected to controllers that control their movement and other functions.

FIG. 8 is a schematic showing a representative system including an information appliance in which various aspects of the present invention may be embodied. Other exemplary systems are also described herein. As will be understood by practitioners in the art from the teachings provided herein, the invention is optionally implemented in hardware and software. In some embodiments, different aspects of the invention are implemented in either client-side logic or server-side logic. As will also be understood in the art, the invention or components thereof may be embodied in a media program component (e.g., a fixed media component) containing logic instructions and/or data that, when loaded into an appropriately configured computing device, cause that apparatus or system to perform according to the invention. As will additionally be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 8 shows information appliance or digital device 800 that may be understood as a logical apparatus (e.g., a computer, etc.) that can read instructions from media 817 and/or network port 819, which can optionally be connected to server 820 having fixed media 822. Information appliance 800 can thereafter use those instructions to direct server or client logic, as understood in the art, to embody aspects of the invention. One type of logical apparatus that may embody the invention is a computer system as illustrated in 800, containing CPU 807, optional input devices 809 and 811, disk drives 815 and optional monitor 805. Fixed media 817, or fixed media 822 over port 819, may be used to program such a system and may represent a disk-type optical or magnetic media, magnetic tape, solid state dynamic or static memory, or the like. In specific embodiments, the aspects of the invention may be embodied in whole or in part as software recorded on this fixed media. Communication port 819 may also be used to initially receive instructions that are used to program such a system and may represent any type of communication connection. Optionally, aspects of the invention are embodied in whole or in part within the circuitry of an application specific integrated circuit (ACIS) or a programmable logic device (PLD). In such a case, aspects of the invention may be embodied in a computer understandable descriptor language, which may be used to create an ASIC, or PLID.

In addition, FIG. 8 also shows mixing station 802, which is operably connected to information appliance 800 via server 820. Optionally, mixing station 802 is directly connected to information appliance 800. During operation, mixing station 802 typically mixes materials with mixing cartridge cavities (e.g., to maintain particles in fluidic materials in suspension, etc.), e.g., as part of an assay or other process. FIG. 8 also shows detector 824, which is optionally included in the systems of the invention. As shown, detector 824 is operably connected to information appliance 800 via server 820. In some embodiments, detector 824 is directly connected to information appliance 800. In certain embodiments, detector 824 is configured to detect detectable signals produced in a cavity of a mixing cartridge positioned on a cartridge support structure of mixing station 802.

C. Example System and Related Process Embodiments

To further illustrate exemplary embodiments of the invention, FIGS. 9 A-G schematically depict a portion of a representative system for nucleic acid amplification product desalting and molecular mass measurement that includes a mixing station as a sub-system component. The measured molecular masses of the amplification products are typically used to determine base compositions of the corresponding amplification products, which are then generally correlated with the identities or organismal sources of the initial template nucleic acids, for example, as part of a research or in-vitro diagnostic application, among many others.

As shown in FIGS. 9 A-G, components of representative system 900 include microplate handling component or system 10, material transfer component 902, mixing station 904, wash stations 906 and 908, sample processing component 910, and sample injector 912. During operation, microplates are typically stored or positioned in input non-priority microplate storage unit 12, output non-priority microplate storage unit 14, priority microplate storage unit 16, microplate processing area 18, and non-priority microplate holding area 20 (e.g., on non-priority microplate holding component 22) of microplate handling component 10. As also shown, microplate handling component 10 also includes barcode reader 36. In the exemplary embodiment shown, barcode reader 36 is configured to read barcodes disposed on microplates when the microplates are disposed in or proximal to non-priority microplate holding area 20, e.g., to track the microplates or samples contained in the microplates in microplate handling system 10. In some embodiments, for example, non-priority microplates are stored in input non-priority microplate storage unit 12 and priority microplates are stored in priority microplate storage unit 16 after target regions of template nucleic acids in those plates have been amplified, e.g., at a separate thermocycling station or nucleic acid amplification component. Essentially any thermal cycling station or device is optionally adapted for use with a system of the invention, such as system 900. Examples of suitable thermocycling devices that are optionally utilized are available from many different commercial suppliers, including Mastercycler® devices (Eppendorf North America, Westbury, N.Y., U.S.A.), the COBAS® AMPLICOR Analyzer (Roche Molecular Systems, Inc., Pleasanton, Calif., U.S.A.), MyCycler and iCycler Thermal Cyclers (Bio-Rad Laboratories, Inc., Hercules, Calif., U.S.A.), and the SmartCycler System (Cepheid, Sunnyvale, Calif., U.S.A.), among many others. In other exemplary embodiments, sample preparation components, nucleic acid amplification components, and related fluid handling or material transfer components are integrated with the systems described herein, e.g., to fully automate a given nucleic acid amplification and analysis process. Instruments that can be adapted for this purpose include, for example, the m2000™ automated instrument system (Abbott Laboratories, Abbott Park, Ill., U.S.A.), the GeneXpert System (Cepheid, Sunnyvale, Calif., U.S.A.), and the COBAS® AmpliPrep® System (Roche Molecular Systems, Inc., Pleasanton, Calif., U.S.A.), and the like.

Microplates are transferred from input non-priority microplate storage unit 12 or priority microplate storage unit 16 to microplate processing area 18 using platform 28 of a microplate transport mechanism. As referred to above and as shown in, e.g., FIGS. 9 F and G, platform 28 is operably connected to X-axis linear motion component 38. X-axis linear motion component 38 includes gantry 40. Platform 28 is operably connected to carriage 42, which moves along gantry 40. As further shown in FIGS. 9 F and G, microplate transport mechanism 26 also includes Y-axis linear motion component 44 operably connected to carriage 42 and to platform 28. Y-axis linear motion component 44 is configured to raise and lower platform 28 along the Y-axis. Suitable linear motion components, motors, and motor drives are generally available from many different commercial suppliers including, e.g., Techno-Isel Linear Motion Systems (New Hyde Park, N.Y., U.S.A.), NC Servo Technology Corp. (Westland, Mich., USA), Enprotech Automation Services (Ann Arbor, Mich., U.S.A.), Yaskawa Electric America, Inc. (Waukegan, Ill., U.S.A.), ISL Products International, Ltd. (Syosset, N.Y., U.S.A.), AMK Drives & Controls, Inc. (Richmond, Va., U.S.A.), Aerotech, Inc. (Pittsburgh, Pa., U.S.A.), HD Systems Inc. (Hauppauge, N.Y., U.S.A.), and the like. Additional detail relating to motors and motor drives are described in, e.g., Polka, Motors and Drives, ISA (2002) and Hendershot et al., Design of Brushless Permanent-Magnet Motors, Magna Physics Publishing (1994), which are both incorporated by reference. Microplate handling components are also described in, e.g., U.S. Provisional Patent App. No. 61/097,510, entitled "MICROPLATE HANDLING SYSTEMS AND RELATED COMPUTER PROGRAM PRODUCTS AND METHODS" filed Sep. 16, 2008 by Hofstadler et al., which is incorporated by reference in its entirety.

Material transfer component 902 includes sample input gantry 914 and sample output gantry 916. Input gantry head 918 is configured to move along sample input gantry 914, whereas output gantry head 920 is configured to move along sample output gantry 916. Input gantry head 918 and output gantry head 920 each include needles that are configured to aspirate and dispense fluidic materials. Further, input gantry head 918 and output gantry head 920 are each configured to be raised and lowered along the Y-axis. During operation of exemplary system 900, the needle or pipetting tip of input gantry head 918 is typically used to aspirate an aliquot of magnetically responsive particles (e.g., magnetically responsive beads, such as BioMag®Plus Amine superparamagnetic microparticles available from Bangs Laboratories, Inc., Fishers, Ind., U.S.A.) that bind nucleic acids from a mixing cartridge positioned at mixing station 904. Nucleic acid purification involving magnetically responsive particles is also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., which are both incorporated by reference in their entirety. Optionally before, but typically after aspirating the aliquot of magnetically responsive particles (e.g., to minimize the possibility of cross-contaminating samples), the needle of input gantry head 918 is also generally used to aspirate an aliquot of an amplification product sample from a selected well of a microplate positioned in microplate processing area 18 of microplate handling system 10. The resulting mixture of magnetically responsive particle and amplification product sample aliquots disposed within the needle of input gantry head 918 is then typically transferred to sample processing component 910 along sample input gantry 914. After dispensing the mixture at sample processing component 910, the needle of input gantry head 918 is typically washed at wash station 906, e.g., to minimize the probability of cross-contaminating samples, prior to repeating this transfer cycle for other amplification product samples contained in the wells of a given microplate (e.g., priority or non-priority microplates) positioned in microplate processing area 18 of microplate handling system 10.

In the embodiment shown, sample processing component 910 is a desalting station that is used to desalt or otherwise purify nucleic acid amplification products in the sample mixture prior to mass spectrometric analysis. Sample processing component 910 includes carrier mechanism 922 (shown as a carousel), which includes a plurality of sample processing units 924. In the illustrated embodiment, each sample processing unit 924 includes cuvette 926 and magnet 928. After a mixture of magnetically responsive particle and amplification product sample aliquots is dispensed into a given cuvette 926, that cuvette is typically rotated in a clockwise direction on carrier mechanism 922 to various positions within sample processing component 910 where various reagents are added to and/or removed from that cuvette (e.g., via various fluidic handling components of manifold 930) as part of the process of purifying the amplification products captured or otherwise bound to the magnetically responsive particles in the mixture. When fluidic materials are removed from the cuvette at a given position within sample processing component 910, the cuvette is typically moved proximal to the magnet of the particular sample processing unit (e.g., cuvette 926 is moved proximal to magnet 928 of sample processing unit 924) using a conveyance mechanism to establish sufficient magnetic communication between the magnet and the magnetically responsive particles such that the magnetically responsive particles are moved to and retained on an internal surface of the cuvette while fluidic materials are removed from the cuvette. At the conclusion of a purification process for a given sample, the purified amplification products are then typically aspirated from the particular cuvette using the needle of output gantry head 920. During or prior this step, the nucleic acid amplification products are eluted from the magnetically responsive particles. After purified amplification products have been removed from a given cuvette, that cuvette is then generally rotated on carrier mechanism 922 into communication with cuvette wash station 927, where the cuvette is washed prior to commencing another purification cycle involving the cuvette and another sample. Sample processing components, such as sample processing component 910 and related desalting/purification methods are also described in, e.g., U.S. Provisional Patent App. No. 61/097,525, entitled "SAMPLE PROCESSING UNITS, SYSTEMS, AND RELATED METHODS" filed Sep. 16, 2008 by Hofstadler et al., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., and Hofstadler et al. (2003) "A highly efficient and automated method of purifying and desalting PCR products for analysis by electrospray ionization mass spectrometry" *Anal Biochem.* 316:50-57, which are each incorporated by reference in their entirety.

Purified and eluted amplification products that have been aspirated from a particular cuvette of sample processing component 910 are typically transported along sample output gantry 916 to sample injector 912 (shown as a two channel time-of-flight injector) using output gantry head 920. That is, the amplification products are typically dispensed from the needle or pipetting tip of output gantry head 920 into one of the two channels of sample injector 912, which generally comprise two independent sample injection syringe pumps that are configured to receive the amplification products. After dispensing the amplification products at sample injector 912, the needle of output gantry head 920 is typically washed at wash station 908 prior to aspirating another purified amplification product sample from sample processing component 910, e.g., to reduce the potential for carryover contamination between samples.

Now referring to FIG. 10, which schematically shows additional components of representative system 900 (sample processing component 910 not shown) from a perspective view. As shown, the additional components include dual sprayer module 932, which includes two independent electrospray ionization sprayers, and time-of-flight mass spectrometer 934. Amplification product samples received at sample injector 912 are typically injected into one of the two sprayers of dual sprayer module 932 for electrospray ionization and mass measurement in time-of-flight mass spectrometer 934. As further shown, the additional components of representative system 900 also include input/output device 936 (shown as a touch screen monitor), computer 937, output device 939 (shown as a printer), reagents and waste module 938, and chassis 940. Input/output device 936, computer 937, and output device 939 are components of a controller of system 900. Controllers are described further herein. Reagents and waste module 938 provide reagent sources and waste receptacles for system 900. Chassis 940 provides mechanical support for microplate handling system 10, sample processing component 910, and other components of system 900. To further illustrate, FIGS. 11 A-C schematically show representative system 900 with an external covering from various views.

In some embodiments, the base compositions of amplification products are determined from detected molecular masses. In these embodiments, base compositions are typically correlated with the identity of an organismal source, genotype, or other attribute of the corresponding template nucleic acids in a given sample. Databases with base compositions and other information useful in these processes are also typically included in these systems. Suitable software and related aspects, e.g., for determining base compositions from detected molecular masses and for performing other aspects of base composition analysis are commercially available from Ibis Biosciences, Inc. (Carlsbad, Calif., U.S.A.).

Particular embodiments of molecular mass-based detection methods and other aspects that are optionally adapted for use with the systems described herein are described in various patents and patent applications, including, for example, U.S. Pat. Nos. 7,108,974; 7,217,510; 7,226,739; 7,255,992; 7,312,036; and 7,339,051; and US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; and WO2007/100397; WO2007/118222, which are each incorporated by reference as if fully set forth herein.

Exemplary molecular mass-based analytical methods and other aspects of use in the systems described herein are also described in, e.g., Ecker et al. (2005) "The Microbial Rosetta Stone Database: A compilation of global and emerging infectious microorganisms and bioterrorist threat agents" *BMC Microbiology* 5(1):19; Ecker et al. (2006) "The Ibis T5000 Universal Biosensor: An Automated Platform for Pathogen Identification and Strain Typing" *JALA* 6(11):341-351.; Ecker et al. (2006) "Identification of *Acinetobacter* species and genotyping of *Acinetobacter baumannii* by multilocus PCR and mass spectrometry" *J Clin Microbiol.* 44(8):2921-32.; Ecker et al. (2005) "Rapid identification and strain-typing of respiratory pathogens for epidemic surveillance" *Proc Natl Acad Sci USA.* 102(22):8012-7; Hannis et al. (2008) "High-resolution genotyping of *Campylobacter* species by use of PCR and high-throughput mass spectrometry" *J Clin Microbiol.* 46(4):1220-5; Blyn et al. (2008) "Rapid detection and molecular serotyping of adenovirus by use of PCR followed by electrospray ionization mass spectrometry" *J Clin Microbiol.* 46(2):644-51; Sampath et al. (2007) "Global surveillance of emerging Influenza virus genotypes by mass spectrometry" *PLoS ONE* 2(5):e489; Sampath et al. (2007) "Rapid identification of emerging infectious agents using PCR and electrospray ionization mass spectrometry" *Ann NY Acad. Sci.* 1102:109-20; Hall et al. (2005) "Base composition analysis of human mitochondrial DNA using electrospray ionization mass spectrometry: a novel tool for the identification and differentiation of humans" *Anal Biochem.* 344(1): 53-69; Hofstadler et al. (2003) "A highly efficient and automated method of purifying and desalting PCR products for analysis by electrospray ionization mass spectrometry" *Anal Biochem.* 316:50-57; Hofstadler et al. (2006) "Selective ion filtering by digital thresholding: A method to unwind complex ESI-mass spectra and eliminate signals from low molecular weight chemical noise" *Anal Chem.* 78(2):372-378.; and Hofstadler et al. (2005) "TIGER: The Universal Biosensor" *Int J Mass Spectrom.* 242(1):23-41, which are each incorporated by reference.

In addition to the molecular mass and base composition analyses referred to above, essentially any other nucleic acid amplification technological process is also optionally adapted for use in the systems of the invention. Other exemplary uses of the systems and other aspects of the invention include immunoassays, cell culturing, cell-based assays, compound library screening, and chemical synthesis, among many others. Many of these as well as other exemplary applications of use in the systems of the invention are also described in, e.g., Current Protocols in Molecular Biology, Volumes I, II, and III, 1997 (F. M. Ausubel ed.); Perbal, 1984, A Practical Guide to Molecular Cloning; the series, Methods in Enzymology (Academic Press, Inc.); Sambrook et al., 2001, Molecular Cloning: A Laboratory Manual, Third Edition, Cold Spring Harbor Laboratory Press, Cold Spring Harbor, N.Y.; Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Berger and Kimmel, Guide to Molecular Cloning Techniques, Methods in Enzymology volume 152 Academic Press, Inc., San Diego, Calif. (Berger), DNA Cloning: A Practical Approach, Volumes I and II, 1985 (D. N. Glover ed.); Immobilized Cells and Enzymes, 1986 (IRL Press); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively), which are each incorporated by reference.

D. Example Kits and Related Methods

In certain embodiments, the mixing cartridges of the invention are provided in kits. To illustrate, in some embodiments, kits include only empty mixing cartridges, whereas in other exemplary embodiments kits also include material disposed in the cavities of mixing cartridges and/or in separate containers. The material included in a given kit typically depends on the intended purpose of the mixing cartridges (e.g., for use in a nucleic acid or protein purification process, for use in a cell culture process or screening application, for use in a painting or printing application, for use in chemical synthetic processes, etc.). Accordingly, non-limiting examples of materials optionally included in kits are magnetically responsive particles (e.g., magnetically responsive beads, etc.), water, solvents, buffers, reagents, cell culture media, cells, paint, ink, biopolymers (e.g., nucleic acids, polypeptides, etc.), solid supports (e.g., controlled pore glass (CPG), etc.), and the like. Kits typically also include instructions for mixing the fluidic materials in the cartridges and/or loading the materials into the cavity of the cartridge. In addition, kits also generally include packaging for containing the cartridge(s), the separate container(s), and/or the instructions.

Kits are typically provided in response to receiving an order from a customer. Orders are received through a variety of mechanisms including, e.g., via a personal appearance by the customer or an agent thereof, via a postal or other delivery service (e.g., a common carrier), via a telephonic communication, via an email communication or another electronic medium, or any other suitable method. Further, kits are generally supplied or provided to customers (e.g., in exchange for a form of payment) by any suitable method, including via a personal appearance by the customer or an agent thereof, via a postal or other delivery service, such as a common carrier, or the like.

E. Example Fabrication Methods and Materials

Mixing cartridges or components thereof, cartridge receiver/rotation assemblies, and system components (e.g., mixing stations, microplate storage units, microplate transport mechanisms, support bases, sample processing components, etc.) are optionally formed by various fabrication techniques or combinations of such techniques including, e.g., machining, embossing, extrusion, stamping, engraving, injection molding, cast molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, $3^{rd}$ Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate mixing cartridges, mixing stations, or components thereof include polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In some embodiments, mixing cartridges or components thereof are fabricated as disposable or consumable components of mixing stations or related systems. In certain embodiments, following fabrication, system components are optionally further processed, e.g., by coating surfaces with a hydrophilic coating, a hydrophobic coating (e.g., a Xylan 1010DF/870 Black coating available from Whitford Corporation (West Chester, Pa.), etc.), or the like, e.g., to prevent interactions between component surfaces and reagents, samples, or the like.

II. Microplate Handling Systems

The invention relates to automated microplate handling and management, and in various embodiments provides systems, computer program products, and related methods that are useful for this purpose. The systems and other aspects of the invention typically process batches of microplates according to a user-selected order or schedule. Unscheduled, high priority or stat samples, however, are also readily introduced into the systems of the invention for processing ahead of lower or non-priority samples that may have been previously scheduled by a user. In certain embodiments, for example, the processing (e.g., addition and/or removal of material to/from the microplate) of a given non-priority microplate can be rapidly halted in deference to the processing of a priority microplate and then be readily resumed once the processing of that priority microplate is completed.

In many pre-existing automated microplate handling systems, samples are processed in batches according to the order in which microplates are initially loaded into microplate storage units (e.g., on a first-in, first-out basis). These systems are generally not configured to readily handle out of sequence samples, such as stat samples that may become prioritized ahead the remaining samples in a pre-loaded batch of microplates. In certain instances, for example, out of sequence priority samples simply cannot be processed until the processing of a given non-priority microplate or batch of non-priority microplates has been completed.

The systems and related aspects of the invention can be used, or adapted for use, in essentially any application that involves microplates. In certain embodiments, for example, microplates comprising nucleic acid amplification reaction mixtures are loaded into microplate storage units of a microplate handling system of the invention. In some of these embodiments, a microplate transport mechanism of the system transports the microplates to a microplate processing area, where material transfer component transfers aliquots of the reaction mixtures from the wells of the microplates to a sample processing system. In these embodiments, the sample processing system is typically used to purify amplification products or amplicons in the reaction mixture aliquots for subsequent detection or other analysis. To further illustrate, in some of these embodiments, the molecular masses of these purified amplicons are measured using a mass spectrometer. The base compositions of the amplicons are typically determined from the measured molecular masses and correlated with an identity or source of target nucleic acids in the amplification reaction mixtures, such as a pathogenic organism.

Particular embodiments of molecular mass-based detection methods and other aspects that are optionally adapted for use with the systems described herein are described in various patents and patent applications, including, for example, U.S. Pat. Nos. 7,108,974; 7,217,510; 7,226,739; 7,255,992; 7,312, 036; and 7,339,051; and US patent publication numbers 2003/0027135; 2003/0167133; 2003/0167134; 2003/ 0175695; 2003/0175696; 2003/0175697; 2003/0187588; 2003/0187593; 2003/0190605; 2003/0225529; 2003/ 0228571; 2004/0110169; 2004/0117129; 2004/0121309; 2004/0121310; 2004/0121311; 2004/0121312; 2004/ 0121313; 2004/0121314; 2004/0121315; 2004/0121329; 2004/0121335; 2004/0121340; 2004/0122598; 2004/ 0122857; 2004/0161770; 2004/0185438; 2004/0202997; 2004/0209260; 2004/0219517; 2004/0253583; 2004/ 0253619; 2005/0027459; 2005/0123952; 2005/0130196 2005/0142581; 2005/0164215; 2005/0266397; 2005/ 0270191; 2006/0014154; 2006/0121520; 2006/0205040; 2006/0240412; 2006/0259249; 2006/0275749; 2006/ 0275788; 2007/0087336; 2007/0087337; 2007/0087338 2007/0087339; 2007/0087340; 2007/0087341; 2007/ 0184434; 2007/0218467; 2007/0218467; 2007/0218489; 2007/0224614; 2007/0238116; 2007/0243544; 2007/ 0248969; WO2002/070664; WO2003/001976; WO2003/ 100035; WO2004/009849; WO2004/052175; WO2004/ 053076; WO2004/053141; WO2004/053164; WO2004/ 060278; WO2004/093644; WO 2004/101809; WO2004/ 111187; WO2005/023083; WO2005/023986; WO2005/ 024046; WO2005/033271; WO2005/036369; WO2005/ 086634; WO2005/089128; WO2005/091971; WO2005/ 092059; WO2005/094421; WO2005/098047; WO2005/ 116263; WO2005/117270; WO2006/019784; WO2006/ 034294; WO2006/071241; WO2006/094238; WO2006/ 116127; WO2006/135400; WO2007/014045; WO2007/ 047778; WO2007/086904; and WO2007/100397; WO2007/ 118222, which are each incorporated by reference as if fully set forth herein.

Exemplary molecular mass-based analytical methods and other aspects of use in the systems described herein are also described in, e.g., Ecker et al. (2005) "The Microbial Rosetta Stone Database: A compilation of global and emerging infectious microorganisms and bioterrorist threat agents" *BMC Microbiology* 5(1):19; Ecker et al. (2006) "The Ibis T5000 Universal Biosensor: An Automated Platform for Pathogen Identification and Strain Typing" *JALA* 6(10:341-351., Ecker et al. (2006) "Identification of *Acinetobacter* species and genotyping of *Acinetobacter baumannii* by multilocus PCR and mass spectrometry" *J Clin Microbiol.* 44(8):2921-32.; Ecker et al. (2005) "Rapid identification and strain-typing of respiratory pathogens for epidemic surveillance" *Proc Natl Acad Sci USA.* 102(22):8012-7; Hannis et al. (2008) "High-resolution genotyping of *Campylobacter* species by use of PCR and high-throughput mass spectrometry" *J Clin Microbiol.* 46(4):1220-5; Blyn et al. (2008) "Rapid detection and molecular serotyping of adenovirus by use of PCR followed by electrospray ionization mass spectrometry" *J Clin Microbiol.* 46(2):644-51; Sampath et al. (2007) "Global surveillance of emerging Influenza virus genotypes by mass spectrometry" *PLoS ONE* 2(5):e489; Sampath et al. (2007) "Rapid identification of emerging infectious agents using PCR and electrospray ionization mass spectrometry" *Ann NY Acad. Sci.* 1102:109-20; Hall et al. (2005) "Base composition analysis of human mitochondrial DNA using electrospray ionization mass spectrometry: a novel tool for the identification and differentiation of humans" *Anal Biochem.* 344(1): 53-69; Hofstadler et al. (2003) "A highly efficient and automated method of purifying and desalting PCR products for analysis by electrospray ionization mass spectrometry" *Anal Biochem.* 316:50-57; Hofstadler et al. (2006) "Selective ion filtering by digital thresholding: A method to unwind complex ESI-mass spectra and eliminate signals from low molecular weight chemical noise" *Anal Chem.* 78(2):372-378.; and Hofstadler et al. (2005) "TIGER: The Universal Biosensor" *Int J Mass Spectrom.* 242(1):23-41, which are each incorporated by reference.

In addition to the molecular mass and base composition analyses referred to above, essentially any other nucleic acid amplification technological process that can be performed in a microplate is also optionally adapted for use in the systems of the invention. Other exemplary uses of the systems and other aspects of the invention include immunoassays, cell culturing, cell-based assays, compound library screening, and chemical synthesis, among many others. Many of these as well as other exemplary applications of use in the systems of the invention are also described in, e.g., Current Protocols in Molecular Biology, Volumes I, II, and III, 1997 (F. M. Ausubel ed.); Perbal, 1984, A Practical Guide to Molecular Cloning; the series, Methods in Enzymology (Academic Press, Inc.); Sambrook et al., 2001, Molecular Cloning: A Laboratory Manual, Third Edition, Cold Spring Harbor Laboratory Press, Cold Spring Harbor, N.Y.; Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Berger and Kimmel, Guide to Molecular Cloning Techniques, Methods in Enzymology volume 152 Academic Press, Inc., San Diego, Calif. (Berger), DNA Cloning: A Practical Approach, Volumes I and II, 1985 (D. N. Glover ed.); Immobilized Cells and Enzymes, 1986 (IRL Press); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively), which are each incorporated by reference. These and many other attributes will be apparent upon reviewing the description provided herein.

A. Exemplary Microplate Handling Systems, Microplate Storage Units, and Computer Program Products As an overview, FIG. 12 schematically illustrates microplate handling system 100 according to one embodiment of the invention. As shown, microplate handling system 100 includes input non-priority microplate storage unit 102 and output non-priority microplate storage unit 104, which are each structured to store multiple stacked microplates. As further shown, microplate handling system 100 also includes priority microplate storage unit 106, which is structured to store a microplate. In some embodiments, priority microplate storage unit 106 includes a cover, e.g., to minimize the possibility contaminating samples disposed the wells of a priority microplate stored in the storage unit. The support structures of input non-priority microplate storage unit 102, output non-priority microplate storage unit 104, and priority microplate storage unit 106 each include retaining mechanisms 107 that are configured to reversibly retain microplates in the cavities of the respective storage units. Non-priority microplates are typically stored in input non-priority microplate storage unit 102 and output non-priority microplate storage unit 104, whereas priority microplates (e.g., microplates having stat samples) needing more urgent or immediate processing are typically stored in priority microplate storage unit 106. Optionally, other numbers of microplate storage units are included in the systems of the invention. In some embodiments, for example, two or more input non-priority microplate storage units, output non-priority microplate storage units, and/or priority microplate storage units (e.g., 3, 4, 5, 6, 7, 8, 9, 10, or more units) are included, e.g., to increase system capacity, to permit longer periods of unattended usage, and the like.

Microplate handling system 100 also includes microplate processing area 108 and non-priority microplate holding area 110. Microplates are typically positioned in microplate processing area 108 for processing, such as the addition and/or removal of materials to/from the wells of the microplates. Although not shown in FIG. 12, a material transfer component (e.g., fluid handling mechanism or the like) is typically disposed proximal to microplate processing area 108 to effect such microplate processing. Non-priority microplate holding area 110 is typically used to store non-priority plates, when the processing of those plates is interrupted by the introduction of a priority microplate into microplate handling system 100 via priority microplate storage unit 106. As shown, non-priority microplate holding area 110 includes non-priority microplate holding components 112, which together form a platform for holding non-priority microplates above support base 114.

To further illustrate, FIGS. 13 A-C schematically depict more detailed perspective views of input non-priority microplate storage unit 102, which is detachable from support base 114 of microplate handling system 100. Detachable microplate storage units typically facilitate microplate loading and transport to and from a given system. In some embodiments, however, microplate storage units are not detachable from microplate handling systems (e.g., are attached to or fabricated integral with other system components). As shown, non-priority microplate storage unit 102 includes support structure 200 that defines cavity 202, which is configured to store multiple vertically stacked microplates. Support structure 200 includes top end 204 and bottom end 206. Non-priority microplate storage unit 102 also includes base structure 208 operably connected to bottom end 206 of support structure 200. An opening (not within view in FIGS. 13 A-C) is disposed through base structure 208 and communicates with cavity 202. The dimensions of the opening are sufficient to accommodate microplates (e.g., microplates having specifications recommended by the Society for Biomolecular Sciences) moving into or out of cavity 202. As also mentioned above, base structure 208 is configured to detachably engage support base 114 of microplate handling system 100.

Although not within view in FIGS. 13 A-C, non-priority microplate storage unit 102 also includes a retaining mechanism (e.g., grippers that are configured to grip the sides of microplates, etc.) operably connected to base structure 208. In some embodiments, retaining mechanisms are operably connected to support structures of microplate storage units, in lieu of or in addition to being connected to base structures. Retaining mechanisms are configured to reversibly retain microplates in the openings and/or in the cavities of microplate storage units. Retaining mechanisms are described further below and in, e.g., U.S. Pat. No. 6,193,102, entitled "Plate Stacker Apparatus," which issued Feb. 27, 2001 to Bevirt et al., which is incorporated by reference.

Non-priority microplate storage unit 102 also includes alignment members 212 operably connected to surfaces of support structure 200. Alignment members 212 are configured to align microplates when the microplates are disposed in cavity 202. As also shown, non-priority microplate storage unit 102 includes cover member 214 that is configured to cover microplates when the microplates are disposed in cavity 202. In the embodiment shown in FIG. 12, output non-priority microplate storage unit 104 of microplate handling system 100 has same structure as input non-priority microplate storage unit 102. In other embodiments, however, input and output non-priority microplate storage units have structures that differ from one another (e.g., have different structural configurations, have different microplate holding capacities, etc.).

As further shown in FIGS. 13 A-C, non-priority microplate storage unit 102 also includes handle 210 that is pivotally attached to support structure 200 and to base structure 208. Handles are typically included, e.g., to facilitate the transport (manually or robotically) of microplate storage units to and from a given microplate handling system. Optionally, handles are pivotally attached only to support structures or to base structures. In some embodiments, handles are attached other than pivotally to support and/or base structures (e.g., in a fixed position that permits microplates to be loaded or unloaded from the particular microplate storage unit, etc.). Handle 210 pivots between an open position (shown in FIG. 13A) and closed (shown in FIG. 13C) or partially closed (shown in FIG. 13B) positions. Top end 204 of support structure 200 accommodates microplates moving into or out of cavity 202 when handle 210 is in the open position.

Handle 210 is shown as a swing arm having ends 217 that are pivotally attached to the base structure 208. Ends 217 of the swing arm extend through base structure 208 and are configured to align base structure 208 relative to support base 114 of microplate handling system 100, when handle 210 is in a closed position (shown in FIG. 13C) and support structure 208 engages the support base 114 of microplate handling system 100. As also shown in FIGS. 13 A-C, slots 216 are disposed through support structure 208, and handle 210 includes sliding members 218 (one not within view in FIGS. 13 A-C) that slide in slots 216, e.g., as handle 210 is raised, lowered, or pivoted.

Microplate handling system 100 also includes microplate transport mechanism 116, which is configured to selectively transport microplates between input non-priority microplate storage unit 102, output non-priority microplate storage unit 104, priority microplate storage unit 106, microplate processing area 108, and/or non-priority microplate holding area 110. Microplate transport mechanism 116 includes platform 118 (shown as a nest) that is structured to support microplates as they are transported between these areas and components of the system. Platform 118 is operably connected to an X-axis linear motion component (not within view in FIG. 12). The X-axis linear motion component microplate transport mechanism 116 is configured to selectively move platform 118 along guide track 120, which is parallel to the X-axis. As shown, platform 118 is configured to move beneath input non-priority microplate storage unit 102, output non-priority microplate storage unit 104, and priority microplate storage unit 106, which are each positioned above support base 114 along guide track 120. Although not completely within view in FIG. 2, the X-axis linear motion component includes a gantry disposed underneath support base 114 in addition to an encoder and stepper motor 122 that effect movement of platform 118 along guide track 120. Other motors, such as servo motors or the like are also optionally utilized. Microplate transport mechanism 116 also includes a Y-axis linear motion component (not within view in FIG. 12) operably connected to platform 118. The Y-axis linear motion component is configured to selectively raise and lower platform 118 along the Y-axis, for example, to obtain microplates from input non-priority microplate storage unit 102 and priority microplate storage unit 106, and to deliver microplates to output non-priority microplate storage unit 104. The Y-axis linear motion component also typically includes a stepper motor, servo motor, or other mechanism that effects movement of platform 118 along the Y-axis. Microplate transport mechanisms are described further below.

In addition, controller 124 (shown as a computer) is operably connected to microplate transport mechanism 116 of microplate handling system 100. Controller 124 is configured to selectively (e.g., in a pre-programmed or a direct user-selected order or sequence) direct microplate transport mechanism 116 to: (a) transport a non-priority microplate from input non-priority microplate storage unit 102 to microplate processing area 108; (b) position the non-priority microplate while in microplate processing area 108 (e.g., move the wells of the non-priority microplate along the X-axis and/or Y-axis relative to a material transfer component, etc.); and (c) transport the non-priority microplate from microplate processing area 108 to non-priority microplate holding area 110 (and position the non-priority microplate on non-priority microplate holding components 112 above support base 114) when a priority microplate (e.g., comprising stat samples or the like) is stored in priority microplate storage unit 106. Controller 124 is also configured to selectively direct microplate transport mechanism 116 to: (d) transport the priority microplate from priority microplate storage unit 106 to microplate processing area 108; (e) position the priority microplate while in microplate processing area 108 (e.g., move the wells of the priority microplate along the X-axis and/or Y-axis relative to a material transfer component, etc.); and (f) transport the priority microplate from microplate processing area 108 to output non-priority microplate storage unit 104 or to priority microplate storage unit 106 (e.g., once processing of the priority microplate is completed). In addition, controller 124 is also configured to selectively direct microplate transport mechanism 116 to: (g) transport the non-priority microplate from non-priority microplate holding area 110 to microplate processing area 108 (e.g., to resume processing the non-priority microplate); and (h) transport the non-priority microplate from microplate processing area 108 to output non-priority microplate storage unit 104 (e.g., once processing of the non-priority microplate is completed). Controllers and exemplary systems are described further below.

As also shown in FIG. 12, microplate handling system 100 also includes barcode reader 126. In the exemplary embodiment shown, barcode reader 126 is configured to read barcodes disposed on microplates when the microplates are disposed in or proximal to non-priority microplate holding area 110, e.g., to track the microplates or samples contained in the microplates in microplate handling system 100, particularly when microplate handling system 100 is included as a subsystem component of a system. Barcode reader 126 is typically operably connected to controller 124, which generally includes or is connected to a database of microplate/sample tracking information. Optionally, a barcode reader is disposed in or proximal to input non-priority microplate storage unit 102, output non-priority microplate storage unit 104, priority microplate storage unit 106, or microplate processing area 108, in lieu of being disposed in or proximal to non-priority microplate holding area 110 as shown, e.g., in FIG. 12. In some embodiments, the microplate handling systems of the invention includes multiple barcode readers.

The controllers of the systems described herein are generally configured to effect microplate transport and positioning. Controllers are typically operably connected to one or more system components, such as motors (e.g., via motor drives), microplate transport mechanisms (e.g., X-, Y- and/or Z-axis motion components, etc.), cleaning components, detectors, fluid sensors, robotic translocation devices, or the like, to control operation of these components. More specifically, controllers are generally included either as separate or integral system components that are utilized to effect, e.g., the movement of microplate retaining mechanisms of microplate storage units, the transport of microplates between system areas or components, the positioning of microplates relative to material transfer components, the detection and/or analysis of detectable signals received from sample materials by detectors, etc. Controllers and/or other system components is/are generally coupled to an appropriately programmed processor, computer, digital device, or other logic device or information appliance (e.g., including an analog to digital or digital to analog converter as needed), which functions to instruct the operation of these instruments in accordance with preprogrammed or user input instructions (e.g., microplate selection and routing, well selection, fluid volumes to be conveyed, etc.), receive data and information from these instruments, and interpret, manipulate and report this information to the user. In certain embodiments, the controller comprises or is operably connected to a database that includes microplate descriptors, such as the well and plate locations of particular sample materials to facilitate sample tracking.

Figure 14:
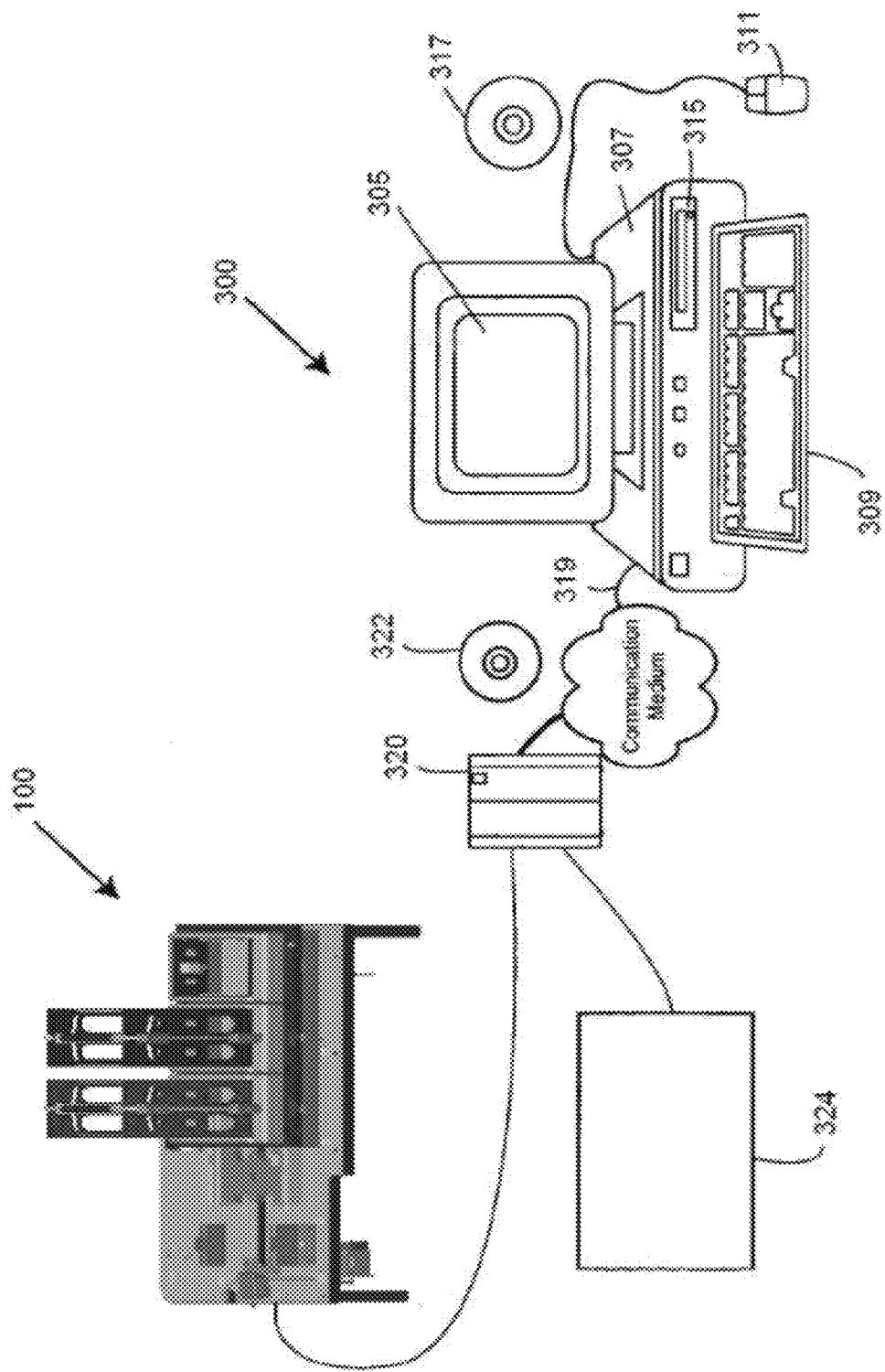
FIG. 14 is a block diagram showing a representative logic device in which various aspects of the present invention may be embodied.

A controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. An exemplary system comprising a computer is schematically illustrated in FIG. 14.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., positioning a microplate in a microplate processing area, aspirating fluidic materials from selected wells of a microplate, or the like. The computer then receives the data from, e.g., sensors/detectors included within the system, and interprets the data, either provides it in a user understood format, or uses that data to initiate further controller instructions, in accordance with the programming, e.g., such as in monitoring detectable signal intensity, microplate positioning, or the like.

More specifically, the software utilized to control the operation of the microplate handling systems of the invention typically includes logic instructions that direct, e.g., (a) transport a non-priority microplate from an input non-priority microplate storage unit of the microplate handling system to a microplate processing area of the microplate handling system; (b) position the non-priority microplate while in the microplate processing area; (c) transport the non-priority microplate from the microplate processing area to a non-priority microplate holding area of the microplate handling system when a priority microplate is stored in a priority microplate storage unit of the microplate handling system; (d) transport the priority microplate from the priority microplate storage unit to the microplate processing area; (e) position the priority microplate while in the microplate processing area; (f) transport the priority microplate from the microplate processing area to an output non-priority microplate storage unit of the microplate handling system or to the priority microplate storage unit; (g) transport the non-priority microplate from the non-priority microplate holding area to the microplate processing area of the microplate handling system; and (h) transport the non-priority microplate from the microplate processing area to the output non-priority microplate storage unit. In some embodiments, the software includes logic instructions for directing a material transfer component to transfer material to and/or from selected wells disposed in a microplate when the microplate is positioned in the microplate processing area. Optionally, the software includes logic instructions for directing a barcode reader of the microplate handling system to read barcodes disposed on microplates. The logic instructions of the software are typically embodied on a computer readable medium, such as a CD-ROM, a floppy disk, a tape, a flash memory device or component, a system memory device or component, a hard drive, a data signal embodied in a carrier wave, and/or the like. Other computer readable media are known to persons of skill in the art. In some embodiments, the logic instructions are embodied in read-only memory (ROM) in a computer chip present in one or more system components, without the use of personal computers.

The computer can be, e.g., a PC (Intel x86 or Pentium chip-compatible DOS™, OS2™, WINDOWS™, WINDOWS NT™, WINDOWS98™, WINDOWS2000™, WINDOWS XP™, WINDOWS Vista™, LINUX-based machine, a MACINTOSH™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., microplate transport, material conveyance to and/or from selected wells of a microplate, assay detection, and data deconvolution is optionally constructed by one of skill using a standard programming language such as Visual basic, C, C++, Fortran, Basic, Java, or the like.

The automated systems of the invention are optionally further configured to detect and quantify absorbance, transmission, and/or emission (e.g., luminescence, fluorescence, etc.) of light, and/or changes in those properties in samples that are arrayed in the wells of a multi-well container, on a substrate surface, or at other material sites. Alternatively, or simultaneously, detectors can quantify any of a variety of other signals from microplates or other containers including chemical signals (e.g., pH, ionic conditions, or the like), heat (e.g., for monitoring endothermic or exothermic reactions, e.g., using thermal sensors) or any other suitable physical phenomenon. In addition to other system components described herein, the systems of the invention optionally also include illumination or electromagnetic radiation sources, optical systems, and detectors. Because the systems and methods of the invention are flexible and allow essentially any chemistry to be assayed, they can be used for all phases of assay development, including prototyping and mass screening. A representative system that includes a microplate handling system as a sub-system component as well as a mass spectrometer is described further below.

In some embodiments, the systems of the invention are configured for area imaging, but can also be configured for other formats including as a scanning imager or as a nonimaging counting system. An area imaging system typically places an entire microplate onto the detector plane at one time. Accordingly, there is typically no need to move photomultiplier tubes (PMTs), to scan a laser, or the like, because the detector images the entire container onto many small detector elements (e.g., charge-coupled devices (CCDs), etc.) in parallel. This parallel acquisition phase is typically followed by a serial process of reading out the entire image from the detector. Scanning imagers typically pass a laser or other light beam over the specimen, to excite fluorescence, reflectance, or the like in a point-by-point or line-by-line fashion. In certain cases, confocal-optics are used to minimize out of focus fluorescence. The image is constructed over time by accumulating the points or lines in series. Nonimaging counting systems typically use PMTs or light sensing diodes to detect alterations in the transmission or emission of light, e.g., within wells of a microplate. These systems then typically integrate the light output from each well into a single data point.

A wide variety of illumination or electromagnetic sources and optical systems can be adapted for use in the systems of the present invention. Accordingly, no attempt is made herein to describe all of the possible variations that can be utilized in the systems of the invention and which will be apparent to one skilled in the art. Exemplary electromagnetic radiation sources that are optionally utilized in the systems of the invention include, e.g., lasers, laser diodes, electroluminescence devices, light-emitting diodes, incandescent lamps, arc lamps, flash lamps, fluorescent lamps, and the like. Exemplary optical systems that conduct electromagnetic radiation from electromagnetic radiation sources to sample containers and/or from microplate to detectors typically include one or more lenses and/or mirrors to focus and/or direct the electromagnetic radiation as desired. Many optical systems also include fiber optic bundles, optical couplers, filters (e.g., filter wheels, etc.), and the like.

Suitable signal detectors that are optionally utilized in these systems detect, e.g., molecular mass, emission, luminescence, transmission, fluorescence, phosphorescence, absorbance, or the like. In some embodiments, the detector monitors a plurality of optical signals, which correspond in position to "real time" results. Example detectors or sensors include PMTs, CCDs, intensified CCDs, photodiodes, avalanche photodiodes, optical sensors, scanning detectors, or the like. Each of these as well as other types of sensors is optionally readily incorporated into the systems described herein. The detector optionally moves relative to microplates or other assay components, or alternatively, microplates or other assay components move relative to the detector. In some embodiments, for example, detection components are coupled to translation components that move the detection components relative to microplates positioned in microplate processing areas of the systems described herein. Optionally, the systems of the present invention include multiple detectors. In these systems, such detectors are typically placed either in or adjacent to, e.g., a microplates or other vessel, such that the detector is in sensory communication with the microplates or other vessel (i.e., the detector is capable of detecting the property of the plate or vessel or portion thereof, the contents of a portion of the plate or vessel, or the like, for which that detector is intended). In certain embodiments, detectors are configured to detect electromagnetic radiation originating in the wells of a multi-well container.

The detector optionally includes or is operably linked to a computer, e.g., which has system software for converting detector signal information into assay result information or the like. For example, detectors optionally exist as separate units, or are integrated with controllers into a single instrument. Integration of these functions into a single unit facilitates connection of these instruments with the computer, by permitting the use of a few or even a single communication port for transmitting information between system components. Detection components that are optionally included in the systems of the invention are described further in, e.g., Skoog et al., Principles of Instrumental Analysis, 6$^{th}$ Ed., Brooks Cole (2006) and Currell, Analytical Instrumentation: Performance Characteristics and Quality, John Wiley & Sons, Inc. (2000), which are both incorporated by reference.

The systems of the invention optionally also include at least one robotic translocation or gripping component that is structured to grip and translocate microplates between components of the automated systems and/or between the systems and other locations (e.g., other work stations, etc.). In certain embodiments, for example, systems further include gripping components that move microplates between positioning components, incubation or storage components, etc. A variety of available robotic elements (robotic arms, movable platforms, etc.) can be used or modified for use with these systems, which robotic elements are typically operably connected to controllers that control their movement and other functions.

FIG. 14 is a schematic showing a representative system including an information appliance in which various aspects of the present invention may be embodied. Other exemplary systems are also described herein. As will be understood by practitioners in the art from the teachings provided herein, the invention is optionally implemented in hardware and software. In some embodiments, different aspects of the invention are implemented in either client-side logic or server-side logic. As will also be understood in the art, the invention or components thereof may be embodied in a media program component (e.g., a fixed media component) containing logic instructions and/or data that, when loaded into an appropriately configured computing device, cause that apparatus or system to perform according to the invention. As will additionally be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 14 shows information appliance or digital device 300 that may be understood as a logical apparatus (e.g., a computer, etc.) that can read instructions from media 317 and/or network port 319, which can optionally be connected to server 320 having fixed media 322. Information appliance 300 can thereafter use those instructions to direct server or client logic, as understood in the art, to embody aspects of the invention. One type of logical apparatus that may embody the invention is a computer system as illustrated in 300, containing CPU 307, optional input devices 309 and 311, disk drives 315 and optional monitor 305. Fixed media 317, or fixed media 322 over port 319, may be used to program such a system and may represent a disk-type optical or magnetic media, magnetic tape, solid state dynamic or static memory, or the like. In specific embodiments, the aspects of the invention may be embodied in whole or in part as software recorded on this fixed media. Exemplary computer program products are described further above. Communication port 319 may also be used to initially receive instructions that are used to program such a system and may represent any type of communication connection. Optionally, aspects of the invention are embodied in whole or in part within the circuitry of an application specific integrated circuit (ACIS) or a programmable logic device (PLD). In such a case, aspects of the invention may be embodied in a computer understandable descriptor language, which may be used to create an ASIC, or PLID.

In addition, FIG. 14 also shows microplate handling system 100, which is operably connected to information appliance 300 via server 320. Optionally, microplate handling system 100 is directly connected to information appliance 300. During operation, microplate handling system 100 typically transports microplates to and/or from selected microplate storage units, e.g., as part of an assay or other process. FIG. 14 also shows detector 324, which is optionally included in the systems of the invention. As shown, detector 324 is operably connected to information appliance 300 via server 320. In some embodiments, detector 324 is directly connected to information appliance 300. In certain embodiments, detector 324 is configured to detect detectable signals produced in the wells of microplates positioned in the microplate processing area of microplate handling system 100. In other embodiments, microplates, or sample materials from those microplates, are transferred (e.g., manually or using a robotic translocation device) to detector 324 to detect detectable signals produced in the wells of microplates or in the sample materials.

B. Exemplary System Embodiment

To further illustrate exemplary embodiments of the invention, FIGS. 15 A-G schematically depict a portion of a representative system for nucleic acid amplification product desalting and molecular mass measurement that includes microplate handling system 100 as a sub-system component. The measured molecular masses of the amplification products are typically used to determine base compositions of the corresponding amplification products, which are then generally correlated with the identities or organismal sources of the initial template nucleic acids, for example, as part of a research or in-vitro diagnostic application, among many others.

As shown in FIGS. 15 A-G, components of representative system 400 include microplate handling system 100, material transfer component 402, mixing station 404, wash stations 406 and 408, sample processing component 410, and sample injector 412. During operation, microplates are typically stored in input non-priority microplate storage unit 102, output non-priority microplate storage unit 104, and priority microplate storage unit 106 of microplate handling system 100. In some embodiments, for example, non-priority microplates are stored in input non-priority microplate storage unit 102 and priority microplates are stored in priority microplate storage unit 106 after target regions of template nucleic acids in those plates have been amplified, e.g., at a separate thermocycling station. Essentially any thermal cycling station or device is optionally adapted for use with a system of the invention, such as system 400. Examples of suitable thermocycling devices that are optionally utilized are available from many different commercial suppliers, including Mastercycler® devices (Eppendorf North America, Westbury, N.Y., U.S.A.), the COBAS® AMPLICOR Analyzer (Roche Molecular Systems, Inc., Pleasanton, Calif., U.S.A.), Mycycler and iCycler Thermal Cyclers (Bio-Rad Laboratories, Inc., Hercules, Calif., U.S.A.), and the SmartCycler System (Cepheid, Sunnyvale, Calif. U.S.A.), among many others. In other exemplary embodiments, sample preparation, thermal cycling, and related fluid handling components are integrated with the systems described herein, e.g., to fully automate a given nucleic acid amplification and analysis process. Instruments that can be adapted for this purpose include, for example, the m2000™ automated instrument system (Abbott Laboratories, Abbott Park, Ill., U.S.A.), the GeneXpert System (Cepheid, Sunnyvale, Calif. U.S.A.), and the COBAS® AmpliPrep® System (Roche Molecular Systems, Inc., Pleasanton, Calif., U.S.A.), and the like.

Microplates are transferred from input non-priority microplate storage unit 102 or priority microplate storage unit 106 to microplate processing area 108 using platform 118 of microplate transport mechanism 116. As referred to above and as shown in, e.g., FIGS. 15 F and G, platform 118 is operably connected to X-axis linear motion component 128. X-axis linear motion component 128 includes gantry 130. Platform 118 is operably connected to carriage 132, which moves along gantry 130. As further shown in FIGS. 15 F and G, microplate transport mechanism 116 also includes Y-axis linear motion component 134 operably connected to carriage 132 and to platform 118. Y-axis linear motion component 134 is configured to raise and lower platform 118 along the Y-axis. Suitable linear motion components, motors, and motor drives are generally available from many different commercial suppliers including, e.g., Techno-Isel Linear Motion Systems (New Hyde Park, N.Y., U.S.A.), NC Servo Technology Corp. (Westland, Mich., USA), Enprotech Automation Services (Ann Arbor, Mich., U.S.A.), Yaskawa Electric America, Inc. (Waukegan, Ill., U.S.A.), ISL Products International, Ltd. (Syosset, N.Y., U.S.A.), AMK Drives & Controls, Inc. (Richmond, Va., U.S.A.), Aerotech, Inc. (Pittsburgh, Pa., U.S.A.), HD Systems Inc. (Hauppauge, N.Y., U.S.A.), and the like. Additional detail relating to motors and motor drives are described in, e.g., Polka, Motors and Drives, ISA (2002) and Hendershot et al., Design of Brushless Permanent-Magnet Motors, Magna Physics Publishing (1994), which are both incorporated by reference.

Material transfer component 402 includes sample input gantry 414 and sample output gantry 416. Input gantry head 418 is configured to move along sample input gantry 414, whereas output gantry head 420 is configured to move along sample output gantry 416. Input gantry head 418 and output gantry head 420 each include needles that are configured to aspirate and dispense fluidic materials. Further, input gantry head 418 and output gantry head 420 are each configured to be raised and lowered along the Y-axis. During operation of exemplary system 900, the needle or pipetting tip of input gantry head 418 is typically used to aspirate an aliquot of magnetically responsive particles (e.g., magnetically responsive beads, such as BioMag®Plus Amine superparamagnetic microparticles available from Bangs Laboratories, Inc., Fishers, Ind., U.S.A.) that bind nucleic acids from magnetically responsive particle source (e.g., a magnetically responsive particle mixing cartridge) positioned at mixing station 404. Magnetically responsive particle sources and mixing stations are also described in, e.g., U.S. Provisional Patent App. No. 61/097,507, entitled "MIXING CARTRIDGES, MIXING STATIONS, AND RELATED KITS, SYSTEMS, AND METHODS" filed Sep. 16, 2008 by Hofstadler et al., which is incorporated by reference in its entirety. Nucleic acid purification involving magnetically responsive particles is also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., which are both incorporated by reference in their entirety. Optionally before, but typically after aspirating the aliquot of magnetically responsive particles (e.g., to minimize the possibility of cross-contaminating samples), the needle of input gantry head 418 is also generally used to aspirate an aliquot of an amplification product sample from a selected well of a microplate positioned in microplate processing area 108 of microplate handling system 100. The resulting mixture of magnetically responsive particle and amplification product sample aliquots disposed within the needle of input gantry head 418 is then typically transferred to sample processing component 410 along sample input gantry 414. After dispensing the mixture at sample processing component 410, the needle of input gantry head 418 is typically washed at wash station 406, e.g., to minimize the probability of cross-contaminating samples, prior to repeating this transfer cycle for other amplification product samples contained in the wells of a given microplate (e.g., priority or non-priority microplates) positioned in microplate processing area 108 of microplate handling system 100.

In the embodiment shown, sample processing component 410 is a desalting station that is used to desalt or otherwise purify nucleic acid amplification products in the sample mixture prior to mass spectrometric analysis. Sample processing component 410 includes carrier mechanism 422 (shown as a carousel), which includes a plurality of sample processing units 424. In the illustrated embodiment, each sample processing unit 424 includes cuvette 426 and magnet 428. After a mixture of magnetically responsive particle and amplification product sample aliquots is dispensed into a given cuvette 426, that cuvette is typically rotated in a counter clockwise direction on carrier mechanism 422 to various positions within sample processing component 410 where various reagents are added to and/or removed from that cuvette (e.g., via various fluidic handling components of manifold 430) as part of the process of purifying the amplification products captured or otherwise bound to the magnetically responsive particles in the mixture. When fluidic materials are removed from the cuvette at a given position within sample processing component 410, the cuvette is typically moved proximal to the magnet of the particular sample processing unit (e.g., cuvette 426 is moved proximal to magnet 428 of sample processing unit 424) using a conveyance mechanism to establish sufficient magnetic communication between the magnet and the magnetically responsive particles such that the magnetically responsive particles are moved to and retained on an internal surface of the cuvette while fluidic materials are removed from the cuvette. At the conclusion of a purification process for a given sample, the purified amplification products are then typically aspirated from the particular cuvette using the needle of output gantry head 420. During or prior this step, the nucleic acid amplification products are eluted from the magnetically responsive particles. After purified amplification products have been removed from a given cuvette, that cuvette is then generally rotated on carrier mechanism 422 into communication with cuvette wash station 427, where the cuvette is washed prior to commencing another purification cycle involving the cuvette and another sample. Sample processing components, such as sample processing component 410 and related desalting/purification methods are also described in, e.g., U.S. Provisional Patent App. No. 62/097,525, entitled "SAMPLE PROCESSING UNITS, SYSTEMS, AND RELATED METHODS" filed Sep. 16, 2008 by Hofstadler et al., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., and Hofstadler et al. (2003) "A highly efficient and automated method of purifying and desalting PCR products for analysis by electrospray ionization mass spectrometry" *Anal Biochem.* 316:50-57, which are each incorporated by reference in their entirety.

Purified and eluted amplification products that have been aspirated from a particular cuvette of sample processing component 410 are typically transported along sample output gantry 416 to sample injector 412 (shown as a two channel time-of-flight injector) using output gantry head 420. That is, the amplification products are typically dispensed from the needle or pipetting tip of output gantry head 420 into one of the two channels of sample injector 412, which generally comprise two independent sample injection syringe pumps that are configured to receive the amplification products. After dispensing the amplification products at sample injector 412, the needle of output gantry head 420 is typically washed at wash station 408 prior to aspirating another purified amplification product sample from sample processing component 410, e.g., to reduce the potential for carryover contamination between samples.

Figure 17A:
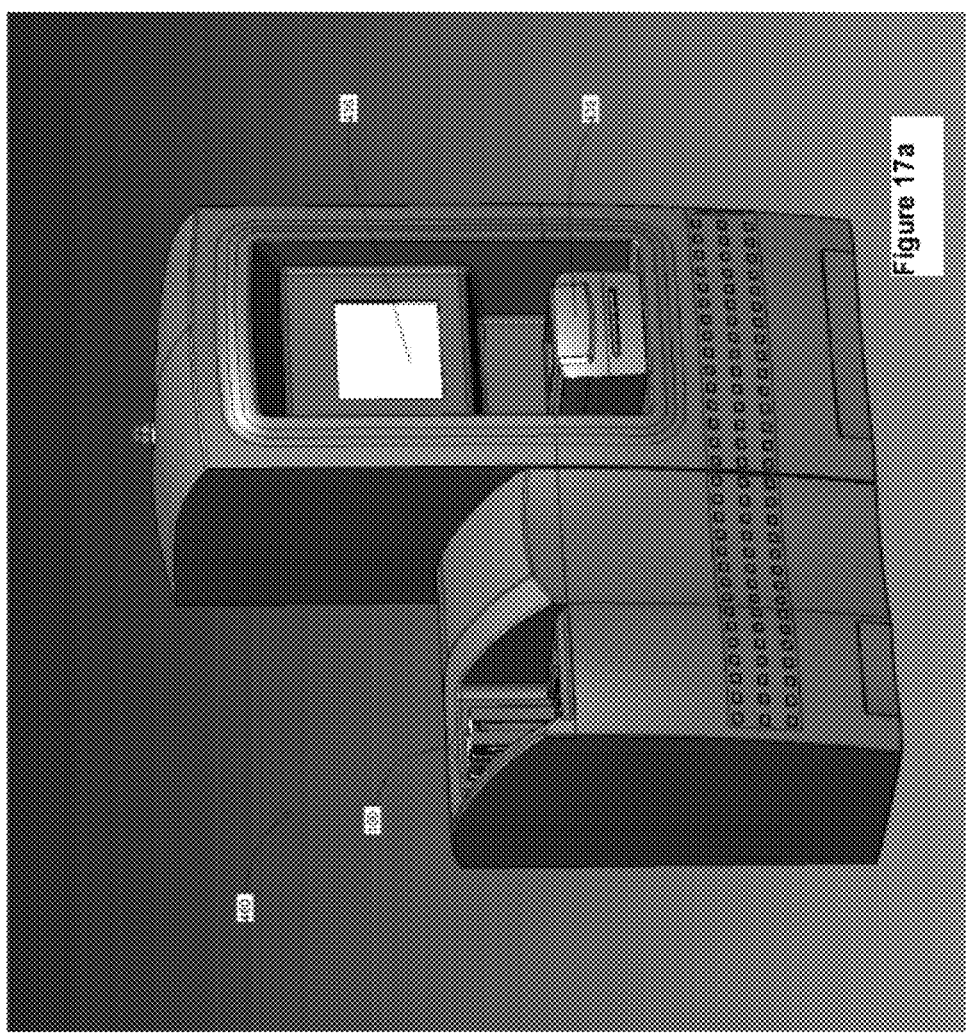
FIG. 17A schematically illustrates the representative system of FIG. 4A with an external covering from a perspective view.
Figure 17B:
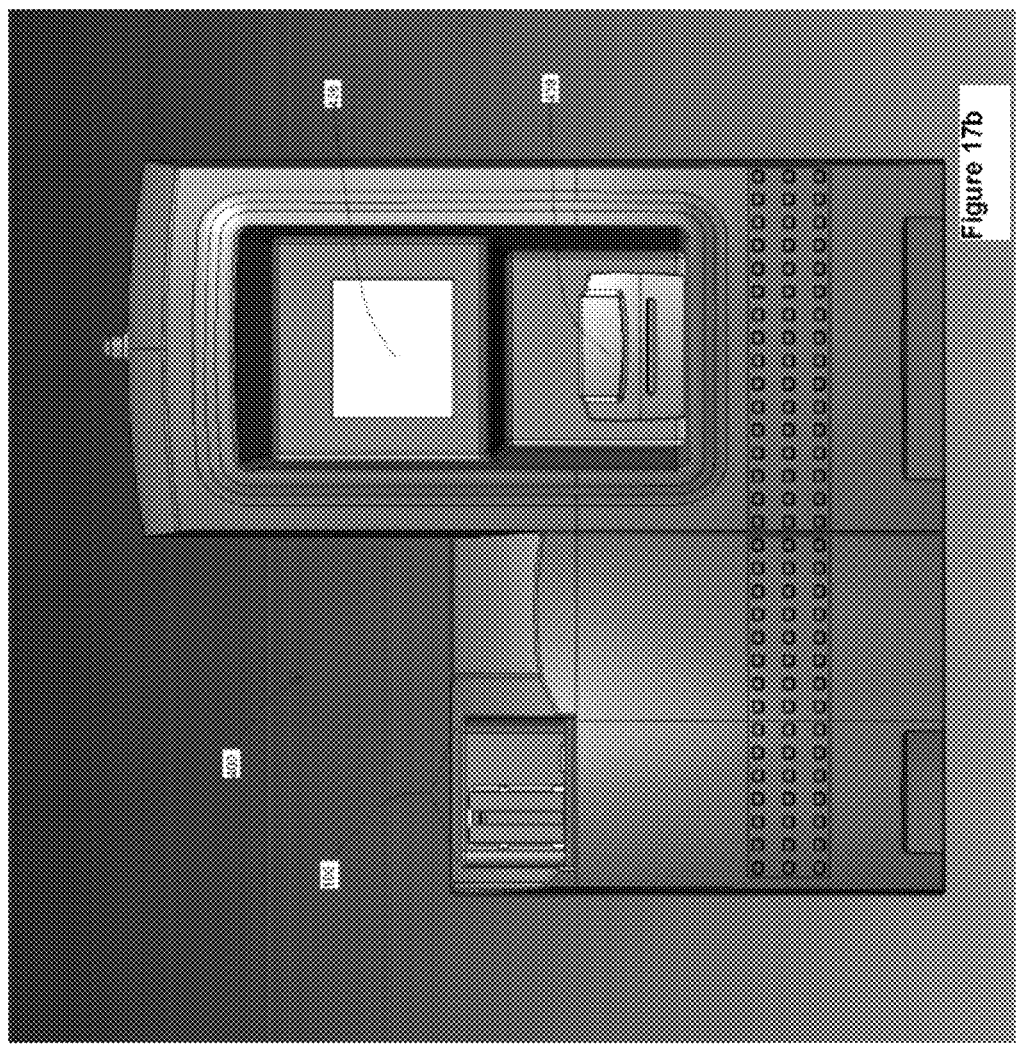
FIG. 17B schematically illustrates the representative system of FIG. 4A with an external covering from a front elevation view.

Now referring to FIG. 16, which schematically shows additional components of representative system 400 (sample processing component 410 not shown) from a perspective view. As shown, the additional components include dual sprayer module 432, which includes two independent electrospray ionization sprayers, and time-of-flight mass spectrometer 434. Amplification product samples received at sample injector 412 are typically injected into one of the two sprayers of dual sprayer module 432 for electrospray ionization and mass measurement in time-of-flight mass spectrometer 434. As further shown, the additional components of representative system 400 also include input/output device 436 (shown as a touch screen monitor), computer 437, output device 439 (shown as a printer), reagents and waste module 438, and chassis 440. Input/output device 436, computer 437, and output device 439 are components of a controller of system 400. Controllers are described further herein. Reagents and waste module 438 provide reagent sources and waste receptacles for system 400. Chassis 440 provides mechanical support for microplate handling system 100, sample processing component 410, and other components of system 400. To further illustrate, FIGS. 17 A-C schematically show representative system 400 with an external covering from various views. In addition, other exemplary methods of using the microplate handling systems and other aspects, as well as related computer program products are also described further herein.

In some embodiments, the base compositions of amplification products are determined from detected molecular masses. In these embodiments, base compositions are typically correlated with the identity of an organismal source, genotype, or other attribute of the corresponding template nucleic acids in a given sample. Suitable software and related aspects, e.g., for determining base compositions from detected molecular masses and for performing other aspects of base composition analysis are commercially available from Ibis Biosciences, Inc. (Carlsbad, Calif., U.S.A.). Nucleic acid base composition analysis is also described in many of the publications referred to herein, including, e.g., U.S. Pat. No. 7,255,992, entitled "METHODS FOR RAPID DETECTION AND IDENTIFICATION OF BIOAGENTS FOR ENVIRONMENTAL AND PRODUCT TESTING," which issued Aug. 14, 2007 to Ecker et al., U.S. Pat. No. 7,226,739, entitled "METHODS FOR RAPID DETECTION AND IDENTIFICATION OF BIOAGENTS IN EPIDEMIOLOGICAL AND FORENSIC INVESTIGATIONS," which issued Jun. 5, 2007 to Ecker et al., U.S. Pat. No. 7,217,510, entitled "METHODS FOR PROVIDING BACTERIAL BIOAGENT CHARACTERIZING INFORMATION," which issued May 15, 2007 to Ecker et al., and U.S. Pat. No. 7,108,974, entitled "METHOD FOR RAPID DETECTION AND IDENTIFICATION OF BIOAGENTS," which issued Sep. 19, 2006 to Ecker et al., which are each incorporated by reference in their entirety.

C. Exemplary Microplate Handling Methods

Figure 18:
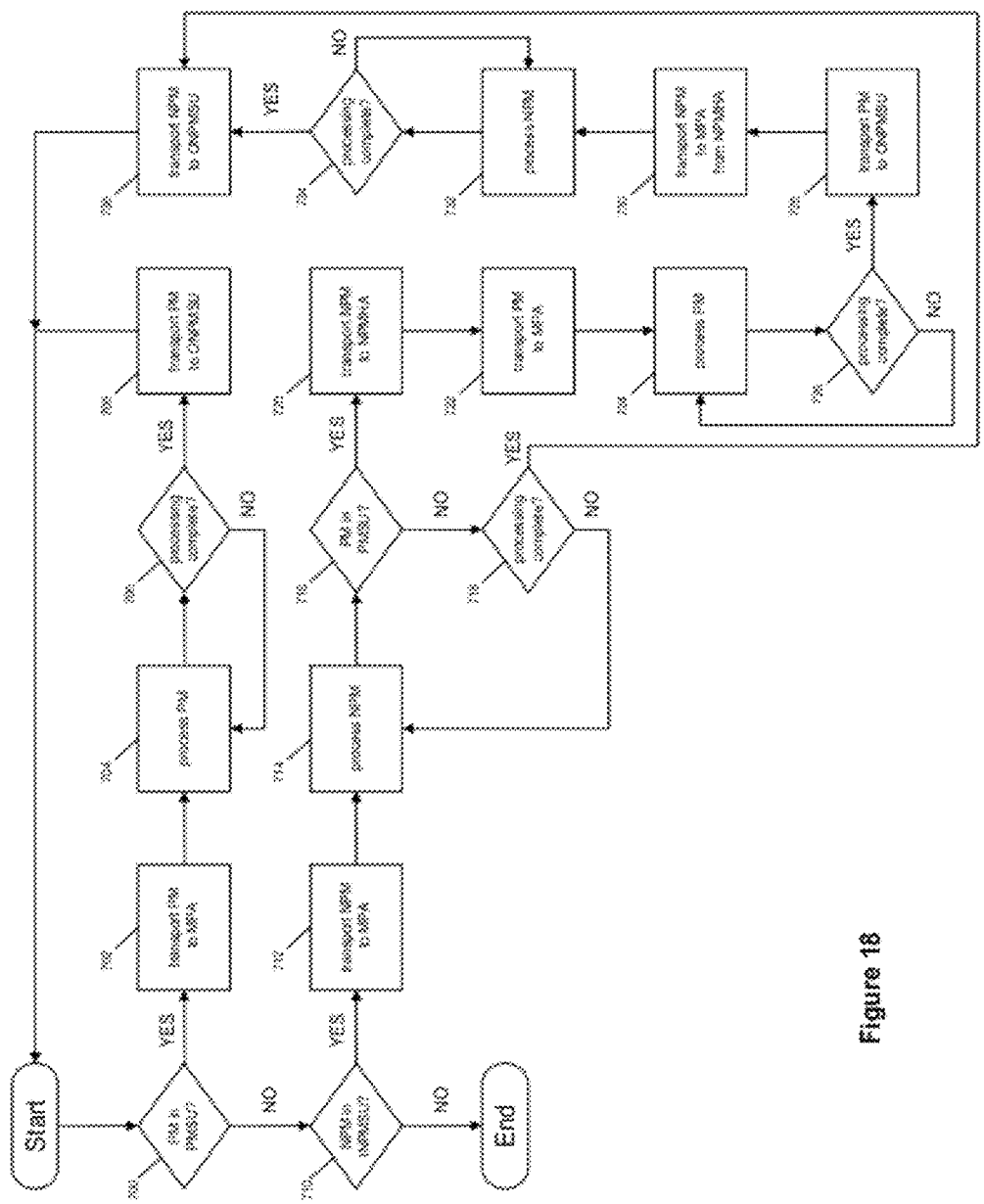
FIG. 18 is a flow chart schematically showing the handling and management of microplates in a microplate handling system according to one embodiment of the invention.

To further illustrate, FIG. 18 is a flow chart that schematically shows the handling or management of microplates in a microplate handling system according to one embodiment of the invention. Referring now also to FIGS. 19 A-G, which schematically depicts aspects of the process illustrated in FIG. 18 in the context of microplate handling system 100. As shown, the illustrated process commences with query 700, which asks whether a priority microplate (PM) is stored or positioned in a priority microplate storage unit (PMSU) of the microplate handling system. If a priority microplate is stored in the priority microplate storage unit, the priority microplate is transported to the microplate processing area (MPA) from the priority microplate storage unit using the microplate transport mechanism of the microplate handling system (step 702). The priority microplate is processed in the microplate processing area (step 704). Microplate processing generally includes positioning a microplate relative to the material handling component of the system so that materials can be added to and/or removed from selected wells of the microplate. After a processing step is concluded (e.g., fluidic material is added to or removed from a selected well), query 706 asks whether the processing of the priority microplate is completed. If processing is not complete, then processing continues. If the processing of the priority microplate is completed, however, the microplate transport mechanism transports the processed priority microplate to the output non-priority microplate storage unit (ONPMSU) (step 708) and as shown, the process starts over.

As further shown in FIG. 18, if no priority microplate is stored in the priority microplate storage unit (query 700), the process also includes querying whether a non-priority microplate (NPM) is stored in the input non-priority microplate storage unit (INPMSU) (query 710). As shown, if no non-priority microplate is present, then the process ends. If a non-priority microplate is stored in the input non-priority microplate storage unit, then the microplate transport mechanism of the system transports the non-priority microplate to the microplate processing area (step 712) and processing of the non-priority microplate commences (step 714). To illustrate, FIG. 19A schematically shows non-priority microplates stored in input non-priority microplate storage unit 102 of microplate handling system 100, and FIG. 19B schematically shows non-priority microplate 101 positioned in microplate processing area 108 of microplate handling system 100 after being transported from input non-priority microplate storage unit 102. After a given processing step is concluded, query 716 asks whether there is a priority microplate in the priority microplate storage unit. If no priority microplate is stored in the priority microplate storage unit, the process continues with query 718, which asks whether the processing of the non-priority microplate is completed. If the processing of the non-priority microplate is not completed, then processing continues. In contrast, if the processing of the non-priority microplate is completed, then the non-priority microplate is transported to the output non-priority microplate storage unit using the microplate transport mechanism (step 736) and as illustrated, the process starts over.

Figure 19G:
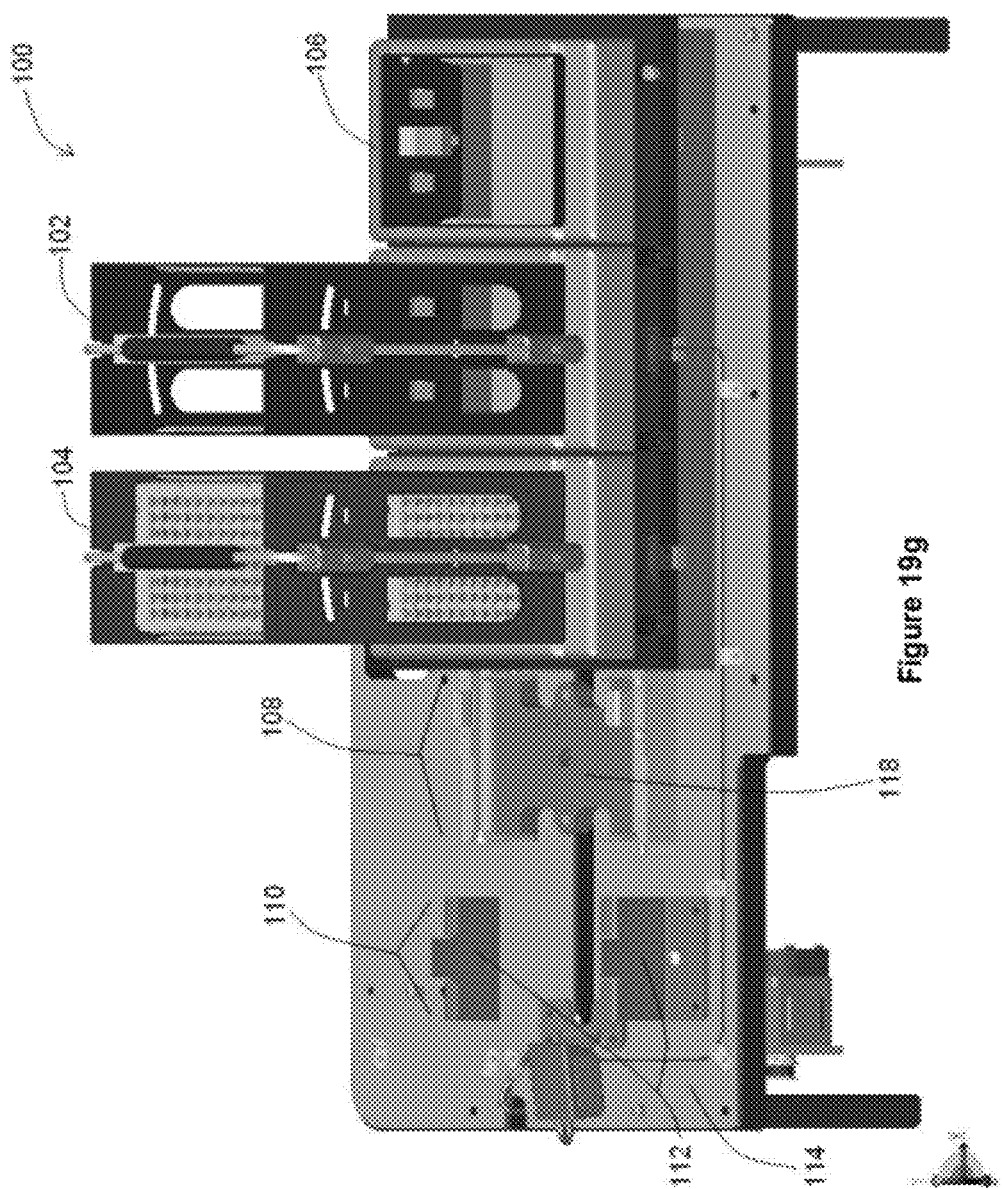
FIG. 19G schematically shows microplates in an output non-priority microplate storage unit of the microplate handling system of FIG. 8A after all of the microplates have been processed using the microplate handling system.
Figure 20A:
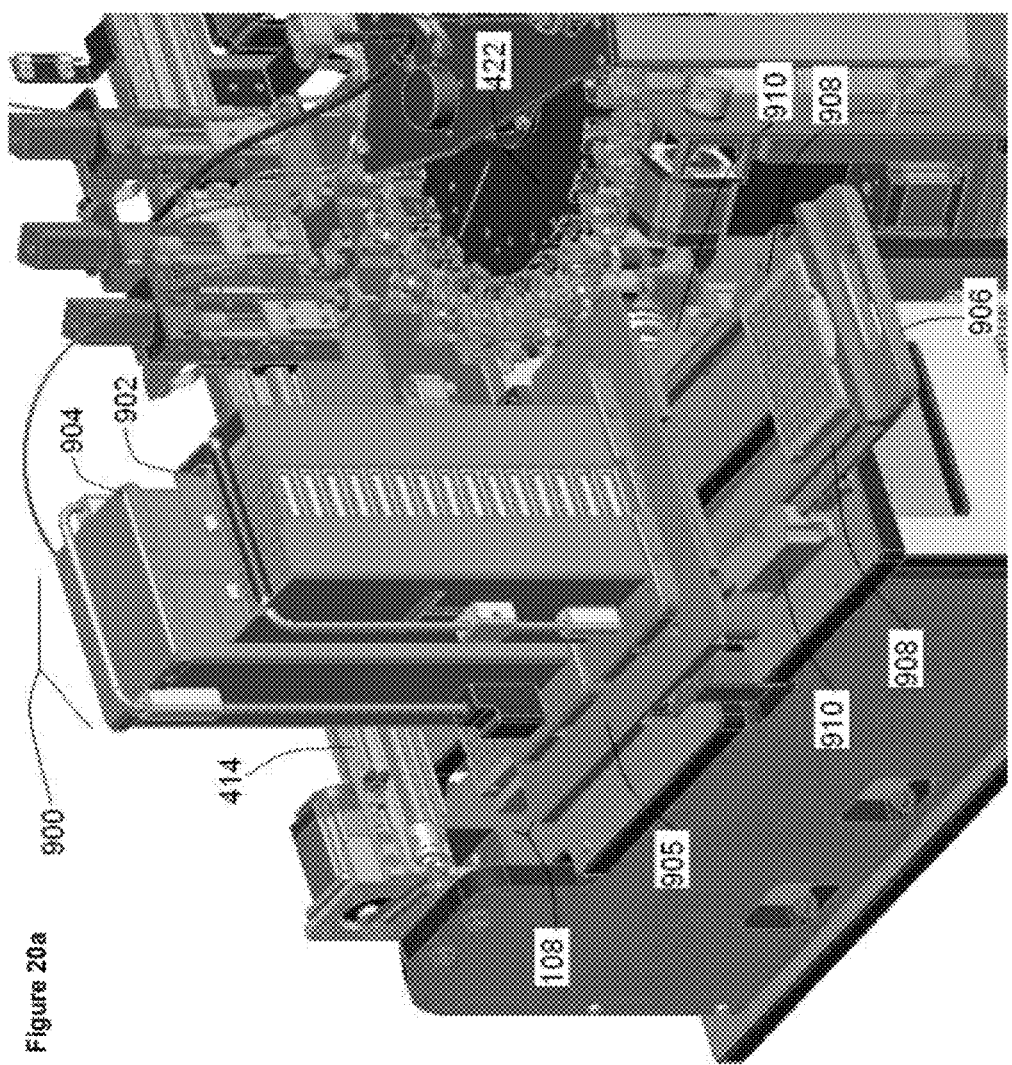
Figure 20C:
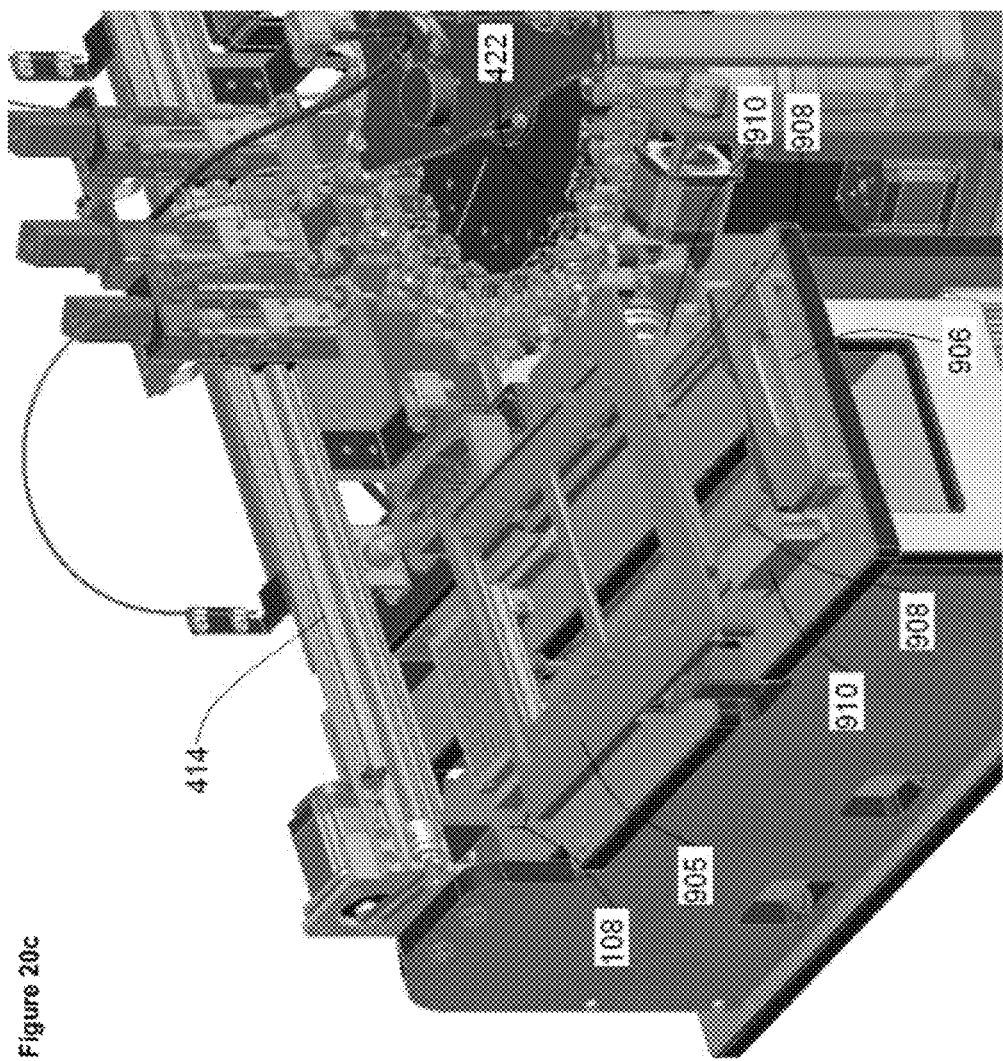
Figure 21A:
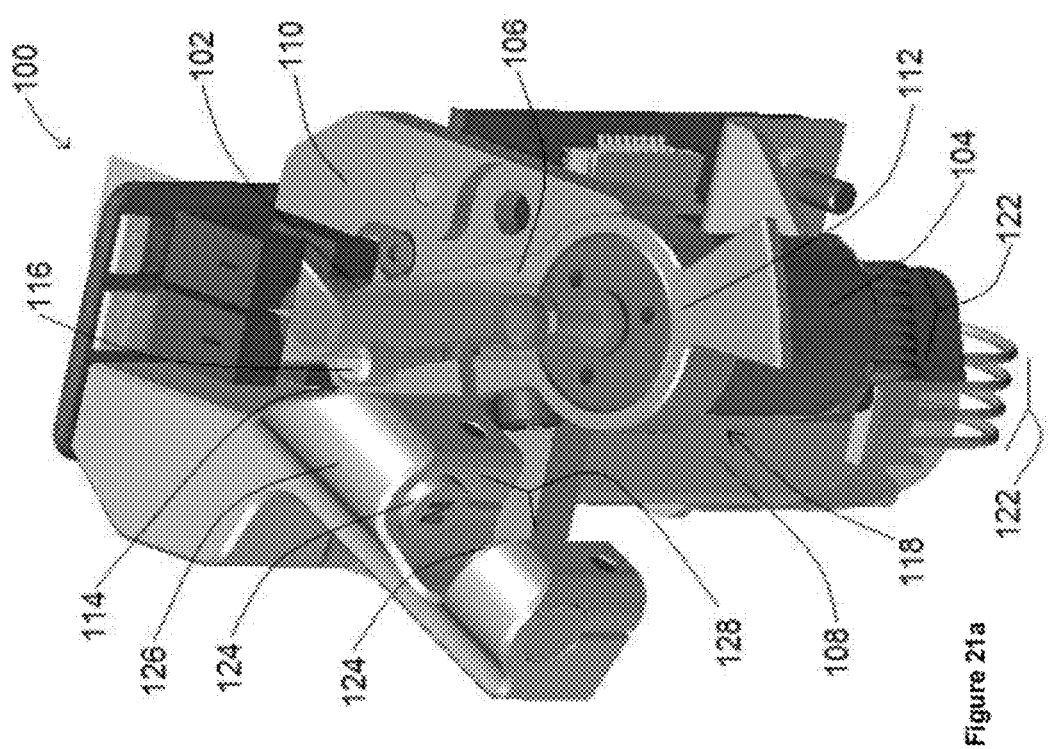
FIG. 21A schematically shows a sample processing unit with a cuvette in a second position from a perspective view according to one embodiment of the invention.
Figure 21B:
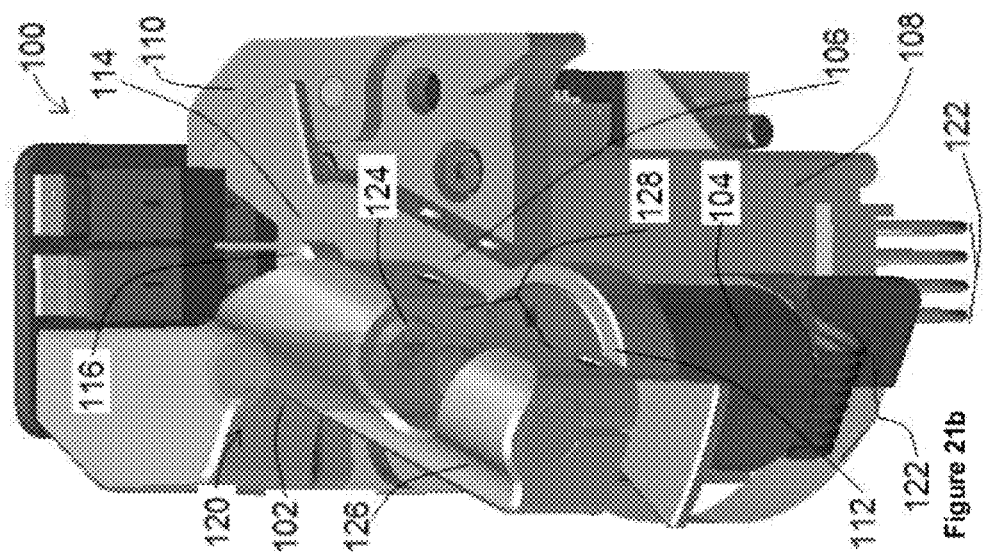
FIG. 21B schematically depicts the sample processing unit of FIG. 1A with the cuvette in a first position from a perspective view.
Figure 21C:
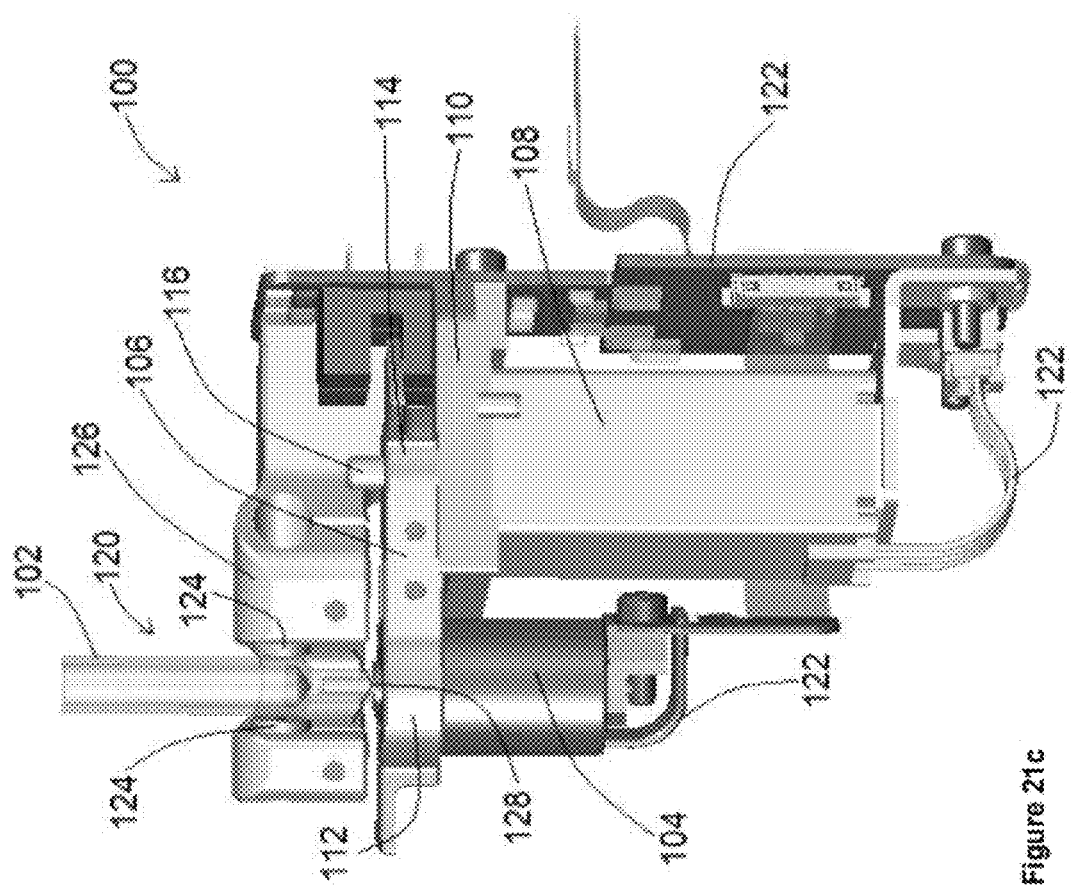
FIG. 21C schematically depicts the sample processing unit of FIG. 1A with the cuvette in a first position from a side elevation view.
Figure 21D:
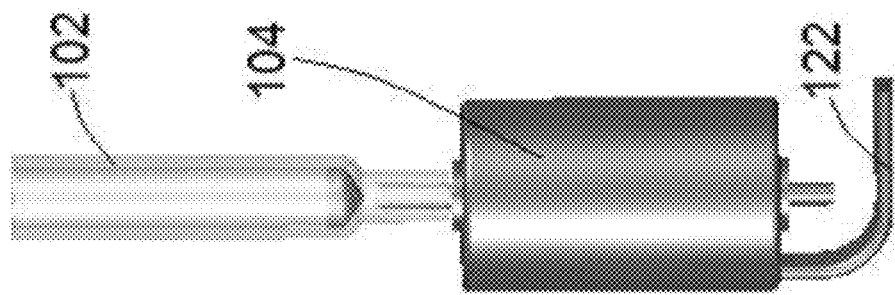
FIG. 21D schematically illustrates a detailed side elevation view of a motor operably connected to a cuvette of the sample processing unit of FIG. 1A.

If the answer to query 716 is that a priority microplate is stored in the priority microplate storage unit, then the non-priority microplate currently positioned in the microplate processing area is transported to the non-priority microplate holding area (NPMHA) using the microplate transport mechanism (step 720). The microplate transport mechanism then transports the priority microplate from the priority microplate storage unit to the microplate processing area (step 722) where processing of the priority microplate begins (step 724). To illustrate, FIG. 19C schematically shows priority microplate 103 stored in priority microplate storage unit 106, while non-priority microplate 101 is positioned in microplate processing area 108 of microplate handling system 100. FIG. 19D schematically depicts priority microplate 103 positioned in microplate processing area 108 of microplate handling system 100 after non-priority microplate 101 has been transported and positioned in non-priority microplate holding area 110. After a processing step is concluded, query 726 asks whether the processing of the priority microplate is completed. As shown, if processing of the priority microplate is not completed, then the processing continues. If processing of the priority microplate is completed, however, the priority microplate is transported to the output non-priority microplate storage unit using the microplate transport mechanism (step 728). The microplate transport mechanism then returns to the non-priority microplate holding area and transports the non-priority microplate, whose processing had been interrupted, to microplate processing area (step 730) to resume processing (step 732). To illustrate, FIG. 19E schematically shows platform 118 in microplate processing area 108 of microplate handling system 100 after the microplate transport mechanism transported priority microplate 103 to output non-priority microplate storage unit 104. To further illustrate, FIG. 19F schematically depicts non-priority microplate 101 positioned in microplate processing area 108 to resume processing after the microplate transport mechanism of microplate handling system 100 transported non-priority microplate 101 from non-priority microplate holding area 110. After a given processing step is concluded, query 734 asks whether the processing of the non-priority microplate is complete. If processing of the non-priority microplate is not completed, then the processing continues. If processing of the non-priority microplate is completed, however, then the microplate transport mechanism transports the non-priority microplate output non-priority microplate storage unit (step 736) and as shown, the process starts over. To further illustrate, FIG. 19G schematically shows microplates in output non-priority microplate storage unit 104 after all of the microplates have been processed using microplate handling system 100.

D. Additional Exemplary Microplate Handling System Embodiments

Figure 20:
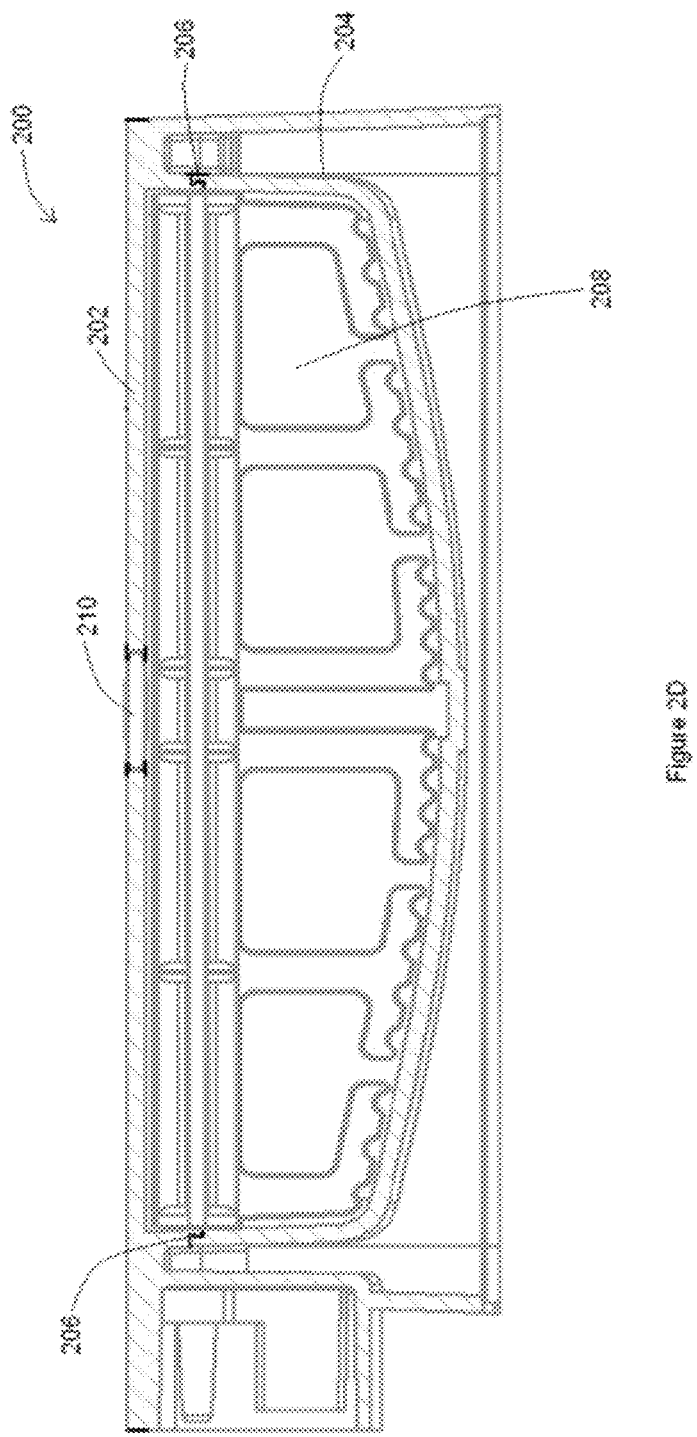
FIG. 20A schematically illustrates selected components of a representative system that includes a microplate handling system as a sub-system component from a perspective view according to one embodiment of the invention in which a support structure of a priority microplate storage unit of the microplate handling system is shown in an open position.
FIG. 20B schematically depicts the representative system of FIG. 9A from another perspective view in which the support structure of the priority microplate storage unit of the microplate handling system is shown in a closed position.
FIG. 20C schematically depicts the representative system of FIG. 9A from another perspective view in which non-priority microplate storage units have been removed from the microplate handling system.
FIG. 20D schematically shows the representative system of FIG. 9A from a top elevation view in which the support structure of the priority microplate storage unit of the microplate handling system is shown in an open position.
FIG. 20E schematically shows the representative system of FIG. 9A from another top elevation view in which the support structure of the priority microplate storage unit of the microplate handling system is shown in a closed position.
FIG. 20F schematically depicts the representative system of FIG. 9A from a side elevation view in which the support structure of the priority microplate storage unit of the microplate handling system is shown in an open position.
FIG. 20G schematically depicts the representative system of FIG. 9A from a side elevation view in which the support structure of the priority microplate storage unit of the microplate handling system is shown in a closed position.
FIG. 20H schematically shows the representative system of FIG. 9A from a front elevation view.
Figure 3D:
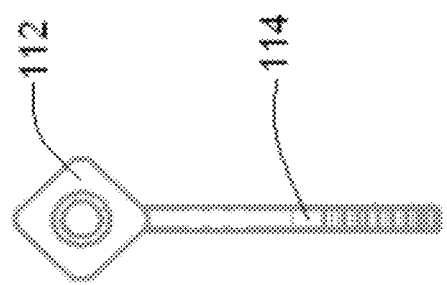
FIG. 3D schematically shows the rotatable member and protrusions of FIG. 3A from a back elevation view.
Figure 3C:
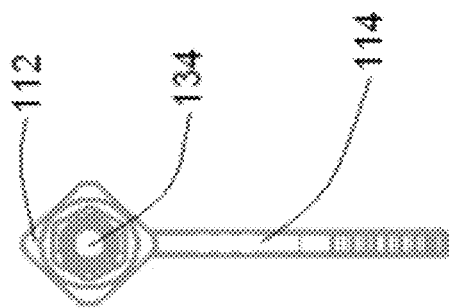
FIG. 3C schematically illustrates the rotatable member and protrusions of FIG. 3A from a front elevation view.
Figure 3E:
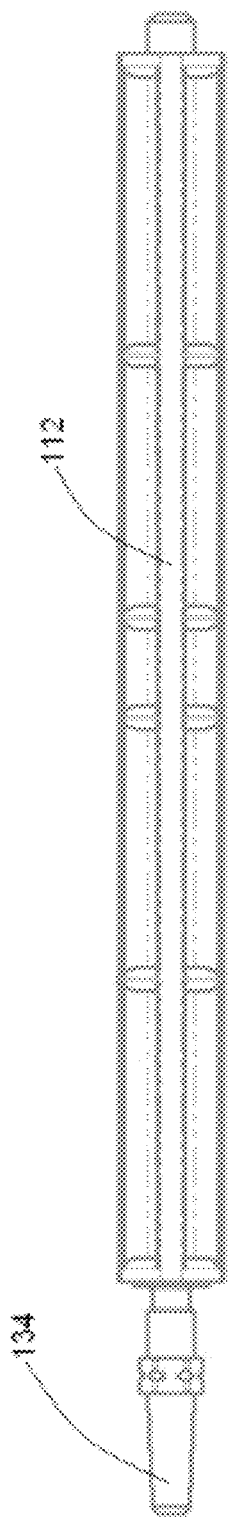
FIG. 3E schematically shows the rotatable member of FIG. 3A from a top view.
Figure 3F:
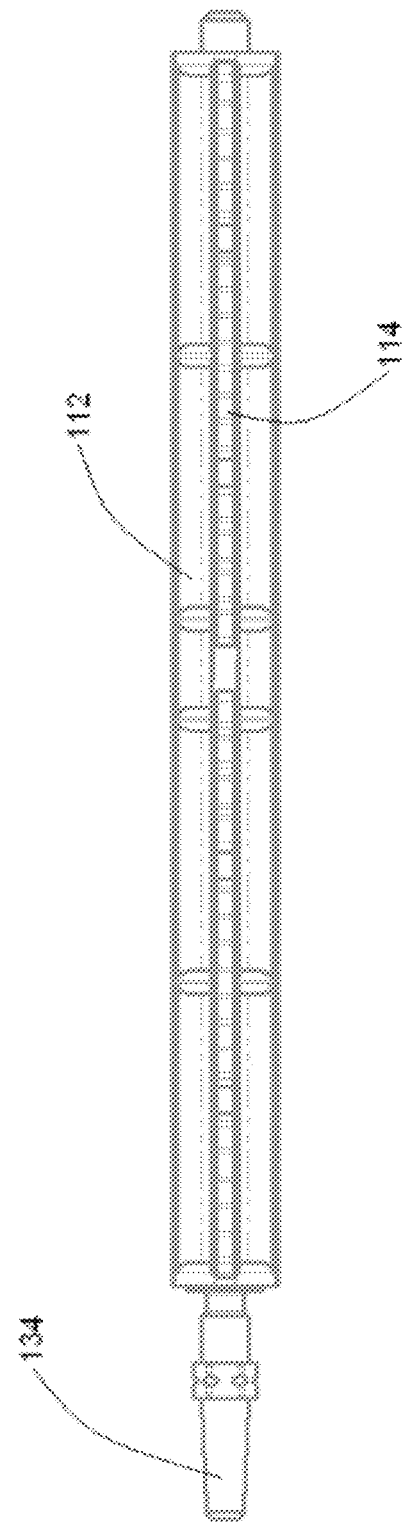
FIG. 3F schematically depicts the rotatable member and protrusions of FIG. 3A from a bottom view.

To illustrate additional representative embodiments, FIGS. 20 A-H schematically depict a portion of the representative system schematically shown in FIGS. 15 A-G in which microplate handling system 900 has been substituted for microplate handling system 100. As shown, microplate handling system 900 includes input non-priority microplate storage unit 902 and output non-priority microplate storage unit 904, which each removably attach to microplate handling system support base 905. As also shown, microplate handling system 900 also includes priority microplate storage unit 906 (shown as a stat tray drawer). Support structure 908 of priority microplate storage unit 906 is operably connected to movement mechanism 910 (shown as guide tracks). Support structure 908 is configured to slide relative to movement mechanism 910 between open and close positions. Priority microplates are typically loaded in priority microplate storage unit 906 when support structure 908 is in an open position. Microplate transport mechanism 116 typically moves priority microplates from priority microplate storage unit 906 when support structure 908 is in a closed position. Additional system features and components are described further herein.

E. Exemplary Fabrication Methods and Materials

System components (e.g., microplate storage units, microplate transport mechanisms, support bases, etc.) are optionally formed by various fabrication techniques or combinations of such techniques including, e.g., machining, embossing, extrusion, stamping, engraving, injection molding, cast molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, 3.sup.rd Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. In certain embodiments, following fabrication, system components are optionally further processed, e.g., by coating surfaces with a hydrophilic coating, a hydrophobic coating (e.g., a Xylan 1010DF/870 Black coating available from Whitford Corporation (West Chester, Pa.), etc.), or the like, e.g., to prevent interactions between component surfaces and reagents, samples, or the like.

III. Sample Processing/Spin Mixing Systems

The invention relates to sample purification, and in various embodiments provides sample processing units, carrier mechanisms, sample processing stations, systems, and related methods that are useful for this purpose. The sample processing units and related aspects of the invention can be used, or adapted for use, in a wide variety of sample purification processes. In certain embodiments, for example, microplates comprising nucleic acid amplification reaction mixtures are loaded into microplate storage units of a microplate handling system. In some of these embodiments, a microplate transport mechanism of the system transports the microplates to a microplate processing area, where a material transfer component transfers aliquots of the reaction mixtures from the wells of the microplates to a sample processing system. In these embodiments, the sample processing system is typically used to purify amplification products or amplicons in the reaction mixture aliquots for subsequent detection or other analysis. To further illustrate, in some of these embodiments, the molecular masses of these purified amplicons are measured using a mass spectrometer, e.g., an electrospray ionization time-of-flight mass spectrometer or the like. The base compositions of the amplicons are typically determined from the measured molecular masses and correlated with an identity or source of target nucleic acids in the amplification reaction mixtures, such as a pathogenic organism.

Particular embodiments of molecular mass-based detection methods and other aspects that are optionally adapted for use with the sample processing units and related aspects of the invention are described in various patents and patent applications, including, for example, U.S. Pat. Nos. 7,108,974; 7,217,510; 7,226,739; 7,255,992; 7,312,036; and 7,339,051; and US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; and WO2007/100397; WO2007/118222, which are each incorporated by reference as if fully set forth herein.

Exemplary molecular mass-based analytical methods and other aspects of use in the sample processing units and systems described herein are also described in, e.g., Ecker et al. (2005) "The Microbial Rosetta Stone Database: A compilation of global and emerging infectious microorganisms and bioterrorist threat agents" *BMC Microbiology* 5(1):19; Ecker et al. (2006) "The Ibis T5000 Universal Biosensor: An Automated Platform for Pathogen Identification and Strain Typing" *JALA* 6(11):341-351.; Ecker et al. (2006) "Identification of *Acinetobacter* species and genotyping of *Acinetobacter baumannii* by multilocus PCR and mass spectrometry" *J Clin Microbiol.* 44(8):2921-32.; Ecker et al. (2005) "Rapid identification and strain-typing of respiratory pathogens for epidemic surveillance" *Proc Natl Acad Sci USA*. 102(22):8012-7; Hannis et al. (2008) "High-resolution genotyping of *Campylobacter* species by use of PCR and high-throughput mass spectrometry" *J Clin Microbiol.* 46(4):1220-5; Blyn et al. (2008) "Rapid detection and molecular serotyping of adenovirus by use of PCR followed by electrospray ionization mass spectrometry" *J Clin Microbiol.* 46(2):644-51; Sampath et al. (2007) "Global surveillance of emerging Influenza virus genotypes by mass spectrometry" *PLoS ONE* 2(5): e489; Sampath et al. (2007) "Rapid identification of emerging infectious agents using PCR and electrospray ionization mass spectrometry" *Ann N Y Acad. Sci.* 1102:109-20; Hall et al. (2005) "Base composition analysis of human mitochondrial DNA using electrospray ionization mass spectrometry: a novel tool for the identification and differentiation of humans" *Anal Biochem.* 344(1):53-69; Hofstadler et al. (2003) "A highly efficient and automated method of purifying and desalting PCR products for analysis by electrospray ionization mass spectrometry" *Anal Biochem.* 316:50-57; Hofstadler et al. (2006) "Selective ion filtering by digital thresholding: A method to unwind complex ESI-mass spectra and eliminate signals from low molecular weight chemical noise" *Anal Chem.* 78(2):372-378.; and Hofstadler et al. (2005) "TIGER: The Universal Biosensor" *Int J Mass Spectrom.* 242(1):23-41, which are each incorporated by reference.

In addition to the molecular mass and base composition analyses referred to above, essentially any other nucleic acid amplification technological process is also optionally adapted for use in the systems of the invention. Other exemplary uses of the systems and other aspects of the invention include numerous biochemical assays, cell culture purification steps, and chemical synthesis, among many others. Many of these as well as other exemplary applications of use in the systems of the invention are also described in, e.g., Current Protocols in Molecular Biology, Volumes I, II, and III, 1997 (F. M. Ausubel ed.); Perbal, 1984, A Practical Guide to Molecular Cloning; the series, Methods in Enzymology (Academic Press, Inc.); Sambrook et al., 2001, Molecular Cloning: A Laboratory Manual, Third Edition, Cold Spring Harbor Laboratory Press, Cold Spring Harbor, N.Y.; Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Berger and Kimmel, Guide to Molecular Cloning Techniques, Methods in Enzymology volume 152 Academic Press, Inc., San Diego, Calif. (Berger), DNA Cloning: A Practical Approach, Volumes I and II, 1985 (D. N. Glover ed.); Immobilized Cells and Enzymes, 1986 (IRL Press); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively), which are each incorporated by reference.

A. Example Sample Processing Units and Carrier Mechanisms

FIGS. 21 A-D schematically illustrate a sample processing unit or components thereof according to one embodiment of the invention. As shown, sample processing unit 100 includes cuvette 102 operably connected to first motor 104 (shown as a brushless DC motor). First motor 104 (i.e., one embodiment of a rotational mechanism) is configured to rotate cuvette 102 around a central longitudinal axis of cuvette 102. As also shown, first motor 104 is operably connected to support member 106 (shown as a swing arm). First motor 104 is optionally configured (e.g., under the control of an appropriately programmed controller) to rotate cuvette 102 in at least one pulsed mode, during which a substantial portion of the time of rotation, a rate of rotation of cuvette 102 exceeds a rate of rotation of sample material in cuvette 102 such that the sample material is sheared away from a surface of cuvette 102, e.g., to effect mixing of the sample material. To further illustrate, first motor 104 is optionally configured (e.g., again under the control of an appropriately programmed controller) to rotate cuvette 102 in at least one oscillating motion, e.g., also to effect mixing of sample materials. Controllers and rotational modes are described further herein.

Support member 106 is also operably connected to second motor 108 (shown as a brushless direct current motor) via mounting bracket 110. Support member 106 includes first end 112 and second end 114. Cuvette 102 is retained proximal to first end 112 of support member 106 via first motor 104, whereas second motor 108 is operably connected to support member 106 proximal to second end 114 of support member 106. Support member 106 is configured to rotate at least partially around a rotational axis extending through and proximal to second end 114 of support member 106. Pin 116 is fixedly coupled to second end 114 of support member 106 and aligned with the rotational axis. Pin 116 is also operably coupled to second motor 108, which effects rotation of cuvette 102 between second position 118 (e.g., a cuvette rotational or spin position) and first position 120 via pin 116 and support member 106. Collectively, second motor 108, pin 116, and support member 106 are components of one embodiment of an exemplary conveyance mechanism. As additionally shown, sample processing unit 100 includes circuitry 122 that electrically connects to first motor 104, second motor 108, and a controller or power source (not shown) to effect control of first motor 104 and second motor 108.

Sample processing unit 100 also includes magnets 124 (shown as permanent magnets) attached to magnet mounting arm 126, e.g., to facilitate certain processing steps that involve magnetically-based separation of materials. In some embodiments, electromagnets are utilized. Magnet mounting arm 126 is operably connected to mounting bracket 110 and holds magnets 124 in substantially fixed positions relative to cuvette 102 and support member 106. Magnets 124 are disposed proximal to receiving space 126. As illustrated, for example, in FIGS. 21B and C, when cuvette 102 is in first position 120, cuvette 102 is located at least partially within receiving space 128.

To further illustrate, FIGS. 22 A and B schematically show sample processing unit 200 from perspective views according to another exemplary embodiment of the invention. As shown, sample processing unit 200 includes only single magnet 202 attached to mounting bracket 204 via magnet mounting arm 206 in a substantially fixed positions relative to cuvette 208, support member 210, and first motor 212. In addition to support member 210, the conveyance mechanism of sample processing unit 200 also includes second motor 214, which conveys cuvette 208 between first position 216 (shown in FIG. 22A) and second position 218 (shown in FIG. 22B).

Figure 23A:
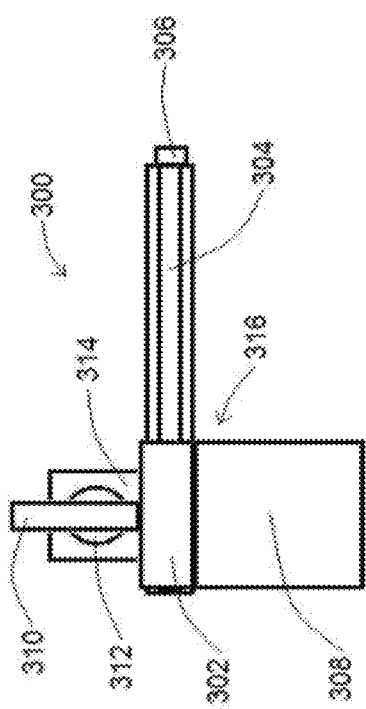
FIG. 23A schematically shows a sample processing unit with a slidable support member in a first position from a front elevation view according to one embodiment of the invention.
Figure 23B:
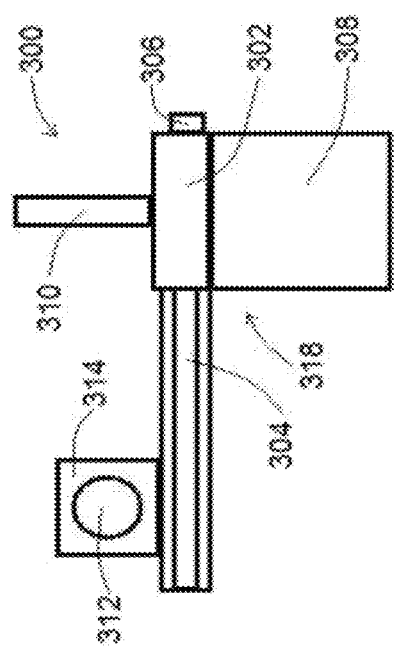
FIG. 23B schematically depicts the sample processing unit of FIG. 3A with the slidable support member in a second position from a perspective view.

The conveyance mechanisms of the sample processing units of the invention include various embodiments. As mentioned above, in certain embodiments, conveyance mechanisms are configured to rotate cuvettes or other types of containers between selected positions (e.g., between spin mixing, detection, and magnetic particle retention positions). Essentially any other mechanism that can convey containers to and from being within magnetic communication with the magnets of the sample processing units described herein is optionally utilized. As a further illustration, conveyance mechanisms include slidable support members in some embodiments. As shown in FIGS. 23 A and B, for example, the conveyance mechanism of sample processing unit 300 includes support member 302 and gantry or linear slide track 304. Linear drive mechanism 306 is configured to move support member 302 along linear slide track 304. Further, rotational mechanism 308 (e.g., a motor or the like) is operably coupled with container 310 via support member 302. In addition, magnet 312 is operably connected to linear slide track 304 in a substantially fixed position via magnet mounting arm 314. Support member 302 and container 310 are shown in first position 316 in FIG. 23A, whereas they are shown in second position 318 in FIG. 23B.

In certain embodiments, carrier mechanisms are operably connected to sample processing units. Carrier mechanisms are typically configured to move sample processing units to one or more locations, e.g., where various processing steps are performed, such as adding and/or removing fluidic materials from sample processing unit containers. Typically, multiple sample processing units are included on a given carrier mechanism, e.g., to enhance the throughput of sample processing applications performed using the carrier mechanism. In some embodiments, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more sample processing units are included on a given carrier mechanism. In addition, essentially any carrier mechanism format that can be used to move sample processing units to selected locations is optionally utilized. In some embodiments, for example, a carrier mechanism includes a carousel that is configured to rotate sample processing units to selected locations. In another representative embodiment, a carrier mechanism includes a conveyor track that is configured to convey sample processing units to one or more locations as desired. Both of these exemplary carrier mechanism embodiments are described further herein. To further illustrate, manifolds for substantially simultaneously distributing fluidic materials to and/or from the containers of multiple sample processing units of a given carrier mechanism are included in certain embodiments, e.g., to enhance process throughput.

Figure 24A:
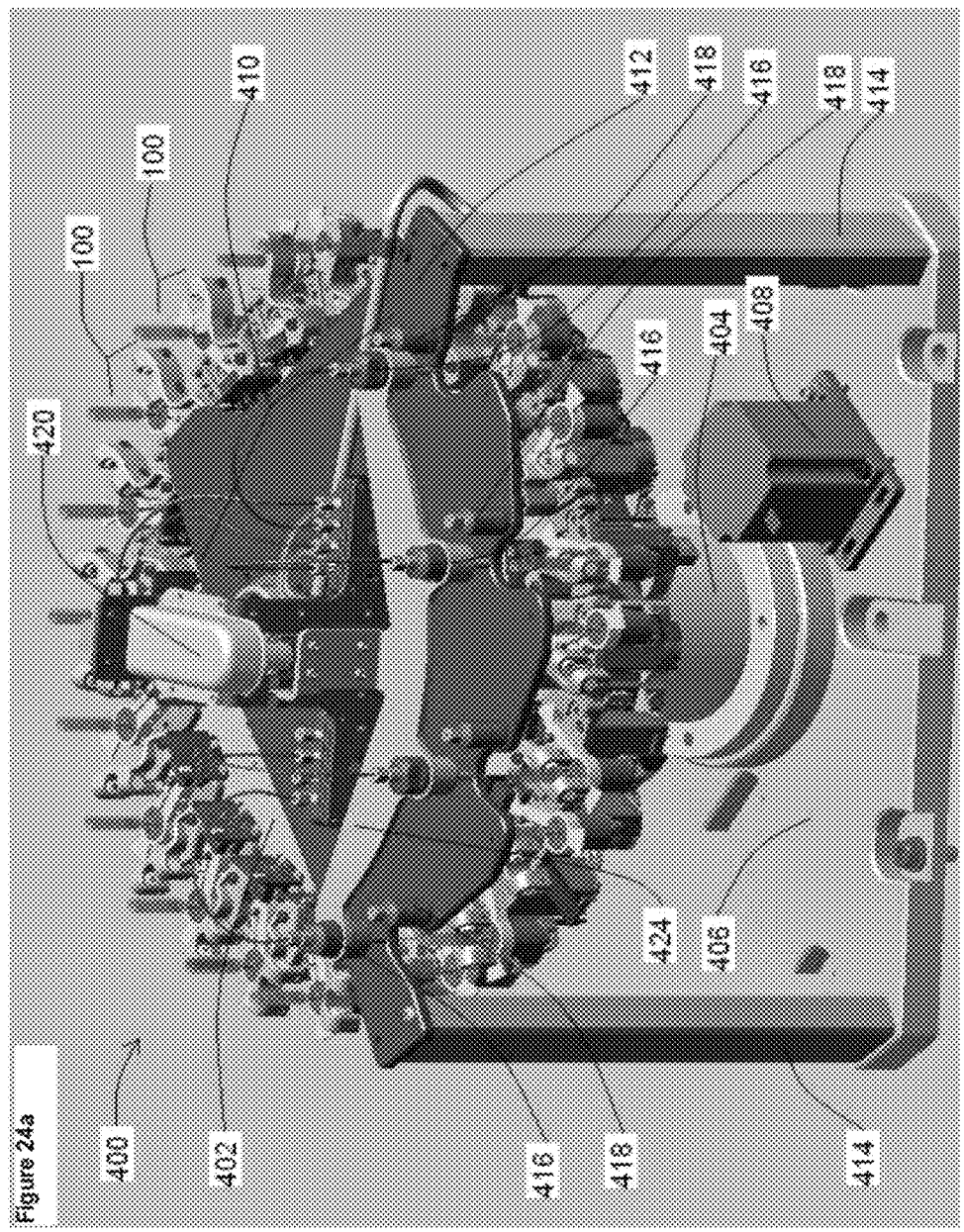
FIG. 24A schematically illustrates a carrier mechanism with a manifold from a perspective view according to one embodiment of the invention.

One embodiment of a carrier mechanism with a manifold is schematically depicted in FIGS. 24 A-F from various points of view. As shown, carousel 400 includes 22 sample processing units 100 mounted on circular support structure 402, which is operably connected to rotating assembly 404. Rotating assembly 404 includes a slip ring or rotary electrical interface that effects rotation of circular support structure 402 and sample processing units 100 to selected positions around carousel 400. Rotating assembly 404 is mounted on support base 406, which provides structural support to carousel 400. Carousel 400 control includes motor 408 (e.g., a stepper motor, such as a Model No. 5704M-10 or 5709L-06PD available from Lin Engineering, Santa Clara, Calif., U.S.A.) and one or more transmissive photomicrosensors (e.g., a Model No. EE-SX1071 available from Omron Electronics LLC, Schaumburg, Ill., U.S.A.).

As additionally shown, sample cleanup station or manifold 410 is also mounted above carousel 400 on manifold support structure 412, which is connected to rotating assembly 404 and manifold support pillars 414. Manifold 410 is used to aspirate and dispense fluidic materials from/into cuvettes 102 of sample processing units 100 as part of sample purification procedures. More specifically, manifold 410 includes aspirate heads 416 and dispense heads 418. Aspirate heads 416 typically fluidly communicate with fluidic material waste containers (not within view) via flexible tubing, whereas dispense heads 418 generally fluidly communicate with fluidic material sources or reservoirs via flexible tubing. Fluidic material is typically conveyed through the tubing using a fluid conveyance mechanism, such as a pump (e.g., a peristaltic pump, a vacuum pump, or the like). Manifold linear motion component 420, which includes manifold stepper motor 422 (e.g., a Model No. 211-13-02 or 211-20-02 available from Lin Engineering, Santa Clara, Calif., U.S.A.), is configured to raise and lower manifold plate 424. As shown, aspirate heads 416 are mounted on manifold plate 424. When fluidic materials are aspirated from cuvettes 102, rotating assembly 404 typically rotates selected cuvettes 102 into alignment with selected aspirate heads 416. Manifold linear motion component 420 then typically lowers aspirate heads 416 such that needles of aspirate heads 416 contact fluidic materials disposed within the selected cuvettes 102 so that selected volumes of the fluidic materials can be aspirated from the selected cuvettes 102. In some of these embodiments, magnetically responsive particles (with bound or otherwise captured nucleic acids or other analytes) are included in the fluidic materials. In these embodiments, the selected cuvettes 102 are typically moved into magnetic communication with magnets 124 of the corresponding sample processing units 100 so that the magnetically responsive particles are retained within the selected cuvettes 102 as the selected aliquots are removed through the needles of the selected aspirate heads 416. After a given fluidic material aspiration step is performed, manifold linear motion component 420 typically raises manifold plate 424 and aspirate heads 416 a sufficient distance such that rotating assembly 404 can rotate cuvettes 102 to other locations without contacting the needles of aspirate heads 416. As further illustrated, dispense heads 418 are mounted in substantially fix positions on manifold support structure 412 such that they can fluidly communicate with cuvettes 102 when cuvettes 102 are positioned beneath and aligned with the needles of dispense heads 418. During operation, e.g., before or after a given aspiration step is performed, rotating assembly 404 typically rotates selected cuvettes 102 into alignment with selected dispense heads 418 so that selected volumes of fluidic material (e.g., reagent mixtures, elution buffers, etc.) can be dispensed into the selected cuvettes 102. Before or after a given aspiration or dispensing step is performed, selected cuvettes 102 are typically spun using first motors 104 of sample processing units 100 to mix fluidic materials in the selected cuvettes 102. Exemplary systems that include carousels and manifolds are described further herein.

Figure 25A:
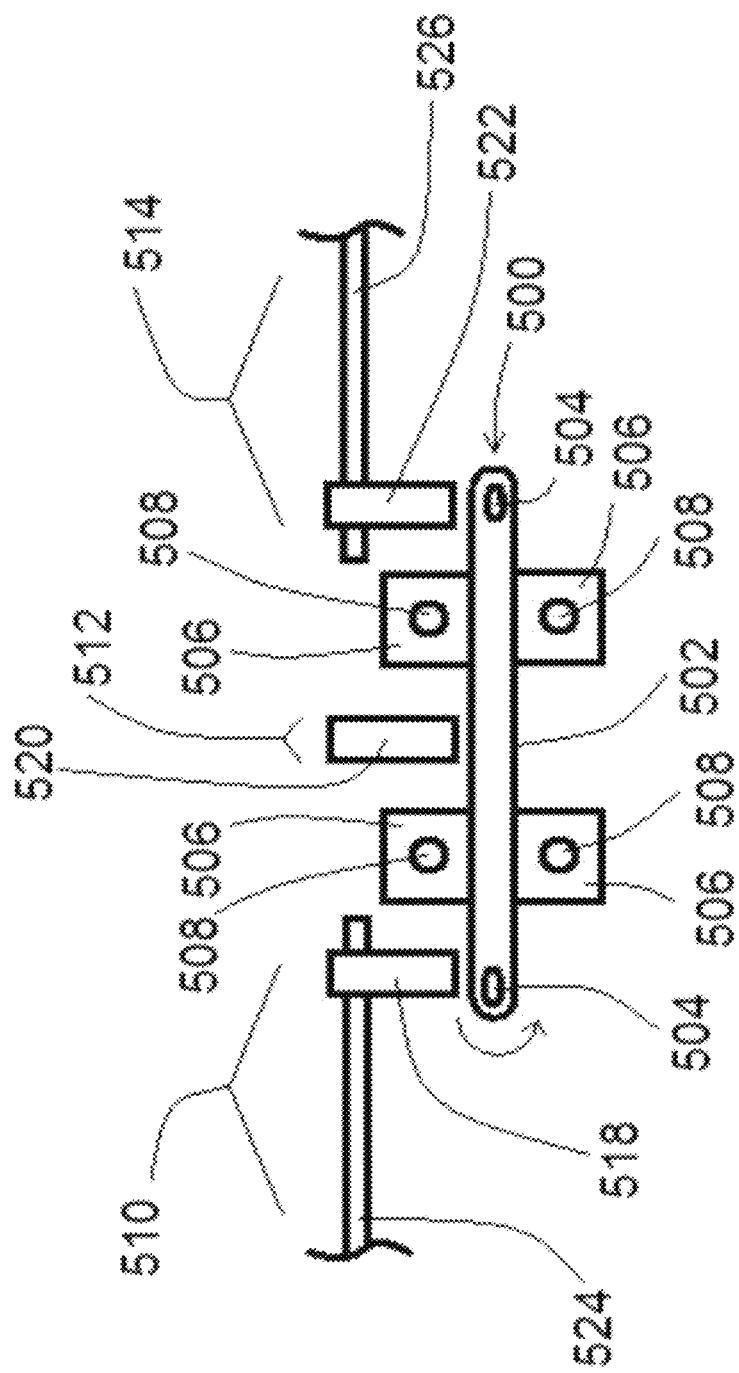
FIG. 25A schematically illustrates a carrier mechanism that includes a conveyor track from a top view according to one embodiment of the invention.
Figure 25B:
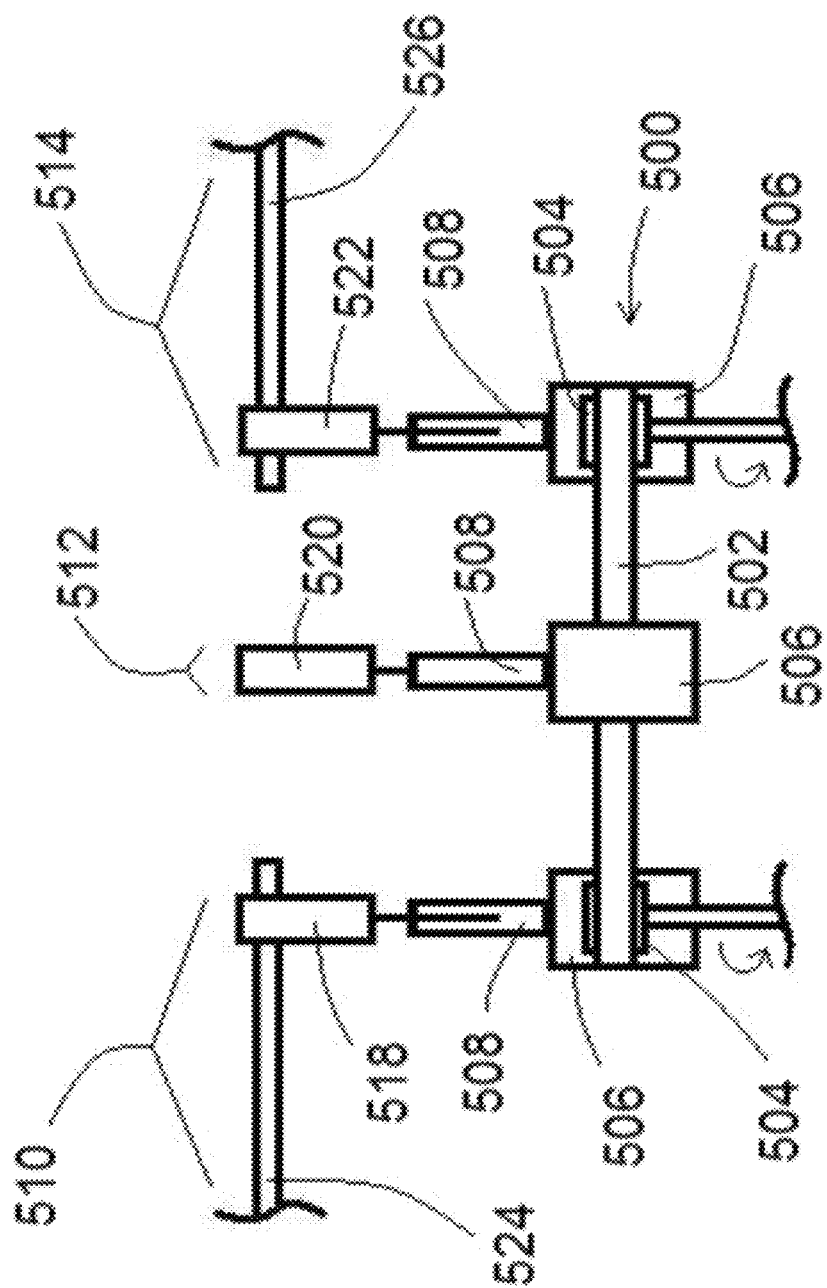
FIG. 25B schematically illustrates the carrier mechanism from FIG. 5A from a side elevation view.

To illustrate another exemplary embodiment, FIGS. 25 A and B schematically depict a carrier mechanism that includes a conveyor track from top and side elevation views, respectively. As shown, carrier mechanism 500 includes conveyor track 502 (e.g., a conveyor belt, etc.), which is configured to rotate counter-clockwise around rotational couplings 504 (e.g., pulleys or the like). Sample processing units 506, which include containers 508, are connected to conveyor track 502. During operation, rotational couplings 504 rotate sample processing units 506 to fluid transfer stations 510, 512, and 516, which include fluid transfer heads 518, 520, and 522, respectively, that each have an aspirate/dispense needle. Fluid transfer heads 518, 520, and 522 are configured to be raised and lowered. As shown, for example, in FIG. 25B, when sample processing units 506 are aligned beneath fluid transfer heads 518, 520, and 522, the heads are typically lowered so that the aspirate/dispense needles can fluidly communicate with containers 508. Note that the container of the sample processing unit depicted on the near side of conveyor track 502 in FIG. 25B partially obscures the needle of fluid transfer head 520, which is lowered into the container of the sample processing unit (not within view in FIG. 25B) on the far side of conveyor track 502. When sample processing units 506 are rotated around rotational couplings 504, transfer heads 518, 520, and 522 are typically raised a sufficient height to permit the unobstructed passage of containers 508 beneath the needles of transfer heads 518, 520, and 522. As also shown, transfer heads 518 and 522 are also configured to move along gantry tracks 524 and 526, respectively.

B. Example Controllers and Related Systems

Controllers are typically operably connected to sample processing units and carrier mechanisms, whether they are used as stand-alone sample processing stations or as system components. The controllers of the sample processing stations and systems described herein are generally configured to effect, e.g. the rotation of sample processing unit containers to mix sample materials in the containers (e.g., in various selectable modes of rotation, etc.), the movement of containers to and from being within magnetic communication with the magnets of sample processing units, the movement of carrier mechanisms to position sample processing units relative to material transfer components, the transfer of materials to and from the containers of sample processing units, the detection of one or more parameters of sample materials disposed in the containers of sample processing units or of aliquots of those materials taken from those containers, and the like. Controllers are typically operably connected to one or more system components, such as motors (e.g., via motor drives), thermal modulating components, detectors, motion sensors, fluidic handling components, robotic translocation devices, or the like, to control operation of these components. More specifically, controllers are generally included either as separate or integral system components that are utilized to effect, e.g., the rotation of the containers of sample processing units according to one or more selectable rotational modes, the transfer of materials to and/or from the containers of sample processing units, the detection and/or analysis of detectable signals received from sample materials by detectors, etc. Controllers and/or other system components is/are generally coupled to an appropriately programmed processor, computer, digital device, or other logic device or information appliance (e.g., including an analog to digital or digital to analog converter as needed), which functions to instruct the operation of these instruments in accordance with preprogrammed or user input instructions (e.g., mixing mode selection, fluid volumes to be conveyed, etc.), receive data and information from these instruments, and interpret, manipulate and report this information to the user.

Figure 26:
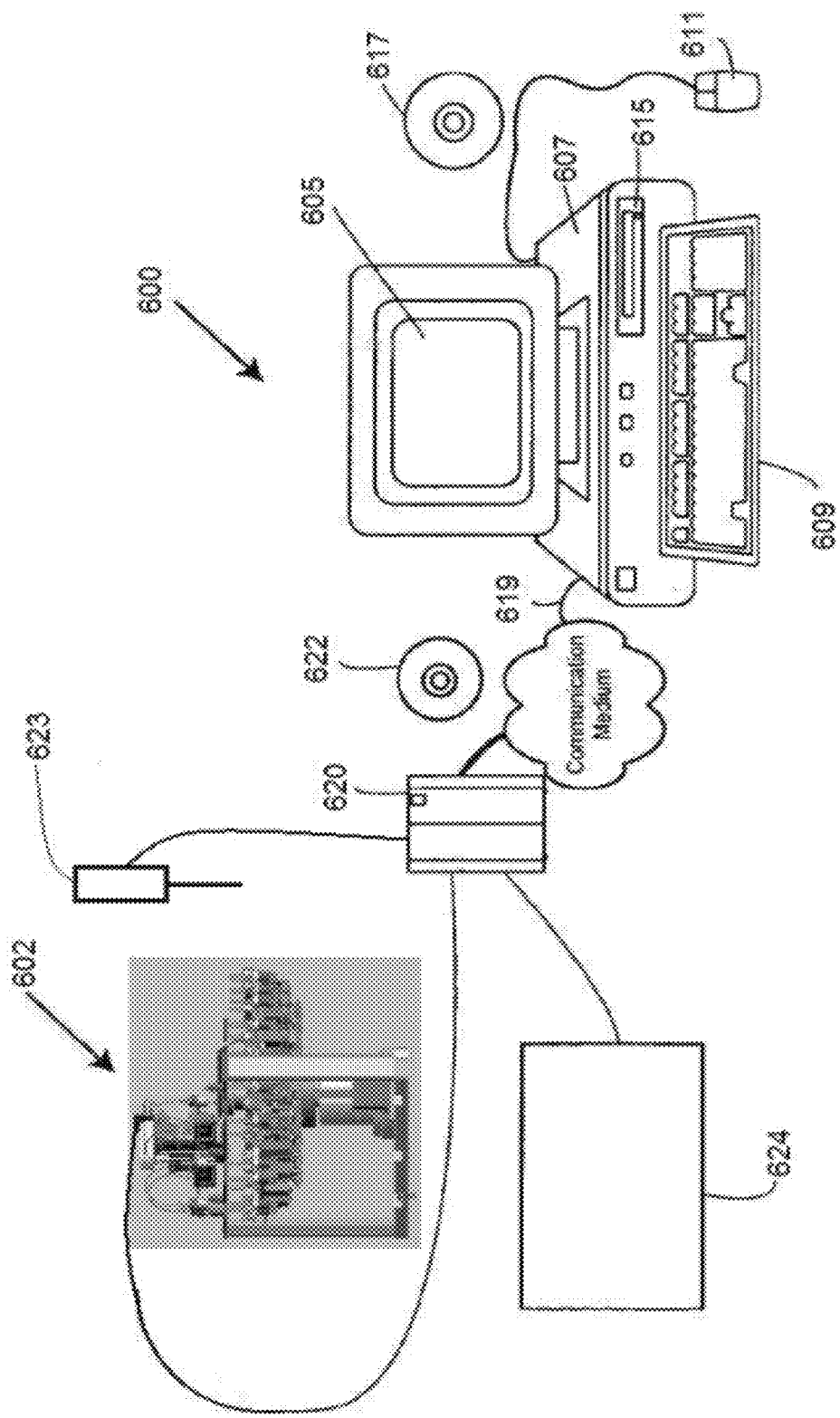
FIG. 26 is a block diagram showing a representative logic device in which various aspects of the present invention may be embodied.

A controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. An exemplary system comprising a computer is schematically illustrated in FIG. 26.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., rotating sample processing unit containers to mix sample materials in the containers, aspirating fluidic materials from sample processing unit containers, dispensing materials into sample processing unit containers, or the like. The computer then receives the data from, e.g., sensors/detectors included within the system, and interprets the data, either provides it in a user understood format, or uses that data to initiate further controller instructions, in accordance with the programming, e.g., such as in monitoring detectable signal intensity, rates or modes of sample processing unit container rotation, or the like.

More specifically, the software utilized to control the operation of the sample processing stations and systems of the invention typically includes logic instructions that selectively direct, e.g., motors to rotate cuvettes in pulsed modes, during which a substantial portion of the time of rotation, a rate of rotation of the cuvettes exceeds a rate of rotation of the samples in the cuvettes such that the samples are sheared away from surfaces of the cuvettes to effect sample mixing, motors to rotate the cuvettes in oscillating motions, and the like. The logic instructions of the software are typically embodied on a computer readable medium, such as a CD-ROM, a floppy disk, a tape, a flash memory device or component, a system memory device or component, a hard drive, a data signal embodied in a carrier wave, and/or the like. Other computer readable media are known to persons of skill in the art. In some embodiments, the logic instructions are embodied in read-only memory (ROM) in a computer chip present in one or more system components, without the use of personal computers.

The computer can be, e.g., a PC (Intel x86 or Pentium chip-compatible DOS™, OS2™, WINDOWS™, WINDOWS NT™, WINDOWS98™, WINDOWS2000™, WINDOWS XP™, WINDOWS Vista™, LINUX-based machine, a MACINTOSHT™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., sample processing unit container rotation, material conveyance to and/or from sample processing unit containers, mixing process monitoring, assay detection, and data deconvolution is optionally constructed by one of skill using a standard programming language such as Visual basic, C, C++, Fortran, Basic, Java, or the like.

The sample processing stations and related systems of the invention optionally include detectors or detection components configured to detect one or more detectable signals or parameters from a given process, e.g., from materials disposed within sample processing unit container or taken therefrom. In some embodiments, systems are configured to detect detectable signals or parameters that are upstream and/or downstream of a given process involving the sample processing units described herein. Suitable signal detectors that are optionally utilized in these systems detect, e.g., pH, temperature, pressure, density, salinity, conductivity, fluid level, radioactivity, luminescence, fluorescence, phosphorescence, molecular mass, emission, transmission, absorbance, and/or the like. In some embodiments, the detector monitors a plurality of signals, which correspond in position to "real time" results. Example detectors or sensors include PMTs, CCDs, intensified CCDs, photodiodes, avalanche photodiodes, optical sensors, scanning detectors, or the like. Each of these as well as other types of sensors is optionally readily incorporated into the sample processing stations and systems described herein. The detector optionally moves relative to the stations, sample containers or other assay components, or alternatively, the stations, sample containers or other assay components move relative to the detector. Optionally, the stations and systems of the invention include multiple detectors. In these stations and systems, such detectors are typically placed either in or adjacent to, e.g., a sample processing unit cuvette or other vessel, such that the detector is in sensory communication with the sample processing unit cuvette or other vessel (i.e., the detector is capable of detecting the property of the cuvette or vessel or portion thereof, the contents of a portion of the cuvette or vessel, or the like, for which that detector is intended).

The detector optionally includes or is operably linked to a computer, e.g., which has system software for converting detector signal information into assay result information or the like. For example, detectors optionally exist as separate units, or are integrated with controllers into a single instrument. Integration of these functions into a single unit facilitates connection of these instruments with the computer, by permitting the use of a few or even a single communication port for transmitting information between system components. Detection components that are optionally included in the systems of the invention are described further in, e.g., Skoog et al., Principles of Instrumental Analysis, 6$^{th}$ Ed., Brooks Cole (2006) and Currell, Analytical Instrumentation: Performance Characteristics and Quality, John Wiley & Sons, Inc. (2000), which are both incorporated by reference.

The sample processing stations and systems of the invention optionally also include at least one robotic translocation or gripping component that is structured to grip and translocate containers or other processing components between components of the stations or systems and/or between the stations or systems and other locations (e.g., other work stations, etc.). A variety of available robotic elements (robotic arms, movable platforms, etc.) can be used or modified for use with these systems, which robotic elements are typically operably connected to controllers that control their movement and other functions.

FIG. 26 is a schematic showing a representative system including an information appliance in which various aspects of the present invention may be embodied. Other exemplary systems are also described herein. As will be understood by practitioners in the art from the teachings provided herein, the invention is optionally implemented in hardware and software. In some embodiments, different aspects of the invention are implemented in either client-side logic or server-side logic. As will also be understood in the art, the invention or components thereof may be embodied in a media program component (e.g., a fixed media component) containing logic instructions and/or data that, when loaded into an appropriately configured computing device, cause that apparatus or system to perform according to the invention. As will additionally be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 26 shows information appliance or digital device 600 that may be understood as a logical apparatus (e.g., a computer, etc.) that can read instructions from media 617 and/or network port 619, which can optionally be connected to server 620 having fixed media 622. Information appliance 600 can thereafter use those instructions to direct server or client logic, as understood in the art, to embody aspects of the invention. One type of logical apparatus that may embody the invention is a computer system as illustrated in 600, containing CPU 607, optional input devices 609 and 611, disk drives 615 and optional monitor 605. Fixed media 617, or fixed media 622 over port 619, may be used to program such a system and may represent a disk-type optical or magnetic media, magnetic tape, solid state dynamic or static memory, or the like. In specific embodiments, the aspects of the invention may be embodied in whole or in part as software recorded on this fixed media. Communication port 619 may also be used to initially receive instructions that are used to program such a system and may represent any type of communication connection. Optionally, aspects of the invention are embodied in whole or in part within the circuitry of an application specific integrated circuit (ACIS) or a programmable logic device (PLD). In such a case, aspects of the invention may be embodied in a computer understandable descriptor language, which may be used to create an ASIC, or PLID.

In addition, FIG. 26 also shows sample processing station 602, which is operably connected to information appliance 600 via server 620. Optionally, sample processing station 602 is directly connected to information appliance 600. During operation, sample processing station 602 typically mixes and retains selected materials (e.g., magnetically responsive particles with captured target materials, etc.) in the cuvettes of the sample processing units of sample processing station 602, e.g., as part of an assay or other process. FIG. 26 also shows material transfer component 623 and detector 624, which are optionally included in the systems of the invention. As shown, material transfer component 623 and detector 624 are operably connected to information appliance 600 via server 620. In some embodiments, material transfer component 623 and/or detector 624 is directly connected to information appliance 600. Material transfer component 623 is typically configured to transfer materials to and/or from the cuvettes of the sample processing units of sample processing station 602. In certain embodiments, detector 624 is configured to detect detectable signals produced in the cuvettes of the sample processing units of sample processing station 602 or in aliquots of materials removed from and/or to be added to those cuvettes.

C. Example Sample Processing System and Related Process Embodiments

To further illustrate exemplary embodiments of the invention, FIGS. 27 A-G schematically depict a portion of a representative system for nucleic acid amplification product desalting and molecular mass measurement that includes a sample processing station as a sub-system component. The measured molecular masses of the amplification products are typically used to determine base compositions of the corresponding amplification products, which are then generally correlated with the identities or organismal sources of the initial template nucleic acids, for example, as part of a research or in-vitro diagnostic application, among many others.

As shown in FIGS. 27 A-G, components of representative system 700 include microplate handling component or system 10, material transfer component 702, mixing station 704, wash stations 706 and 708, sample processing component 710, and sample injector 712. During operation, microplates are typically stored or positioned in input non-priority microplate storage unit 12, output non-priority microplate storage unit 14, priority microplate storage unit 16, microplate processing area 18, and non-priority microplate holding area 20 (e.g., on non-priority microplate holding component 22) of microplate handling component 10. As also shown, microplate handling component 10 also includes barcode reader 36. In the exemplary embodiment shown, barcode reader 36 is configured to read barcodes disposed on microplates when the microplates are disposed in or proximal to non-priority microplate holding area 20, e.g., to track the microplates or samples contained in the microplates in microplate handling system 10. In some embodiments, for example, non-priority microplates are stored in input non-priority microplate storage unit 12 and priority microplates are stored in priority microplate storage unit 16 after target regions of template nucleic acids in those plates have been amplified, e.g., at a separate thermocycling station or nucleic acid amplification component. Essentially any thermal cycling station or device is optionally adapted for use with a system of the invention, such as system 700. Examples of suitable thermocycling devices that are optionally utilized are available from many different commercial suppliers, including Mastercycler® devices (Eppendorf North America, Westbury, N.Y., U.S.A.), the COBAS® AMPLICOR Analyzer (Roche Molecular Systems, Inc., Pleasanton, Calif., U.S.A.), Mycycler and iCycler Thermal Cyclers (Bio-Rad Laboratories, Inc., Hercules, Calif., U.S.A.), and the SmartCycler System (Cepheid, Sunnyvale, Calif., U.S.A.), among many others. In other exemplary embodiments, sample preparation components, nucleic acid amplification components, and related fluid handling or material transfer components are integrated with the systems described herein, e.g., to fully automate a given nucleic acid amplification and analysis process. Instruments that can be adapted for this purpose include, for example, the m2000™ automated instrument system (Abbott Laboratories, Abbott Park, Ill., U.S.A.), the GeneXpert System (Cepheid, Sunnyvale, Calif. U.S.A.), and the COBAS® AmpliPrep® System (Roche Molecular Systems, Inc., Pleasanton, Calif., U.S.A.), and the like.

Microplates are transferred from input non-priority microplate storage unit 12 or priority microplate storage unit 16 to microplate processing area 18 using platform 28 of a microplate transport mechanism. As referred to above and as shown in, e.g., FIGS. 27 F and G, platform 28 is operably connected to X-axis linear motion component 38. X-axis linear motion component 38 includes gantry 40. Platform 28 is operably connected to carriage 42, which moves along gantry 40. As further shown in FIGS. 27 F and G, microplate transport mechanism 26 also includes Y-axis linear motion component 44 operably connected to carriage 42 and to platform 28. Y-axis linear motion component 44 is configured to raise and lower platform 28 along the Y-axis. Suitable linear motion components, motors, and motor drives are generally available from many different commercial suppliers including, e.g., Techno-Isel Linear Motion Systems (New Hyde Park, N.Y., U.S.A.), NC Servo Technology Corp. (Westland, Mich., USA), Enprotech Automation Services (Ann Arbor, Mich., U.S.A.), Yaskawa Electric America, Inc. (Waukegan, Ill., U.S.A.), ISL Products International, Ltd. (Syosset, N.Y., U.S.A.), AMK Drives & Controls, Inc. (Richmond, Va., U.S.A.), Aerotech, Inc. (Pittsburgh, Pa., U.S.A.), HD Systems Inc. (Hauppauge, N.Y., U.S.A.), and the like. Additional detail relating to motors and motor drives are described in, e.g., Polka, Motors and Drives, ISA (2002) and Hendershot et al., Design of Brushless Permanent-Magnet Motors, Magna Physics Publishing (1994), which are both incorporated by reference. Microplate handling components are also described in, e.g., U.S. Provisional Patent App. No. 61/097, 510, entitled "MICROPLATE HANDLING SYSTEMS AND RELATED COMPUTER PROGRAM PRODUCTS AND METHODS" filed Sep. 16, 2008 by Hofstadler et al., which is incorporated by reference in its entirety.

Material transfer component 702 includes sample input gantry 714 and sample output gantry 716. Input gantry head 718 is configured to move along sample input gantry 714, whereas output gantry head 720 is configured to move along sample output gantry 716. Input gantry head 718 and output gantry head 720 each include needles that are configured to aspirate and dispense fluidic materials. Further, input gantry head 718 and output gantry head 720 are each configured to be raised and lowered along the Y-axis. During operation of exemplary system 700, the needle or pipetting tip of input gantry head 718 is typically used to aspirate an aliquot of magnetically responsive particles (e.g., magnetically responsive beads, such as BioMag®Plus Amine superparamagnetic microparticles available from Bangs Laboratories, Inc., Fishers, Ind., U.S.A.) that bind nucleic acids from a mixing cartridge positioned at mixing station 704. Magnetically responsive particle sources and mixing stations are also described in, e.g., U.S. Provisional Patent App. No. 61/097,507, entitled "MIXING CARTRIDGES, MIXING STATIONS, AND RELATED KITS, SYSTEMS, AND METHODS" filed Sep. 16, 2008 by Hofstadler et al., which is incorporated by reference in its entirety. Nucleic acid purification involving magnetically responsive particles is also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., which are both incorporated by reference in their entirety. Optionally before, but typically after aspirating the aliquot of magnetically responsive particles (e.g., to minimize the possibility of cross-contaminating samples), the needle of input gantry head 718 is also generally used to aspirate an aliquot of an amplification product sample from a selected well of a microplate positioned in microplate processing area 18 of microplate handling system 10. The resulting mixture of magnetically responsive particle and amplification product sample aliquots disposed within the needle of input gantry head 718 is then typically transferred to sample processing component 710 along sample input gantry 714. After dispensing the mixture at sample processing component 710, the needle of input gantry head 718 is typically washed at wash station 706, e.g., to minimize the probability of cross-contaminating samples, prior to repeating this transfer cycle for other amplification product samples contained in the wells of a given microplate (e.g., priority or non-priority microplates) positioned in microplate processing area 18 of microplate handling system 10.

In the embodiment shown, sample processing station or component 710 is a desalting station that is used to desalt or otherwise purify nucleic acid amplification products in the sample mixture prior to mass spectrometric analysis. Sample processing component 710 includes carrier mechanism 722 (shown as a carousel), which includes a plurality of sample processing units 724. In the illustrated embodiment, each sample processing unit 724 includes cuvette 726 and magnet 728. After a mixture of magnetically responsive particle and amplification product sample aliquots is dispensed into a given cuvette 726, that cuvette is typically rotated in a counter-clockwise direction on carrier mechanism 722 to various positions within sample processing component 710 where various reagents (e.g., washes with ammonium bicarbonate and/or MeOH, etc.) are added to and/or removed from that cuvette (e.g., via various fluidic handling components of manifold 730) as part of the process of purifying the amplification products captured or otherwise bound to the magnetically responsive particles in the mixture. When fluidic materials are removed from the cuvette at a given position within sample processing component 710, the cuvette is typically moved proximal to the magnet of the particular sample processing unit (e.g., cuvette 726 is moved proximal to magnet 728 of sample processing unit 724) using a conveyance mechanism to establish sufficient magnetic communication between the magnet and the magnetically responsive particles such that the magnetically responsive particles are moved to and retained on an internal surface of the cuvette while fluidic materials are removed from the cuvette. At the conclusion of a purification process for a given sample, the purified amplification products are then typically aspirated from the particular cuvette using the needle of output gantry head 720. During or prior this step, the nucleic acid amplification products are eluted (e.g., using a solution that includes piperidine, imidazole, MeOH, and optionally peptide calibration standards (used as part of subsequent mass spectrometric analyses), or the like) from the magnetically responsive particles. After purified amplification products have been removed from a given cuvette, that cuvette is then generally rotated on carrier mechanism 722 into communication with cuvette wash station 727, where the cuvette is washed prior to commencing another purification cycle involving the cuvette and another sample. Sample desalting/purification methods are also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., and Hofstadler et al. (2003) "A highly efficient and automated method of purifying and desalting PCR products for analysis by electrospray ionization mass spectrometry" *Anal Biochem.* 316:50-57, which are each incorporated by reference in their entirety.

Purified and eluted amplification products that have been aspirated from a particular cuvette of sample processing component 710 are typically transported along sample output gantry 716 to sample injector 712 (shown as a two channel time-of-flight injector) using output gantry head 720. That is, the amplification products are typically dispensed from the needle or pipetting tip of output gantry head 720 into one of the two channels of sample injector 712, which generally comprise two independent sample injection syringe pumps that are configured to receive the amplification products. After dispensing the amplification products at sample injector 712, the needle of output gantry head 720 is typically washed at wash station 708 prior to aspirating another purified amplification product sample from sample processing component 710, e.g., to reduce the potential for carryover contamination between samples.

Figure 29A:
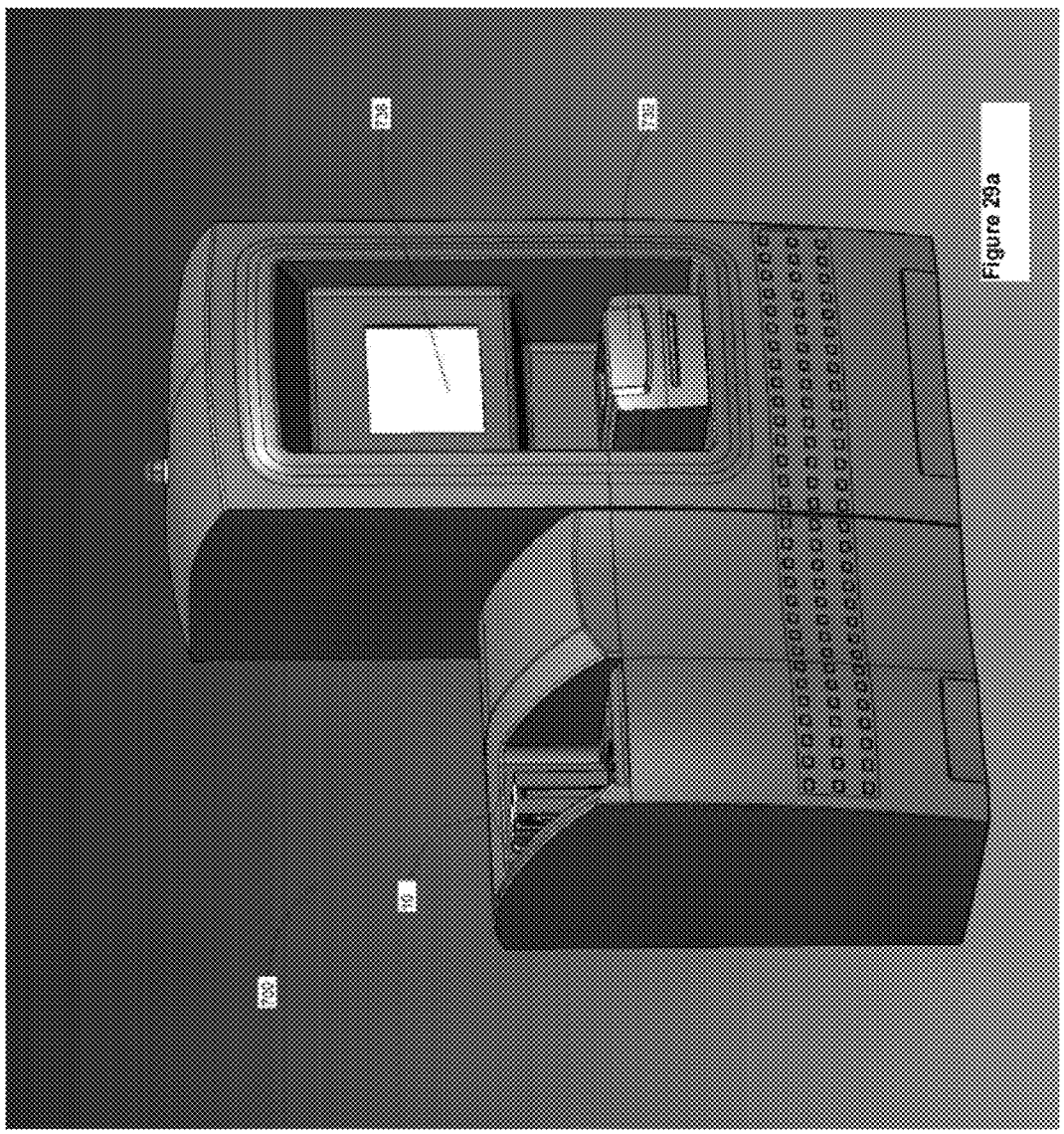
FIG. 29A schematically illustrates the representative system of FIG. 7A with an external covering from a perspective view.
Figure 29B:
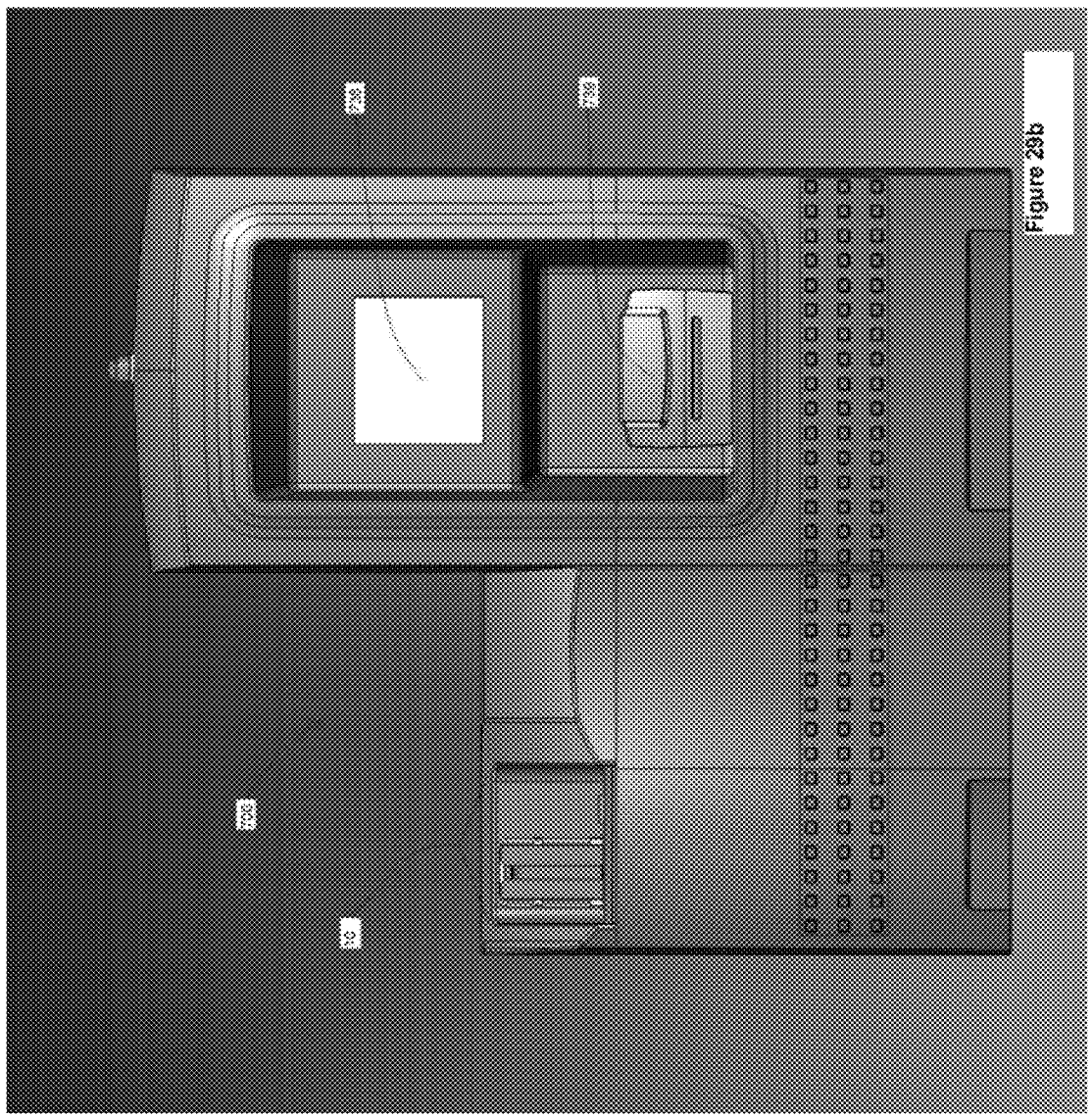
FIG. 29B schematically illustrates the representative system of FIG. 7A with an external covering from a front elevation view.
Figure 29C:
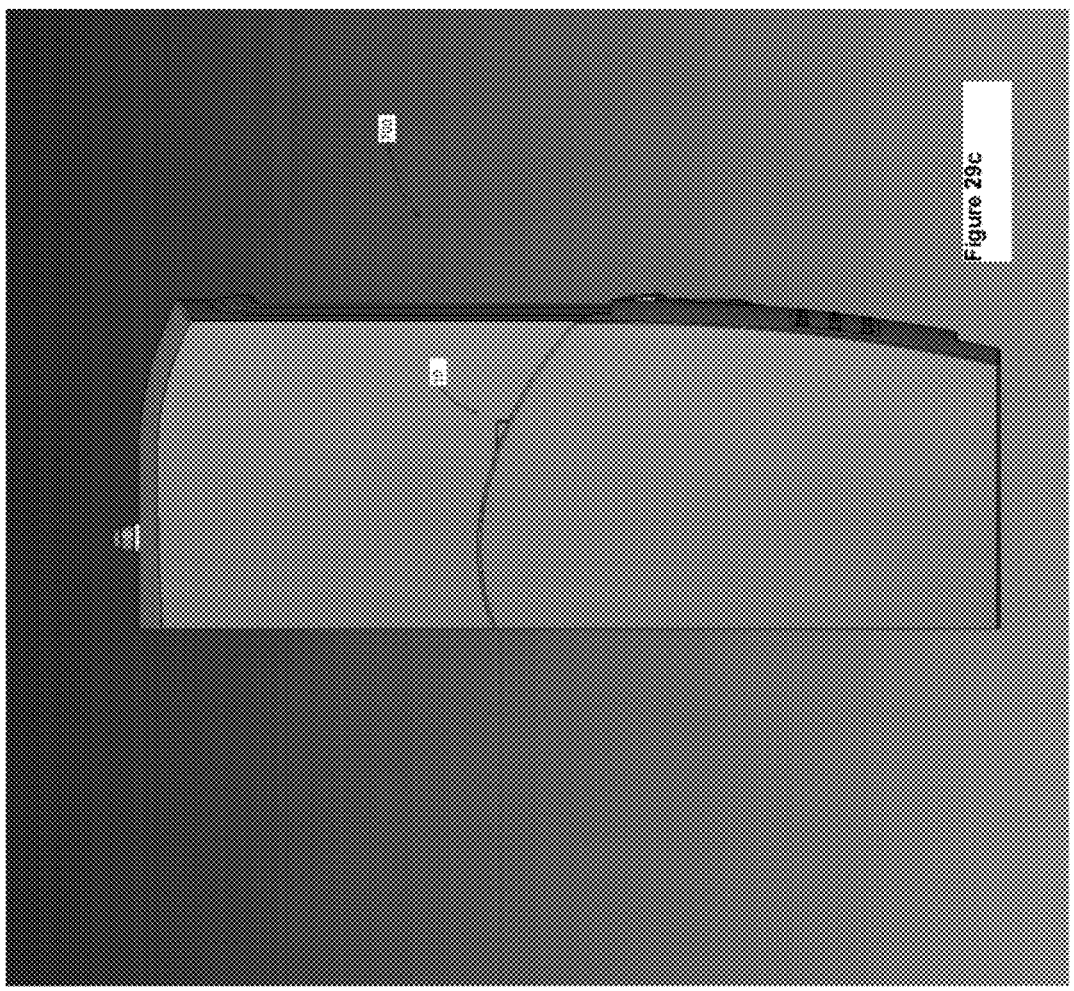
FIG. 29C schematically shows the representative system of FIG. 7A with an external covering from a side view.

Now referring to FIG. 28, which schematically shows additional components of representative system 700 (sample processing component 710 is not shown so that other system components are within view) from a perspective view. As shown, the additional components include dual sprayer module 732, which includes two independent electrospray ionization sprayers, and time-of-flight mass spectrometer 734. Amplification product samples received at sample injector 712 are typically injected into one of the two sprayers of dual sprayer module 732 for electrospray ionization and mass measurement in time-of-flight mass spectrometer 734. As further shown, the additional components of representative system 700 also include input/output device 736 (shown as a touch screen monitor), computer 737, output device 739 (shown as a printer), reagents and waste module 738, and chassis 740. Input/output device 736, computer 737, and output device 739 are components of a controller of system 700. Controllers are described further herein. Reagents and waste module 738 provide reagent sources and waste receptacles for system 700. Chassis 740 provides mechanical support for microplate handling system 10, sample processing component 710, and other components of system 700. To further illustrate, FIGS. 29 A-C schematically show representative system 700 with an external covering from various views.

In some embodiments, the base compositions of amplification products are determined from detected molecular masses. In these embodiments, base compositions are typically correlated with the identity of an organismal source, genotype, or other attribute of the corresponding template nucleic acids in a given sample. Suitable software and related aspects, e.g., for determining base compositions from detected molecular masses and for performing other aspects of base composition analysis are commercially available from Ibis Biosciences, Inc. (Carlsbad, Calif., U.S.A.). Nucleic acid base composition analysis is also described in many of the publications referred to herein, including, e.g., U.S. Pat. No. 7,255,992, entitled "METHODS FOR RAPID DETECTION AND IDENTIFICATION OF BIOAGENTS FOR ENVIRONMENTAL AND PRODUCT TESTING," which issued Aug. 14, 2007 to Ecker et al., U.S. Pat. No. 7,226,739, entitled "METHODS FOR RAPID DETECTION AND IDENTIFICATION OF BIOAGENTS IN EPIDEMIOLOGICAL AND FORENSIC INVESTIGATIONS," which issued Jun. 5, 2007 to Ecker et al., U.S. Pat. No. 7,217,510, entitled "METHODS FOR PROVIDING BACTERIAL BIOAGENT CHARACTERIZING INFORMATION," which issued May 15, 2007 to Ecker et al., and U.S. Pat. No. 7,108,974, entitled "METHOD FOR RAPID DETECTION AND IDENTIFICATION OF BIOAGENTS," which issued Sep. 19, 2006 to Ecker et al., which are each incorporated by reference in their entirety.

D. Fabrication Methods and Materials

Sample processing units or components thereof, carrier mechanisms or components thereof, and station or system components (e.g., mixing stations, microplate storage units, microplate transport mechanisms, support bases, etc.) are optionally formed by various fabrication techniques or combinations of such techniques including, e.g., machining, embossing, extrusion, stamping, engraving, injection molding, cast molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, $3^{rd}$ Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate sample processing units, carrier mechanisms, manifolds, or components thereof include metal (e.g., steel, aluminum, etc.), glass, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, system components are optionally further processed, e.g., by coating surfaces with a hydrophilic coating, a hydrophobic coating (e.g., a Xylan 1010DF/870 Black coating available from Whitford Corporation (West Chester, Pa.), etc.), or the like, e.g., to prevent interactions between component surfaces and reagents, samples, or the like.

E. Examples

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

A. PCR Product Purification and Desalting Example

1. PCR Product Purification

PCR products were thoroughly purified and desalted before ESI MS. This step typically precedes ESI-MS analysis, because PCR salts and buffer components generally have a deleterious effect on the ESI process. Even small amounts of salts (<1 µmol/L) will typically significantly reduce ESI sensitivity, owing to the appearance of multiple cation adducts in the mass spectra. The protocol used in this example is based on a weak anion-exchange method, in which amplified DNA was bound to a weak anion-exchange resin coated on the outside of magnetic bead particles. Unconsumed deoxynucleoside triphosphates, salts, and other low-molecular-weight species that could interfere with subsequent ESI-MS analysis were removed using a sample processing station system described herein and the PCR cleanup process outlined as follows:

1. Loaded 40 µL PCR Product and 50 µL magnetic bead solution into a clean cuvette;
2. Mixed the beads for 4.5 minutes to allow the DNA to bind the magnetic beads;
3. Positioned the cuvette at the magnet for 30 seconds to separate the beads from the solution;
4. Aspirated the liquid from the cuvette and dispensed 80 µL of 100 mM ammonium bicarbonate in a 50:50 methanol:water solution;
5. Resuspended and washed the beads by mixing for 35 seconds;
6. Positioned the cuvette at the magnet for 15 seconds to separate the beads from the solution;
7. Aspirated the liquid from the cuvette and dispensed 80 µL of 100 mM ammonium bicarbonate in a 50:50 methanol:water solution;
8. Resuspended and washed the beads by mixing for 35 seconds;
9. Positioned the cuvette at the magnet for 15 seconds to separate the beads from the solution;

10. Aspirated the liquid from the cuvette and dispensed 80 μL of 50:50 methanol:water solution;

11. Resuspended and washed the beads by mixing for 35 seconds;

12. Positioned the cuvette at the magnet for 15 seconds to separate the beads from the solution;

13. Aspirated the liquid from the cuvette and dispensed 40 μL of 25 mM piperidine and 25 mM imidazole in 35:65 methanol:water solution;

14. Resuspended the magnetic beads and allowed time for the DNA to elute from the beads for 2 minutes;

15. Positioned the cuvette at the magnet for 30 seconds to separate the beads from the solution; and 16. Aspirated the solution and injected into the ESI-MS for analysis. TOTAL PCR PRODUCT CLEANUP TIME=10 minutes 2. Cuvette Cleaning Protocol The cuvette cleaning protocol utilized to clean the cuvette after PCR products were purified and desalted was as follows:

1. Dispensed 160 μL of 25 mM piperidine and 25 mM imidazole in 35:65 methanol:water solution and mixed for 15 seconds;

2. Aspirated solution and dispensed 160 μL of clean (Type I) water into the cuvette;

3. Mixed for 15 seconds; and

4. Aspirated liquid from cuvette.
TOTAL CUVETTE CLEANUP TIME=2 minutes

3. ESI-TOF Mass Spectrometry

Figure 30:
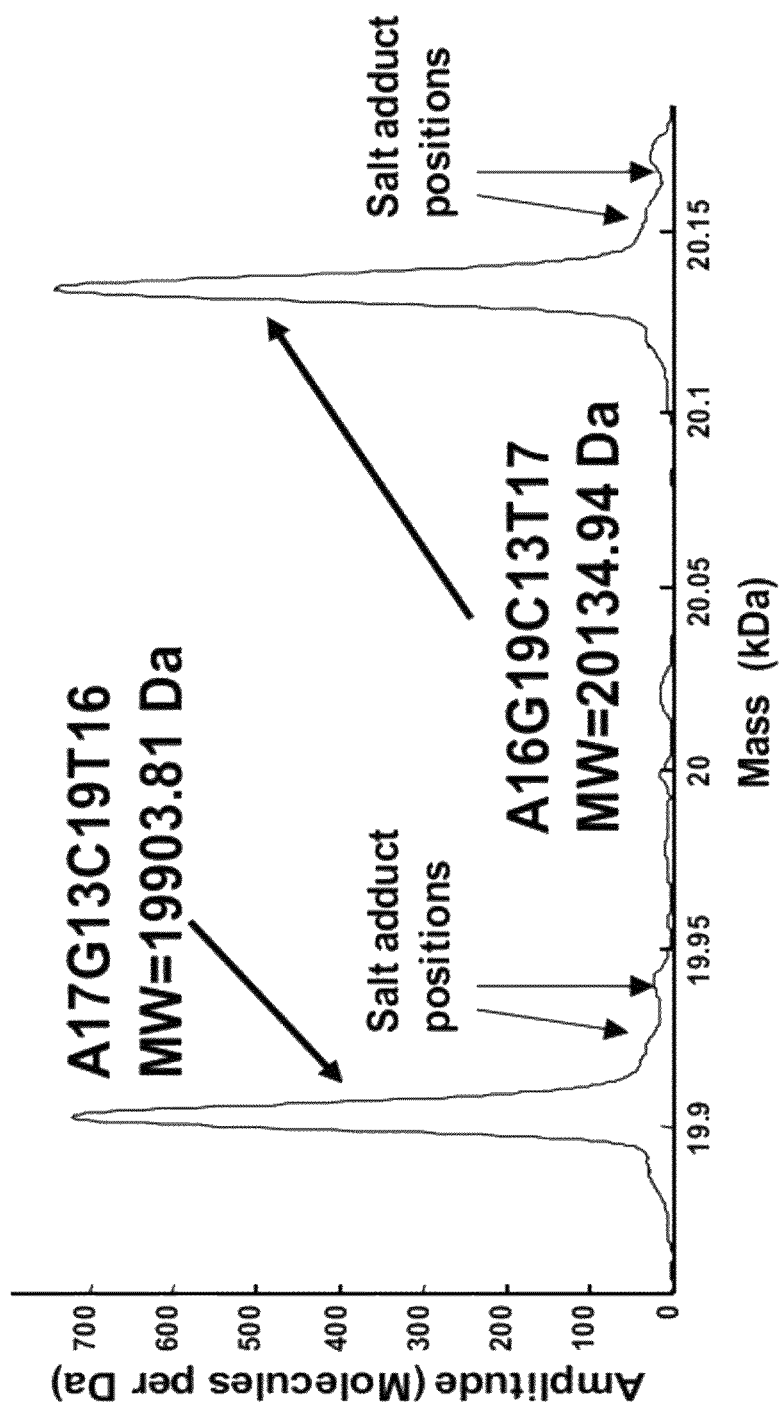
FIG. 30 is a mass spectrum obtained for a 65-mer PCR product following a purification and desalting protocol described herein. The two peaks correspond to sense and antisense strands of the PCR amplicons, which separate under the conditions of ESI. Low amplitude salt adducts indicated effective cleanup of the PCR product.

A Bruker Daltonics (Billerica, Mass., U.S.A.) MicroTOF-ESI time-of-flight (TOF) mass spectrometer was used to analyze purified and desalted PCR products in this example. Ions from the ESI source underwent orthogonal ion extraction and were focused in a reflectron prior to detection. Ions were formed in the standard MicroTOF-ESI source, which was equipped with an off-axis sprayer and glass capillary. For operation in the negative ion mode, the atmospheric pressure end of the glass capillary was biased at 3500 V relative to the ESI needle during data acquisition. A countercurrent flow of dry $N_2$ gas was employed to assist in the desolvation process. External ion accumulation was employed to improve ionization duty cycle during data acquisition and to enhance sensitivity in the m/z range of interest. In this example, each 75 μs scan was comprised of 75,000 data points (a 37.5 μs delay followed by a 37.5 μs digitization event at 2 GHz). For each spectrum, 660 000 scans were co-added. Example data obtained from this analysis is shown in FIG. 30.

IV. Ionization Probe Assemblies

The invention relates to ionization probe assemblies that are useful in spraying and ionizing sample materials, and in various embodiments provides individual sub-components, software, control components, and related methods employing the assemblies. In some embodiments, the ionization probe assemblies are configured to substantially continuously introduce sample materials into ion source housings of molecular mass measurement systems via multiple probes that are individually configured to discontinuously spray or otherwise introduce sample materials into the ion source housings. In some embodiments, for example, probes of the ionization probe assemblies are configured to duty cycle between spray and rinse positions that are substantially electrically isolated from one another.

A. Example Systems

Figure 31:
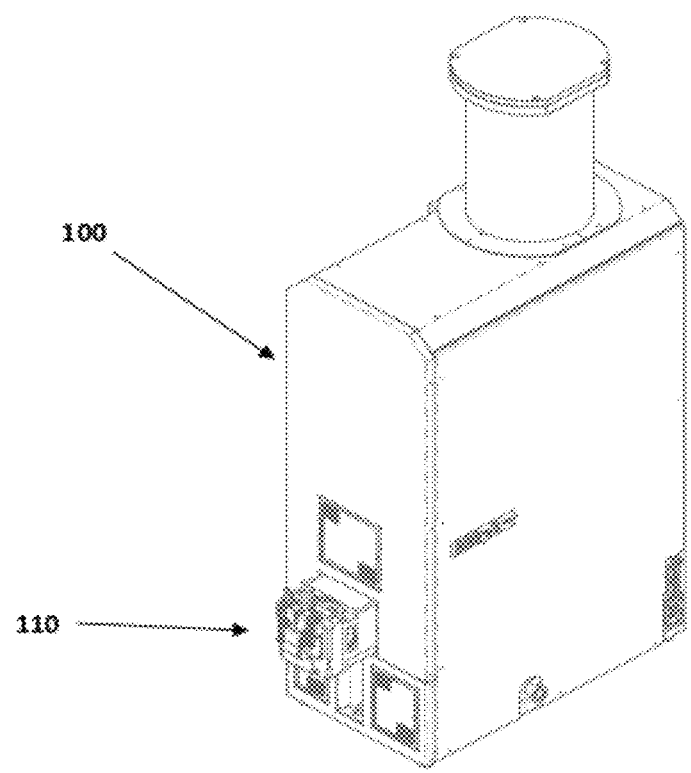
FIG. 31 schematically shows a dual sprayer mounted on a time of flight spectrometer (TOF).
Figure 32:
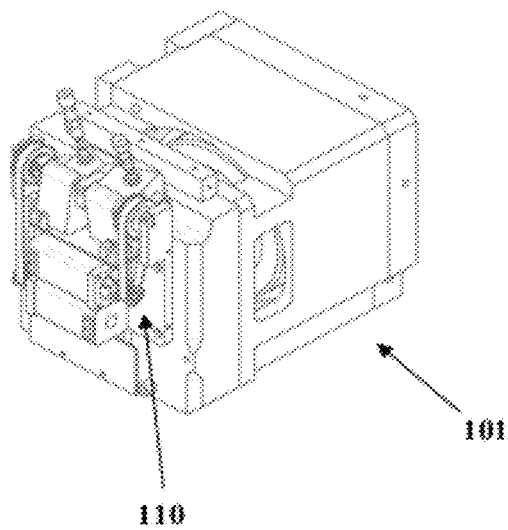
FIG. 32 schematically shows a dual sprayer mounted on a TOF chamber.
Figure 33:
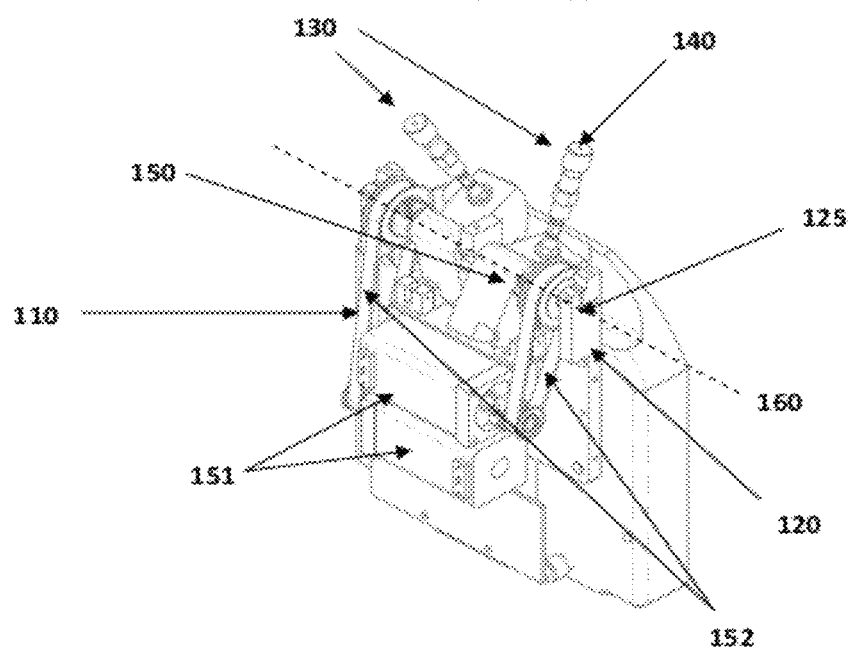
FIG. 33 schematically shows an exemplary dual sprayer with two probes mounted on an ion source housing.

FIG. 31 shows a representative time of flight spectrometer (TOF) 100 having an exemplary dual sprayer 110 mounted thereon. FIG. 32 shows the dual sprayer 110 mounted on a TOF chamber 101, showing the chamber detached from the TOF. FIG. 33 shows the dual sprayer 110 separate from the TOF or the TOF chamber. The dual sprayer 110 comprises an ionization probe assembly that includes at least one probe mounting structure 120 and two probes 130 that are movably coupled to the probe mounting structure 120. Any number of configurations may be used to movably couple the probes 130 to the probe mounting structure 120, so long as the desired position and movement of the probes 130 is provided. The probes 130 are configured to discontinuously introduce sample aliquots into the TOF chamber 101 (not shown in FIG. 33). Samples are introduced into a probe via a probe opening 140. The probe 130 may be mounted on a probe conveyance mechanism 150, operably connected to the probe. The probe conveyance mechanism 150 is configured to convey the probe between at least a first position and at least a second position. As shown in FIG. 33, the two probes 130 are configured to pivot around an axis 160 permitting movement from the first position to the second position. The first position is substantially electrically isolated from the second position. The dual sprayer 110 may comprise least two independent probes 130 that are movably coupled to the probe mounting structure 120. Each probe is movably coupled to the probe mounting structure 120 via a pivot mechanism 125. The probe conveyance mechanism 150 comprises a motor 151 operably connected to a pivot mechanisms 125 via belt drive 152.

Figure 34:
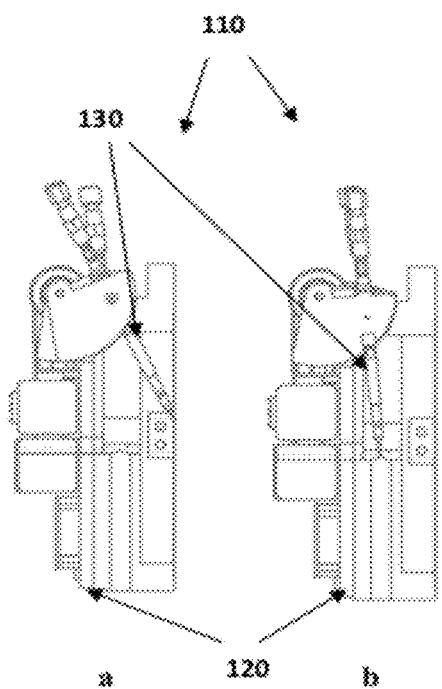
FIG. 34a schematically shows an exemplary dual sprayer with the proximal probe in a sprayer position.
FIG. 34b schematically shows an exemplary dual sprayer with the proximal probe in a rinse position.

FIGS. 34a and 34b show a side view of the dual sprayer 110. In FIG. 34a, the front-most probe 130 is shown in the second position, or "spray" position. In FIG. 34b the front-most probe 130 is shown in the first position, or "rinse" position. A cavity is disposed in or proximal to the probe mounting structure 120 to permit movement of the probe 130 into the second position. The cavity typically comprises the second position. In some of these embodiments, the cavity fluidly communicates with at least one outlet. The probes 130 are generally independently movably coupled to the probe mounting structure 120. In certain embodiments, the probe mounting structure 120 includes at least one view port 123 (FIG. 38) to permit viewing of the probes. The one or more view ports 123 (FIG. 38) may comprise a glass, plastic, ceramic or other transparent material to provide a window located on any desired region of the mounting structure 120.

Figure 35:
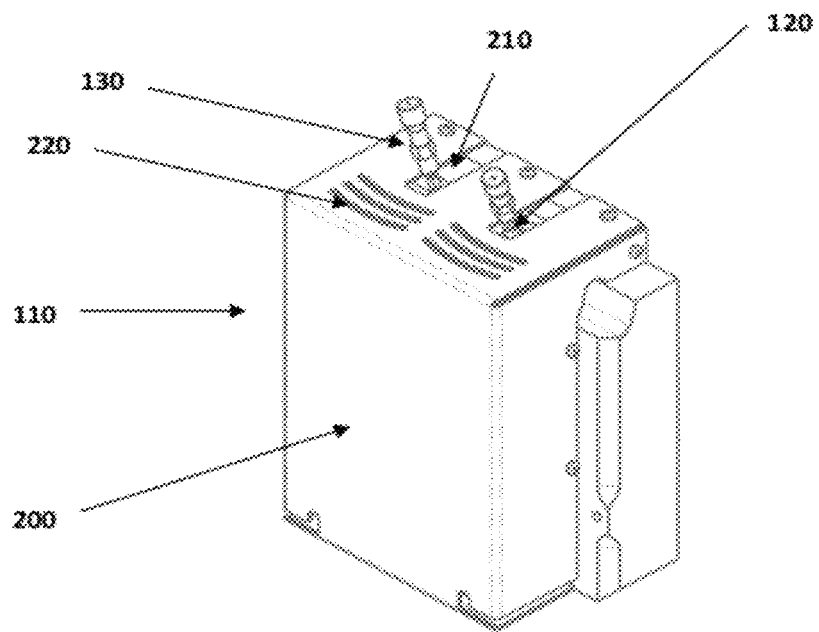
FIG. 35 schematically shows a cover covering a dual sprayer mounted on an ion source housing.

FIG. 35 shows a dual sprayer 110 comprising a cover 200 affixed to and covering the mounting structure 120. The cover 200 may be made of any desired material and can substantially or partially cover the mounting structure 120. The cover 200 may be affixed to the mounting structures by screws, bolts, clamps, pins, or via any other connection means. The cover may comprise one or more slots or openings 210 to allow the probe(s) 130 to stick through the cover 200 and permit the probe(s) 130 to move uninhibited by the cover 200. The cover 200 may further comprise one or more slots or openings that serve as vents 220 to permit air to circulate in and out of the cover 200. One or more fans or pumps (not shown) may also be employed to assist in circulation of air or other gasses throughout the system.

Figure 36:
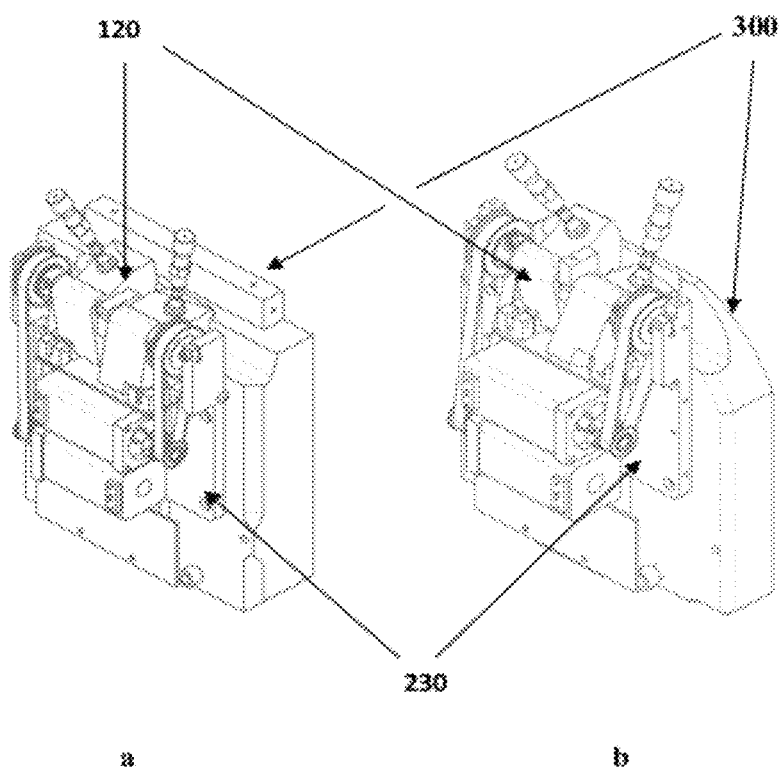
FIG. 36a schematically shows an exemplary dual sprayer with a mounting structure mounted on an ion source housing.
FIG. 36b schematically shows an exemplary dual sprayer with a mounting structure mounted on an alternative ion source housing.

As shown in FIGS. 36a and 36b, the probe mounting structure 120 may comprise an ion source housing back plate 230 that is configured to operably connect to an ion source housing 300. FIGS. 36a and 36b show alternative ion source housing back plates 230 configured for attachment to two different ion source housing 300 configurations. The ion source housing back plate 230 typically comprises at least one alignment feature (not shown) that is structured to align the ion source housing back plate 230 relative to the ion source housing 300 when the ion source housing back plate 230 operably connects to the ion source housing 300.

Examples of alignment features include, but are not limited to, markings, grooves, alignment holes, alignment pegs, and the like.

As shown in FIG. 37, the probe 130 comprises at least one channel 131 disposed through a length of the probe 130. The probe 130 may comprise at least one sprayer needle 132 that fluidly communicates with the channel 131. A nebulizer gas source and/or nebulizer gas sheath 133 fluidly communicates with the channel. The probe 130 may also comprise a thermal modulator, configured to modulate a temperature of the probe 130, comprising a nebulizer gas heater 134 and a controller circuit board 135.

As shown in FIG. 38, a first mounting 121 component is operably connected to the probe mounting structure 120. The first mounting component is configured to engage at least a second mounting component (not shown) that is operably connected to an ion source housing 300 (not shown in FIG. 38) when the probe mounting structure 120 is mounted on the ion source housing 300 (not shown in FIG. 38). The first 121 and second (not shown) mounting components may comprise hinge and/or latch components or any other means to moveably attached the mounting structure 120 to the ion source housing 300.

The probe may be movably coupled to the probe mounting structure 120 via a slide mechanism 400. The slide mechanism 400 comprises at least two probes 130, substantially fixedly coupled to the slide mechanism 400, and capable of sliding between a first position and a second position. The first position 130a comprises a spray position and the second position comprises at least first 130b and second 130c rinse positions that are each substantially electrically isolated from the spray position. When a first probe 130 is in the spray position 130a, a second probe 130 is in the second rinse position 130b, and when the second probe 130 is in the spray position 130a, the first probe is in the first rinse position 130c. The slide mechanism 400 comprises a probe support plate 420 coupled to the probe mounting structure 120 via a linear slide 410, and the probe is mounted on the probe support plate 420. The probe slide mechanism comprises a dual acting pneumatic cylinder 430 operably connected to the probe mounting structure 120 and to the probe support plate 420.

As shown in FIG. 38, an ion source housing back plate 230 comprises one or more surfaces that define at least one spray orifice 139. The dual sprayer assembly 110 also includes at least one rinse cavity 136 that is at least partially disposed within the ion source housing back plate 230 in which the rinse cavity 136 fluidly communicates with at least one outlet 138. The dual sprayer assembly 110 also includes at least one probe support structure 120 coupled to the ion source housing back plate 230 via at least one linear slide 410, and at least one probe 130 substantially fixedly mounted on the probe support structure 120. The probe conveyance mechanism 150 is operably connected to the probe support structure 120. The probe conveyance mechanism 150 is configured to selectively convey the probe support structure 120, such that the probe 130 slides between the spray orifice 139 and the rinse cavity 136 through the opening.

In some embodiments, the invention provides a molecular mass measurement system. The system includes time of flight spectrometer (TOF) 100 that comprises at least one ion source housing 300, and at least one dual sprayer assembly 110 operably connected to the ion source housing 300. The dual sprayer assembly 110 comprises: at least one probe mounting structure 120; at least one probe 130 that comprises a probe opening 140 that can serve as a fluid inlet and a sprayer needle 132 that can serve as a fluid outlet in which the probe opening 140 communicates with the sprayer needle 132 via a channel 131. The probe 130 is movably coupled to the probe mounting structure 120, which probe is configured to discontinuously introduce sample aliquots into the ion source housing 300; and at least one probe conveyance mechanism 150 operably connected to the probe 130, which probe conveyance mechanism 150 is configured to convey the probe 130 between a spray position 130a and a rinse position 130b in which the spray position 130a is substantially electrically isolated from the rinse position 130b.

In some embodiments, the present invention provides a controller configured to selectively direct the ionization probe assembly 110 to: (a) convey the probe from the rinse position 130b to the spray position 130a; (b) spray at least one sample aliquot into the ion source housing 300 from the sample source when the probe is in the spray position 130a; (c) convey the probe from the spray position 130a to the rinse position 130b; and (d) rinse the probe with rinse fluid from a rinse fluid source when the probe is in the rinse position 130b. In some embodiments, a rinse fluid source is contained on or within the TOF spectrometer 100, TOF chamber 101, or the dual sprayer assembly 110 or is located externally to the sprayer and spectrometer devices.

In some embodiments, the system includes at least one additional system component selected from, e.g., at least one nucleic acid amplification component; at least one sample preparation component; at least one microplate handling component; at least one mixing station; at least one material transfer component; at least one sample processing component; at least one database; and the like.

In some embodiments, the invention provides a computer program product that includes a computer readable medium having one or more logic instructions for directing an ionization probe assembly of a molecular mass measurement system as shown in FIGS. 39a and b: (a) convey a first probe 130 from a first rinse position 130b to a first spray position 130a of the molecular mass measurement system, wherein the first rinse position 130b and the first spray position 130a are substantially electrically isolated from one another; (b) convey a second probe from a second spray position 130c to a second rinse position 130d of the molecular mass measurement system, wherein the second spray position 130c and the second rinse position 130d are substantially electrically isolated from one another; (c) spray at least a first sample aliquot into an ion source housing 300 of the molecular mass measurement system via the first probe 130 when the first probe is in the first spray position 130a; (d) rinse the second probe 130 when the second probe is in the second rinse position 130d; (e) convey the first probe from the first spray position 130a to the first rinse position 130b; (f) convey the second probe from the second rinse position 130d to the second spray position 130c; (g) spray at least a second sample aliquot into the ion source housing of the molecular mass measurement system via the second probe 130 when the second probe is in the second spray position 130c; and, (h) rinse the first probe 130 when the first probe 130 is in the first rinse position 130b. In some embodiments, the computer program product includes at least one logic instruction for directing the dual spray assembly 110 of the molecular mass measurement system to modulate a temperature of the first probe and/or second probe 130 using at least one thermal modulator operably connected to the first probe and/or second probe. In certain embodiments, the logic instructions are configured to direct the dual spray assembly 110 to execute (a) substantially simultaneously with (b), (c) substantially simultaneously with (d), (e) substantially simultaneously with (f), and/or (g) substantially simultaneously with (h). Typically, a controller of the molecular mass measurement system comprises the logic instructions.

In another aspect, the invention provides a method of spraying sample aliquots into an ion source housing of a molecular mass measurement system. The method includes (a) conveying a first probe 130 from a first rinse position 130b to a first spray position 130a of the molecular mass measurement system in which the first rinse position 130b and the first spray position 130a are substantially electrically isolated from one another and wherein the first spray position 130a is in fluid communication with the ion source housing 300; and (b) conveying a second probe 130 from a second spray position 130c to a second rinse position 130d of the molecular mass measurement system, wherein the second spray position 130c and the second rinse position 130d are substantially electrically isolated from one another. The method also includes (c) spraying at least a first sample aliquot into the ion source housing 300 via the first probe 130 when the first probe 130 is in the first spray position 130a; (d) rinsing the second probe 130 when the second probe 130 is in the second rinse position 130d; and (e) conveying the first probe 130 from the first spray position 130a to the first rinse position 130b. In addition, the method also includes (f) conveying the second probe 130 from the second rinse position 130d to the second spray position 130c in which the second spray position 130c is in fluid communication with the ion source housing 300; (g) spraying at least a second sample aliquot into the ion source housing 300 of the molecular mass measurement system via the second probe 130 when the second probe 130 is in the second spray position 130c; and (h) rinsing the first probe 130 when the first probe is in the first rinse position 130b, thereby spraying the sample aliquots into the ion source housing 300 of the molecular mass measurement system. In certain embodiments, the method includes performing (a) substantially simultaneously with (b), (c) substantially simultaneously with (d), (e) substantially simultaneously with (f), and/or (g) substantially simultaneously with (h).

In some embodiments, the method includes modulating a temperature of the first probe and/or second probe using at least one thermal modulator operably connected to the first probe 130 and/or second probe 130. Typically, the method includes ionizing the first sample aliquot and the second sample aliquot when the first sample aliquot and the second sample aliquot are sprayed into the ion source housing 300. The method also generally includes measuring a molecular mass of at least one component of the first sample aliquot and/or the second sample aliquot using the molecular mass measurement system.

In some embodiments, the component of the first sample aliquot and/or the second sample aliquot comprises at least one nucleic acid molecule. In these embodiments, the method generally comprises determining a base composition of the nucleic acid molecule from the molecular mass of the nucleic acid molecule. In certain of these embodiments, the method includes correlating the base composition of the nucleic acid molecule with an identity or property of the nucleic acid molecule.

In some embodiments, the present invention provides determination of base compositions of the amplicons are typically determined from the measured molecular masses and correlated with an identity or source of target nucleic acids in the amplification reaction mixtures, such as a pathogenic organism. Particular embodiments of molecular mass-based detection methods and other aspects that are optionally adapted for use with the sample processing units and related aspects of the invention are described in various patents and patent applications, including, for example, U.S. Pat. Nos. 7,108,974; 7,217,510; 7,226,739; 7,255,992; 7,312,036; and 7,339,051; and US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; and WO2007/100397; WO2007/118222, which are each incorporated by reference as if fully set forth herein.

Exemplary molecular mass-based analytical methods and other aspects of use in the sample processing units and systems described herein are also described in, e.g., Ecker et al. (2005) "The Microbial Rosetta Stone Database: A compilation of global and emerging infectious microorganisms and bioterrorist threat agents" *BMC Microbiology* 5(1):19; Ecker et al. (2006) "The Ibis T5000 Universal Biosensor: An Automated Platform for Pathogen Identification and Strain Typing" *JALA* 6(11):341-351.; Ecker et al. (2006) "Identification of *Acinetobacter* species and genotyping of *Acinetobacter baumannii* by multilocus PCR and mass spectrometry" *J Clin Microbiol.* 44(8):2921-32.; Ecker et al. (2005) "Rapid identification and strain-typing of respiratory pathogens for epidemic surveillance" *Proc Natl Acad Sci USA.* 102(22):8012-7; Hannis et al. (2008) "High-resolution genotyping of *Campylobacter* species by use of PCR and high-throughput mass spectrometry" *J Clin Microbiol.* 46(4):1220-5; Blyn et al. (2008) "Rapid detection and molecular serotyping of adenovirus by use of PCR followed by electrospray ionization mass spectrometry" *J Clin Microbiol.* 46(2):644-51; Sampath et al. (2007) "Global surveillance of emerging Influenza virus genotypes by mass spectrometry" *PLoS ONE* 2(5): e489; Sampath et al. (2007) "Rapid identification of emerging infectious agents using PCR and electrospray ionization mass spectrometry" *Ann N Y Acad. Sci.* 1102:109-20; Hall et al. (2005) "Base composition analysis of human mitochondrial DNA using electrospray ionization mass spectrometry: a novel tool for the identification and differentiation of humans" *Anal Biochem.* 344(1):53-69; Hofstadler et al. (2003) "A highly efficient and automated method of purifying and desalting PCR products for analysis by electrospray ionization mass spectrometry" *Anal Biochem.* 316:50-57; Hofstadler et al. (2006) "Selective ion filtering by digital thresholding: A method to unwind complex ESI-mass spectra and eliminate signals from low molecular weight chemical noise" *Anal Chem.* 78(2):372-378.; and Hofstadler et al. (2005) "TIGER: The Universal Biosensor" *Int J Mass Spectrom.* 242(1):23-41, which are each incorporated by reference.

In addition to the molecular mass and base composition analyses referred to above, essentially any other nucleic acid amplification technological process is also optionally adapted for use in the systems of the invention. Other exemplary uses of the systems and other aspects of the invention include numerous biochemical assays, cell culture purification steps, and chemical synthesis, among many others. Many of these as well as other exemplary applications of use in the systems of the invention are also described in, e.g., Current Protocols in Molecular Biology, Volumes I, II, and III, 1997 (F. M. Ausubel ed.); Perbal, 1984, A Practical Guide to Molecular Cloning; the series, Methods in Enzymology (Academic Press, Inc.); Sambrook et al., 2001, Molecular Cloning: A Laboratory Manual, Third Edition, Cold Spring Harbor Laboratory Press, Cold Spring Harbor, N.Y.; Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Berger and Kimmel, Guide to Molecular Cloning Techniques, Methods in Enzymology volume 152 Academic Press, Inc., San Diego, Calif. (Berger), DNA Cloning: A Practical Approach, Volumes I and II, 1985 (D. N. Glover ed.); Immobilized Cells and Enzymes, 1986 (IRL Press); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively), which are each incorporated by reference.

In some embodiments, one or more controllers and/or computers may be operably attached to devices of the present invention to select conditions under which molecular mass measurement are made using a device of the present invention. The controllers and/or computers configured to operate with devices described herein are generally configured to effect, e.g. temperature, sample volume, number of runs, sample switching, probe rinsing conditions, spray conditions, etc. Controllers and/or computers are typically operably connected to one or more system components, such as motors (e.g., via motor drives), thermal modulating components, detectors, motion sensors, fluidic handling components, robotic translocation devices, or the like, to control operation of these components. Controllers and/or other system components is/are generally coupled to an appropriately programmed processor, computer, digital device, or other logic device or information appliance (e.g., including an analog to digital or digital to analog converter as needed), which functions to instruct the operation of these instruments in accordance with preprogrammed or user input instructions (e.g., mixing mode selection, fluid volumes to be conveyed, etc.), receive data and information from these instruments, and interpret, manipulate and report this information to the user.

A controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

In some embodiments, a computer includes appropriate software for receiving user instructions, either in the form of user input into a set of parameter fields, e.g., in the form of preprogrammed instructions, e.g., preprogrammed for a variety of different specific operations. The software then converts these instructions to appropriate language for instructing the operation of one or more controllers to carry out the desired operation, e.g., rinsing probe, switching fluids, taking mass measurements, or the like. The computer then receives the data from, e.g., sensors/detectors included within the system, and interprets the data, either provides it in a user understood format, or uses that data to initiate further controller instructions, in accordance with the programming.

More specifically, the software utilized to control the operation of the devices and systems of the invention typically includes logic instructions that selectively direct, e.g., motors to more probes, rate of probe movement, rate of sampling, data acquisition, and the like. The logic instructions of the software are typically embodied on a computer readable medium, such as a CD-ROM, a floppy disk, a tape, a flash memory device or component, a system memory device or component, a hard drive, a data signal embodied in a carrier wave, and/or the like. Other computer readable media are known to persons of skill in the art. In some embodiments, the logic instructions are embodied in read-only memory (ROM) in a computer chip present in one or more system components, without the use of personal computers.

The computer can be, e.g., a PC (Intel x86 or Pentium chip-compatible DOS™, OS2™, WINDOWS™, WINDOWS NT™, WINDOWS98™, WINDOWS2000™, WINDOWS XP™, WINDOWS Vista™, LINUX-based machine, a MACINTOSH™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., sample processing unit container rotation, material conveyance to and/or from sample processing unit containers, mixing process monitoring, assay detection, and data deconvolution is optionally constructed by one of skill using a standard programming language such as Visual basic, C, C++, Fortran, Basic, Java, or the like.

Devices and systems of the invention may also include at least one robotic translocation or gripping component that is structured to grip and translocate fluids, containers, or other components between components of the devices or systems and/or between the devices or systems and other locations (e.g., other work stations, etc.). A variety of available robotic elements (robotic arms, movable platforms, etc.) can be used or modified for use with these systems, which robotic elements are typically operably connected to controllers that control their movement and other functions.

Devices, systems, components thereof, and station or system components of the present invention are optionally formed by various fabrication techniques or combinations of such techniques including, e.g., machining, embossing, extrusion, stamping, engraving, injection molding, cast molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, $3^{rd}$ Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate devices or systems of the present invention, or components thereof include metal (e.g., steel, aluminum, etc.), glass, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, system components are optionally further processed, e.g., by coating surfaces with a hydrophilic coating, a hydrophobic coating (e.g., a Xylan 1010DF/870 Black coating available from Whitford Corporation (West Chester, Pa.), etc.), or the like, e.g., to prevent interactions between component surfaces and reagents, samples, or the like.

V. Lift and Mount Component

The present invention provides devices, apparatuses, and systems for lifting and mounting of clinical- and research-related equipment. In certain embodiments, for example, the present invention provides a lifting and mounting system for mass spectrometers (e.g., time of flight (TOF) mass spectrometers (MS)). In some embodiments, the present invention provides an apparatus, unit, assembly, system, rack, shelve, and/or device for mounting, storing, protecting, supporting, shelving, and/or holding a device, unit, apparatus, instrument, piece of equipment, etc. (e.g. mass spectrometers (e.g. TOF-MS, MALDI-TOF-MS, LC-MS, ESI-MS), chromatography equipment (e.g. high performance liquid chromatograph (HPLC), fast protein liquid chromatograph (FPLC), liquid chromatograph (LC), gas chromatograph (GC), supercritical-fluid chromatography (SFC), capillary electrokinetic chromatograph (CEC), etc.), scintillation counter, microscope systems (e.g. confocal microscope), spectrometer (e.g. IR spectrometer, UV-Vis. spectrometer, microwave spectrometer, x-ray spectrometer, emission spectrometer, fluorescence spectrometer, nuclear magnetic resonance spectrometer, etc.), x-ray generator, computers, etc.). Biomedical, biochemical, and biophysical research and clinical instruments may be large, unwieldy, and difficult to move and/or store. Further, research and clinical equipment may be delicate, containing precision elements that should be transported and stored with great care and sensitivity. In some embodiments, the present invention provides an apparatus for mounting, supporting, and storing clinical and research devices and equipment in a safe, effective manner. In some embodiments, an apparatus of the present invention is configured to support biomedical, biochemical, and/or biophysical devices and related equipment (e.g. computer, printer, reagents, power source, display unit, control unit, accessory units, etc.). In some embodiments, devices and equipment may be accessed by a user, manipulated, and used while stored in an apparatus of the present invention. In some embodiments, the present invention provides an apparatus for mounting, supporting, storing, and using a TOF-MS and any related equipment or accessories (e.g. computer, display, printer, reagents, nucleic acid or protein processing components (e.g., thermocyclers), etc.).

Illustrative embodiments of the apparatuses are described in more detail below. The invention is not limited to these particular embodiments.

As shown in FIG. 40, in some embodiments, the present invention provides an apparatus 100 for mounting and supporting a device 200 (exemplified as a TOF-MS in the figure). The apparatus provides a structural assembly 110 for supporting a device 200, and a mounting assembly 130 for mounting and unmounting the device 200 onto and off of the structural assembly 110.

In some embodiments, the apparatus 100 comprises a structural assembly 110. The structural assembly 110 comprises a plurality of support members (e.g. bars, rails, posts, beams, walls, etc.) including four vertical support members 111 (although more or less can be used), a front base member 112, a front support member 113, and two side support members 114 (one not within view in FIG. 40), a rear support member 115, rear restraint member 116, rear vertical member 117, two side restraint members 118 (one not within view in FIG. 40), two upper support members 119, and two top support members 120. The support members 120 provide support for the apparatus 100, the device 200, and the mounting assembly 130. Configurations of the support members other than the embodiments depicted in FIG. 40 are also contemplated. For example, additional side restraint members 118 and rear restraint members 116 may be utilized to provide additional support and restraint for the device 200, multiple rear vertical members 117, or additional top support members 120 may play roles in attaching and supporting the mounting assembly 130. Likewise, one or more of the support or restraint members may be absent, so long as sufficient architecture is present to mount the device 200. Attached to the side support members 114, rear support member 115, and front support member 113 is a platform member 121 which provides a placement location for the device 200, when mounted.

In some embodiments, the apparatus 100 comprises a mounting assembly 130. The mounting assembly 130 is configured to perform a lifting operation and a retracting operation. The lifting operation of the mounting assembly 130 is performed by two device engagement members 131, a device stability member 132, a primary lift rod 133, a secondary lift rod 134, four rod engagement members 135, a rod connection member 136, a lift motor 137 (e.g., a stepper motor, a servo motor, or the like), two side lift members 138, a front lift member 139, and a top lift member 140. In some embodiments, device engagement members 131 comprise straps or belts which extend from a rod engagement member 135 attached to the primary lift rod 133 to a second rod engagement member 135 attached to the secondary lift rod 134. The device engagement members 131 are configured to extend to the level of the front base member 112 and beneath the device 200. In some embodiments, rod engagement members 135 comprise wheels or tracks on the primary lift rod 133 and secondary lift rod 134 which are configured to engage the device engagement members and provide stability of the interaction between the device engagement members 131 and the primary lift rod 133 and secondary lift rod 134 during lifting. In some embodiments, the lift motor 137 is functionally attached to the primary lift rod 133. Turning of the lift motor 137 results in simultaneous turning of the primary lift rod 133. The rod connection member 136 engages both the primary lift rod 135 and the secondary lift rod 134. Turning of the primary lift rod 133 results in turning of the secondary lift rod 134 through the action of the rod connection member 136. Therefore, turning of the lift motor 137 results in the simultaneous turning of the primary lift rod 133 and the secondary lift rod 134 in the same rotary direction. Turning of the primary lift rod 133 and secondary lift rod 134 causes the device engagement members 131 to retract, thereby lifting the device 200 up from the level of the front base member 112. The lift motor 137, primary lift rod 133, secondary lift rod 134, rod engagement members 135, rod connection member 136, and device engagement members 131 are configured to lift the device 200 so that the bottom of the device 200 is higher than the level of the platform member 121. One or more device stability members 132 extend around the device 200 and the device engagement members 131 to stabilize and secure the device 200 during lifting. Support for the mounting assembly 130 during lifting is provided by two side lift members 138, a front lift member 139, and a top lift member 140.

In some embodiments, the retracting operation of the mounting assembly 130 is performed by a retraction member 141 and the retraction motor 142 (e.g., a stepper motor, a servo motor, or the like). Movement of the refraction member 141 by the retraction motor 142 results in the retraction of the primary lift rod 134 and secondary lift rod 134, as well as the attached rod engagement members 135, device engagement members 131, device stability member 132, rod connection member 136, and lift motor 137 into the mounted position above the platform member 121.

Upon retraction, the mounting assemble 130 is configured to lower the device 200 onto the platform assembly 118. Lowering of the device 200 is carried out by turning of the lift motor 137 in the opposite direction as during lifting. Turning of the lift motor 137 results in rotation of the primary lift rod 133, movement of the rod connection member 136, rotation of the secondary lift member 134, extension of the device engagement members 131, and lowering of the device 200 onto the platform member 118. Upon placement of the device 200 onto the platform member 121, the side lift members 138 and front lift member 139 can be removed or retracted, and the top lift member 140 can adopt a collapsed conformation (SEE FIG. 41). The same lowering mechanism is performed when the mounting assembly 130 is in the extended conformation to lower a device 200 onto the ground in front of the apparatus 100. In some embodiments, additional support structures are included to increase the load bearing capacity of the side lift members 138 and the front lift member 139. For example, in some embodiments, one or more additional support members, straps, cables, or other components connect the front lift member 139 and/or the side lift members 138 (or any other component of the mounting assembly 130) to the structural assembly 110, for example, to the support members 120 of the structural assembly 110.

In some embodiments, the apparatus 100 comprises an accessory assembly 150. In some embodiments the accessory assembly 150 attaches to the structural assembly 110 at the front base member 112, vertical support members 111, rear restraint member 116, side restraint member 118, front support member 113, and rear restraint member 116. The accessory assembly 150 comprises the front base member 112, front support member 113, accessory vertical member 151, accessory side restraint 152, accessory support members 153, accessory side support 154, accessory vertical support 155, accessory base member 156, and accessory top restraint 157. Many configurations of the accessory assembly 150 are within the scope of the present invention. For example, in some embodiments the accessory assembly 150 comprises front and rear accessory top restraints 157. In some embodiments, the accessory assembly 150 comprises a rear accessory base member. In some embodiments, the accessory assembly 150 lacks an accessory side restraint 152 and accessory top restraint 157. In some embodiments, the apparatus 100 lacks an accessory assembly 150. In some embodiments, the apparatus 100 comprises multiple accessory assemblies 150 (e.g. located in front, right side, left side, rear, serially connected, etc.).

In some embodiments, the mounting assembly 130 comprises a lifting assembly and a retracting assembly. In some embodiments, the lifting assembly and a retracting assembly comprise separate motors (e.g. 137 and 142). In some embodiments, a single motor drives the lifting assembly and the retracting assembly (e.g. 137). In some embodiments, a motor engages both the retracting assembly and the lifting assembly. In some embodiments, the lifting assembly is driven by a motor (e.g. 137). In some embodiments, the lifting motor is electric powered (e.g. AC powered, battery powered, etc.). In some embodiments, the lifting motor powers the lifting assembly by directly turning one or more gears, chains, belts, rods (e.g. 133), etc. In some embodiments, the lifting motor (e.g. 137) powers the lifting assembly by indirectly turning one or more gears, chains, belts, rods (e.g. 134), etc. In some embodiments, one or more gears or rods (e.g. 133 or 134) turned by the lifting motor (e.g. 137) directly engage one or more device engagement members (e.g. 131). In some embodiments, one or more gears or rods (e.g. 133 or 134) turned by the lifting motor (e.g. 137) indirectly engage one or more device engagement members (e.g. through a chain, through a belt, through one or more gears, through a rod engagement member (e.g. 135), etc.). In some embodiments, a lifting motor (e.g. 137) directly turns a primary lift rod (e.g. 133), and indirectly (e.g. via a chain, via one or more gears, etc.) turns a secondary lifting rod (e.g. 134). In some embodiments, a primary (e.g. 133) and/or secondary lift rod (e.g. 134) is functionally attached to one or more device engagement members (e.g. 131). In some embodiments, a lifting motor turns a primary lift rod (e.g. 133) and a secondary lift rod (e.g. 134) in the same direction (e.g. clockwise or counterclockwise). In some embodiments, a lifting motor turns a primary lift rod (e.g. 133) and a secondary lift rod (e.g. 134) in opposite directions (e.g. clockwise and counterclockwise). In some embodiments, turning of a primary lift rod (e.g. 133) and/or a secondary lift rod (e.g. 134) and/or the rod engagement members (e.g. 135) results in retracting of one or more device engagement members (e.g. 131). In some embodiments, device engagement members (e.g. 131) comprise straps, cords, chains, cables, ropes, latches, hooks, etc. In some embodiments device engagement members (e.g. 131) are positioned under a device (e.g. 200) in order to lift the device (e.g. 200). In some embodiments device engagement members (e.g. 131) are attached to a device (e.g. 200) in order to lift the device (e.g. 200). In some embodiments device engagement members (e.g. 131) are configured to fit with a specific make, model, or type of device (e.g. 200). In some embodiments, device engagement members (e.g. 131) are generically configured to fit with all, most, or many large research or clinical devices (e.g. 200). In some embodiments, retracting one or more device engagement members (e.g. 131) via the lifting assembly results in lifting an attached or engaged device (e.g. 200).

In some embodiments, the retracting assembly is operatively associated, functionally associated, and/or attached to the lifting assembly. In some embodiments, the retracting assembly is configured to shuttle the lifting assembly from an extended conformation (SEE FIG. 40) (e.g. extended beyond the front or rear of the structural assembly 110) to a retracted conformation (SEE FIG. 41) (e.g. retracted within the structural assembly 110, above the platform member 121). In some embodiments, the retracting assembly is configured to shuttle the lifting assembly from a retracted conformation (SEE FIG. 41) to an extended conformation (SEE FIG. 40). In some embodiments, the retracting assembly is powered by a motor (e.g. electric motor). In some embodiments, the retracting assembly is powered by the same motor as the lifting assembly. In some embodiments, the retracting assembly is powered by a different motor from the lifting assembly (e.g. 142). In some embodiments, the retracting motor (e.g. 142) turns one or more gears, rods, belts, and/or chains (e.g. retraction member 141) which result in extending or retracting the lifting assembly.

The present invention is not limited to the configurations depicted in the drawings (SEE FIG. 40-44). In some embodiments, the structural assembly 110 may be of any suitable configuration. In some embodiments, the structural assembly 110 comprises walls, windows, doors, drawers, shelves, panels, etc. In some embodiments, the structural assembly 110 comprises wheels, casters, sliders, etc. In some embodiments, the structural assembly 110 is mobile. In some embodiments, the structural assembly 110 is stationary. In some embodiments, the structural assembly 110 is configured to be attached to a wall or external support. In some embodiments, the structural assembly 110 is free standing.

In some embodiments, the structural assembly 110 comprises one or more vertical support members 111 (e.g. 1, 2 3, 4, 5, 6, 7, 8, 9, 10, 11, 12 13, 14, 15, 16, 17 18, 19, 20, >20). In some embodiments, vertical support members 111 are located at the corners of the structural assembly 110. In some embodiments vertical support members 111 are located along the front, right, left, or rear sides of the structural assembly 110. In some embodiments, vertical support members 111 extend from the bottom of the structural assembly 110 to the top of the structural assembly 110. In some embodiments, vertical support members 111 do not extend to the bottom of the structural assembly 110. In some embodiments, vertical support members 111 do not extend to the top of the structural assembly 110. In some embodiments, vertical support members 111 are attached to or in contact with other elements within the structural assembly 110 (e.g. front base member 112, front support member 113, side support member 114, rear support member 115, rear restraint member 116, side restraint member 118, upper support member 119, top support member 120, platform member 121, etc.), mounting assembly 130 (e.g. primary lift rod 133, secondary lift rod 134, lift motor 137, side lift member 138, front lift member 139, top lift member 140, retraction member 141, retraction motor 142, etc.), and/or accessory assembly 150 (e.g. accessory vertical member 151, accessory side restraint 152, accessory support member 153, accessory side support 154, accessory vertical support 155, accessory base member 156, accessory top restraint 157, etc.). In some embodiments, vertical support members 111 are attached to or in contact with other elements within the structural assembly 110, mounting assembly 130, and/or accessory assembly 150 through connector pieces (e.g. brackets, joints, connectors, screws, etc.).

In some embodiments, the structural assembly 110 comprises one or more front base members 112 (e.g. 1, 2 3, 4, 5, 6, 7, 8, 9, 10, >10). In some embodiments, a front base member 112 is positioned along the front of the apparatus 100. In some embodiments, a front base member 112 is positioned along the right, rear, or left side of the structural assembly 110. In some embodiments, a front base member comprises a portion of the structural assembly 110 and/or the accessory assembly 150. In some embodiments, a front base member extends from a corner of the structural assembly 110 and/or the accessory assembly 150 to another corner. In some embodiments, one or both ends of a front base member terminates within the side of the structural assembly 110 and/or the accessory assembly 150 (e.g. not at a corner). In some embodiments, one or more front base members 112 are attached to or in contact with other elements within the structural assembly 110 (e.g. vertical support member 111 side support member 114, rear support member 115, rear vertical member 117, platform member 121, etc.), mounting assembly 130, and/or accessory assembly 150 (e.g. accessory vertical member 151, accessory side restraint 152, accessory support member 153, accessory side support 154, accessory vertical support 155, accessory base member 156, accessory top restraint 157, etc.) through direct interaction of through connector pieces (e.g. brackets, joints, connectors, screws, etc.).

In some embodiments, the structural assembly 110 comprises one or more front support members 113 (e.g. 1, 2 3, 4, 5, 6, 7, 8, 9, 10, >10), side support members 114 (e.g. 1, 2 3, 4, 5, 6, 7, 8, 9, 10, >10), and/or rear support members 115 (e.g. 1, 2 3, 4, 5, 6, 7, 8, 9, 10, >10). In some embodiments, a front support member 113 is positioned along the front of the apparatus 100. In some embodiments, a side support member 114 is positioned along the right or left side of the apparatus 100. In some embodiments, a rear support member 115 is positioned along the rear of the apparatus 100. In some embodiments, a front support member 113, side support member 114, and/or rear support member 115 is positioned along the front, right, rear, and/or left side of the structural assembly 110. In some embodiments, a front support member 113, side support member 114, and/or rear support member 115 comprises a portion of the structural assembly 110 and/or the accessory assembly 150. In some embodiments, a front support member 113, side support member 114, and/or rear support member 115 extends from a corner of the structural assembly 110 and/or the accessory assembly 150 to another corner. In some embodiments, one or both ends of a front support member 113, side support member 114, and/or rear support member 115 terminates within the side of the structural assembly 110 and/or the accessory assembly 150 (e.g. not at a corner). In some embodiments, one or more front support member 113, side support member 114, and/or rear support member 115 are attached to or in contact with other elements within the structural assembly 110 (e.g. vertical support member 111, rear vertical member 117, platform member 121, etc.), mounting assembly 130, and/or accessory assembly 150 (e.g. accessory vertical member 151, accessory side restraint 152, accessory support member 153, accessory side support 154, accessory vertical support 155, accessory base member 156, accessory top restraint 157, etc.) through direct interaction of through connector pieces (e.g. brackets, joints, connectors, screws, etc.). In some embodiments, one or more front support member 113, side support member 114, and/or rear support member 115 are attached to or in contact with (e.g. direct or through one or more connector pieces) one or more front support member 113, side support member 114, and/or rear support member 115.

In some embodiments, the apparatus 100 comprises one or more rear restraint members 116 (e.g. 1, 2 3, 4, 5, 6, 7, 8, 9, 10, >10), side restraint members 118 (e.g. 1, 2 3, 4, 5, 6, 7, 8, 9, 10, >10), accessory side restraints 152 (e.g. 1, 2 3, 4, 5, 6, 7, 8, 9, 10, >10), and/or accessory top restraints 157 (e.g. 1, 2 3, 4, 5, 6, 7, 8, 9, 10, >10). In some embodiments, one or more rear restraint members 116, side restraint members 118, accessory side restraints 152, and/or accessory top restraints 157 are configured to provide structural support for the apparatus 100 and/or device 200. In some embodiments, one or more rear restraint members 116, side restraint members 118, accessory side restraints 152, and/or accessory top restraints 157 are configured to restrain a device 100 and/or accessory equipment, and prevent a device 100 and/or accessory equipment from falling, slipping, dislodging, and/or shifting. In some embodiments, one or more rear restraint members 116, side restraint members 118, accessory side restraints 152, and/or accessory top restraints 157 extend from a corner of the structural assembly 110 and/or the accessory assembly 150 to another corner. In some embodiments, one or more rear restraint members 116, side restraint members 118, accessory side restraints 152, and/or accessory top restraints 157 terminates within the side of the structural assembly 110 and/or the accessory assembly 150 (e.g. not at a corner). In some embodiments, one or more rear restraint members 116, side restraint members 118, accessory side restraints 152, and/or accessory top restraints 157 comprise a linear element, corner element, and/or bent element. In some embodiments, one or more rear restraint members 116, side restraint members 118, accessory side restraints 152, and/or accessory top restraints 157 are attached to or in contact with (e.g. direct or through one or more connector pieces) one or more elements within the structural assembly 110 (e.g. vertical support member 111, rear vertical member 117, platform member 121, etc.), mounting assembly 130, and/or accessory assembly 150 (e.g. accessory vertical member 151, accessory side restraint 152, accessory support member 153, accessory side support 154, accessory vertical support 155, accessory base member 156, accessory top restraint 157, etc.).

In some embodiments, the structural assembly 110 comprises one or more rear vertical members 117 (e.g. 1, 2 3, 4, 5, 6, 7, 8, 9, 10, 11, 12 13, 14, 15, 16, 17 18, 19, 20, >20). In some embodiments, rear vertical members 117 are located at the corners of the structural assembly 110. In some embodiments rear vertical members 117 are located along the front, right, left, or rear sides of the structural assembly 110. In some embodiments, rear vertical members 117 extend from the bottom of the structural assembly 110 to the top of the structural assembly 110. In some embodiments, rear vertical members 117 do not extend to the bottom of the structural assembly 110. In some embodiments, rear vertical members 117 do not extend to the top of the structural assembly 110. In some embodiments, rear vertical members 117 are attached to or in contact with other elements within the structural assembly 110 (e.g. front base member 112, front support member 113, side support member 114, rear support member 115, rear restraint member 116, side restraint member 118, upper support member 119, top support member 120, platform member 121, etc.), mounting assembly 130 (e.g. primary lift rod 133, secondary lift rod 134, lift motor 137, side lift member 138, front lift member 139, top lift member 140, retraction member 141, refraction motor 142, etc.), and/or accessory assembly 150 (e.g. accessory vertical member 151, accessory side restraint 152, accessory support member 153, accessory side support 154, accessory vertical support 155, accessory base member 156, accessory top restraint 157, etc.). In some embodiments, rear vertical members 117 are attached to or in contact with other elements within the structural assembly 110, mounting assembly 130, and/or accessory assembly 150 through connector pieces (e.g. brackets, joints, connectors, screws, etc.).

In some embodiments, the apparatus 100 of the present invention provides one or more platform members 121 (e.g. 1, 2, 3, 4, 5, 6, 7, 8, 9, 10, >10). In some embodiments, a platform member of the present invention is part of the structural assembly 110, mounting assembly 130, accessory assembly 150, and/or bridges 2 or more portions of the apparatus 100 (e.g. structural assembly 110 and accessory assembly 150). In some embodiments, a platform assembly 121 is configured to support a device 100, accessory, or other equipment, devices, apparatus, etc. In some embodiments, a platform assembly 121 is custom designed to fit and/or interact with a specific device 100 (e.g. mass spectrometer (e.g. TOF-MS)). In some embodiments, a platform assembly 121 comprises attachment elements for interacting with a device 100. In some embodiments, a platform assembly 121 provides a generic platform for supporting and interacting with general clinical and research equipment. In some embodiments, a platform assembly is directly or indirectly supported by vertical support members 111, front base members 112, front support members 113, side support members 114, rear support members 115, rear vertical members 117, accessory vertical members 151, accessory support members 153, accessory side supports 154, accessory vertical supports 155, and/or accessory base members 156.

In some embodiments, one or more accessory vertical members 151, accessory support member 153, accessory side support 154, accessory vertical support 155, and/or accessory base member 156 are configured to provide similar functions to the corresponding elements in the structural assembly 110. The accessory elements are configured to support the accessory assembly 150 and any accessory devices, equipment, and/or accessory units. In some embodiments, an apparatus 100 comprises one or more accessory assemblies 150 located on the front, rear, right, or left sides of the structural assembly 110. In some embodiments, an apparatus 100 lacks an accessory assembly 150.

In some embodiments, the mounting assembly 130 comprises one or more device engagement members 131 (e.g. 1, 2, 3, 4, 5, 6, 7, 8, 9, 10, 11, 12 13, 14, 15, 16, 17 18, 19, 20, >20). In some embodiments, device engagement members 131 provide an interface between the mounting assembly 130 and the device 200, during the lifting, retracting, and lowering processes. In some embodiments, a device engagement member 131 comprises a strap, belt, cord, cable, latch, platform, scoop, elevator, arm, etc. In some embodiments, a device engagement member 131 attaches directly to a device 200 (e.g. to the exterior). In some embodiments, a device engagement member 131 traverses around, under, or through a device 200.

In some embodiments, the structural assembly, mounting assembly, and accessory assembly comprise a plurality of materials (e.g. metal, alloys, plastics, etc.). In some embodiments, an apparatus of the present invention comprises one or more metals, alloys, plastics, polymers, natural materials, synthetic materials, fabrics, fibers, etc. In some embodiments, an apparatus of the present invention comprises one or more metals including but not limited to aluminum, antimony, boron, cadmium, cesium, chromium, cobalt, copper, gold, iron, lead, lithium, manganese, mercury, molybdenum, nickel, platinum, palladium, rhodium, silver, tin, titanium, tungsten, vanadium, and zinc. In some embodiments, a device of the present invention comprises one or more alloys including but not limited to alloys of aluminum (e.g., Al—Li, alumel, duralumin, magnox, zamak, etc.), alloys of iron (e.g., steel, stainless steel, surgical stainless steel, silicon steel, tool steel, cast iron, Spiegeleisen, etc.), alloys of cobalt (e.g., stellite, talonite, etc.), alloys of nickel (e.g., German silver, chromel, mu-metal, monel metal, nichrome, nicrosil, nisil, nitinol, etc.), alloys of copper (beryllium copper, billon, brass, bronze, phosphor bronze, constantan, cupronickel, bell metal, Devarda's alloy, gilding metal, nickel silver, nordic gold, prince's metal, tumbaga, etc.), alloys of silver (e.g., sterling silver, etc.), alloys of tin (e.g., Britannium, pewter, solder, etc.), alloys of gold (electrum, white gold, etc.), amalgam, and alloys of lead (e.g., solder, terne, type meta, etc.). In some embodiments, a device of the present invention comprises one or more plastics including but not limited to Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc. In some embodiments, elements of a device of the present invention a device of the present invention may also comprise glass, textiles (e.g., from animal (e.g. wool), plant (e.g. cotton, flax, etc.), mineral, and/or synthetic sources (e.g. polyester, etc.), liquids, etc.

VI. Asprirate Needle

In some embodiments, the present invention provides aspirate needles for use in the systems and methods described in this application that avoid problems associated with operating in magnetic environments. In certain embodiments, one or more aspirate needles in the systems of the present invention are composed of polyetheretherketone tubing (e.g., PEEK tubing), or similar type tubing, in conjunction with a stainless steel over-sheath that does not extend to the end of the tubing (see, e.g., FIG. 51), although any suitable non-magnetizable material may be used. The tubing is, for example, guided and held straight by the over sheath of stainless steel tubing for its near-full length (e.g., except the last few mm). Only the plastic tubing touches the aspirate fluid. In certain embodiments, there are no internal fluid connection junctions with the tubing employed. In some embodiments, the assembly shown in FIG. 51 is spring-loaded (spring inside the white Delrin hub) for +/−1 mm of height tolerance, as the probe touches off on the bottom of the cylindrical cuvette. In certain embodiments, the size of the tube is about 1/16" OD.

Work conducted during development of embodiments of the present invention, found the configuration described above overcame problems found when employing a stainless steel needle, which saw magnetic particle build-up at the tip over time, due to induced magnetism. This was caused by the fact that the probe is operating in a highly magnetic field in certain embodiments (e.g., see the nickel-plated neodymium magnets on either side of the cuvette in FIG. 51). It was determined that cutting and polishing the stainless tip, created some slight magnetic properties, which was enough to be generate problems after aspirating 5000 or more wells. The aspirate needle embodiments discussed above, and shown in FIG. 51, overcome such limitations.

VII. Reagent Rack and Signal Light

In some embodiments, the present invention provides systems for bioagent detection that comprise a reagent rack that can be accessed from the front on an intergrated system, although any suitable location may be employed. In some preferred embodiments, the rack is removable or partially removable from the remainder of the system to facility exchange of reagent containers. For example, as shown in FIG. 52 the rack containing the reagent bottles can be swung forward into a loading position. The reagent rack can also then be swung back into a run position as shown in FIG. 53.

In certain embodiments, the integrated detection system (shown in FIGS. 52 and 53) has a signal light or audio alarm (e.g., located on top of the integrated system as shown in FIGS. 52 and 53). In particular embodiments, this signal light or audio alarm is configured to alert the user of the integrated system that, for example, one or more of the reagent bottles is low or empty (or could simply indicate good status of all reagents), or could indicate that the integrated system was experiencing some internal problem that required user attention. In certain embodiments, the signal light has one color (e.g., blue) that indicates that all systems are working properly and/or all reagent bottles are not low; has a second color (e.g., amber) that indicates that there is a minor problem or that one or more of the reagent bottles is getting low; and has a third color (e.g., red) to indicate a system stopping problem or that one of the reagents bottles is empty. In some embodiments, a light or other indicator on the outside (e.g., top) of the system housing indicates a problem or potential problem. A secondary set of signals (e.g., lights) is contained under the reagent bottles themselves indicating which of the bottles has in inappropriate volume or other problem. Thus, the first external alarm indicates a general problem and the bottle-specific lights indicate more specifically where the problem resides. The volume of the reagent vessels can be assessed via any desired capacitive level sensing component or method, including visual methods, weight, or the like.

FIG. 54 shows one embodiments of the signal light of the present invention. FIG. 54A shows the signal light with the translucent cover covering LED lights. FIG. 54B shows the cover removed from the light, showing the internal LED light system. FIG. 54C shows a close up view of the LED light system, which is composed of 3 roes of 120 degree angle LED's (blue, red, and amber) which has variable intensity for each. In certain embodiments, the signal light is configured to display 3 colors (e.g., red, blue and amber), with intensity controlled by a PCB circuit, which is a USB peripheral for the intergrated system. In certain embodiments, the signal light has the dimensions such as, fore example, 6"×9"×4" tall.

VIII. Reagent Level Sensing Component

In certain embodiments, the integrated systems of the present invention have a plurality of liquid reagent bottles. In particular embodiments, the integrated system is configured to light up the reagent bottles with a color that is indicative of its liquid level status (e.g., empty is one color, low is a second color, and acceptable or full is a third color). In this regard, a user does not have to examine the individual reagent bottles to determine the status of each bottle.

In certain embodiments, the user is alerted to the status of reagent bottles by placing Light Emitting Diodes (LEDs) below PolyEthyleneGlycol-bottles or any material bottle (e.g., as shown in FIG. 55B). The status of the system or functional unit is communicated via the LEDs causing the bottle to illuminate with color or sequence of flashes. The illuminated bottle therefore indicates status. FIG. 55A shows three bottles, with two of the bottle (left and right) being one color to indicate an acceptable reagent level, and the middle bottle being a different color indicating a low level of reagent in this bottle.

In some embodiments, the presence or fill-status of the reagent bottles is detected by capacitive level sensing (or any other method that can sense reagent level or weight). In particular embodiments, according to sequences or combinations programmed as a user may decide, two individual banks of hi-brite LEDs (e.g., blue and amber) are available to be illuminated. In particular embodiments, the sensor is "normally open," so that the presence of at least some acceptable level of reagent is required to confirm the bottle is in place. Selective pattern diffusers on the LED window are used to highlight the meniscus.

In some embodiments, the "waste bottle full" sensor is "normally closed," so if a wire is broken, the logic state is the same as if the bottle is full. A second reflective IR sensor may be used to detect that the waste bottle is physically present. The "bottle present" sensor may have a short detection range (approx. 1"), to prevent false triggering on other objects.

In certain embodiments, the LED's, directly mounted to the sensor control-interface PCB are housed in a spill-proof area below the bottles. In particular embodiments, the LED's are standard commercial size, readily available, and dissipate approximately ½ watt per station for each color.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

We claim:

1. A system, comprising:
    at least one sample container handling component that comprises at least one non-priority sample container storage unit and at least one priority sample container storage unit that each store at least one sample container that is configured to contain one or more samples;
    at least one mixing station that comprises at least one mixing container and at least one mixing mechanism that is configured to mix at least one composition comprising magnetically responsive particles disposed in the mixing container, wherein said mixing container comprises a cartridge that comprises:
        at least one body structure comprising one or more surfaces that define a cavity having upper and lower portions;
        at least one rotatable member extending at least partially along an axis that is substantially horizontally disposed in the upper portion of the cavity; and
        at least one protrusion extending outward from the rotatable member and into the lower portion of the cavity;
    at least one sample processing component that comprises:
        at least one sample processing unit that comprises:
            at least one sample processing vessel that is configured to contain at least one sample comprising at least one magnetically responsive particle;
            at least one magnet that generates, or is configured to generate, at least one magnetic field at least proximal to the sample processing vessel; and
        at least one carrier mechanism operably connected to the sample processing unit, which carrier mechanism is configured to move the sample processing unit to one or more locations;
    at least one detection component that is configured to detect at least one detectable property of at least one sample component;
    at least one material transfer component that is configured to transfer material to and/or from the sample container handling component, the mixing station, the sample processing component, and/or the detection component;
    at least one controller operably connected to, and configured to effect operation of, the sample container handling component, the mixing station, the sample processing component, and/or the detection component; and,
    at least one base composition database.

2. The system of claim 1, wherein the non-priority sample container storage unit and the priority sample container storage unit are each configured to store at least one microplate.

3. The system of claim 1, wherein the sample processing vessel comprises at least one cuvette.

4. The system of claim 1, wherein the magnet is in a substantially fixed position.

5. The system of claim 1, wherein the detection component comprises at least one mass spectrometer.

6. The system of claim 1, wherein the detection component comprises at least one biopolymer sequencing component.

7. The system of claim 1, comprising at least one sample preparation component and/or at least one nucleic acid amplification component.

8. The system of claim 1, comprising:
    at least one sample container processing area;
    at least one non-priority sample container holding area; and,
    at least one sample container transport mechanism that is configured to transport one or more sample containers between the non-priority sample container storage unit, the priority sample container storage unit, the priority sample container storage unit, the sample container processing area, and/or the non-priority sample container holding area.

9. The system of claim 8, wherein the controller is configured to selectively direct the sample container transport mechanism to:
    transport a non-priority sample container from the non-priority sample container storage unit to the sample container processing area;
    position the non-priority sample container while in the sample container processing area;
    transport the non-priority sample container from the sample container processing area to the non-priority sample container holding area when a priority sample container is stored in the priority sample container storage unit;
    transport the priority sample container from the priority sample container storage unit to the sample container processing area;
    position the priority sample container while in the sample container processing area;
    transport the priority sample container from the sample container processing area to the non-priority sample container storage unit or to the priority sample container storage unit;
    transport the non-priority sample container from the non-priority sample container holding area to the sample container processing area; and
    transport the non-priority sample container from the sample container processing area to the non-priority sample container storage unit.

10. The system of claim 1, wherein the mixing mechanism comprises at least one cartridge receiver/rotation assembly that comprises:
    at least one cartridge support structure that supports the body structure of the cartridge; and
    a rotational mechanism operably connected to the rotatable member.

11. The system of claim 10, wherein the controller is configured to selectively direct the rotational mechanism to rotate the rotatable member in an initiation mode or in a maintenance mode, wherein a rate of rotation of the rotatable member is greater in the initiation mode than in the maintenance mode.

12. The system of claim 1, wherein the sample processing unit comprises:
    at least a first motor operably connected to the sample processing vessel, which first motor is configured to rotate the sample processing vessel around a central longitudinal axis of the sample processing vessel;
    at least one support member operably connected to the first motor; and,
    at least a second motor operably connected to the support member, which second motor is configured to rotate the sample processing vessel between at least first and second positions, wherein at least the first position is within magnetic communication with the magnet when the magnet generates the magnetic field.

13. The system of claim 12, wherein the controller is configured to effect one or more of: the magnet to generate the magnetic field, the first motor to rotate the sample processing vessel, the second motor to rotate the sample processing vessel between the first and second positions, the carrier mechanism to move the sample processing unit to the one or more locations, or the material transfer component to transfer the material to and/or from the sample processing vessel.

14. The system of claim 12, wherein the controller is configured to effect the first motor to rotate the sample processing vessel in one or more selectable modes.

15. A system, comprising:
at least one sample container handling component that comprises at least one non-priority sample container storage unit and at least one priority sample container storage unit that each store at least one sample container that is configured to contain one or more samples;
at least one mixing station that comprises at least one mixing container and at least one mixing mechanism that is configured to mix at least one composition comprising magnetically responsive particles disposed in the mixing container, wherein said mixing container comprises a cartridge that comprises:
 at least one body structure comprising one or more surfaces that define a cavity having upper and lower portions;
 at least one rotatable member extending at least partially along an axis that is substantially horizontally disposed in the upper portion of the cavity; and
 at least one protrusion extending outward from the rotatable member and into the lower portion of the cavity;
at least one sample processing component that comprises:
 at least one sample processing unit that comprises:
  at least one sample processing vessel that is configured to contain at least one sample comprising at least one magnetically responsive particle;
  at least one magnet that generates, or is configured to generate, at least one magnetic field at least proximal to the sample processing vessel; and
 at least one carrier mechanism operably connected to the sample processing unit, which carrier mechanism is configured to move the sample processing unit to one or more locations;
at least one detection component that is configured to detect at least one detectable property of at least one sample component;
at least one material transfer component that is configured to transfer material to and/or from the sample container handling component, the mixing station, the sample processing component, and/or the detection component; and
at least one controller operably connected to, and configured to effect operation of, the sample container handling component, the mixing station, the sample processing component, and/or the detection component.

16. The system of claim 15, wherein the non-priority sample container storage unit and the priority sample container storage unit are each configured to store at least one microplate.

17. The system of claim 15, wherein the sample processing vessel comprises at least one cuvette.

18. The system of claim 15, wherein the magnet is in a substantially fixed position.

19. The system of claim 15, wherein the detection component comprises at least one mass spectrometer.

20. The system of claim 15, wherein the detection component comprises at least one biopolymer sequencing component.

21. The system of claim 15, comprising at least one sample preparation component and/or at least one nucleic acid amplification component.

22. The system of claim 15, comprising at least one database.

23. The system of claim 15, comprising:
at least one sample container processing area;
at least one non-priority sample container holding area; and,
at least one sample container transport mechanism that is configured to transport one or more sample containers between the non-priority sample container storage unit, the priority sample container storage unit, the priority sample container storage unit, the sample container processing area, and/or the non-priority sample container holding area.

24. The system of claim 23, wherein the controller is configured to selectively direct the sample container transport mechanism to:
transport a non-priority sample container from the non-priority sample container storage unit to the sample container processing area;
position the non-priority sample container while in the sample container processing area;
transport the non-priority sample container from the sample container processing area to the non-priority sample container holding area when a priority sample container is stored in the priority sample container storage unit;
transport the priority sample container from the priority sample container storage unit to the sample container processing area;
position the priority sample container while in the sample container processing area;
transport the priority sample container from the sample container processing area to the non-priority sample container storage unit or to the priority sample container storage unit;
transport the non-priority sample container from the non-priority sample container holding area to the sample container processing area; and
transport the non-priority sample container from the sample container processing area to the non-priority sample container storage unit.

25. The system of claim 15, wherein the mixing mechanism comprises at least one cartridge receiver/rotation assembly that comprises:
at least one cartridge support structure that supports the body structure of the cartridge; and
a rotational mechanism operably connected to the rotatable member.

26. The system of claim 25, wherein the controller is configured to selectively direct the rotational mechanism to rotate the rotatable member in an initiation mode or in a maintenance mode, wherein a rate of rotation of the rotatable member is greater in the initiation mode than in the maintenance mode.

27. The system of claim 15, wherein the sample processing unit comprises:
at least a first motor operably connected to the sample processing vessel, which first motor is configured to rotate the sample processing vessel around a central longitudinal axis of the sample processing vessel;

at least one support member operably connected to the first motor; and, at least a second motor operably connected to the support member, which second motor is configured to rotate the sample processing vessel between at least first and second positions, wherein at least the first position is within magnetic communication with the magnet when the magnet generates the magnetic field.

28. The system of claim 27, wherein the controller is configured to effect one or more of: the magnet to generate the magnetic field, the first motor to rotate the sample processing vessel, the second motor to rotate the sample processing vessel between the first and second positions, the carrier mechanism to move the sample processing unit to the one or more locations, or the material transfer component to transfer the material to and/or from the sample processing vessel.

29. The system of claim 27, wherein the controller is configured to effect the first motor to rotate the sample processing vessel in one or more selectable modes.

* * * * *